US011473088B2

(12) United States Patent
Kopchick et al.

(10) Patent No.: US 11,473,088 B2
(45) Date of Patent: Oct. 18, 2022

(54) METHOD OF TREATING CANCER AND METHOD OF SENSITIZING CANCER CELLS TO THE ACTION OF CHEMOTHERAPEUTIC AGENTS VIA GROWTH HORMONE RECEPTOR ANTAGONISTS OR KNOCK DOWN

(71) Applicant: Ohio University, Athens, OH (US)

(72) Inventors: John J. Kopchick, Athens, OH (US); Reetobrata Basu, Athens, OH (US)

(73) Assignee: Ohio University, Athens, OH (US)

( * ) Notice: Subject to any disclaimer, the term of this patent is extended or adjusted under 35 U.S.C. 154(b) by 0 days.

(21) Appl. No.: 16/464,742

(22) PCT Filed: Dec. 1, 2017

(86) PCT No.: PCT/US2017/064188
§ 371 (c)(1),
(2) Date: May 29, 2019

(87) PCT Pub. No.: WO2018/102670
PCT Pub. Date: Jun. 7, 2018

(65) Prior Publication Data
US 2019/0309308 A1 Oct. 10, 2019

Related U.S. Application Data

(60) Provisional application No. 62/429,273, filed on Dec. 2, 2016.

(51) Int. Cl.
| | | |
|---|---|---|
| A61K 38/27 | (2006.01) | |
| C12N 15/113 | (2010.01) | |
| A61K 47/60 | (2017.01) | |
| A61P 35/00 | (2006.01) | |
| A61K 33/243 | (2019.01) | |
| A61K 31/337 | (2006.01) | |
| A61K 31/352 | (2006.01) | |
| A61K 31/437 | (2006.01) | |
| A61K 31/704 | (2006.01) | |
| C07K 16/28 | (2006.01) | |
| A61K 31/713 | (2006.01) | |

(52) U.S. Cl.
CPC ........ *C12N 15/1138* (2013.01); *A61K 31/337* (2013.01); *A61K 31/352* (2013.01); *A61K 31/437* (2013.01); *A61K 31/704* (2013.01); *A61K 31/713* (2013.01); *A61K 33/243* (2019.01); *A61K 38/27* (2013.01); *A61K 47/60* (2017.08); *A61P 35/00* (2018.01); *C07K 16/2869* (2013.01); *C07K 2317/76* (2013.01); *C12N 2310/11* (2013.01); *C12N 2310/14* (2013.01)

(58) Field of Classification Search
CPC ............ C12N 15/1138; C12N 2310/11; C12N 2310/14; A61K 33/24; A61K 31/713; A61K 47/60; A61K 33/243; A61K 31/337; A61K 31/352; A61K 31/437; A61K 31/704; A61K 38/27; A61P 35/00; C07K 16/2869; C07K 2317/76
See application file for complete search history.

(56) References Cited

U.S. PATENT DOCUMENTS

| | | | |
|---|---|---|---|
| 2007/0243192 A1* | 10/2007 | Wicha | G01N 33/57492 424/138.1 |
| 2014/0356359 A1* | 12/2014 | Siebel | A61P 35/00 424/133.1 |

FOREIGN PATENT DOCUMENTS

| | | |
|---|---|---|
| WO | 03090785 A1 | 11/2003 |
| WO | 2004078922 A2 | 9/2004 |

OTHER PUBLICATIONS

Arumugam, Arunkumar et al., "Growth Hormone Receptor Silencing Enhances the Sensitivity of Breast Cancer Cells to Chemotherapy By Inhibiting MDR1 and BCRP", Endocrine Reviews, The Endocrine Society, US, vol. 35, No. 3, Suppl. S, May 31, 2014 (May 31, 2014), pp. MON-0330.
Basu, Reetobrata et al., "Growth Hormone Receptor Knockdown Sensitizes Human Melanoma Cells to Chemotherapy by Attenuating Expression of ABC Drug Efflux Pumps", Hormones and Cancer, Springer New York LLC, US, vol. 8, No. 3, Mar. 14, 2017 (Mar. 14, 2017), pp. 143-156.

(Continued)

*Primary Examiner* — J. E. Angell
(74) *Attorney, Agent, or Firm* — Wood Herron & Evans LLP

(57) ABSTRACT

Various aspects of the present invention relate to a method of treating cancer in a subject having cancer cells, wherein the cancer cells possess at least one growth hormone receptor, and wherein the method includes controlling an action of the growth hormone receptor. In various non-limiting embodiments, controlling an action of the growth hormone receptor may occur via knock down of the growth hormone receptor, or may be caused by inhibiting growth hormone action, such as via the use of antibodies directed against growth hormone or the growth hormone receptor. Methods may also relate to administering an antagonist of the growth hormone receptor, and administering at least one anti-tumor drug in concert with administration of the antagonist. Another aspect may include a method of maintaining an anti-tumor drug in cancer cells of a subject by controlling an action of at least one growth hormone receptor in the cancer cells.

23 Claims, 82 Drawing Sheets

(56) References Cited

OTHER PUBLICATIONS

Basu, Reetobrata et al., "Targeting growth hormone receptor in human melanoma cells attenuates tumor progression and epithelial mesenchymal transition via suppression of multiple oncogenic pathways", Oncotarget, vol. 8, No. 13, Mar. 28, 2017 (Mar. 28, 2017), pp. 21579-21598.

Chien, Chia-Hung et al., "Growth hormone is increased in the lungs and enhances experimental lung metastasis of melanoma in DJ-1 KO mice", BMC Cancer, vol. 16, No. 1, Nov. 8, 2016 (Nov. 8, 2016).

Fan, Yong et al., "Evolution of Hepatic Steatosis to Fibrosis and Adenoma Formation in Liver-Specific Growth Hormone Receptor Knockout Mice", Frontiers in Endocrinology, vol. 5, Dec. 18, 2014 (Dec. 18, 2014), 10 pages.

International Search Report in International Patent Application No. PCT/US2017/064188, dated Jun. 6, 2018, 9 pgs.

Minoia, Mariella et al., "Growth Hormone Receptor Blockade Inhibits Growth Hormone-Induced Chemoresistance by Restoring Cytotoxic-Induced Apoptosis in Breast Cancer Cells Independently of Estrogen Receptor Expression", Journal of Clinical Endocrinology and Metabolism, vol. 97, No. 6, Jun. 1, 2012 (Jun. 1, 2012), pp. E907-E916.

Pawlowski, K. M. et al., "Growth hormone receptor (ghr) RNAi decreases proliferation and enhances apoptosis in CMT-U27 canine mammary carcinoma cell line", Veterinary and Comparative Oncology, vol. 10, No. 1, May 2, 2011 (May 2, 2011), pp. 2-15.

Subramani, Ramadevi et al., "Growth hormone receptor inhibition decreases the growth and metastasis of pancreatic ductal adenocarcinoma", Experimental & Molecular Medicine, vol. 46, No. 10, Oct. 1, 2014 (Oct. 1, 2014), pp. e117-e117.

Wang, Zhuohua et al., "Disruption of Growth Hormone Signaling Retards Early Stages of Prostate Carcinogenesis in the C3(1)/T Antigen Mouse", Endocrinology, vol. 146, No. 12, Dec. 1, 2005 (Dec. 1, 2005), pp. 5188-5196.

Written Opinion in International Patent Application No. PCT/US2017/064188, dated Jun. 6, 2018, 15 pgs.

Zhang, X. et al., "Inhibition of estrogen-independent mammary carcinogenesis by disruption of growth hormone signaling", Carcinogenesis, vol. 28, No. 1, Jan. 1, 2007 (Jan. 1, 2007), pp. 143-150.

Zhou, Dong et al., "Effect of combination therapy of siRNA targeting growth hormone receptor and 5-fluorouracil in hepatic metastasis of colon cancer", Oncology Letters, vol. 10, No. 6, Sep. 30, 2015 (Sep. 30, 2015), pp. 3505-3509.

Zhou, Dong, et al., "siRNA-targeted inhibition of growth hormone receptor in human colon cancer SW480 cells", World Journal of Gastroenterology, vol. 19, No. 44, Jan. 1, 2013 (Jan. 1, 2013), pp. 8108-8113.

Chen, Y-J, You M-L, Chong Q-Y, Pandey V, Zhuang Q-S, Liu D-X, Ma L, Zhu T, Lobie P. Autocrine Human Growth Hormone Promotes Invasive and Cancer Stem Cell-Like Behavior of Hepatocellular Carcinoma Cells by STAT3 Dependent Inhibition of CLAUDIN-1 Expression. Int J Mol Sci [Internet]. 2017; 18: 1274. doi: 10.3390/ijms18061274.

Goyal, L, Muzumdar MD, Zhu AX. Targeting the HGF/c-MET Pathway in Hepatocellular Carcinoma. Clin Cancer Res [Internet] 2013; 19: 2310-8. doi: 10.1158/1078-0432.CCR-12-2791.

Hu, C-T, Wu J-R, Cheng C-C, Wu W-S. The Therapeutic Targeting of HGF/c-Met Signaling in Hepatocellular Carcinoma: Alternative Approaches. Cancers (Basel) [Internet] 2017; 9: 58. doi: 10.3390/cancers9060058.

Kelley, RK, Verslype C, Cohn AL, Yang T-S, Su W-C, Burris H, Braiteh F, Vogelzang N, Spira A, Foster P, Lee Y, Van Cutsem E., Cabozantinib in hepatocellular carcinoma: results of a phase 2 placebo-controlled randomized discontinuation study. Ann Oncol Off J Eur Soc Med Oncol [Internet]. Oxford University Press; 2017 [cited Oct. 24, 2017]; 28: 528-34. doi: 10.1093/annonc/mdw651.

* cited by examiner

METHOD OF TREATING CANCER AND METHOD OF SENSITIZING CANCER CELLS TO THE ACTION OF CHEMOTHERAPEUTIC AGENTS VIA GROWTH HORMONE RECEPTOR ANTAGONISTS OR KNOCK DOWN

CROSS-REFERENCE TO RELATED APPLICATION

This application claims priority to and the benefit of the filing date of U.S. Patent Application Ser. No. 62/429,273, entitled "Method of Treating Cancer and Method of Sensitizing Cancer Cells to the Action of Chemotherapeutic Agents via Growth Hormone Receptor Antagonists or Knock Down," filed on Dec. 2, 2016, the disclosure of which is incorporated by reference herein in its entirety.

FIELD OF THE INVENTION

The present invention relates generally to methods of treating cancers, and more specifically to methods of treating cancer via interference with growth hormone receptor.

BACKGROUND OF THE INVENTION

This section is intended to introduce the reader to various aspects of art that may be related to various aspects of the present invention, which are described and/or claimed below. This discussion is believed to be helpful in providing the reader with background information to facilitate a better understanding of various aspects of the present invention. Accordingly, it should be understood that these statements are to be read in this light, and not as admissions of prior art.

Melanoma (a word derived from the Greek words—melas, "dark" and oma "tumor") is an ancient disease, dating back to $5^{th}$ century BC with the earliest physical evidence found in the 2,400-year-old mummies of the pre-Colombian era. In modern times, melanoma is considered the most aggressive and treatment-resistant form of human skin cancer, with an annual incidence of 73,870 in 2015 with a total of approximately 1,000,000 patients in the USA. The estimated mortality from melanoma in the US in 2015 is 9,970 and includes children, adolescents and adults. Fair skinned people have the highest propensity to acquire melanoma, with males (28.2%) having a higher predisposition than females (16.8%). More than 10,000 men and women in the United States and 60,000 worldwide are expected to die of melanoma in 2016, which globally claims about five lives per hour.

The number of new cases annually has been rising steadily in the last 30 years, during which the five-year survival rate increased from 86% (1985) to 93% (2012), albeit with a poor quality of life. Studies indicate increased UV exposure, use of tanning beds, hormone replacement therapies as well as improved and increased diagnostic screening, as the underlying causes of heightened melanoma incidence. Melanoma usually occurs in the exposed parts of the body—face, neck, hands and feet—but can also be found in any anatomical site occupied by melanocytes, like the gastrointestinal, genitourinary and respiratory mucosa, and the choroidal layers of the eye.

Chemotherapeutic interventions for melanoma often result in drug resistance that may occur by several cellular mechanisms. The development of a melanoma vaccine has enjoyed limited success. However, in the last five years, a number of highly efficacious immunotherapies, e.g. CTLA-4 antibody, ipilimumab; PD-1/PD-L1 antibody, and pembrolizumab, and targeted therapies, e.g. V600E BRAF inhibitor and vemurafenib, have been approved by the FDA. Several additional therapeutic regimens are in various stages of development. In spite of these promising advancements in melanoma therapy, some areas of concern remain. For instance, effective therapy with one of the most successful melanoma drugs, pembrolizumab, requires pre-existence of active cytotoxic T-cells in the system while resistance to most other known chemotherapies, including ipilimumab and vemurafenib, has been reported.

Indeed, melanoma is unique among other types of cancers in possessing multiple robust mechanisms of chemotherapeutic resistance. This includes abundant expression of a repertoire of drug efflux pumps, melanosomal sequestration of drugs in melanosomes during melanogenesis, as well as upregulation of epithelial-mesenchymal transition (EMT) markers. However, molecular echanisms to define melanoma drug-resistance are lacking.

SUMMARY OF THE INVENTION

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

As described above, cancers, such as melanoma, may possess robust mechanisms of chemotherapeutic resistance. And molecular mechanisms to define such drug resistance are lacking. However, as now elucidated by the present inventors, reducing the effects of growth hormone (GH) may be used to prevent and/or treat cancer in a subject. And so, one aspect of the present invention may include a method of treating cancer in a subject having cancer cells, wherein the method includes reducing one or more effects of growth hormone. Further, any mechanism to reduce the effects of GH may be used. Exemplary mechanisms include growth hormone receptor knock down (GHR-KD), administering antibodies against GH and/or growth hormone receptor (GHR), and administering GHR antagonists, among others. GHR-KD may be accomplished by administering small interfering RNA (siRNA) sequences to the subject, but other methods of GHR-KD may be used.

Thus, one aspect of the present invention may include a method of treating cancer in a subject having cancer cells, wherein the cancer cells include at least one growth hormone receptor, and wherein the method includes controlling an action of the growth hormone receptor. Further, one aspect of the present invention may include a method of treating cancer in a subject having cancer cells, wherein the cancer cells include at least one growth hormone receptor, and wherein the method includes controlling an action of the growth hormone receptor via knock down of the growth hormone receptor.

Another aspect of the present invention may include a method of treating cancer in a subject having cells including at least one growth hormone receptor, wherein the method includes controlling an action of the growth hot receptor, and administering a sub-$EC_{50}$ dose of at least one anti-tumor drug.

Another aspect of the present invention may include a method of treating cancer in a subject having cells including at least one growth hormone receptor, wherein the method includes controlling an action of the growth hormone receptor by administering an antagonist of the growth hormone receptor, and administering at least one anti-tumor drug in concert with administration of the antagonist.

Another aspect of the present invention may include a method of treating cancer in a subject having cancer cells, said cancer cells including at least one growth hormone receptor, wherein the method includes controlling an action of the growth hormone receptor, wherein the controlling an action of the growth hormone receptor is caused by inhibiting growth hormone action. This inhibition may be effected via the use of antibodies (such as antibodies directed against the growth hormone receptor, or antibodies directed against growth hormone.

Another aspect of the present invention may include a method of treating cancer in a subject having cancer cells, said cancer cells possessing at least one growth hormone receptor, wherein the method includes reducing serum insulin-like growth factor 1 (IGF1) levels below the normal serum IGF1 level of the subject.

Another aspect of the present invention may include a method of maintaining an anti-tumor drug in cancer cells of a subject by controlling an action of at least one growth hormone receptor in the cancer cells. In this aspect of the present invention, the controlling of an action of the growth hot mone receptor may include: knock down of the growth hormone receptor; co-administration of an antagonist of the growth hot mane receptor with the anti-tumor drug; inhibiting growth hormone action via antibodies directed against growth hormone; or inhibiting growth hormone action via antibodies directed against the growth hormone receptor.

BRIEF DESCRIPTION OF THE DRAWINGS

The accompanying drawings, which are incorporated in and constitute a part of this specification, illustrate embodiments of the invention and, together with the general description of the invention given above and the detailed description of the embodiments given below, serve to explain the principles of the present invention.

DETAILED DESCRIPTION

Figure 1:
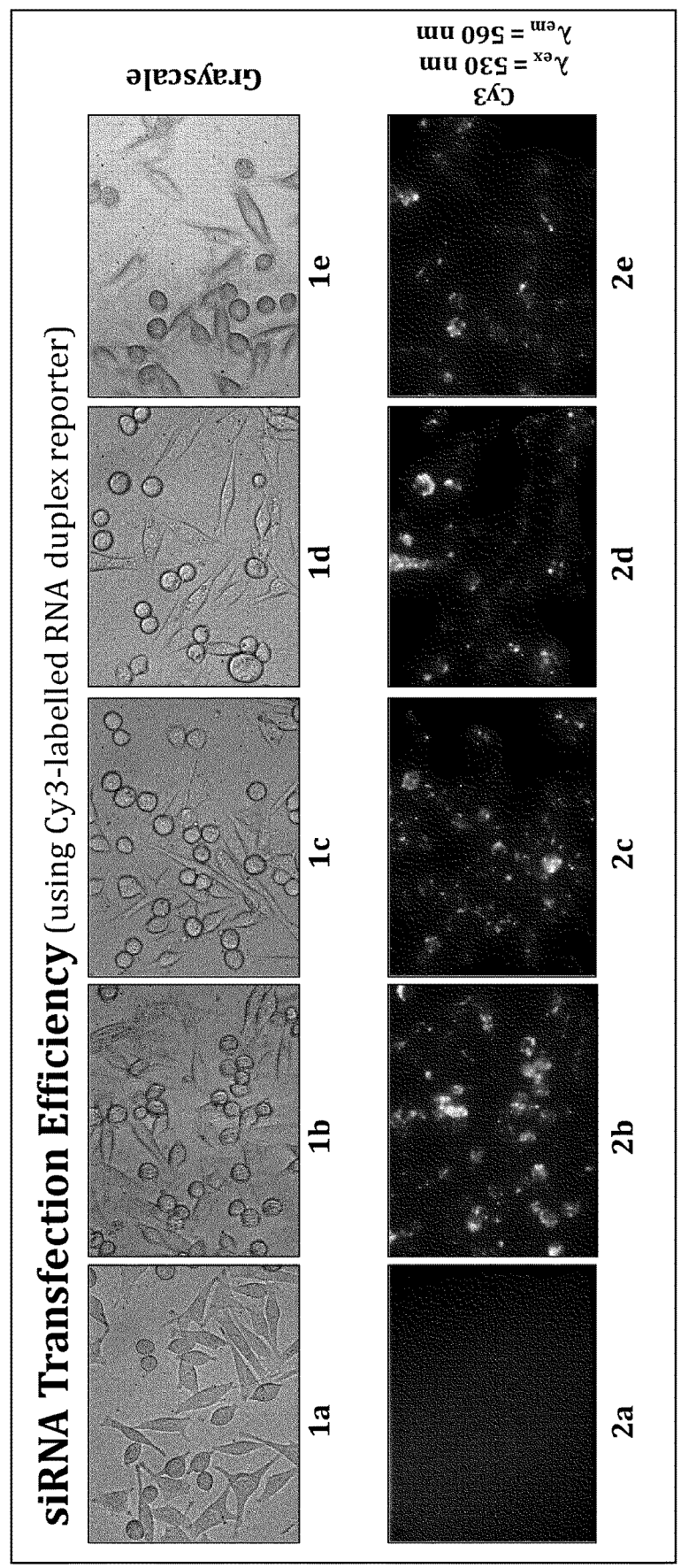
FIG. 1 includes microphotographs showing siRNA transfection efficiency in SK-MEL-28 cells [plated at 10,000 cells/cm$^2$ and treated with either 20 nM GHR-specific siRNA (siRNA-A—1b, 2b; siRNA-B—1c, 2c; siRNA-C, 1d, 2d) or scramble-siRNA (1e, 2e); with untreated cells being treated with only transfection reagent (1a, 2a)]. Cy3 labelled scramble reporter siRNA was used to confirm transfection.
Figure 2A:
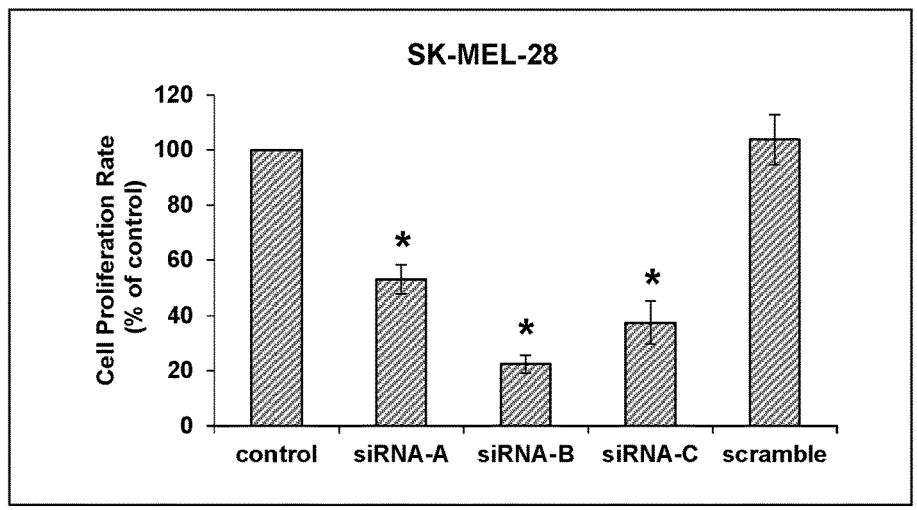
FIGS. 2A-2C include graphs showing the siRNA optimization for the process of GHR knock-down (KD) on melanoma cell proliferation, with FIG. 2A showing SK-MEL-28 cells, FIG. 2B showing MALME-3M cells, and FIG. 2C showing SK-MEL-5 cells.
Figure 2B:
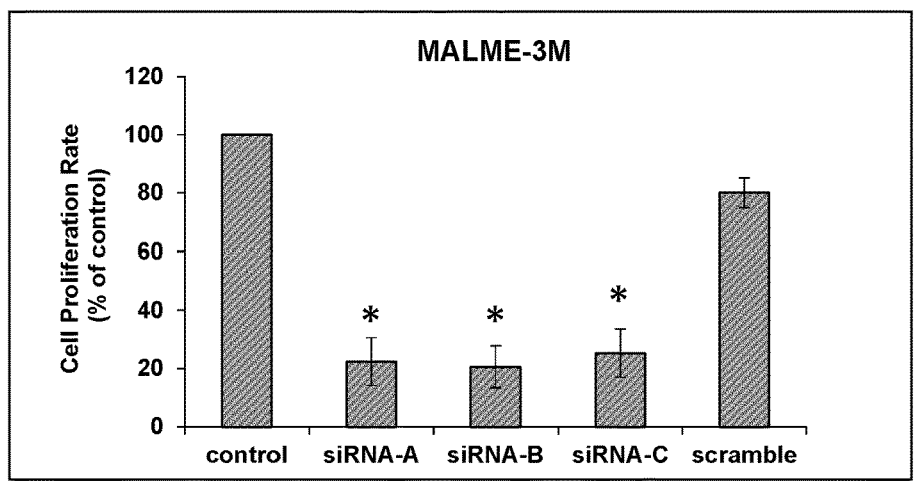
Figure 2C:
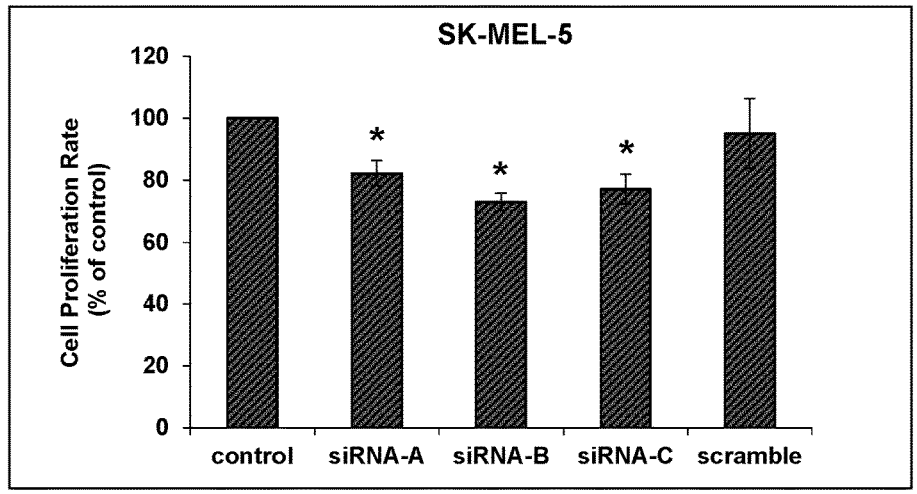

One or more specific embodiments of the present invention will be described below. To provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described above, reducing the effects of growth hormone (GH) may be used to prevent and/or treat cancer in a subject. And so, one aspect of the present invention may include a method of treating cancer in a subject having cancer cells, wherein the method includes reducing one or more effects of growth hormone. Further, any mechanism to reduce the effects of GH may be used. Exemplary mechanisms include growth hormone receptor knock down (GHR-KD), administering antibodies against GH and/or growth hormone receptor (GHR), and administering GHR antagonists, among others. GHR-KD may be accomplished by administering small interfering RNA (siRNA) sequences to the subject, but other methods of GHR-KD may be used.

Thus, one aspect of the present invention may include a method of treating cancer in a subject having cancer cells, wherein the cancer cells including at least one growth hormone receptor, and wherein the method includes controlling an action of the growth hormone receptor. Further, one aspect of the present invention may include a method of treating cancer in a subject having cancer cells, wherein the cancer cells including at least one growth hormone receptor, and wherein the method includes controlling an action of the growth hormone receptor via knock down of the growth hormone receptor.

In this aspect of the present invention, the subject may be a human in certain embodiments. And, while the aspects of the present invention are contemplated for treating cancer in general, and many different types of cancers more specifically, in certain embodiments, the cancer to be treated may be chosen from breast cancer, colorectal cancer, prostate cancer, hepatic cell carcinoma, and melanoma.

Further, as described above, the method of this aspect of the present invention may involve controlling an action of a growth hormone receptor via knock down of the growth hormone receptor. In particular embodiments, the knock down of the growth hormone receptor may be performed by siRNA mediated knock down. And, in further embodiments, the knock down of the growth hormone receptor may be via anti-sense RNA directed against the growth hormone receptor. In yet further embodiments, the knock down of the growth hot mone receptor may be caused by an antibody specific to the growth hormone receptor.

Another aspect of the present invention may include a method of treating cancer in a subject having cells including at least one growth hormone receptor, wherein the method includes controlling an action of the growth hormone receptor, and administering a sub-$EC_{50}$ dose of at least one anti-tumor drug.

In this aspect of the present invention, (like the previous aspect described above), the subject may be a human in certain embodiments. And, while the aspects of the present invention are contemplated for treating cancer in general, and many different types of cancers more specifically, in certain embodiments, the cancer to be treated may be chosen from breast cancer, colorectal cancer, prostate cancer, hepatic cell carcinoma, and melanoma.

Further in this aspect of the present invention, while it is contemplated that the method may be amenable for use with any anti-tumor drug (or any of a number of anti-tumor drugs), in certain embodiments, the anti-tumor drug may be chosen from cisplatin, doxorubicin, oridonin, paclitaxel, and vemurafenib.

Further, as described above, the method of this aspect of the present invention may involve controlling an action of a growth hormone receptor via knock down of the growth hormone receptor. In particular embodiments, the knock down of the growth hormone receptor may be performed by siRNA mediated knock down. And, in further embodiments, the knock down of the growth hormone receptor may be via anti-sense RNA directed against the growth hormone receptor. In yet further embodiments, the knock down of the growth hormone receptor may be caused by an antibody specific to the growth hormone receptor.

Further, the controlling an action of the growth hormone receptor may directly lead to inhibiting growth hormone action. And, this may be caused in turn by antibodies directed against growth hormone.

Further, the controlling an action of the growth hormone receptor may include administering an antagonist of the growth hormone receptor. And, in certain embodiments, the antagonist of the growth hormone receptor may be pegvisomant.

Another aspect of the present invention may include a method of treating cancer in a subject having cells including at least one growth hormone receptor, wherein the method includes controlling an action of the growth hormone receptor by administering an antagonist of the growth hormone receptor, and administering at least one anti-tumor drug in concert with administration of the antagonist.

In this aspect of the present invention, (like the previous aspects described above), the subject may be a human in certain embodiments. And, while the aspects of the present invention are contemplated for treating cancer in general, and many different types of cancers more specifically, in certain embodiments, the cancer to be treated may be chosen from breast cancer, colorectal cancer, prostate cancer, hepatic cell carcinoma, and melanoma.

Further in this aspect of the present invention, while it is contemplated that the method may be amenable for use with any anti-tumor drug (or any of a number of anti-tumor drugs), in certain embodiments, the anti-tumor drug may be chosen from cisplatin, doxorubicin, oridonin, paclitaxel, and vemurafenib. And, while it is contemplated that the method may be amenable for use with any GHR antagonist (or any of a number of GHR antagonists), in certain embodiments, the antagonist of the growth hormone receptor may be pegvisomant.

Another aspect of the present invention may include a method of treating cancer in a subject having cancer cells, said cancer cells including at least one growth hormone receptor, wherein the method includes controlling an action of the growth hormone receptor, wherein the controlling an action of the growth hormone receptor is caused by inhibiting growth hormone action. This inhibition may be effected via the use of antibodies (such as antibodies directed against the growth hormone receptor, or antibodies directed against growth hormone.

Again, in this aspect of the present invention, (like the previous aspects described above the subject may be a human in certain embodiments. And, while the aspects of the present invention are contemplated for treating cancer in general, and many different types of cancers more specifically, in certain embodiments, the cancer to be treated may be chosen from breast cancer, colorectal cancer, prostate cancer, hepatic cell carcinoma, and melanoma.

In certain embodiments of this aspect of the invention, the inhibiting of the growth hormone action may be caused by antibodies directed against growth hormone. And, in certain embodiments, the inhibiting of the growth hormone action may be caused by antibodies directed against growth hormone receptor.

Another aspect of the present invention may include a method of treating cancer in a subject having cancer cells, said cancer cells including at least one growth hormone receptor, wherein the method includes reducing serum insulin-like growth factor 1 (IGF1) levels below the normal serum IGF1 level of the subject.

In certain embodiments of this aspect, the reducing of serum IGF1 levels may be performed by controlling an action of the growth hot mane receptor. And, the controlling an action of the growth hormone receptor may include administering an antagonist of the growth hormone receptor. And, while it is contemplated that the method may be amenable for use with any GHR antagonist (or any of a number of GHR antagonists), in certain embodiments, the antagonist of the growth hormone receptor may be pegvisomant.

Another aspect of the present invention may include a method of maintaining an anti-tumor drug in cancer cells of a subject by controlling an action of at least one growth hormone receptor in the cancer cells. In this aspect of the present invention, the controlling of an action of the growth hormone receptor may include: knock down of the growth hormone receptor; co-administration of an antagonist of the growth hormone receptor with the anti-tumor drug; inhibiting growth hormone action via antibodies directed against growth hormone; or inhibiting growth hormone action via antibodies directed against the growth hormone receptor.

Again, in this aspect of the present invention, (like the previous aspects described above), the subject may be a human in certain embodiments. And, while the aspects of the present invention are contemplated for treating cancer in general, and many different types of cancers more specifically, in certain embodiments, the cancer to be treated may be chosen from breast cancer, colorectal cancer, prostate cancer, hepatic cell carcinoma, and melanoma.

Further, as described above, the method of this aspect of the present invention may involve (in one embodiment) controlling an action of a growth hormone receptor via knock down of the growth hormone receptor. In particular embodiments, the knock down of the growth hormone receptor may be performed by siRNA mediated knock down. And, in further embodiments, the knock down of the growth hormone receptor may be via anti-sense RNA directed against the growth hormone receptor. In yet further embodiments, the knock down of the growth hormone receptor may be caused by an antibody specific to the growth hormone receptor.

Further, as described above, this aspect may include (in one embodiment) co-administration of an anti-tumor drug with a GHR antagonist. While it is contemplated that the method may be amenable for use with any anti-tumor drug (or any of a number of anti-tumor drugs), in certain embodiments, the anti-tumor drug may be chosen from cisplatin, doxorubicin, oridonin, paclitaxel, and vemurafenib. And, while it is contemplated that the method may be amenable for use with any GHR antagonist (or any of a number of GHR antagonists), in certain embodiments, the antagonist of the growth hormone receptor may be pegvisomant.

Further, and more specifically, one disclosed aspect is a method of attenuating cancer properties of cells by control of GHR action. The cells may be any type of cancer cells, such as melanoma cells, for example. Another aspect is a method of improving a response to chemotherapeutic agents by control of GHR action.

Cancer properties of any cell expressing GHRs may be attenuated in accordance with this invention. GHRs have been implicated in the growth and function of cancer cells associated with breast cancer, colorectal cancer, prostate cancer, and melanoma, for example. Any cancer that exhibits increased levels of GHR in the cancer cells may be a target. A biopsy may be used to determine if such increased levels are present in the subject.

GHR action may be controlled via administration of GHR antagonists, such as pegvisomant. Further, GHR action may be controlled via siRNA mediated GHR-KD or any other means of deactivating or downregulating GHR action. As used herein, the terms "growth hormone receptor knock down" and "GHR-KD" mean decreasing the amount and/or action of the growth hormone receptor.

In one aspect, the effects of the administration of excess hGH or the disruption of GH induced signaling on several GH induced intracellular signaling pathways and downstream proliferative effects in tumor cell growth are used to disrupt cancer progression by taking advantage of GH-GHR interaction. Attenuation of the phosphorylation states of multiple intracellular signaling molecules is attainable by the methods disclosed, as are differential, yet significant changes in RNA levels of GH, prolactin, insulin, IGF1, IGF2, and their cognate receptors, which appear to increase insulin/IGF receptors. Indeed, as used herein GH antagonism may refer not only to a direct action on the GHR but also anything that ultimately lowers serum IGF1. The RNA interference (RNAi)-mediated downregulation of GH action in the melanoma cells translates into a decrease in cell proliferation, migration, invasion, and colony formation on soft agar assays. GH/GHR action in human melanoma cells provides a unique model of GH-regulated multiple critical cellular processes in the tumor. Further, the dependence of the melanoma cells on the GH/GHR interaction validates these interactions as pharmacological targets of intervention in melanoma therapy.

A comprehensive analysis of GH-GHR action in human melanoma cells exposes a definitive regulation of key intracellular signaling pathways, such as the JAK, STAT (1, 3, and 5), SRC, ERK1/2, AKT, and mTOR, which may be critical mediators of early gene activation and drug resistance in melanoma and other forms of cancer. Observed robust GH-dependent modulation of RNA expressions of hepatocyte growth factor (HGF), the HGF-receptor MET, and Erb-B2 tyrosine receptor kinase 3 (ERBB3) in human melanoma cells may indicate a possible involvement of GH on mechanisms of therapy refractoriness in melanoma. Further, melanoma cells may express endogenous GH and the GHR, as well as relatively high levels of receptors of the insulin family (IR, IGF1R and EGF2R). The expression levels of the insulin and IGF receptor family may be modulated by GH action, as described herein.

GH putatively occupies a central regulatory role in melanoma cell physiology and may be involved in the control of multiple mechanisms of melanoma growth and progression.

In one aspect, GHR-KD or other downregulation of GHR may be used for the control of four human melanoma cell lines derived from the NCI-60 panel of human cancer cells. The cells were either treated with hGH or had their GHR expression abrogated using GHR-specific siRNA to mimic a transient but acute inhibition of GH action. The subsequent RNA levels and variations of key components of the GH/IGF axis were then examined to determine the efficacy of the treatments. Human melanoma cells have endogenous GH and GHR, with the GH/IGF1 axis affecting expression of multiple genes. Signaling networks in the melanoma cell are GH-dependent and were significantly upregulated in presence of GH and also were severely suppressed following GHR-KD. GHR-KD in melanoma cells significantly suppressed characteristic tumor phenotypes associated with proliferation and metastasis of cancer cells, including melanoma cells.

In another aspect, treatment of melanoma cells with sub-$EC_{50}$ doses of anti-cancer drugs, in parallel with blocking GHR action, may result in a significant suppression of major pathways and processes associated with drug resistance. This may provide a direct opportunity to reduce the dosage of anti-cancer chemotherapy by several folds while at least maintaining an equivalent level of tumor clearance. In turn, these effects may allow patients and clinicians to better manage costs and side-effects associated with cancer therapy. The suppression of GHR expression using siRNA leads to a marked reduction in RNA- and protein expression of ATP binding cassette transporters (ABC transporters), significant downregulation of key modulators of the melanogenesis pathway, including the microphthalmia-associated transcription factor (MITF) and its target tyrosinase related protein 1 (TYRP1), and a significant reversal in the RNA and protein levels of markers of epithelial mesenchymal transition (EMT). Many anti-cancer drugs have been approved for a variety of cancers, but certain anti-tumor agents such as cisplatin, doxorubicin, paclitaxel, and vemurafenib are used against melanoma, while compounds such as oridonin are under study to determine possible therapeutic targets. A large hurdle in treating melanoma is its intrinsic development of resistance to a given therapy fueled largely by the abundant expression of a repertoire of xenobiotic efflux pumps of the ABC transporter family as well as possible mechanisms of drug sequestration in melanosomes. Following GHR-KD, melanoma cells exhibit significantly longer drug retention and increased sensitivity to even sub-$EC_{50}$ doses of anti-cancer drugs. Therefore, GHR reduction or suppression of GH action can be utilized in combination with other US Food and Drug Administration (FDA) and European Union approved chemo-therapies with established and/or novel anti-tumor compounds. Thus, an approach of concomitant GHR antagonism or down regulation with conventional therapies may provide improved therapeutic interventions. This approach may not only lead to a more effective treatment plan for a given cancer, but may reduce the required drug dosages. This in turn may lower any physiological side-effects of the drugs and the associated cost burden.

In another aspect, a method of treating a human patient for cancer includes controlling the effects of GHR in cancer cells. One manner of controlling the effects of GHR in cancer cells is by administering a GHR antagonist, such as pegvisomant for example. Pegvisomant is a recombinant protein that mimics the interaction of GH with GHR. If pegvisomant is administered as a GHR antagonist, dosages may be varied to cause a physiological effect, e.g., a lowering of serum insulin like growth factor 1 (IGF 1). For instance, the dosage may be 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, or even higher. To determine the correct dosage of pegvisomant, the serum concentrations of IGF 1 may be monitored, with dosage adjusted in 5 tug increments to achieve and maintain normal serum EGF1 levels.

In another aspect, a mechanism for preventing cancer in a human patient is described. The effects of active GHR-induced intracellular signaling may be reduced or controlled in a prophylactic manner to prevent the growth and spread of cancer within the human patient. Such a prophylactic treatment may be indicated, for example, where the patient presents with polyps and/or other precancerous symptoms.

The following examples may provide further explanation of the described subject matter.

EXAMPLES

Example 1

In this Example 1, the inventors demonstrated that (I) GHR expression in melanoma cells was abrogated by siRNA; (2) GHR-KD suppresses human melanoma cell migration, invasion, colony formation, and proliferation; (3) GH-GHR action regulates phosphorylation states of intracellular signaling intermediates in human melanoma cells; and (4) targeting GHR remodels RNA expression of members of the IGF family of proteins and suppresses oncogenic receptors on/in human melanoma cells. And so, in this Example 1, the inventors present mechanistic details of GH-GHR action in human melanoma cells, and an indication that the GH-GHR pair could be an important marker of metastatic melanoma.

Materials and Methods

Cell Culture and GH Treatment

Human malignant melanoma cell lines (part of NCI-60 panel of human cancer cells)—SK-MEL-5 (#HTB-70), SK-MEL-28 (#HTB-72), MALME-3M (#HTB-64), MDA-MB-435S (#HTB-1.29), and not mal human skin fibroblast cells MALME-3 (#HTB-102) cells—were obtained from American Type Culture Collection (ATCC; Manassas, Va.). SK-MEL-5 and SK-MEL-28 were grown and maintained in EMEM media (ATCC #30-2003), while MALME-3M and MDA-MB-435S were grown in IMDM (ATCC #30-2005) and RPMI-1640 (ATCC #30-2001) respectively, as indicated by ATCC protocols. Complete growth media was supplemented with 5% fetal bovine serum (FBS; ATCC # 30-2020) and 1× antibiotic-antimycotic (Thermo Fisher Scientific #15240). MALME-3 cells were grown in McCoy's medium (ATCC #30-2007) supplemented with 15% FBS and 1× antibiotic-antimycotic. Cells were grown at 37° C. in 5% $CO_2$ in a humidified incubator. Half the media was replaced every 48 hr. No hGH was present in the media or added externally unless specifically noted. Tissue culture treated sterile T-75 and T-25 flasks and 6-, 12-, 24-, and 96-well plates (Corning, N.Y.) were used. Trypsinization was performed using 0.25% Trypsin/0.53 mM EDTA in Hank's balanced salt solution (HBSS) without calcium or magnesium (ATCC #30-2101) for 5 min at 37° C. in 5% $CO_2$.

For hGH treatment, 16 hours after seeding (or 24 hours post-transfection), the cells were serum-starved for 2 hours in serum-free growth media, and hGH (phosphate buffered saline was used as control where applicable) was added at the noted concentrations (0-, 5-, 50-, and 150 ng/ml). Cells were subsequently incubated for 24 hours before evaluating RNA levels. Recombinant hGH was purchased from Antibodies Online (#ABIN2017921, Atlanta, Ga.).

Transfection

Transfection was performed using siLentFect lipid reagent (Biorad #170-3360, Hercules, Calif.) following the manufacturer's protocol. Pre-designed siRNA duplexes against human GHR (Origene #SR301794, Rockville, Md.) at different concentrations were evaluated, and 20 nM was found to be optimum for decreasing the GHR RNA by >85%. Mock transfections were performed using universal scrambled negative control siRNA-duplex (Origene #SR30004). TYE-563-fluorescent labeled siRNA duplex (Origene #SR30002) was used as the transfection control. Cells were trypsinized, counted using a Countess Automated Cell Counter (Life Technologies, Carlsbad, Calif.), and seeded at 25,000-30,000 cells/$cm^2$, the cells being allowed to attach for 16-18 hours. The growth media was replaced with fresh antibiotic free complete growth medium just prior to transfection. A pre-incubated mix of 20 nM siRNA duplex (scramble or GHR specific) and siLentFect reagent at 1:1 molar ratio was added to the cells and incubated at 37° C. in 5% $CO_2$. Media was changed to complete growth medium plus antibiotics after 24 hours. RNA levels were analyzed 48 hours post-transfection, and protein levels were analyzed at 60 hours post-transfection.

RNA Extraction and RT-qPCR

RNA extraction was performed using the IBI-Trizol based total RNA purification kit (MidSci #IB47632, St. Louis, Mo.), and reverse transcription was performed using Maxima First Strand cDNA synthesis kit (Thermo Fisher Scientific #K1642, Waltham, Mass.) following the manufacturers' protocols. Real time-quantitative PCR and melt curve analysis were performed using Maxima SYBR-Green qPCR master mix (Thermo Fisher Scientific #K0241) and a T100 thermal cycler (Biorad #1861096, Hercules, Calif.). RNA and DNA concentrations were estimated using a Nanodrop2000 (Thermo Fisher Scientific, Waltham, Mass.) spectrophotometer. Primers were obtained from Sigma-Aldrich for the following human genes, with primer efficiency being experimentally confirmed: GAPDH, b-Actin, GHR, GHRHR, SOCS2, IGF1, IGF1R, IGF2, IGF2R, PRL, PRLR, insulin (Ins), IR, IGFBP2, IGFBP3, EGFR, HGF, cMET and ERBB3. Each sample represented a pool of two replicates per experiment. Experiments were performed at least three times. Each qPCR for individual genes and every treatment for every cell type was performed in triplicates.

Protein Extraction

Total protein was collected 60 hours post-transfection. The conditioned growth media for each treatment type were collected separately for subsequent analysis of secreted proteins. Total protein was extracted from the cells using RIPA buffer (Sigma-Aldrich #R-0278, St. Louis, Mo.) mixed with 1.5× Halt protease and phosphatase inhibitor cocktail (Thermo-Fisher #78442, Waltham, Mass.), following the manufacturer's protocol. Briefly, cells were washed twice with chilled sterile 1× phosphate buffered saline (PBS). Thereafter, chilled RIPA buffer at 1 ml per million cells was added and incubated for 5 min. at 4° C. Then, the cells were rapidly scraped for cell lysis. The cell lysate was clarified by centrifuging at 8,000× g for 10 min. at 4° C., and the supernatant was collected and stored at −80° C. for subsequent use. Each sample was a pool of three replicates per experiment and each experiment was performed three times.

Protein concentration was estimated in duplicates and two dilutions (1:2, 1:4), using the Bradford reagent (Sigma-Aldrich #B6916) and 1 mg/ml bovine serum albumin as standards. Absorbance at 595 nm was measured using Spectramax250 (Molecular Devices, Sunnyvale, Calif.) and SoftmaxPro v4.7.1 software.

Western Blotting (WB)

Briefly, cell lysates were separated by SDS-PAGE and transferred to nitrocellulose membrane by a wet-transfer method at 70 mA over 14 hours at 4° C. and blocked with 5% non-fat dry milk (NFDM) or 5% bovine serum albumin (BSA) in 1× TBS-T (Tris buffered saline, pH 17.2 with 0.1% Triton-X100) for 12-16 hours at 4° C. with gentle rocking. Membranes were then incubated with primary antibody (at the specific dilutions cited below) for 12-16 hours at 4° C. with gentle rocking. Membranes were then washed for 5 min. 3 times with 1× TBS-T and incubated with corresponding secondary antibodies (at the specific dilutions cited below) for 2 hours at 25° C. Membranes were then washed for 5 min. 4 times with 1× TBS-T, treated with West Femto Chemiluminiscence detection reagents (Thermo Fisher Scientific), and the chemiluminiscence signal was captured using a GelDoc (Biorad) fluorescence reader. Densitometric analysis of the blots was performed by measured band-intensity from the area-under-curve using ImageJ software.

Primary antibodies at specific dilutions were used to detect the following human proteins: GH (Rabbit, 1:100, Abcam #ab155276), GHR (Mouse, 1:300, SCBT #137185; Goat, 1:100, R&D Systems #AF1210; Rabbit, 1:200, Abcam #ab134078), STAT5 (Rabbit, 1:100, CST #9358S), P(Y694/Y699)-STAT5 (Rabbit, 1:100, ActiveMotif #39617, 39618), P(Y701)-STAT1 (Rabbit, 1:100, CST #7649), P(Y705)-STAT3 (Rabbit, 1:100, CST #9145), STAT3 (Rabbit, 1:200, CST #4904), STAT1 (Rabbit, 1:200, CST #9175), p44/42 MAPK (Erk1/2) (Rabbit, 1:2000, CST #9102S), P-p44/42 MAPK (Erk1/2) (Rabbit, 1:3000, CST #4370P), Akt (Rabbit, 1:2000, CST #4685S), P-Akt (Rabbit, 1:1000, CST #4058S), P-Jak2 (Rabbit, 1:200, GeneTex#61122; Rabbit, 1:100, CST #8082), JAK2 (Mouse, 1:200, Sigma Aldrich # SAB4200483), mTOR (Rabbit, 1:1000, CST #2983), P-mTOR (Ser2448) (Rabbit, 1:2000, CST #5536), P-mTOR (Ser2481) (Rabbit, 1:2000, CST #2974), Raptor (Rabbit, 1:500, CST #2280), Rictor (Rabbit, 1:500, CST#2114), GbL (Rabbit, 1:1000, CST #3274), b-Actin (Goat, 1:3000, SCBT #sc1616), GAPDH (Goat, 1:3000, SCBT #sc20357), P(51524)-BRCA1 (Rabbit, 1:500, CST#9009), P(S139)-histone H2A.X (Rabbit, 1:1000, CST #9718), histone H2A.X (Rabbit, 1:1000, CST #2595), Caspase-3 (Rabbit, 1:1000, CST#9665), cleaved (Asp175)-Caspase-3 (Rabbit, 1:1000, CST #9664), P(Y416)-SFK (Rabbit, 1:200, CST #2101), P(Y416)-SRC (Rabbit, 1:200, CST #6943), and SRC (Rabbit, 1:500, AbcaM #47405), Secondary antibodies used were anti-rabbit HRP-linked IgG (Donkey, 1:2000, CST #7074P2), anti-goat HRP-linked IgG (Donkey, 1:1000, SCBT #sc2020), anti-rabbit HRP-linked IgG (Donkey, 1:2000, GE #NA934), and anti-mouse HRP-linked IgG (Rat, 1:1000, Antibodies Online #ABIN1589975).

Immunofluorescence (IF)

Cells were seeded at 10,000 cells/cm$^2$ in 8-well chamber slides, and transfection was performed as described above. Transfection media was replaced with antibiotic containing complete growth media after 24 hours, and cells were fixed after 36 additional hours (a total of 60 hours post-transfection). The cells were washed twice with 1× PBS and fixed with 4% freshly-prepared formaldehyde (pH 6.9) for 15 min. at 25° C. It was also possible to use 100% methanol for fixation. After fixation, cells were permeabilized with 0.2% Triton-X100 in 1× PBS for 15 min. at 25° C., followed by blocking with 1% BSA for 4 hours at 25° C. Incubation time was 12 hours at 4° C. for primary antibody and 2 hours at 25° C. for secondary antibody. Finally, the slides were washed four times with 1× PBS, and the sample was mounted with Fluoroshield mounting medium containing DAN (Abeam #ab104139, Cambridge, UK) and covered with a 60 mm coverslip. The edges were then sealed with nail-polish, and the mounted sample was stored at 4° C. for microscopy. Microscopic imaging was performed using a Nikon Eclipse E600 compound fluorescent microscope fitted with a Nikon DS-Fi1CC camera (Nikon, Tokyo, Japan) and NIS-Elements BR3.2 imaging software. Sera used were rabbit anti-human-Ki67 monoclonal antibody with AlexaFluor488 tag (Abeam #ab154201, 1:300 dilutions); rabbit anti-human GER monoclonal antibody (Abeam #ab134078, 1:250 dilution); and rat anti-rabbit secondary antibody with AlexaFluor488 tag (Life Technologies #R37116, 1:500 dilution).

Cell Proliferation Assay

A 1% (w/v) resazurin (Sigma-Aldrich #R7017) solution in 1× PBS was made and filter-sterilized. The final concentration of resazurin in the assay was 0.004%. Inside the proliferating cells, mildly fluorescent blue resazurin is reduced to a bright pink fluorescent product called resorufin (stable for 4 hours), which allows for a quantitative measure of the percentage of proliferating cells. In all cases, cells were incubated at 37° C. in 5% $CO_2$ for 45-60 min. for adequate sensitivity of detection. Briefly, cells were seeded at 10,000 cells/cm$^2$ into 96-well plates and transfected as described above. The resazurin assay was performed 60 hours after transfection (unless specified otherwise) and resorufin absorbance was measured at 570 nm (reference wavelength=600 nm) using Spectramax250 (Molecular Devices, Sunnyvale, Calif.) and SoftmaxPro software.

Cell Migration Assay

Cell migration assays are standard methods of estimating the repair and regenerative properties of cells. In this example, the Radius Cell Migration Assay design from Cell Biolabs (Cell Biolabs #CBA-125, San Diego, Calif.) was used, and experiments were performed as per the manufacturer's protocol. In this assay, a 24-well plate containing a non-toxic, 0.68 mm biocompatible hydrogel spot is present at the center of the well, which spot prevents the attachment of cells. siRNA treated cells were trypsinized 48 hours post-transfection, counted, and seeded at 5000 cells/well in a pretreated hydrogel spot-containing 24-well plate. The hydrogel spot was gently removed after 24 hours incubation at 37° C. in 5% $CO_2$. The cells were allowed to migrate for up to 48 hours at 37° C. in 5% $CO_2$. Images were captured every 24 hours using a 4× objective (total magnification 40×) employing an inverted Olympus IX70 microscope fitted with a Retiga 1300 camera (QImaging, Surrey, BC). Total uncovered area at the beginning and end of assay were quantitated using ImageJ software, Experiments were performed in triplicates.

Cell Invasion Assay

The 96-well 3D spheroid BME cell invasion assay (Trevigen, Gaithersburg, Md.) was used to evaluate the ability of cells to invade surrounding tissue. Tumor spheroids are better representatives of tumors in-vivo, compared to tumor cells in a Boyden chamber, as is used in multiple invasion assay designs. Briefly, siRNA (scramble or GHR specific) treated melanoma cells were trypsinized 48 hours after transfection, counted, and seeded at 5000 cells/well in a 96-well spheroid formation plate, followed by incubation for 72 hours at 37° C. in 5% $CO_2$ to allow spheroid formation. Thereafter, the invasion matrix was added, followed by addition of 50 ng/ml hGH-containing culture medium as a chemoattractant. The invasive behavior of the cells was monitored every 24 hours for up to 72 hours. Images were taken every 24 hours using a 4× objective (total magnification 40×) using an inverted Olympus IX70 microscope fitted with a Retiga 1300 camera (QImaging, Surrey, BC). Total pixels at the beginning and end of assay were quantitated using ImageJ software. Experiments were performed in triplicate.

Clonogenicity Assay

Colony formation on soft agar or anchorage independent colonization is considered to be a very stringent test for malignant transformation of cells and a hallmark of cancer. Ability of the tumor cell to develop colonies on soft agar reflects a reduced dependence for extracellular growth promoting factors, independence from the control of neighboring cells (like keratinocytes in the case of melanocytes), and infinite capacity to proliferate. In this example, the CytoSelect 96-well format (Cell Biolabs #CBA-130, San Diego, Calif.) was employed, which format provides a timely (one week) and quantitative (fluorometric) readout of the total colonies formed. Experiments were performed as per the manufacturer's protocol. Briefly, a 0.6% base agar medium containing 1× RPMI-1640 (10% FBS) was prepared and allowed to settle for 30 min. at 4° C. siRNA treated cells were trypsinized 48 hours after transfection, counted, and seeded at 5000 cells/well in a 0.4% top agar layer also containing 1× RPMI-1640 (10% FBS), being allowed to settle for 15 min. at 4° C. Finally, 100 μl of pre-warmed culture media containing 50 μg/ml hGH was added at the top of the culture and incubated for 7 days at 37° C. in 5% $CO_2$. The media was then removed, the agar was solubilized, and the cells were lysed in situ. Total DNA content was measured using the CyQuant GR dye (kit component), and fluorescence was measured at 485 (ex)/520 nm (em) using a spectramax M2 fluorescence plate reader (Molecular Devices, Sunnyvale, Calif.) and SoftMax Pro v6.2.1 software. Experiments were performed in quadruplicate.

Statistical Analyses

Parametric and non-parametric statistical analyses for comparing RNA levels were performed using R software (ver3.0.2). For RT-qPCR analysis of RNA, the levels were first normalized against two reference genes (GAPDH and beta-actin), and the $2^{-ddc}t$ values were compared by Wilcoxon signed rank test for significance. A p-value less than 0.05 was considered as significant. The densitometric analyses, clonogenicity, migration and invasion, and resazurin based assays, were compared by a paired student's T-test, and ANOVA was performed (using GraphPad Prism software) to compare for significance ($p<0.05$ was considered significant).

Results

GHR expression in melanoma cells was abrogated by siRNA: The four human melanoma cells selected for this example (SK-MEL-28 cells, SK-MEL-5 cells, MALME-3M cells, and MDA-MB-435 cells) reportedly express GHR and are responsive to exogenous hGH treatment. However, the GHR protein level in these cell lines was not known. The siRNA and concentration were carefully selected, as was the transfection efficiency for the melanoma cell lines (see FIGS. 1 and 2A-2C). For purposes of this example, the siRNA concentration used was 20 nM. In particular, and as shown in FIG. 1, SK-MEL-28 cells were plated at 10,000 cells/cm² and treated with either 20 nM GHR-specific siRNA [siRNA-A (shown in panels 1b, and 2b; of FIG. 1); siRNA-B (shown in panels 1c and 2c of FIG. 1); siRNA-C (shown in panels 1d and 2d of FIG. 1)] or scramble-siRNA (shown in panels 1e and 2e of FIG. 1). Untreated cells were treated with only transfection reagent (shown in panels 1a and 2a of FIG. 1), The cells were photographed in grayscale (top row of FIG. 1) and at 630 mn (bottom row of FIG. 1). A Cy3-siRNA duplex at 10 nM was used as a reporter. Red fluorescence in FIG. 1 indicated successful transfection. While not shown in FIG. 1, identical results to the SK-MEL-28 cells were also obtained with SK-MEL-5, MALME-3M and MDA-MB-435 cells.

And, to optimize siRNA effect of GHR knock-down (KD) on melanoma cell proliferation (see FIGS. 2A-C), SK-MEL-28 cells (FIG. 2A), MALME-3M cells (FIG. 2B), and SK-MEL-5 cells (FIG. 2C) were transfected with 20 nM of either GHR-siRNA or scramble siRNA for 24 hr., and cell proliferation was checked 60 hr. post-transfection using 0.04% resazurin (as described in the methods) and absorbance was read at 570 nm (600 nm=reference wavelength). While not shown in FIGS. 2A-2C, data for MDA-MB-435 cells was obtained showing similar results) [*, $p<0.05$, Students t-test].

Figure 3A:
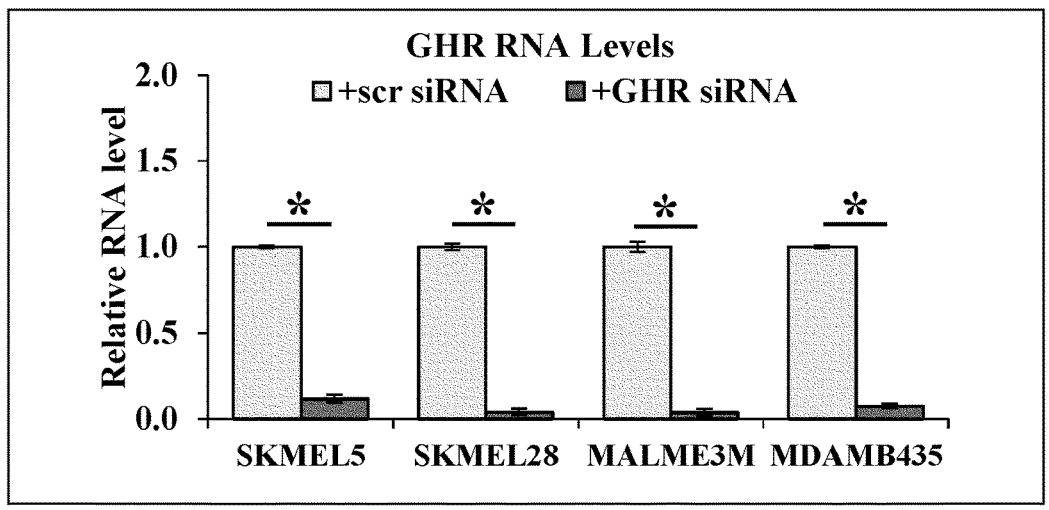
FIGS. 3A-3C include graphs showing that GHR RNA and protein levels are suppressed following siRNA mediated KD in melanoma cells.
Figure 3B:
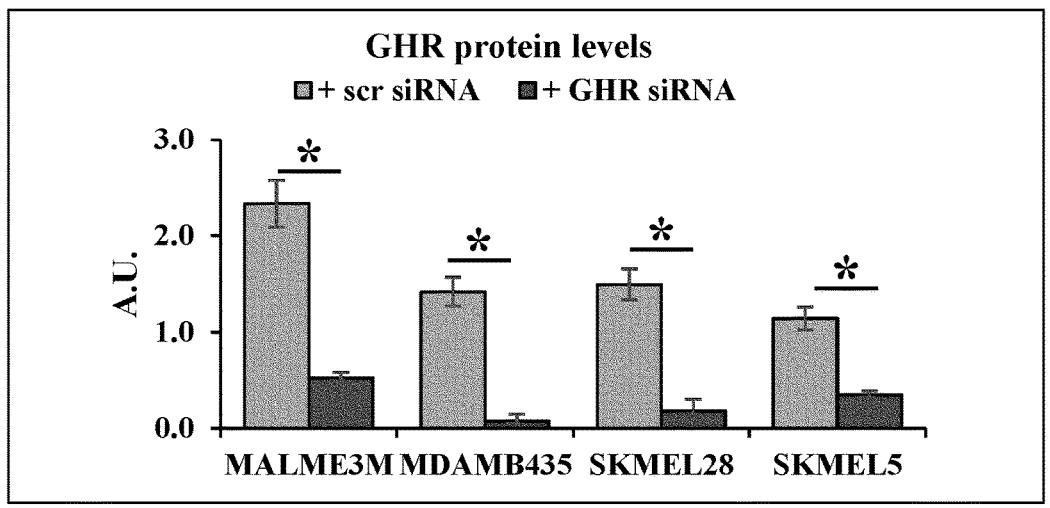
Figure 3C:
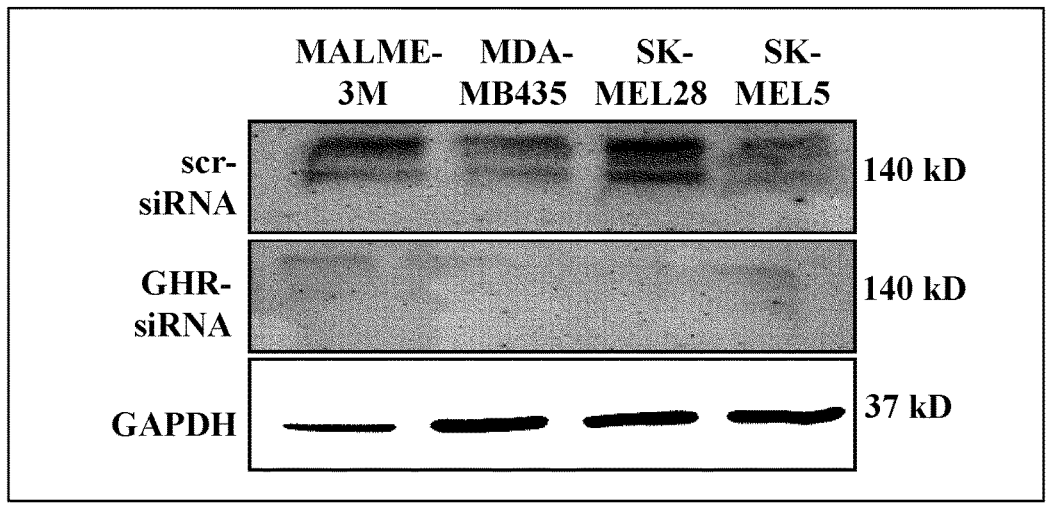

In order to verify and quantify GHR RNA in the cell lines, the RNA collected 48 hours post-transfection from the cells was subjected to RT-qPCR analysis using primers against GHR coding exons. As shown in FIGS. 3A-3C, the results showed high levels of GHR RNA in all four melanoma cells, which levels were inhibited by almost 90% following GHR-KD [FIG. 3A, which shows almost 90% reduction in mRNA levels was achieved in all four cell lines. Expressions were normalized against expression of beta-actin and GAPDH as reference genes (*, $p<0.05$, Wilcoxon sign rank test, n=6)].

The amount of GHR protein in these cells was also analyzed. Cell lysates collected 60 hours post-transfection showed an almost complete inhibition of GHR protein following the siRNA treatment, when compared to the corresponding scramble-transfected controls (FIG. 3C). Densitometry analyses of the WB confirmed a significant (70%-95%) reduction in GHR protein in the melanoma cells. In order to further validate these results, immunofluorescence staining for GHR on these cells was performed 60 hours post-transfection. Differential yet high levels of expression of GHR in the cells was observed, with the GHR protein increasing in order from SKMEL-5, MDAMB-435, MALME-3M and SKMEL-28. The trend was also seen in the WB from the cell lysates as shown in FIGS. 3A-3C.

Figure 4:
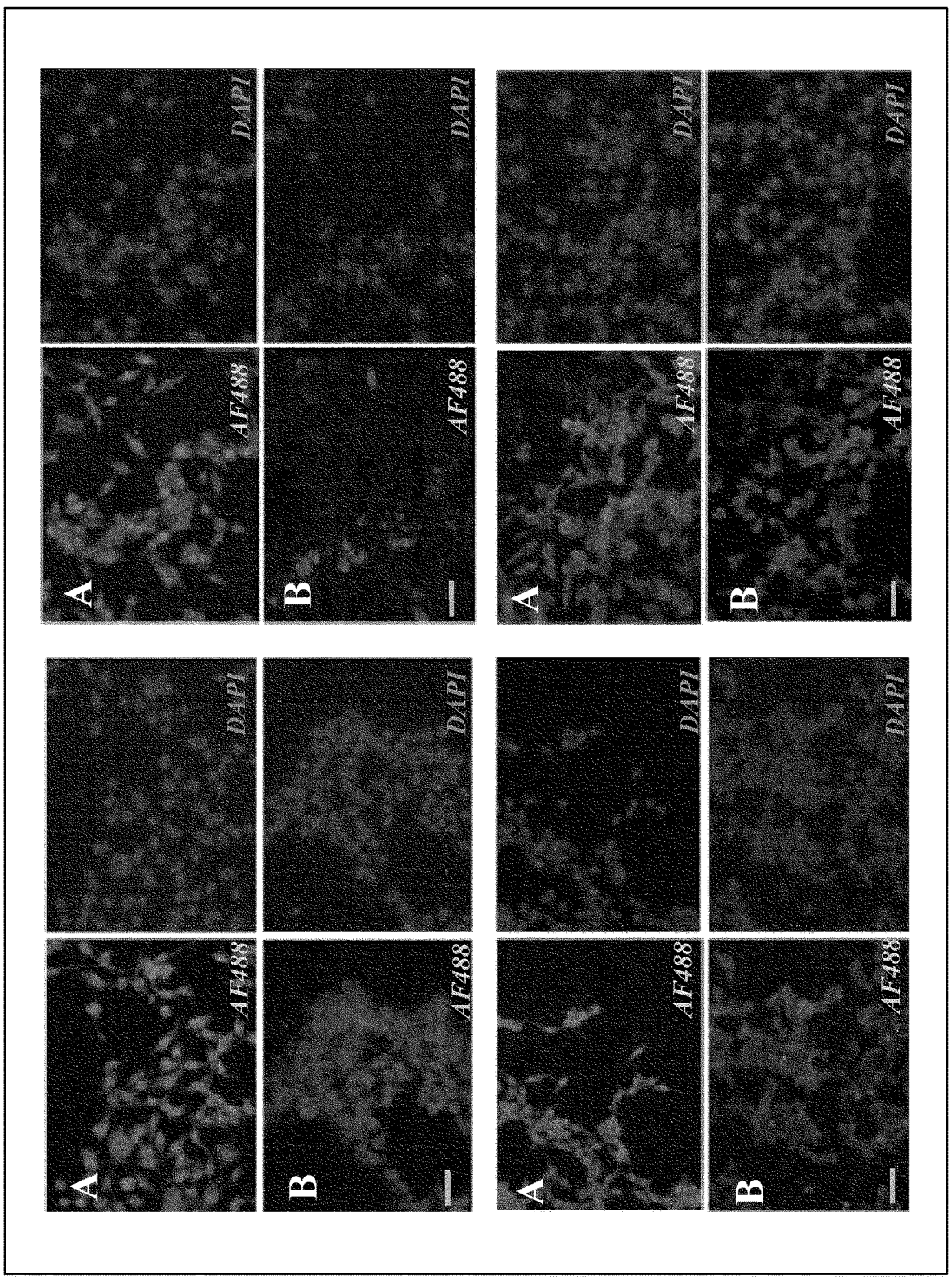
FIG. 4 includes microphotographs showing that GHR expression is abrogated following siRNA mediated KD in melanoma cells (top left to bottom right—SK-MEL-28, MALME-3M, MDA-MB-435, SK-MEL-5).

Following siRNA mediated GHR-KD a dramatic decrease was observed in the immunofluorescence levels indicative of GHR protein expression, in all the four cell lines, compared to the scramble-siRNA (scr-siRNA) treated controls (see FIG. 4). In that FIG. 4, in each of the four boxes, top row (A) shows melanoma cells transfected with scramble siRNA while the bottom row (B) shows melanoma cells transfected with GHR-siRNA. In each box the left column shows cellular DNA stained with DAPI (blue) while the right column shows the same cells labeled with AlexaFluor 488 (green)-conjugated (goat) secondary antibody to rabbit IgG specific for hGHR. From the average of four pictures per cell, maximum GHR-specific fluorescent signal was in the order of SKMEL-28>MALME-3M>MDAMB-435>SK-MEL-5—a trend also seen in WB analyses. ICC/IF was performed on cells 48 hours after transfection.

GHR-KD suppresses human melanoma cell migration, invasion, colony formation, and proliferation: The effect of GHR-KD on tumor phenotypes, including proliferation, migration, invasion, and clonogenicity, was analyzed. Migration and invasion are parameters in tumor cell interaction with its microenvironment and cancer metastasis. Various assays are employed to quantify these parameters. When choosing an appropriate assay, the seven day stability of siRNA mediated knock-down of gene expression following transfection may be a consideration.

Figure 5:
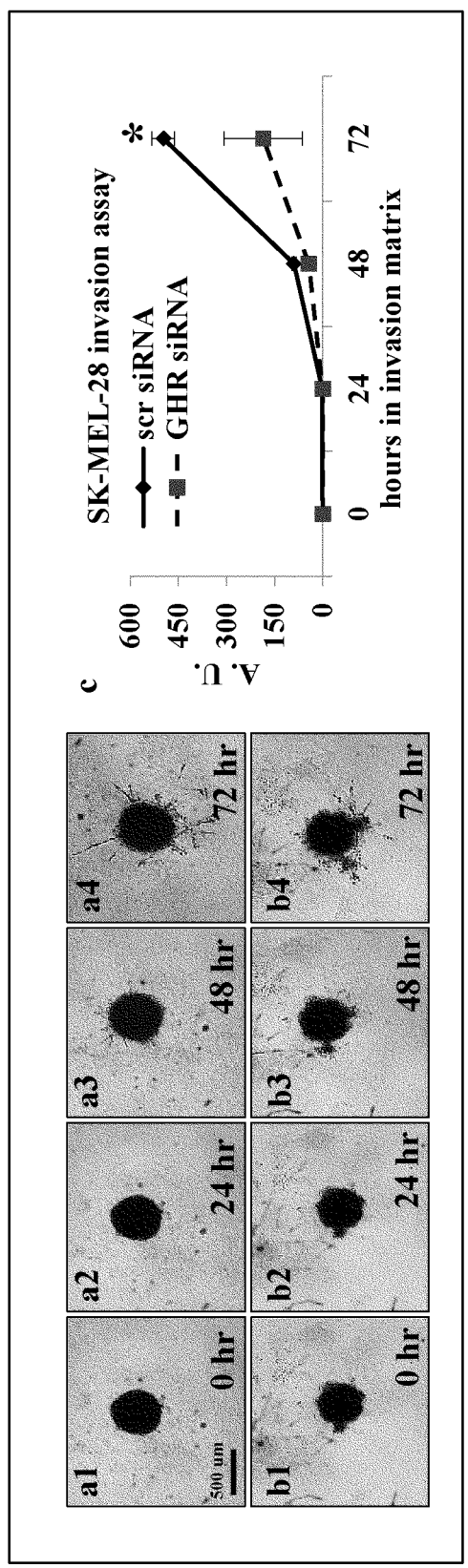
FIG. 5 includes microphotographs and graphs showing that growth hormone receptor knock-down (GHR-KD) attenuates invasive properties in human melanoma cell (SK-MEL-28).
Figure 7:
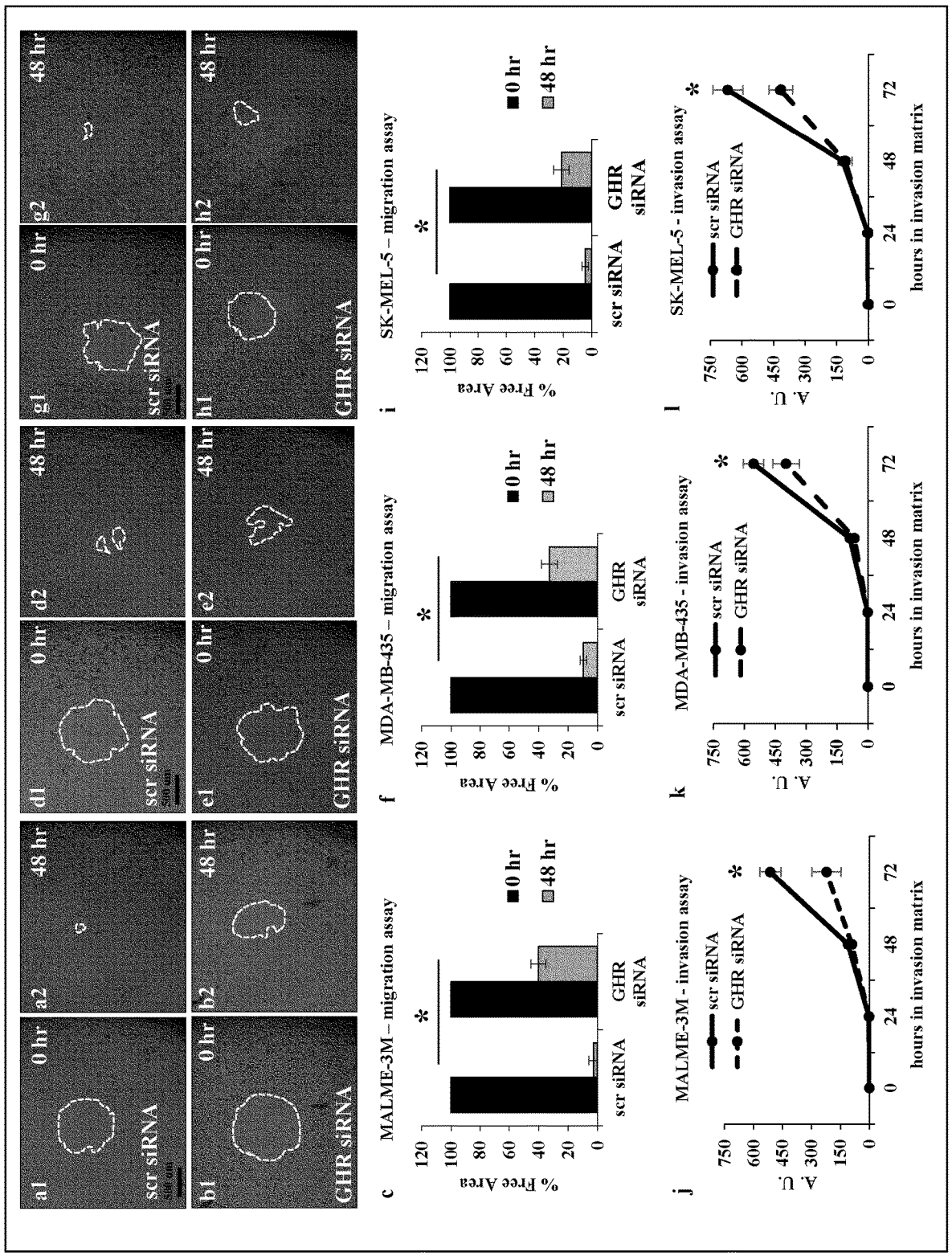
FIG. 7 includes microphotographs and graphs showing that GHR knock-down attenuates migration and invasion in human melanoma cells—MALME-3M, MDA-MB-435, and SK-MEL-5.

To analyze the effects of GHR-KD within a relevant time, a commercially available 3-dimensional spheroid assay was used to visualize and quantitate the invasion of melanoma spheroids into a basement membrane protein containing hydrogel matrix with all four cell types. The assay used a three-day observation window starting 48 hours post-transfection with scr- or GHR-siRNA. Invasion capacity decreased by a minimum of 28% in MDA-MB-435 cells to as much as 62% in SK-MEL-28 cells following GHR-KD (see FIG. 5 and panels j-1 of FIG. 7), More specifically, as shown in FIG. 5, SK-MEL-28 cells transfected with scramble (scr) (shown in panels a1-a4 of FIG. 5) or GHR-siRNA (shown in panels b1-b4 of FIG. 5) were seeded onto U-bottom 96-well plates at 5000 cells/well and allowed to form a spheroid. A hydrogel invasion matrix was added above the spheroid and cells were monitored for up to 72 hr. in presence of 50 ng/mL hGH. Total pixels representing structural extensions from the spheroid were calculated using ImageJ software and reflected the invasive ability of the melanoma cells (as shown in panel c of FIG. 5). A significant decrease in spheroid invasion was noted following GHR-KD. And, as shown in panels j-1 of FIG. 7, MALME-3M cells (FIG. 7, panel j), MDA-MB-435 cells (FIG. 7, panel k), and SK-MEL-5 cells (FIG. 7, panel l) transfected with scramble (scr)- or GHR-siRNA were seeded onto U-bottom 96-well plates at 5000 cells/well and allowed to form a spheroid. A hydrogel invasion matrix was added above the spheroid and cells were monitored for up to 72 hr. in presence of 50 ng/mL hGH. Total pixels representing structural extensions from the spheroid were calculated using ImageJ software and reflected the invasive ability of the melanoma cells. A significant decrease in spheroid invasion was noted following GHR-KD. [*, $p<0.05$, Students t-test, n=3]

Figure 6:
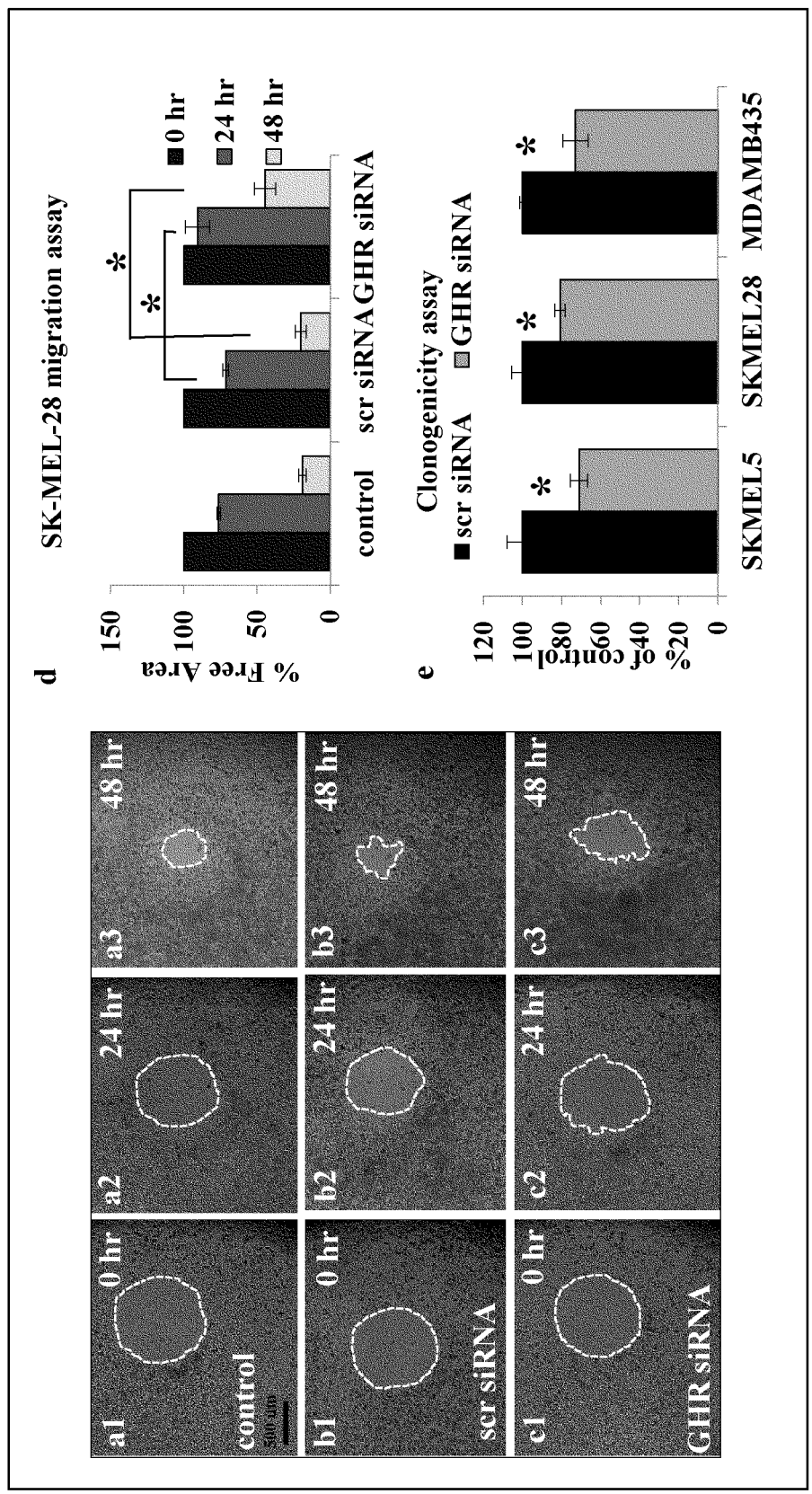
FIG. 6 includes further microphotographs and graphs showing that growth hormone receptor knock-down (GHR-KD) attenuates migration and clonogenicity in human SK-MEL-28 melanoma cells.

To assay the migratory capacity of the melanoma cell lines, the transfected cells were allowed to converge on a small circular area in the center of the culture well for up to 48 hours. The percentage free area at the end time point was calculated using ImageJ. A 2-fold reduction in migration level of SK-MEL-28 cells occurred following GHR-KD, while for MALME-3M cells, the difference was 15-fold when compared against scr-siRNA treated controls (see panels a-d of FIG. 6, and panels a-i of FIG. 7). More specifically, as shown in FIG. 6, SK-MEL-28 cells transfected with scr- (shown in panels b1-b3 of FIG. 6) or GHR-siRNA (shown in panels c1-c3 of FIG. 6) as well as un-transfected controls (shown in panels a1-a3 of FIG. 6) were allowed to migrate into a 0.68 mm circular spot at the center of the well, in presence of 50 ng/mL hGH for up to 48 hr. The percentage free area was calculated using ImageJ software and reflected the decrease/inhibition in migration (see panel d of FIG. 6). A significant decrease in migration was noted following GHR-KD. Similar results for migration and invasion assays with MALME-3M, MDA-MB-435 and SK-MEL-5 cells are presented in FIGS. 2A-2C. And, as shown in panels a-i of FIG. 7, MALME-3M cells (FIG. 7, panels a-c), MDA-MB-435 cells (FIG. 7, panels d-f), and SK-MEL-5 cells (FIG. 7, panels g-i) transfected with scr- or GHR-siRNA were allowed to migrate into a 0.68 mm circular spot at the center of the well, in presence of 50 ng/mL hGH for up to 48 hr. The percentage free area was calculated using ImageJ software and reflected the decrease/inhibition in migration. A significant decrease in migration was noted following GHR-KD.

Colony formation on soft agar assay was next examined using a high-throughput fluorescent readout. This assay is a widely used method for evaluating the malignant transformation of cells. A significant reduction, ranging from 19% (SK-MEL-28) to 28% (SK-MEL-5) in colony formation following GHR-KD was observed despite the presence of hGH in the media (see panel e of FIG. 6—showing SK-MEL-5, SK-MEL-28 and MDA-MB-435 cells transfected with 20 nM scramble or GHR-siRNA allowed to form colonies on soft agar for 7 days in presence of 50 ng/mL hGH; the cells were lysed at the end time point and total DNA was quantified using a fluorescent readout, showing a significant decrease in total number of colonies). No marked increase in melanoma migration, invasion, or clonogenicity was observed upon incubation with excess GH (up to 150 ng/ml), although there was a trend towards an increase for each (data not shown).

Figure 8A:
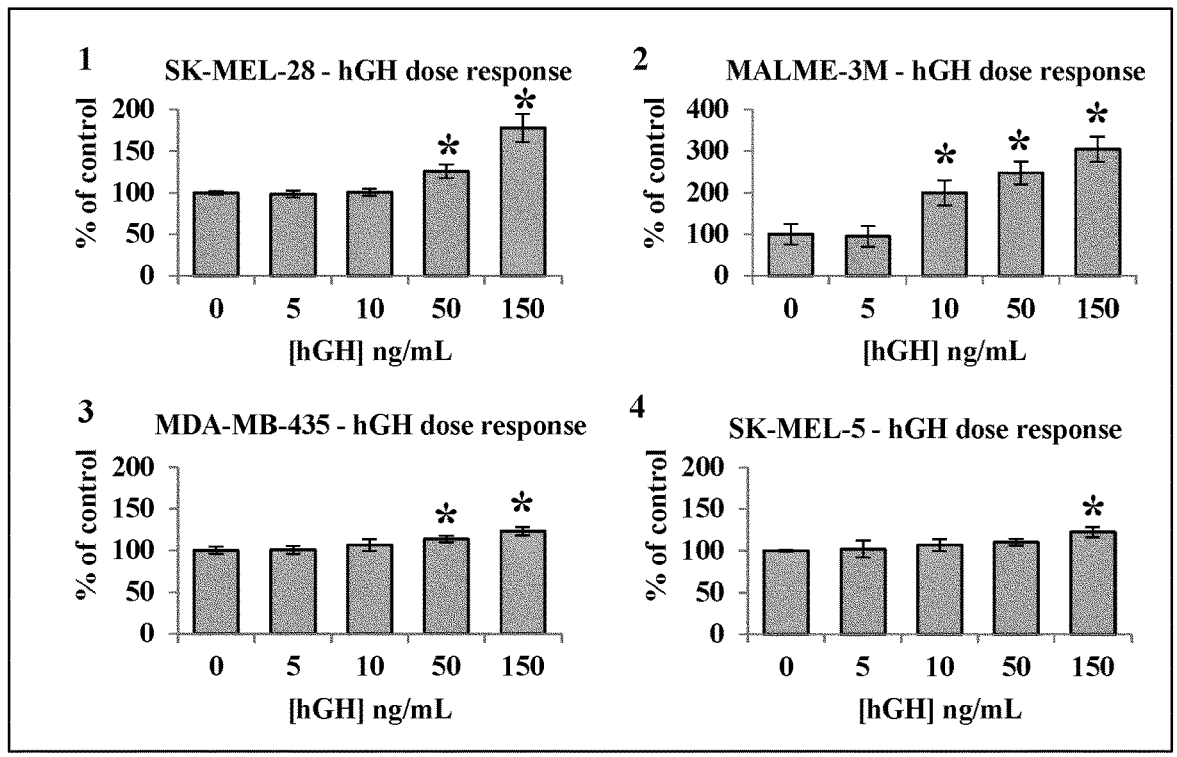
FIGS. 8A-8B include graphs showing that GH-excess promotes, while GHR-KD attenuates human melanoma cell proliferation FIGS. 9A-9I include photographs and graphs showing that GH-excess promotes, and GHR-KD attenuates, multiple oncogenic intracellular signaling pathways in human melanoma cells.

The cell proliferation of the four melanoma cell lines in response to increasing doses (5, 50 and 150 ng/ml) of recombinant hGH was also evaluated. A significant difference in cell proliferation was observed at a minimum hGH concentration of 50 ng/ml (serum concentration in media 1%). Cell proliferation induced by hGH-excess ranged between 10% (SK-MEL-5) to as much as 248% (MALME-3M) at 50 ng/ml hGH; while at the supra-physiological levels (150 ng/mL), the increase in proliferation ranged from 22% (SK-MEL-5) to more than 300% (MALME-3M) (see FIG. 8A). More specifically, SK-MEL-28 cells (FIG. 8A, panel 1), MALME-3M cells (FIG. 8A, panel 2), MDA-MB-435 cells (FIG. 8A, panel 3), and SK-MEL-5 cells (FIG. 8A, panel 4) were treated with increasing doses of hGH for 48 hr. and cell proliferation was estimated using a resazurin-based metabolic assay. As noted above, a significant increase in cell proliferation was noted at and above 50 ng/mL hGH treatment.

Figure 8B:
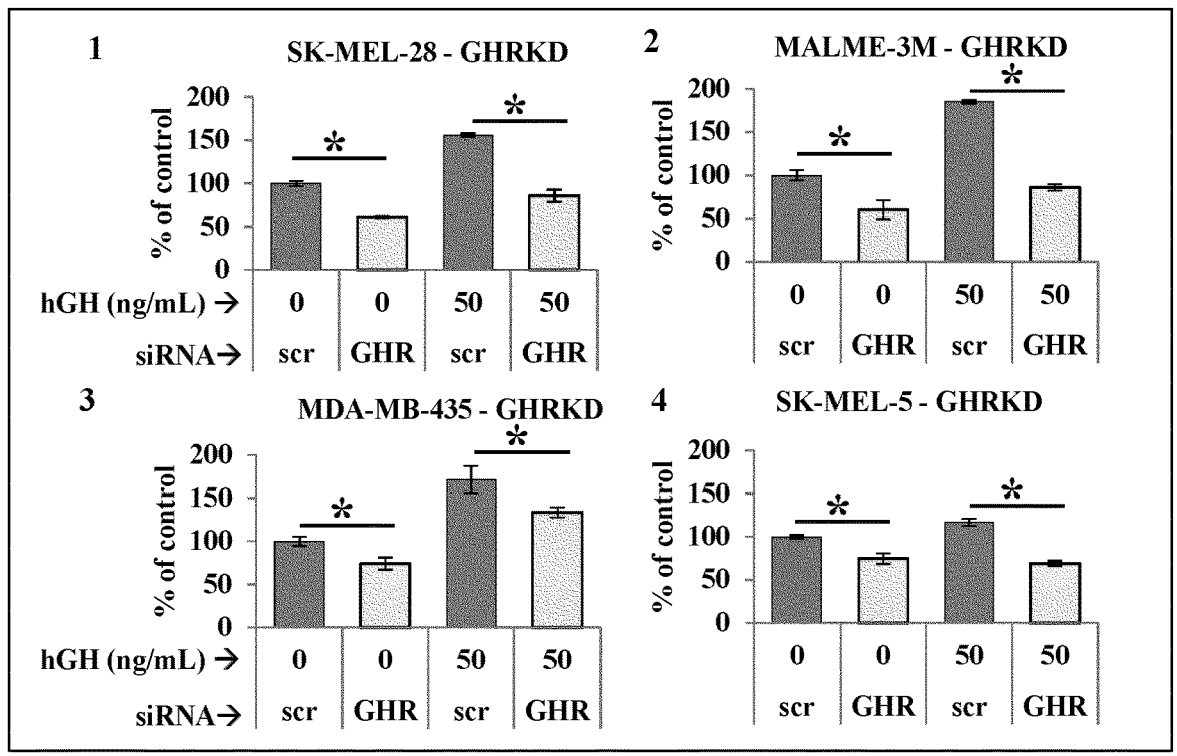

On the other hand, a pronounced drop in proliferation levels in all the cell lines was seen when GHR was knocked down. Melanoma cell proliferation decreased by 24% (MDA-MB-435) to 40% (MALME-3M) in GHR-KD cells, even when no GH was added externally, while the trend remained similar even when 50 ng/ml hGH was present in the media (see FIG. 8B). More specifically, SK-MEL-28 cells (FIG. 8B, panel 1), MALME-3M cells (FIG. 8B, panel 2), MDA-MB-435 cells (FIG. 8B, panel 3), and SK-MEL-5 cells (FIG. 8B, panel 4) were transfected with 20 nM scramble or GHR-siRNA for 24 hr. and grown for 48 hr. in presence or absence of 50 ng/mL hGH. Cell proliferation was estimated using resazurin-based metabolic assay. A significant decrease in cell proliferation was noted following GHR-KD. Averages of at least four independent experiments performed in quadruplicate were taken [*, $p<0.05$, Students t-test]. The results may indicate that human melanoma cells utilize GH-GHR interaction to drive aggressive tumor phenotypes.

Possible intracellular signaling networks under GH control that may be responsible for translating the GH-GHR interaction to the above described phenotypes involving tumor progression were investigated next.

GH-GHR action regulates phosphorylation states of intracellular signaling intermediates in human melanoma cells: In order to assess the effects of GHR-KD on the activation states of GH regulated shared oncogenic signaling pathways, scr-siRNA or GHR-siRNA transfected human melanoma cells, at 60 hours post-transfection, were treated with 50 ng/ml hGH for 20 minutes, and phosphorylation levels of intracellular signaling intermediates were analyzed by WB. Results are described below, and shown in FIGS. 9A-9I, 10A-10L, and 11A-11I. For the results described and shown in FIGS. 9A-I, SK-MEL-28 cells, 24 hr post-transfection with either scramble (scr)-siRNA or GHR-siRNA were treated for ten mins with GH and lysed as described. WB was performed using appropriate antibodies. Densitometry analyses of individual blots was performed using ImageJ software and the ratio of phosphorylated vs. total protein levels against untreated scr-siRNA transfected controls. Overall, excess GH increased while GHR-KD decreased phosphorylation states. Similar results for MALME-3M, MDA-MB-435 and SK-MEL-5 human melanoma cells are presented in FIGS. 10A-10L. [In FIGS. 10A-10L, relative RNA expression was quantified for GH, PRL, IGF1, GHR, PRLR, IGF1R, IGF2R, GHRHR, IGFBP2, IGFBP3 and SOCS2 in MALME-3M melanoma cells following addition of 0, 5, 50 and 150 ng/mL hGH or following GHR-KD, in presence or absence of 0 and 50 ng/mL hGH. In all cases, exogenous hGH treatment was for 24 hr. ERNA levels were normalized against expression of beta-actin and GAPDH as reference genes. [*, $p<0.05$, Wilcoxon sign rank test, n=4],] Blots from individual experiments were quantified and the mean of three blots per antibody was taken. Protein levels were normalized against expression of β-actin. [*, $p<0.05$, Students t test, n=3]. And, for the results described and shown in FIGS. 11A-11I, WB was performed using appropriate antibodies. Densitometry analyses of individual blots was performed using ImageJ software and the ratio of phosphorylated vs. total protein levels against untreated scr-siRNA transfected controls. Overall, excess GH increased while GHR-KD decreased phosphorylation states. Blots from individual experiments were quantified and the mean of three blots per antibody was taken. Protein levels were normalized against expression of β-actin. [*, $p<0.05$, Students t test, n=3]

Figure 9A:
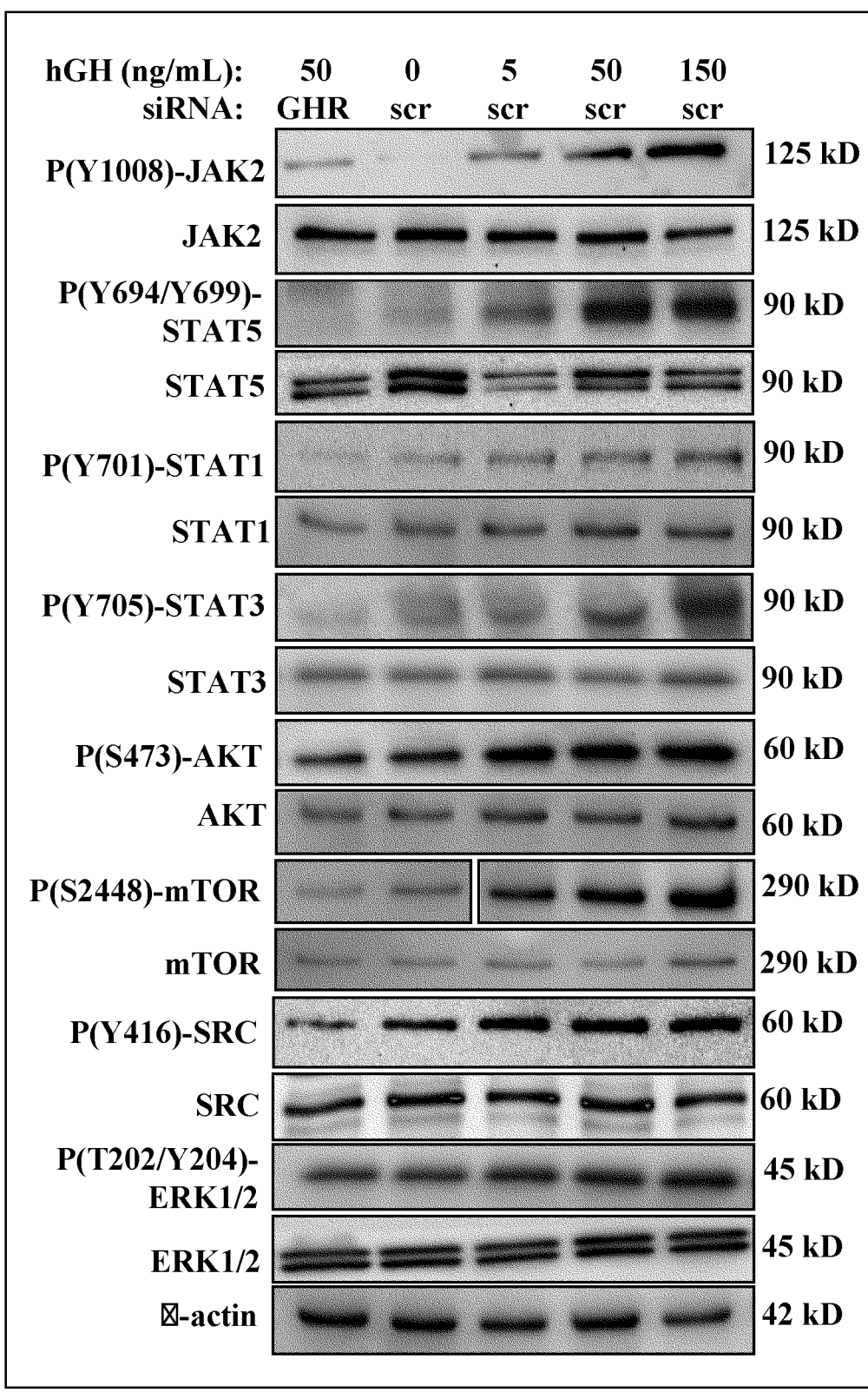
Figure 9B:
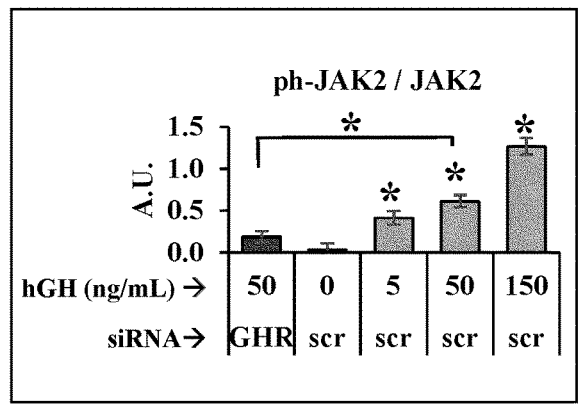
Figure 9C:
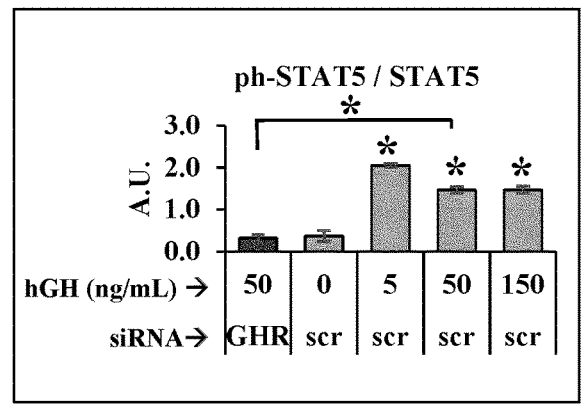
Figure 9D:
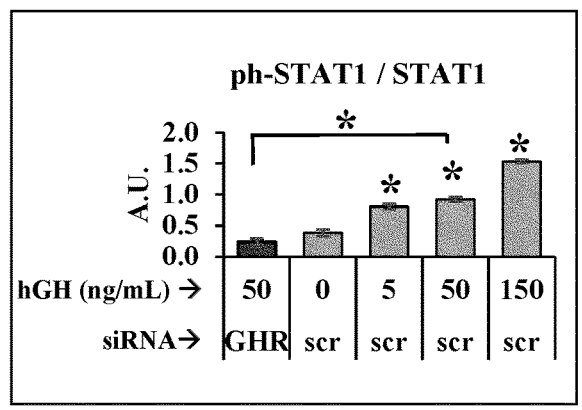
Figure 9E:
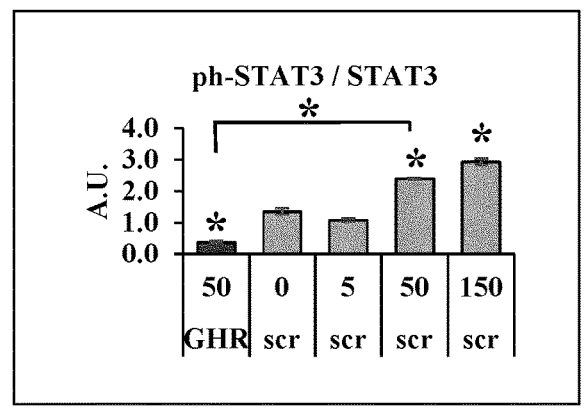
Figure 9F:
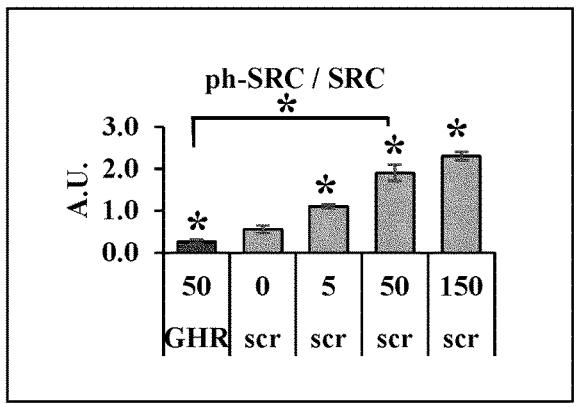
Figure 9G:
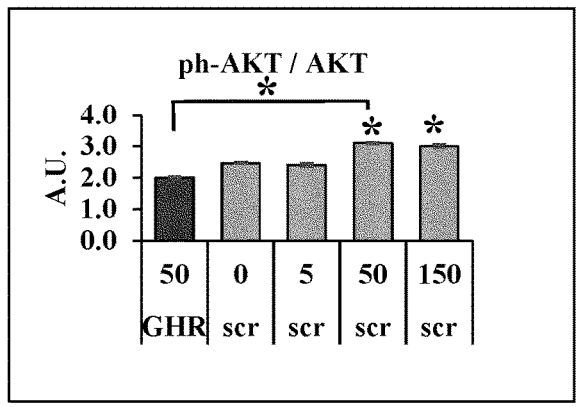
Figure 9H:
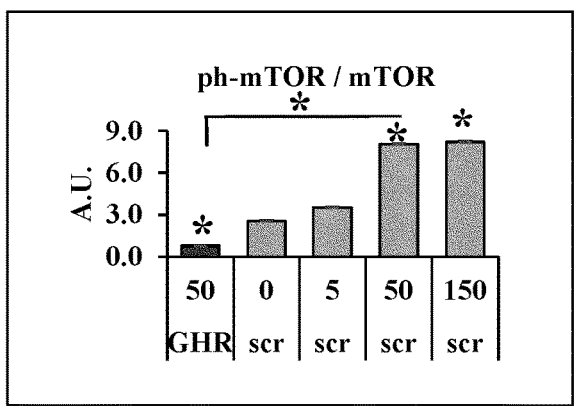
Figure 9I:
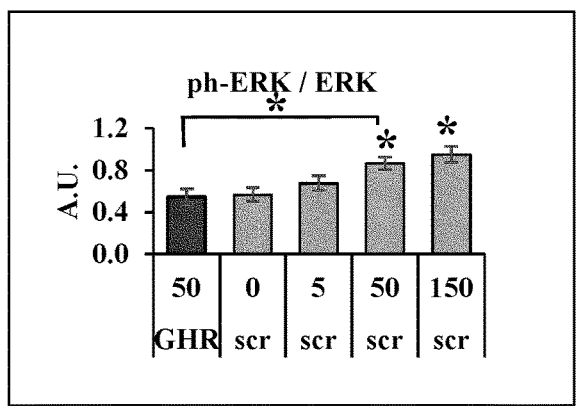
Figure 10A:
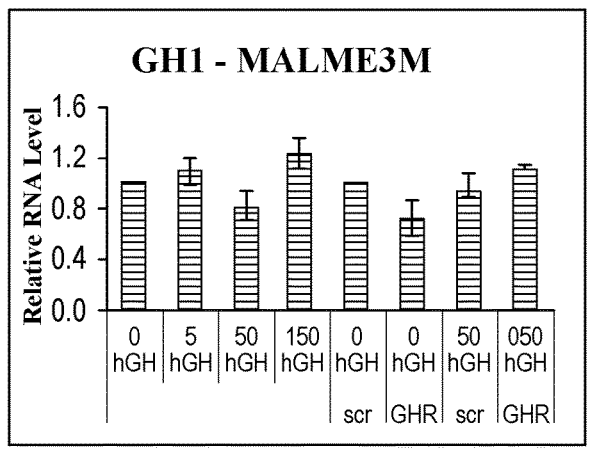
FIGS. 10A-10L include graphs showing a comparison of changes in RNA level expression of key components of GH/GF-1 axis in MALME-3M cells.
Figure 10B:
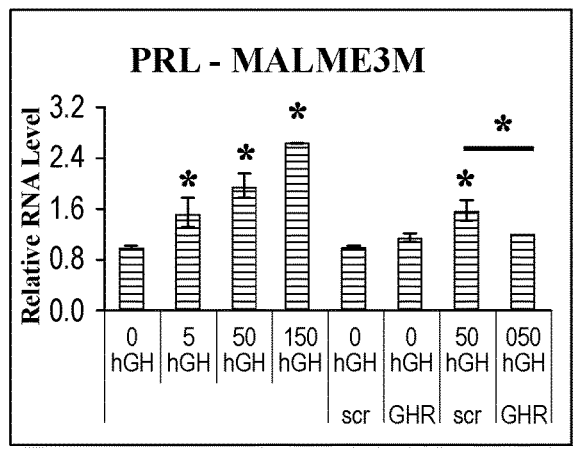
Figure 10C:
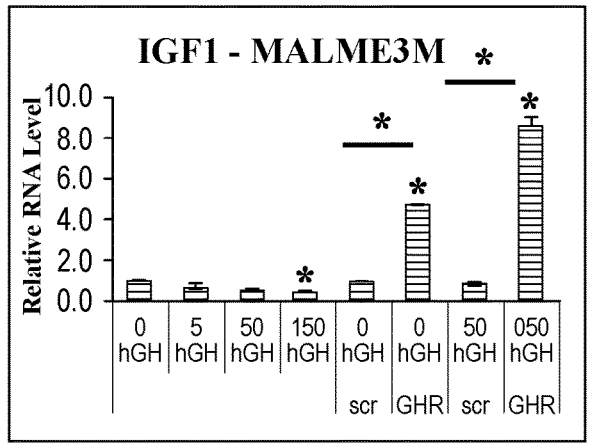
Figure 10D:
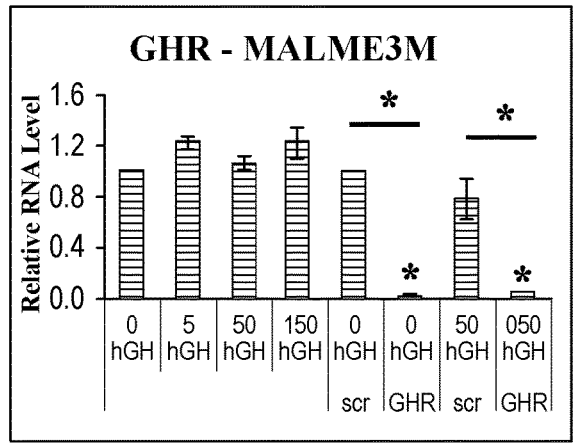
Figure 10E:
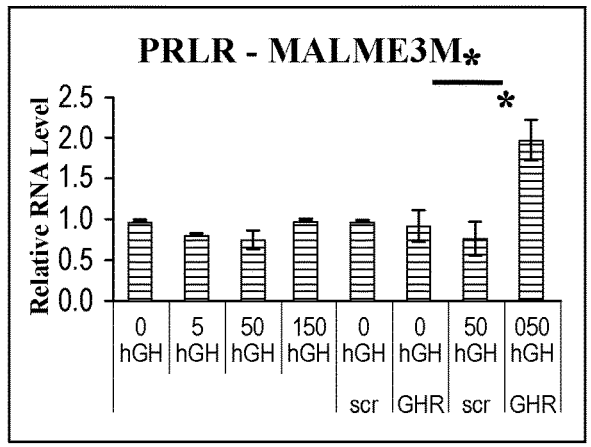
Figure 10F:
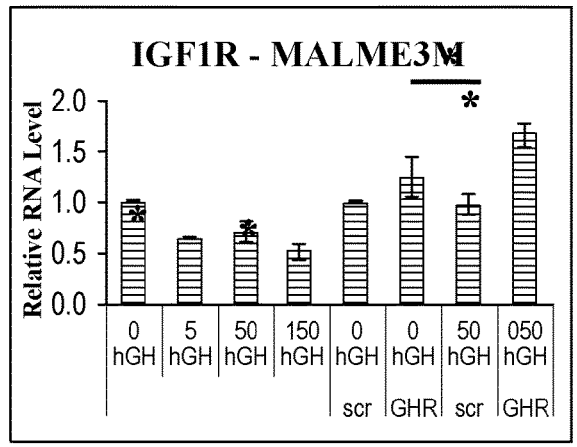
Figure 10G:
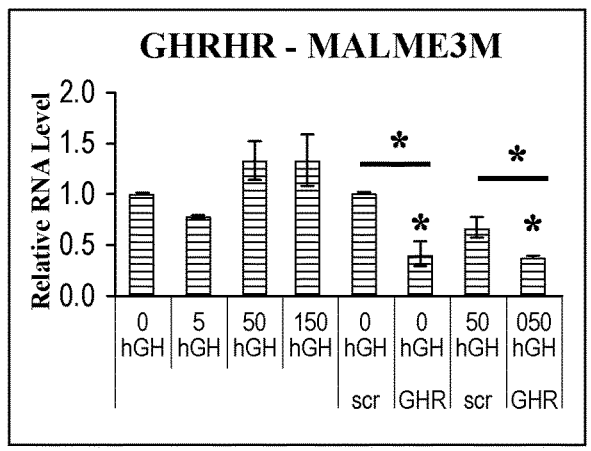
Figure 10H:
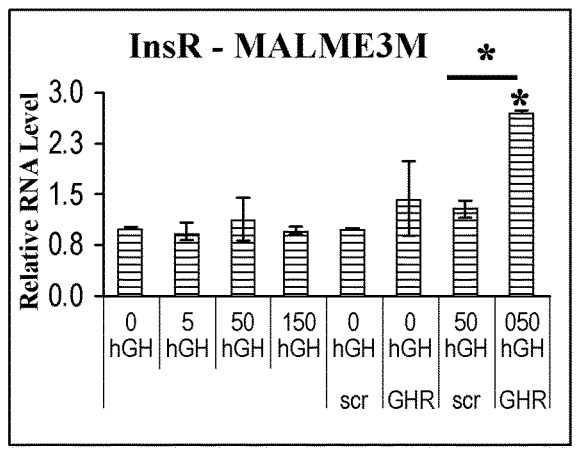
Figure 10I:
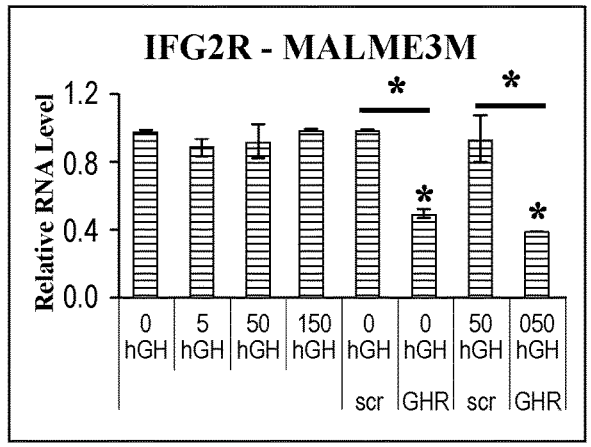
Figure 10J:
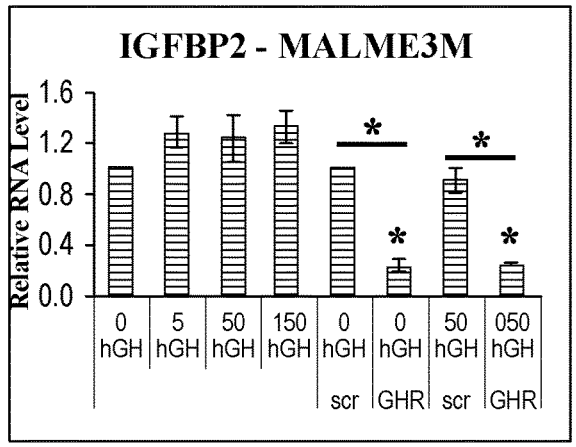
Figure 10K:
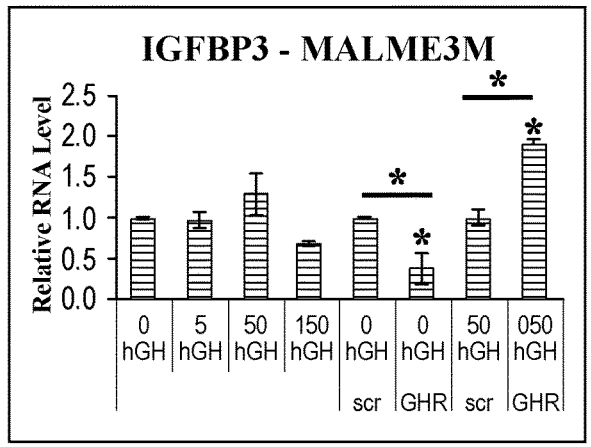
Figure 10L:
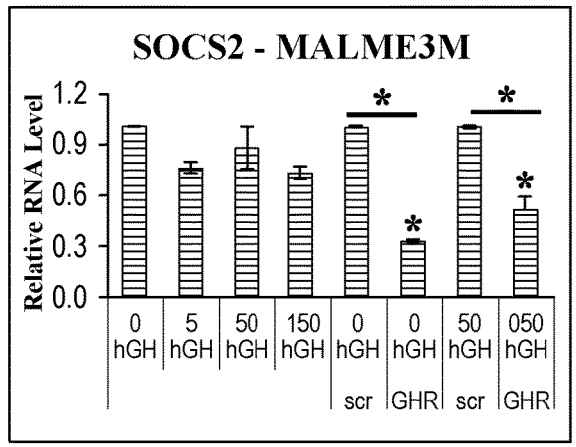
Figure 11A:
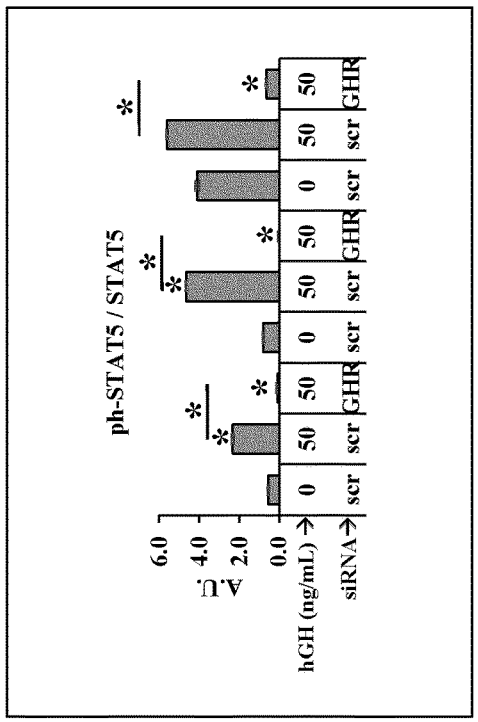
FIGS. 11A-11I include graphs and photographs showing that GH-excess promotes, and GHR-KD attenuates, phosphorylation levels of multiple critical intracellular signaling pathways in human melanoma cells.
Figure 11B:
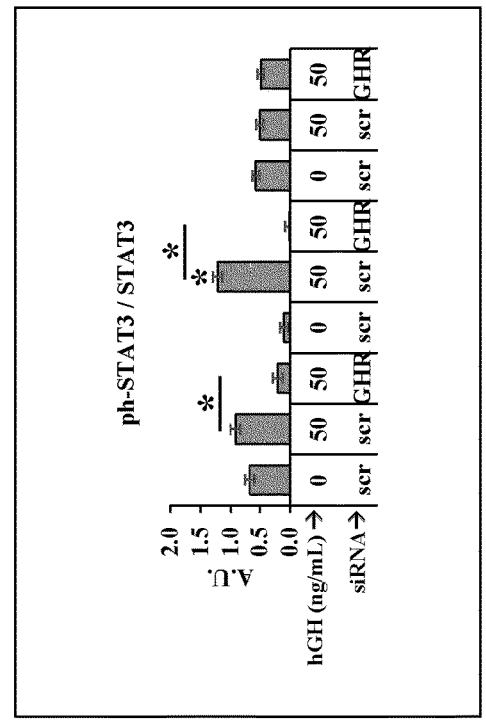
Figure 11C:
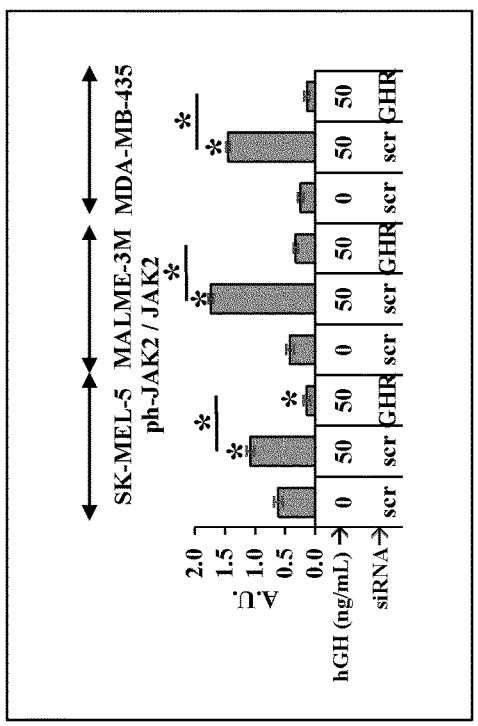
Figure 11D:
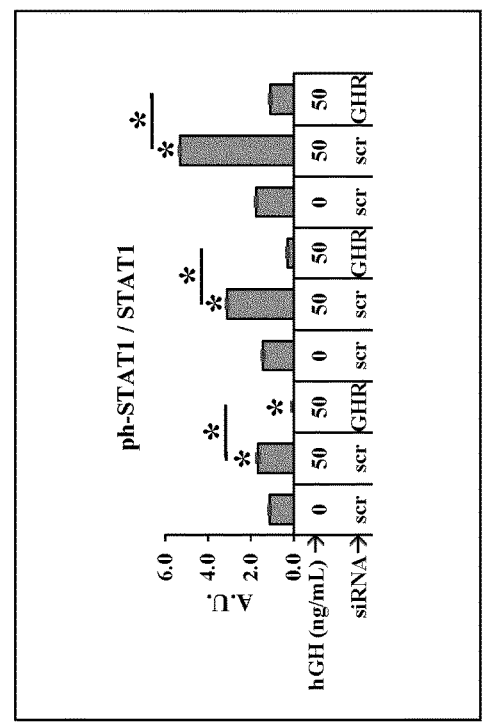
Figure 11F:
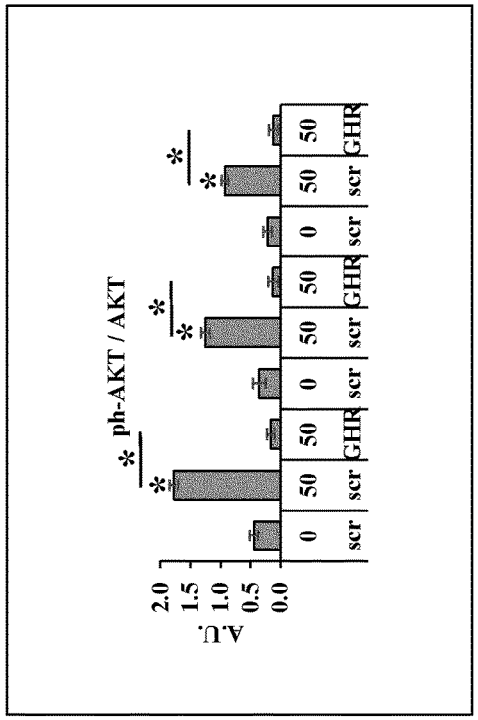
Figure 11H:
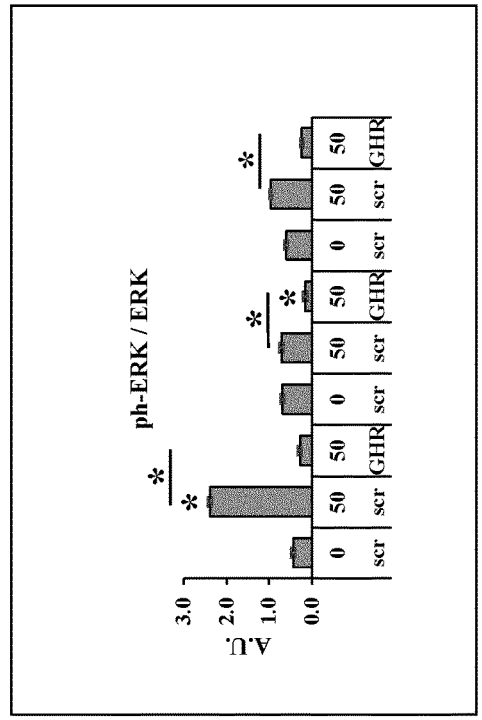
Figure 11E:
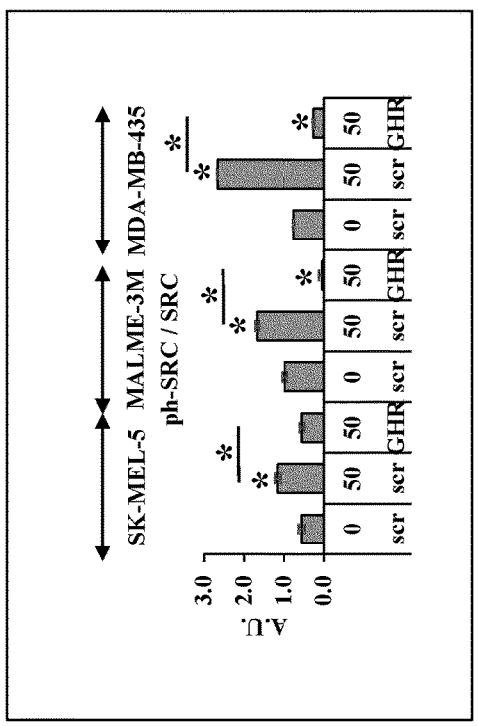
Figure 11G:
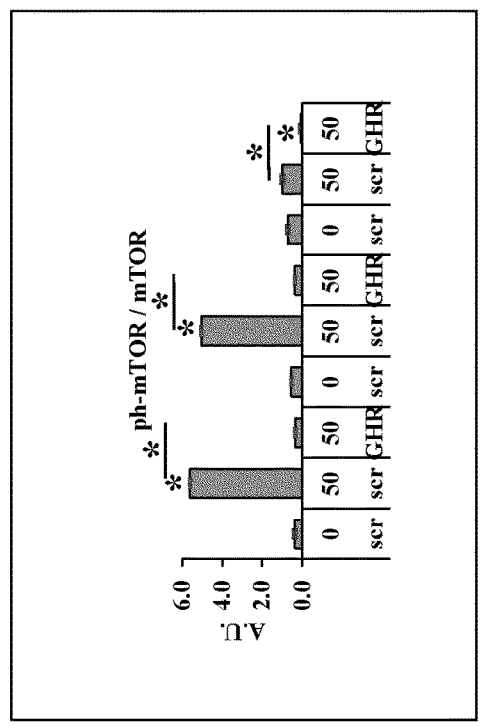
Figure 11I:
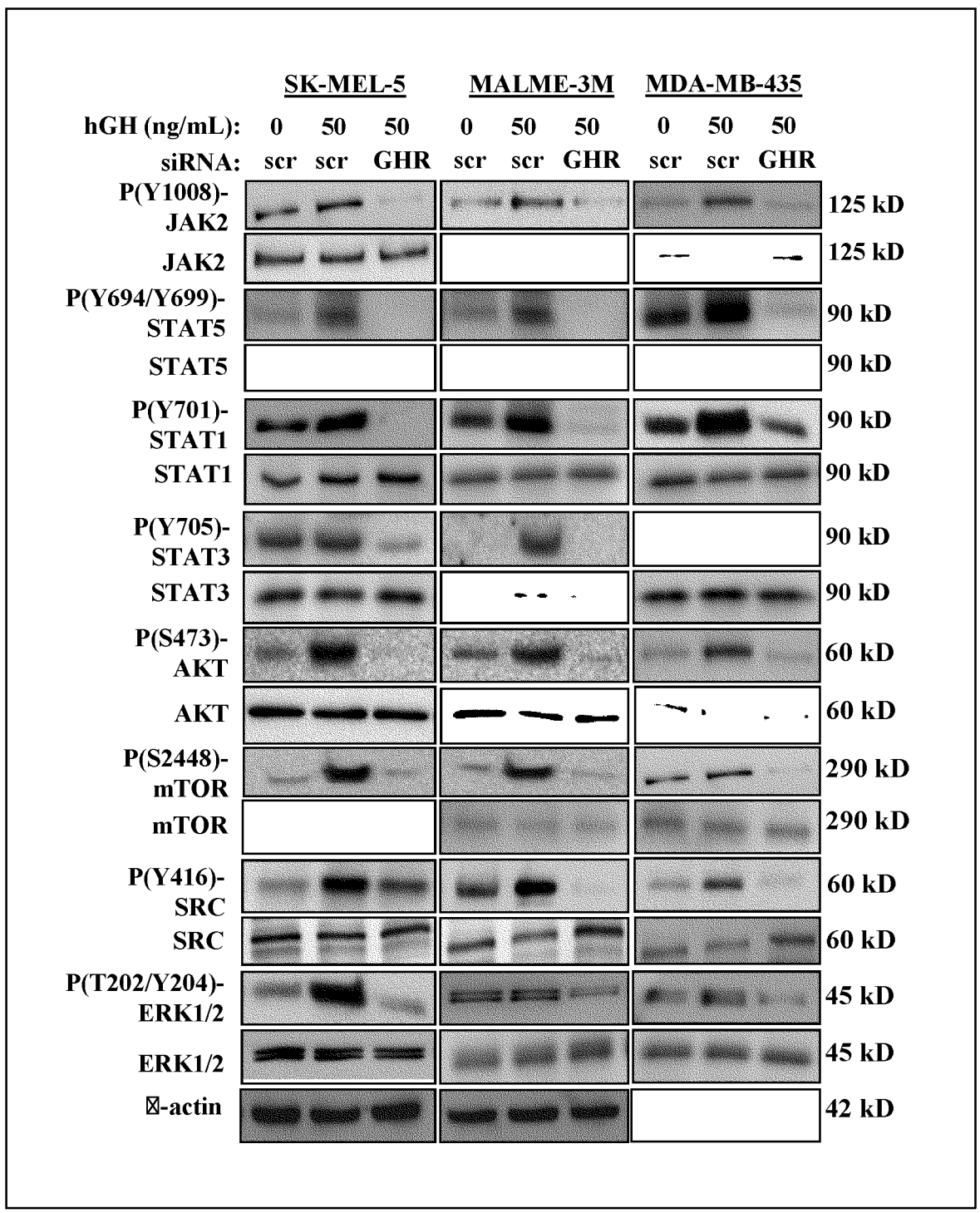

As shown in FIGS. 9A-9I and 11A-11I, a dependence of various signaling pathways on the GH-GHR interaction in all four human melanoma cells was observed (FIGS. 9A and 11I). Densitometry analyses revealed that GH induced a robust increase in phosphorylation levels of JAK2 (FIGS. 9B, 11A) as well as of SRC (FIGS. 9F, 11E), supporting findings in other cellular lines. In fact, the increases in GH-induced phosphorylation of JAK2, e.g., 1.7-fold (SK-MEL-5) to 6.1-fold (SK-MEL-28), and SRC, e.g., 1.7 fold (MALME-3M) to 3.5 fold (SK-MEL-28), were found to be dose-dependent (FIGS. 9B, 9F). Even in the presence of 50 ng/ml hGH in the medium, GHR-KD resulted in as much as 75%-90% lower activation of JAK2 and SRC than corresponding control, often to below the basal activation states observed across the four cell lines (FIGS. 9B, 9F).

Continuing to refer to FIGS. 9A-9I and 11A-11I, additional routes of GH induced signaling situated downstream of JAK2 and SRC were investigated, including GH-induced increases in phosphorylation states of STAT5 (FIGS. 9C, 11B), STAT1 (FIGS. 9D, 11C), STAT3 (FIGS. 9E, 11D), as well as of AKT (FIGS. 9G, 11F), mTOR (FIGS. 9H, 11G), and ERK1/2 (FIGS. 9I, 11H) in all four human melanoma cell lines. STAT5 phosphorylation increased by 4.1-fold (SK-MEL-28) to 5.8-fold (MALME-3M) at 50 ng/ml hGH; while GHR-KD effected an 80%-90% reduction of the same (FIGS. 9, 11B), STAT1 and STAT3 phosphorylation levels were upregulated at 50 ng/ml hGH, e.g., MALME-3M with its 2.2-fold increase in STAT1 phosphorylation level and 11.9-fold increase in STAT3 phosphorylation level and SK-MEL-28 with its 2.4-fold increase in STAT1 phosphorylation level and 1.9-fold increase in STAT3 phosphorylation level, while GHR-KD suppressed phosphorylation significantly across all four cells (FIGS. 9D, 9E, 11C, 11D). Activated (tyrosine phosphorylated) GHR, in presence of 50 ng/ml hGH, was found to increase AKT and its downstream target, mTOR, phosphorylation levels up to 4-fold and 15-fold respectively in SK-MEL-5 cells, while GHR-KD suppressed the same by more than 90% in all cases (FIGS. 11F, 11G). The ERK1/2 levels were similarly upregulated by GH in three of four melanoma cell lines, with a 5-fold increase in SK-MEL-5 cells (FIG. 11H). GHR-KD also suppressed ERK1/2 phosphorylation by 80% in human melanoma cell lines, even in presence of GH.

These signaling pathways are oncogenic "drivers" or enhancers in several human cancers, including melanoma. Thus, these results, dealing with both excess GH and GHR depletion, show that the GH-GHR pair and interaction thereof regulates aggressive tumor phenotypes by exerting control over the activation states of certain oncogenic signaling mediators.

Targeting GHR remodels RNA expression of members of the IGF family of proteins and suppresses oncogenic receptors on/in human melanoma cells: induced intracellular signaling may be associated with that of several other hormones, including prolactin (PRL), insulin (Ins), IGF-1, and IGF-2, and their respective cognate receptors, PRL receptor (PRLR), insulin receptor (IR), IGF-1 receptor (IGF1R) and IGF-2 receptor (IGF2R). In addition, GH action may be correlated with expression of IGF binding proteins (IGFBP), e.g., IGFBP-2 and IGFBP-3. GH and PRL belong to the same family of class I cytokines, which possess a few similar actions on tissues. Additionally, human skin may be an extra-pituitary site where both these cytokines and their cognate receptors (GHR and PRLR) may be expressed. Thus, the endogenous RNA levels of GH, as well as PRL and PRLR, in human melanoma were also quantified.

Figure 12A:
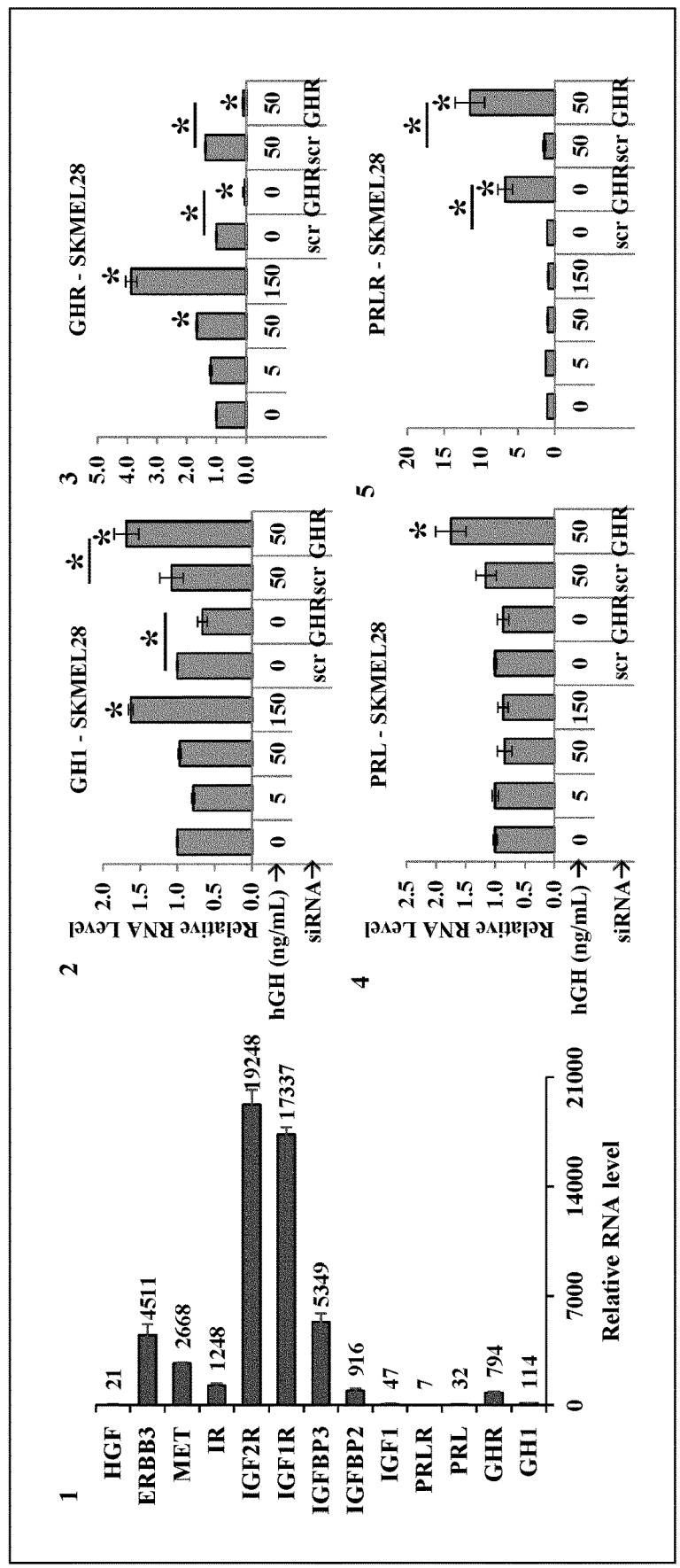
FIGS. 12A-12B include graphs showing RT-qPCR analysis of GH-IGF axis in human melanoma cells.
Figure 12B:
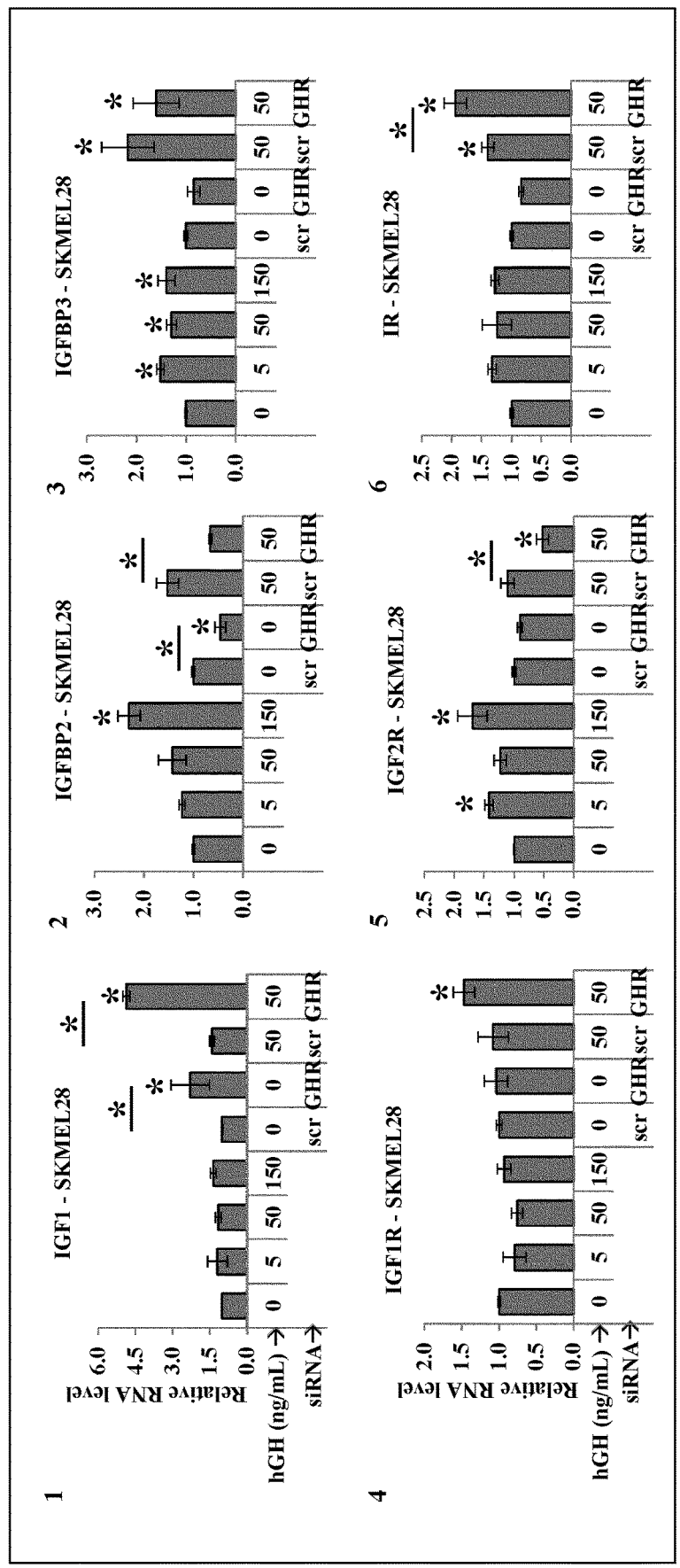
Figure 13A:
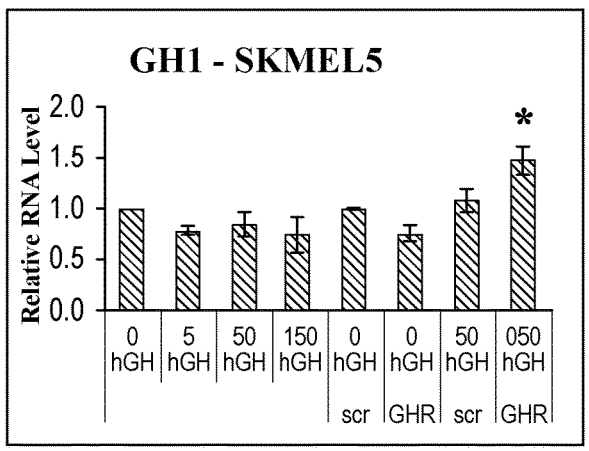
FIGS. 13A-13L include graphs showing a comparison of changes in RNA level expression of key components of GH/IGF-1 axis in SK-MEL-5 cells.
Figure 13B:
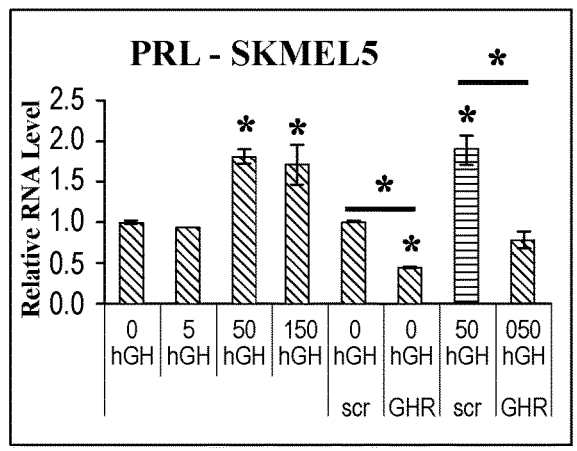
Figure 13C:
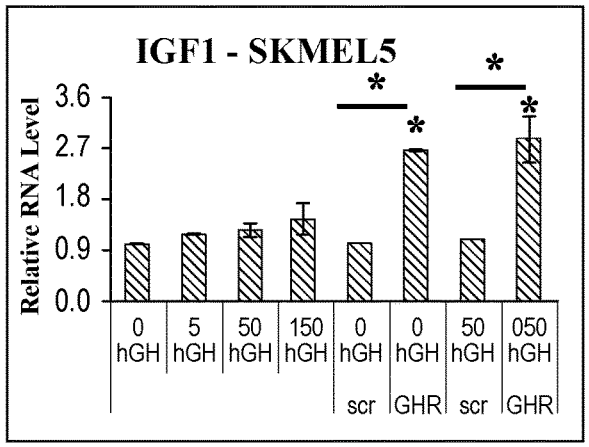
Figure 13D:
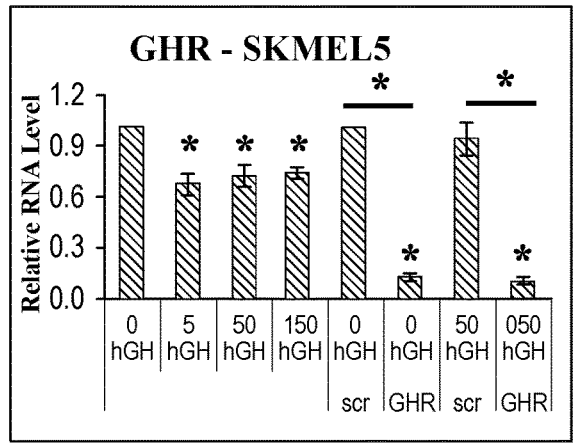
Figure 13E:
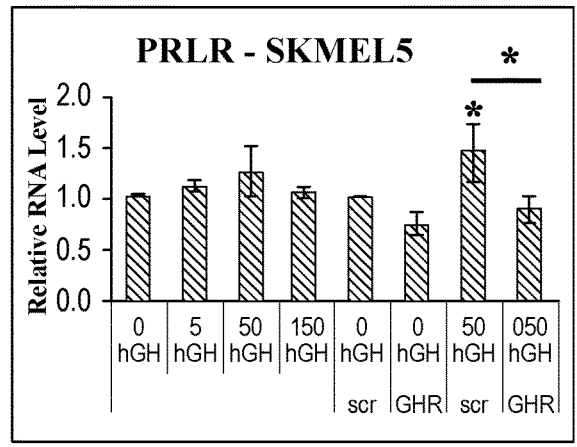
Figure 13F:
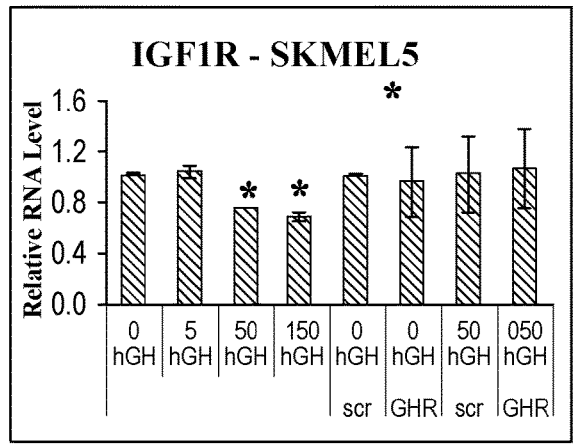
Figure 13G:
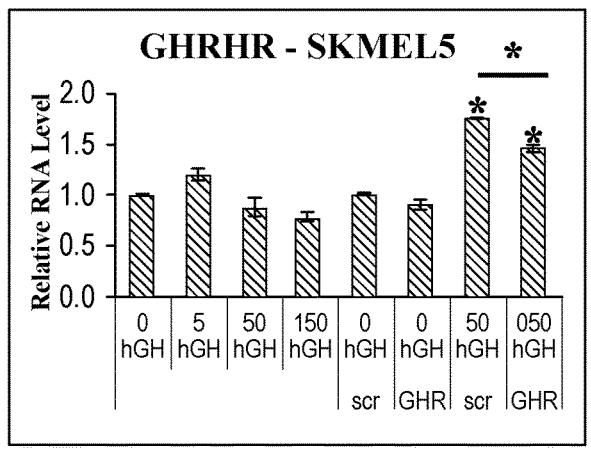
Figure 13H:
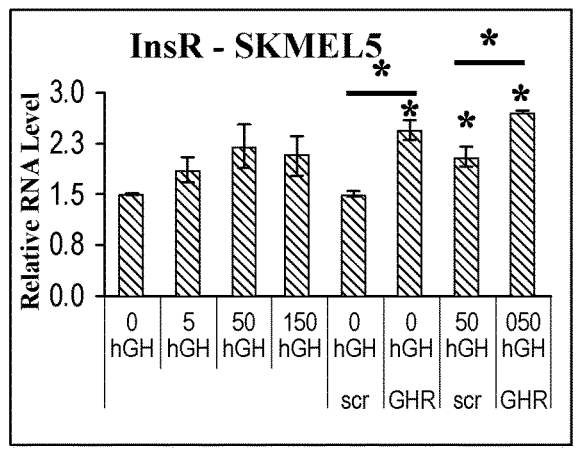
Figure 13I:
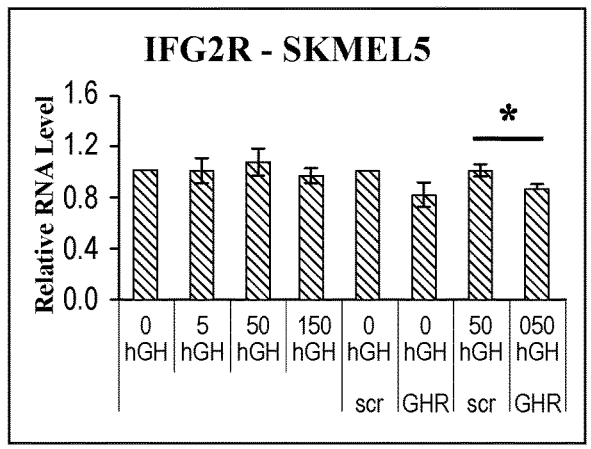
Figure 13J:
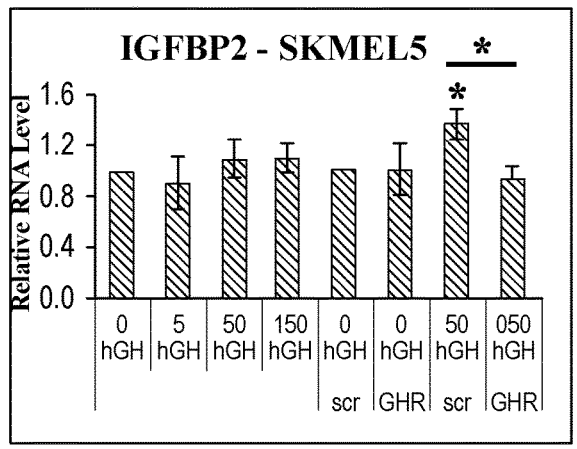
Figure 13K:
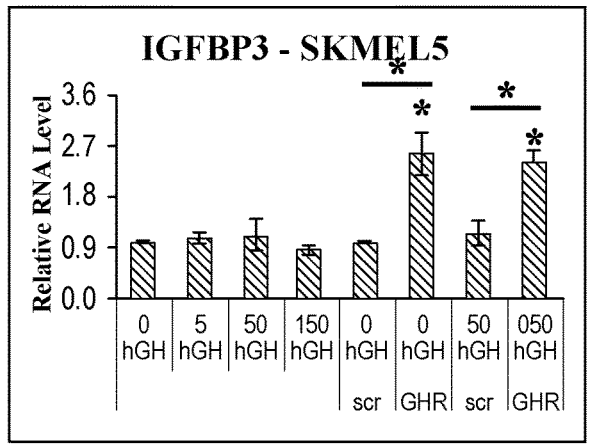
Figure 13L:
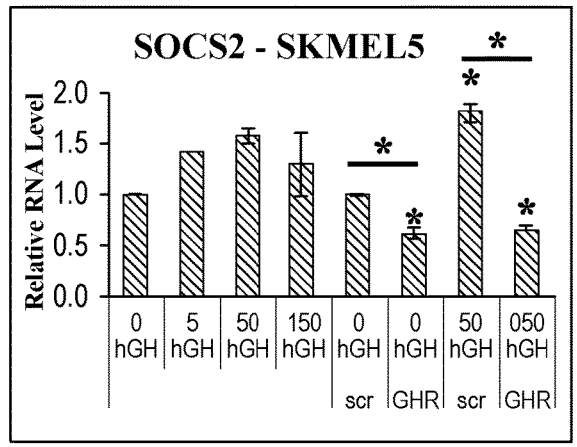
Figure 14A:
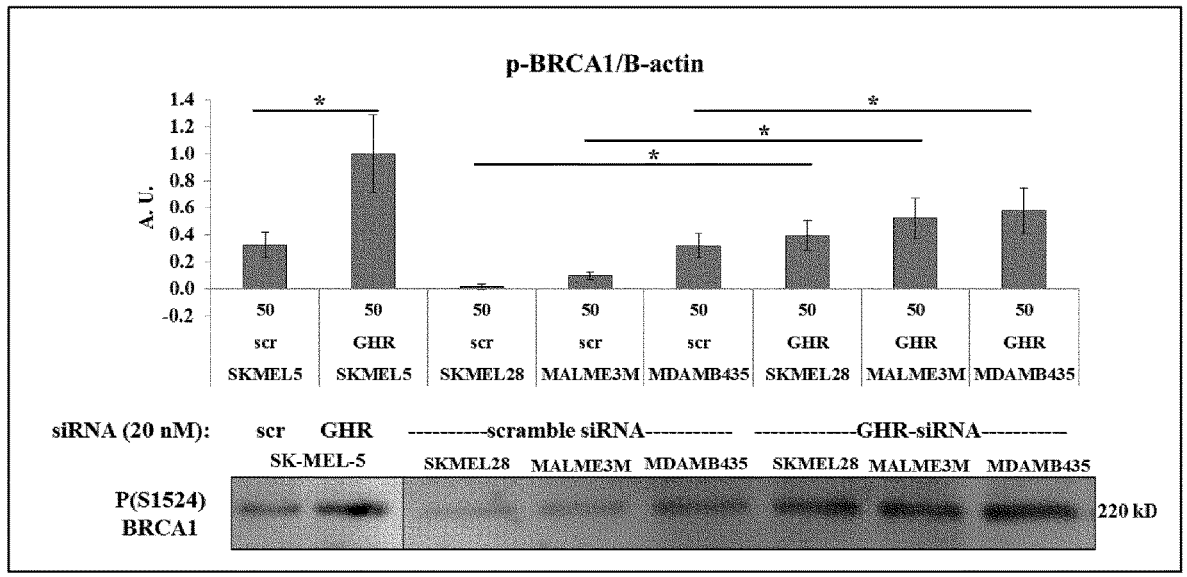
FIGS. 14A-14B include graphs and photographs showing a change in markers of DNA damage following GHR-KD.
Figure 14B:
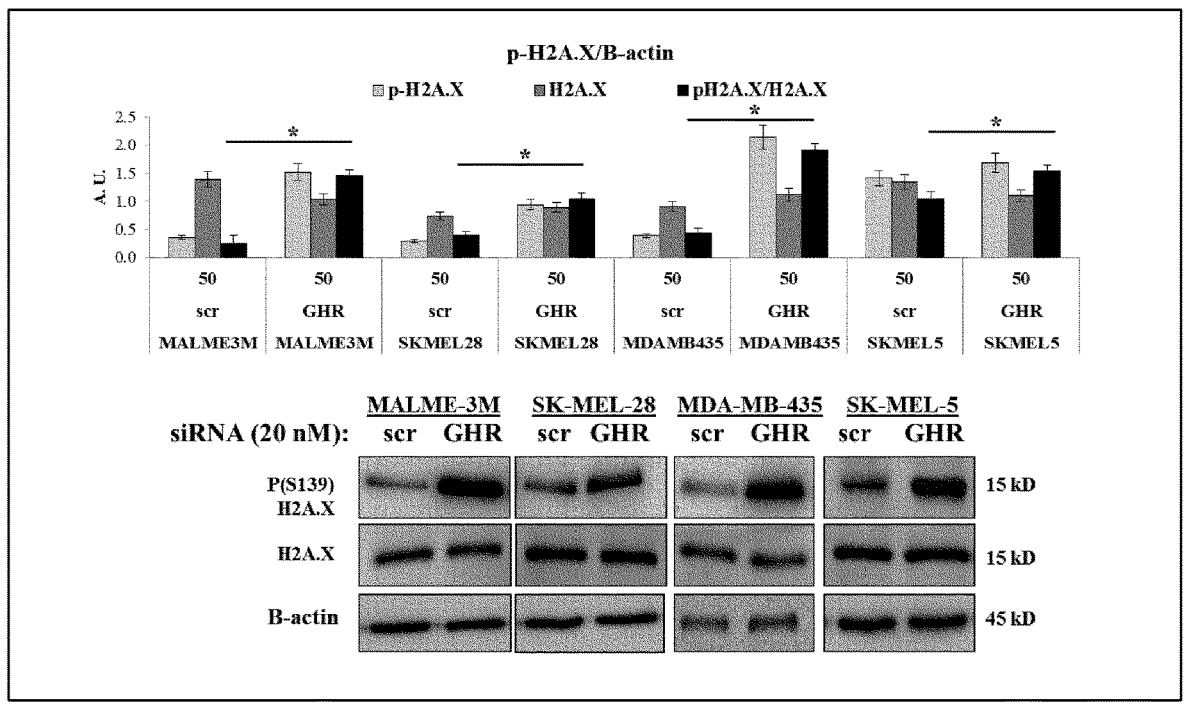
Figure 15:
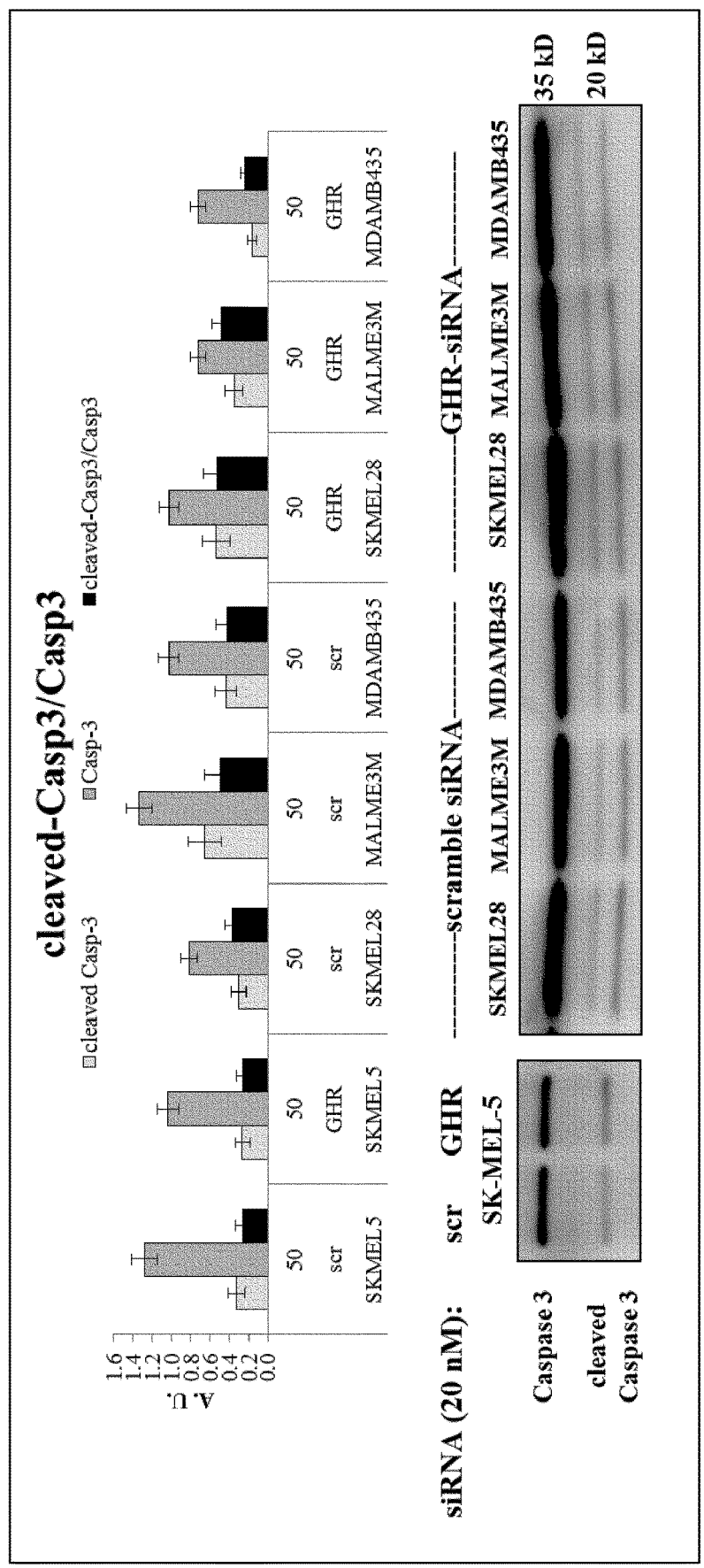
FIG. 15 includes graphs and photographs showing a change in markers of apoptosis following GHR-KD.
Figure 16:
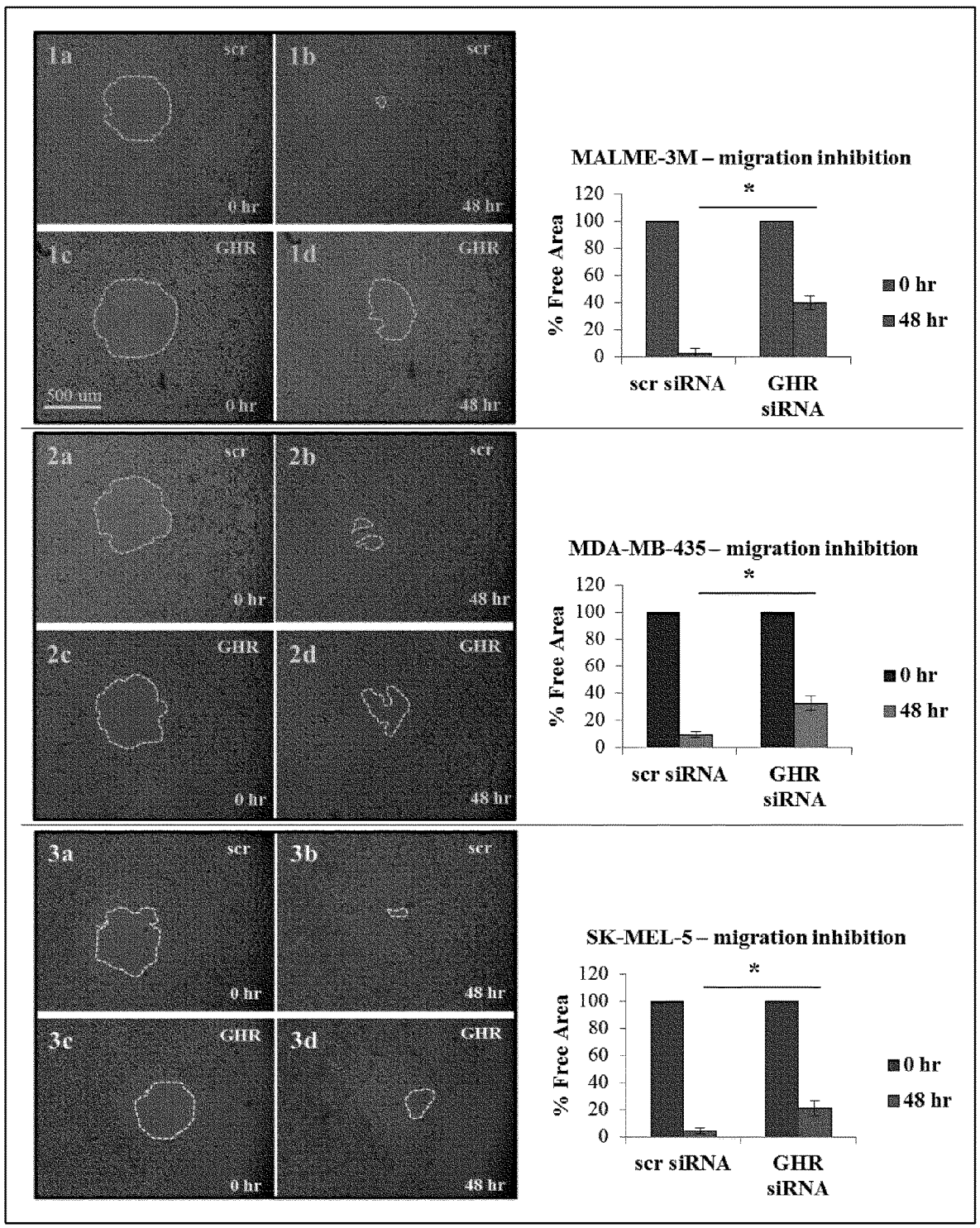
FIG. 16 includes graphs and photographs showing the effect of GHR knock down (KD) on melanoma cell migration.

And so—referring now to FIGS. 12A-12B, 17A-17C, 18A-18F, 19A-19F, and 20A-20F—RT-qPCR analysis of GH-IGF axis in human melanoma cells (FIGS. 12A-12B) and RT-qPCR analysis of GH-GHR and PRL-PRLR pairs in human melanoma cells (FIGS. 17A-17C) was performed. As shown in FIGS. 12A and 12B, and for the results described below, the RT-qPCR analysis was of RNA extracted from SK-MEL-28 cells following addition of 0, 5, 50 and 150 ng/mL hGH or following GHR-KD, in presence or absence of 0 and 50 ng/mL hGH. Results are discussed below. And, while not shown in FIGS. 12A and 12B, similar results for MALME-3M, MDA-MB-435 and SK-MEL-5 human melanoma cells are presented in FIGS. 13A-13L, 17A-17C, 18A-18F, 19A-19F, and 20A-20F. In FIGS. 13A-13L, (which shows a comparison of changes in RNA level expression of key components of GH/IGF-1 axis in SK-MEL-5 cells), relative RNA expression was quantified for GH, PRL, IGF1, GHR, PRLR, IGF1R, IGF2R, GHRHR, IGFBP2, IGFBP3 and SOCS2 in SK-MEL-5 melanoma cells following addition of 0, 5, 50 and 150 ng/mL hGH or following GHR-KD, in presence or absence of 0 and 50 ng/mL hGH. In all cases, exogenous hGH treatment was for 24 hr. RNA levels were normalized against expression of beta-actin and GAPDH as reference genes. [*, p<0.05, Wilcoxon sign rank test, n=4], In FIGS. 14A and 14B, (which shows a change in markers of DNA damage following GHR-KD), changes in phosphorylation levels of BRCA1 and histone H2A.X were evaluated using antibodies recognizing phospho-serine 1524-BRCA1 and phospho-serine 139-H2A.X. The p-H2A.X112A.X ratio was specifically compared as the indicator of relative level of phosphorylation. The p-BRCA1 values were significantly upregulated following GHR-KD but p-BRCA1/BRCA1 ratio was not evaluated. Cells were grown in presence of 50 ng/mL exogenous GH and protein level changes were estimated 60 hr. post-transfection. [*, p<0.05, Students t test, n=3]. In FIG. 15, (which shows a change in markers of apoptosis following GHR-KD), changes in protein levels of caspase-3 and cleaved caspase-3 were evaluated following GHR-KD in the presence of 50 ng/mL hGH. And in FIG. 16, (which shows the effect of GHR knock down (KD) on melanoma cell migration), (1) MALME-3M (panels 1a-1d and top graph), (2) MDA-MB-435 (panels 2a-2d and middle graph), and (3) SK-MEL-5 cells (panels 3a-3d and bottom graph) transfected with 20 nM scramble (panels a and b in the photographs) or GHR-siRNA (panels c and d in the photographs) were allowed to migrate into a circular spot at the center of the well, in presence of 50 ng/mL hGH for up to 48 hr. The percentage free area at the end time point was calculated using ImageJ software and reflected the decrease/inhibition in migration. A significant decrease in migration was noted following GHR-KD. [*, p<0.05, Students t-test, n=3]. In all cases, exogenous hGH treatment was for 24 hr. RNA levels were normalized against expression of β-actin and GAPDH as reference genes [*, p<0.05, Wilcoxon sign rank test, n=4]. And, in FIGS. 17A-17C, relative RNA levels of GH, GHR, PRL, and PRLR, following RT-qPCR of RNA extracted from MALME-3M, MDA-MB-435, and SK-MEL-5 cells following addition of 0, 5, 50 and 150 ng/mL hGH or following GHR-KD, in presence or absence of 0 and 50 ng/mL hGH, are shown. Results are discussed below. In all cases, exogenous hGH treatment was for 24 hr. RNA levels were normalized against expression of β-actin and GAPDH as reference genes. [*, p<0.05, Wilcoxon sign rank test, n=4]

Figure 17A:
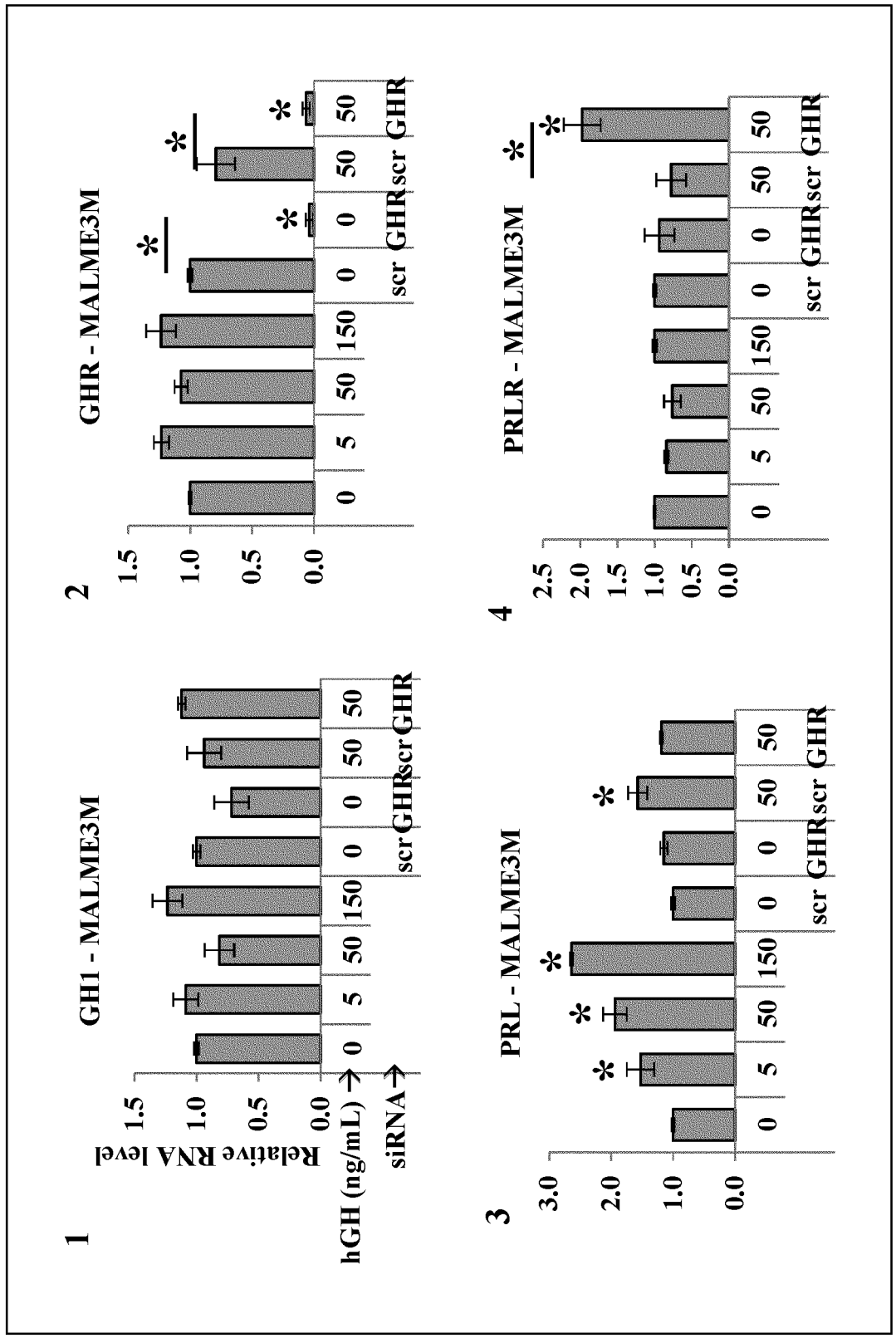
FIGS. 17A-17C include graphs showing RT-qPCR analysis of GH-GHR and PRL-PRLR pairs in human melanoma cells.
Figure 17B:
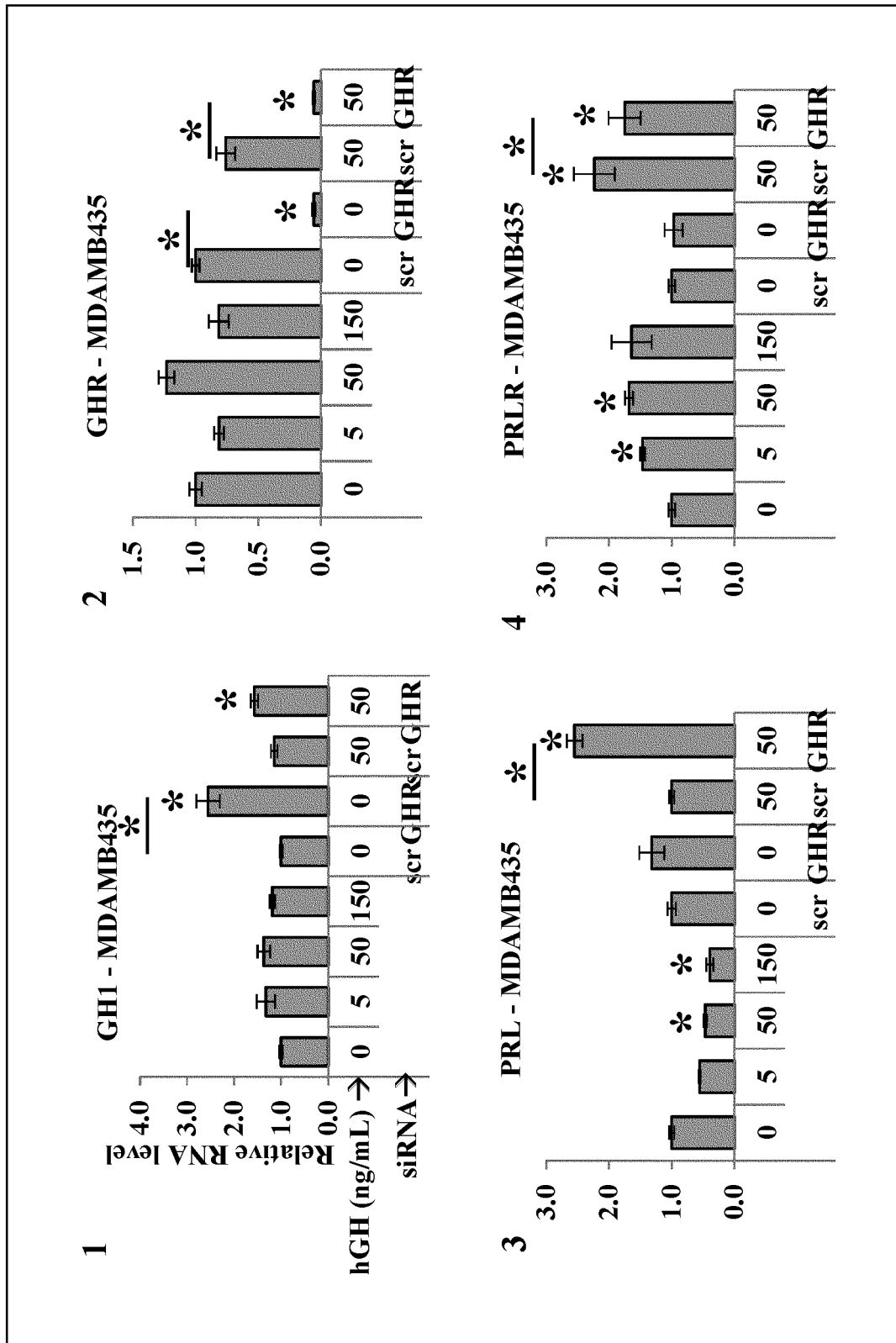
Figure 17C:
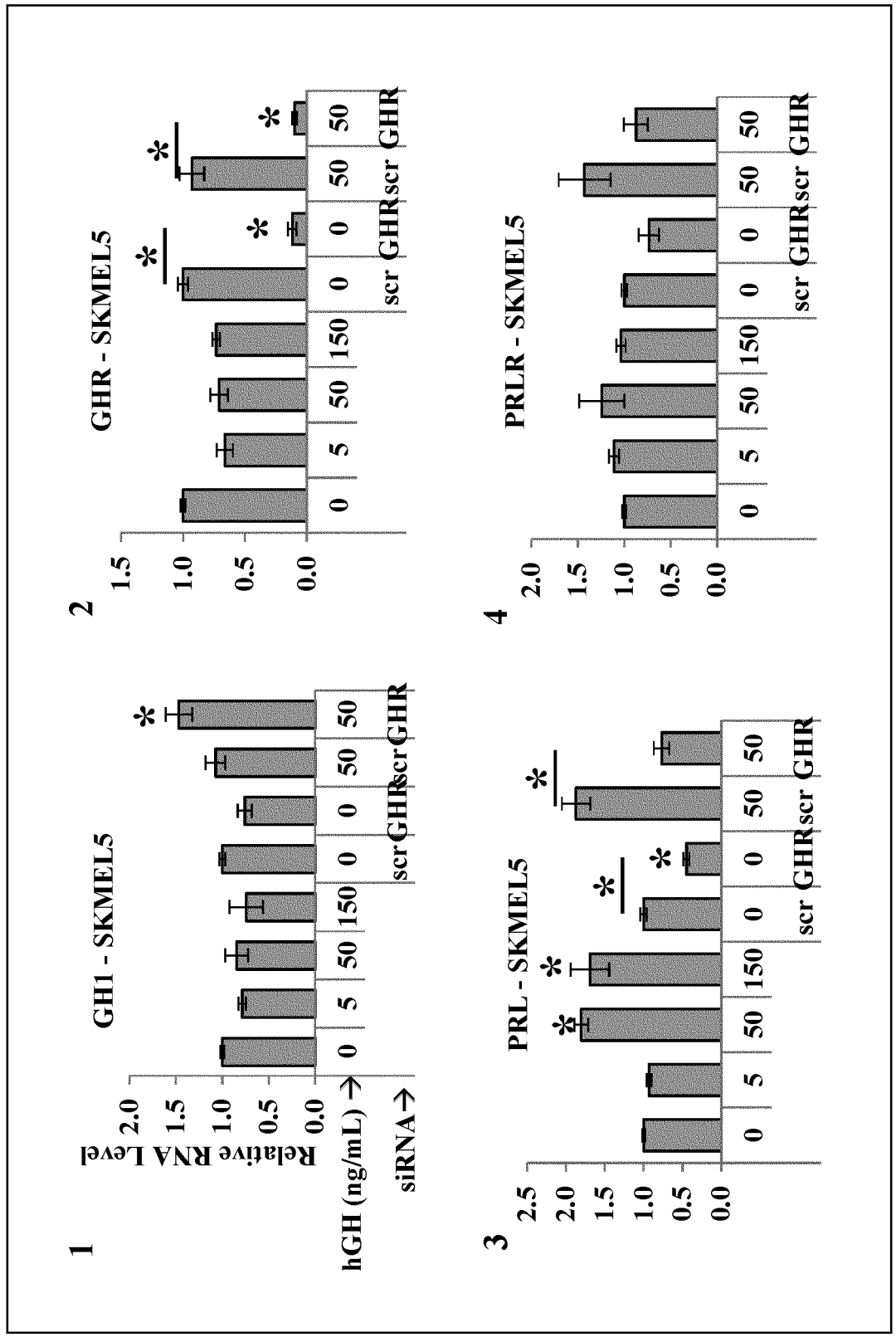

In all four melanoma cells, a relatively high level of GH RNA [panels 1 and 2 of FIG. 12A and FIGS. 17A-C] was observed, potentially indicating a mechanism of intrinsic GH production and the possibility of autocrine action in these GHR-expressing human melanoma cells. PRL and PRLR were detectable, but at levels 4-fold and 110-fold lower than GH and GHR levels, respectively, in SK-MEL-28 cells (FIG. 12A, panel 1). A similar level of RNA expression was observed in all four melanoma cell lines. In the SK-MEL-28 cells, GHR knockdown resulted in a 1.7-fold rise in GH and PRL (FIG. 12A, panels 2 and 3), which was closely reflected in other cell lines (FIGS. 17A, panel 3; 17B, panel 1; 17B, panel 3; 17C, panel 1). A 6- to 10-fold rise in PRLR levels was found with a concomitant 8- to 10-fold drop in GHR levels in SK-MEL-28 cells (FIG. 12A, panels 4 and 5). This significant rise in PRLR with drop in GHR expression was seen also in MALME-3M and MDA-MB-435 cells (FIGS. 17A, panel 4, and 17B, panel 4). Without intending to be bound by any particular theory, this data-set suggests a compensatory rise in PRL dependency of the melanoma cells, in absence of GH action, potentially caused by abrogation of GHR expression.

IGF1 may be elevated in melanoma patients, relative to non-melanoma human subjects, and the IGF1-IGF1R system may be involved with autocrine/paracrine regulation of melanoma growth. The network of Ins, IGF1, and IGF2, as well as their cognate receptors (IR, IGF1R, IGF2R) and binding proteins (IGFBPs), may be involved with melanoma disease progression. Thus, the levels of these species were examined following the perturbation of the GH-GHR axis by either addition of exogenous hGH or GHR-KD. No IGF2 or insulin RNA expression in the melanoma cell lines was observed. However, low levels of IGF1 and very high levels (25-fold greater than GHR) of IGF1R and IGF2R expression were observed (FIG. 12A, panel 1). Insulin receptors (IRs) were also detected at equivalent levels with GHR (FIG. 12A, panel 1). Although GH-excess did not cause any consistent variation in the levels of the low amounts of IGF1 RNA detected, GHR-KD resulted in a 2-fold (MDA-MB-435) to 8.6-fold (MALME-3M) increase of IGF1 RNA in the four melanoma cells (panel 1 of FIG. 12B, and FIGS. 18A, 19A, and 20A). Although excess GH caused no consistent variation in the RNA levels, a differential pattern of regulation of the IGF receptors following GHR-KD was observed. In SK-MEL-28 (FIG. 12B) and MALME-3M (FIGS. 18A-18F) cells, GHR-KD resulted in an increase in the level of IGF1R (1.5-fold) and IR (2-fold), as well as a drop in IGF2R (2-fold). FIGS. 18A-18F show the RT-qPCR analysis of components of IGF axis in MALME-3M cells. Relative RNA levels of IGF1 (FIG. 18A), IGFBP2 (FIG. 18B), IGFBP3 (FIG. 18C), IGF1R (FIG. 18D), IGF2R (FIG. 18E) and IR (FIG. 18F), following RT-qPCR of RNA extracted from MALME-3M cells following addition of 0, 5, 50 and 150 ng/mL hGH or following GHR-KD, in presence or absence of 0 and 50 ng/mL hGH. In all cases, exogenous hGH treatment was for 24 hr. RNA levels were normalized against expression of β-actin and GAPDH as reference genes. [*, p<0.05, Wilcoxon sign rank test, n=4]

Without intending to be bound by any particular theory, the net effect of this remodeling of IGF receptor distribution may help explaining the dynamicity in targeting receptor tyrosine kinases in melanoma. IGF-binding proteins 2 (IGFBP2) and 3 (IGFBP3) were expressed at relatively high levels in SK-MEL-28 (FIG. 12A, panel 1) and may have differential roles in melanoma progression. Increasing IGFBP2 level may correlate with progression to metastasis and may actively drive proliferation in melanoma. An increase in IGFBP2 RNA levels in SK-MEL-28 cells at high GH levels and a significant decrease following GHR-KD (FIG. 12B, panel 2) were observed. This 2-fold (SK-MEL-28) to 4-fold (MALME-3M) decrease in IGFBP2 levels subsequent to GHR-KD was observed in all melanoma cell lines (FIGS. 18B, 19B, and 20B—with FIGS. 19A-19F showing RT-qPCR analysis of components of IGF axis in MDA-MB-435 cells, and FIGS. 20A-20F showing RT-qPCR analysis of components of IGF axis in SK-MEL-5 cells).

Figure 18A:
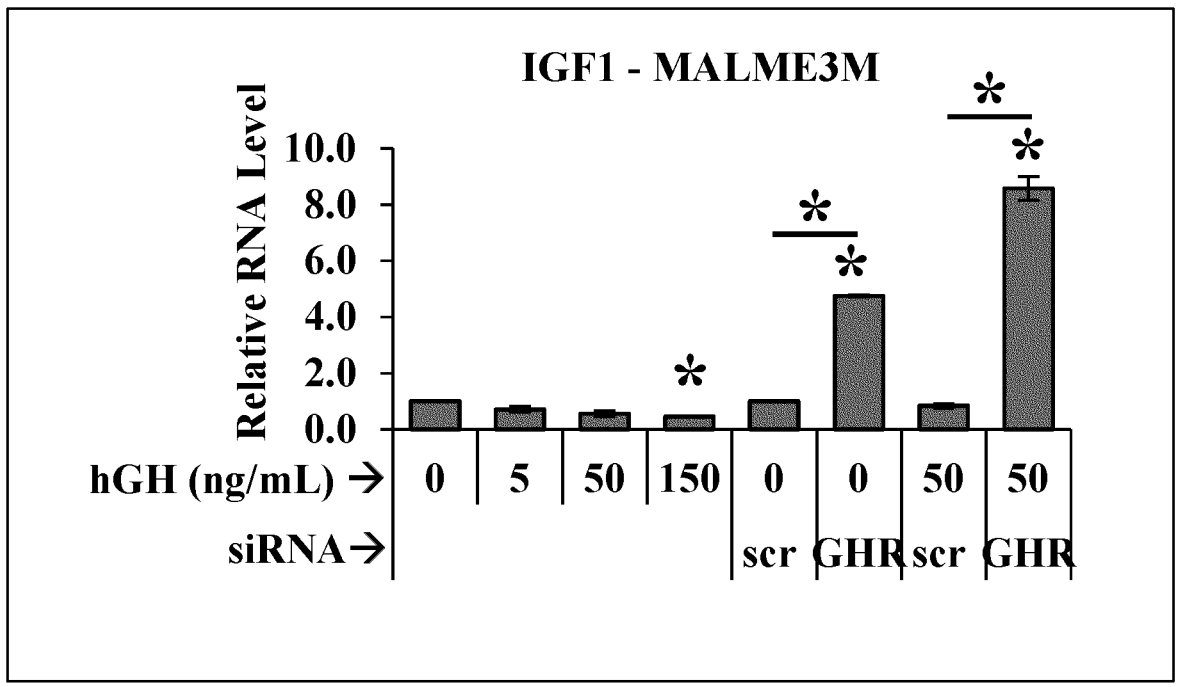
FIGS. 18A-18F include graphs showing RT-qPCR analysis of components of IGF axis in MALME-3M cells.
Figure 18B:
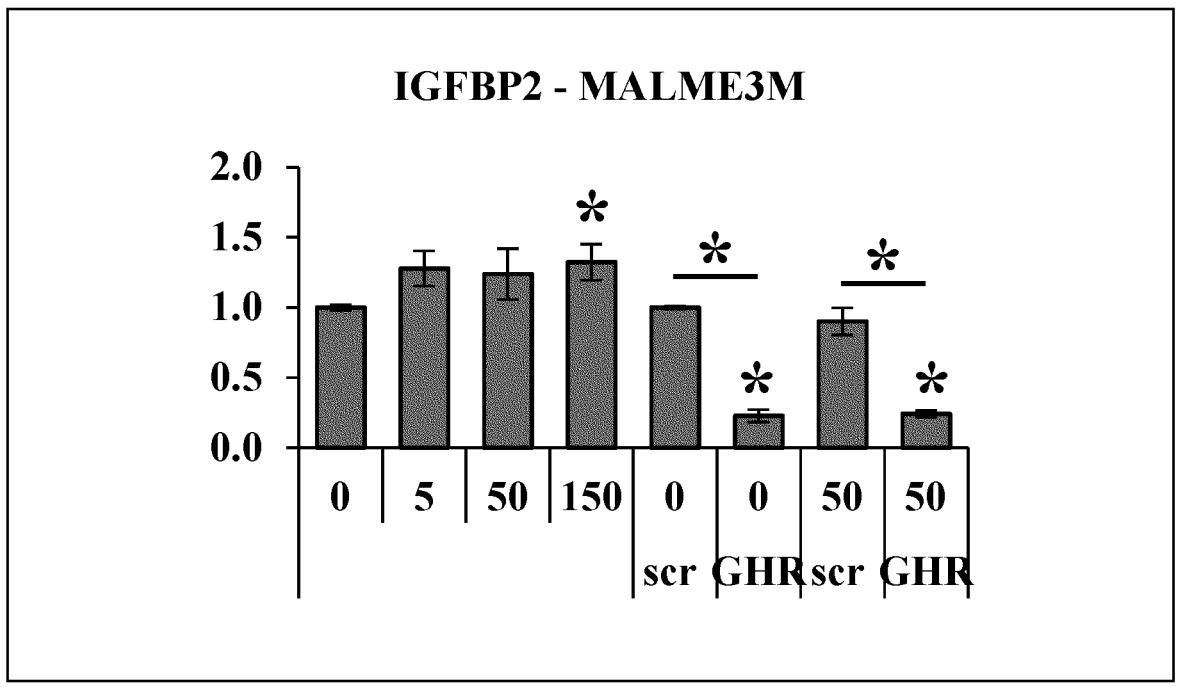
Figure 18C:
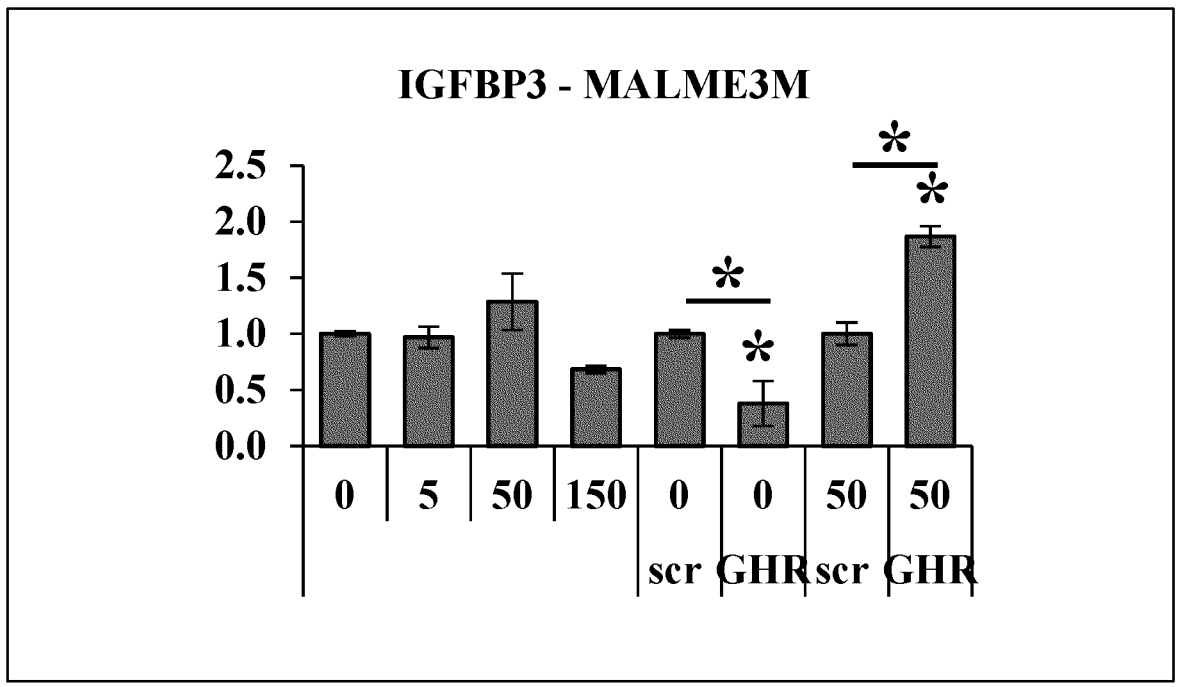
Figure 18D:
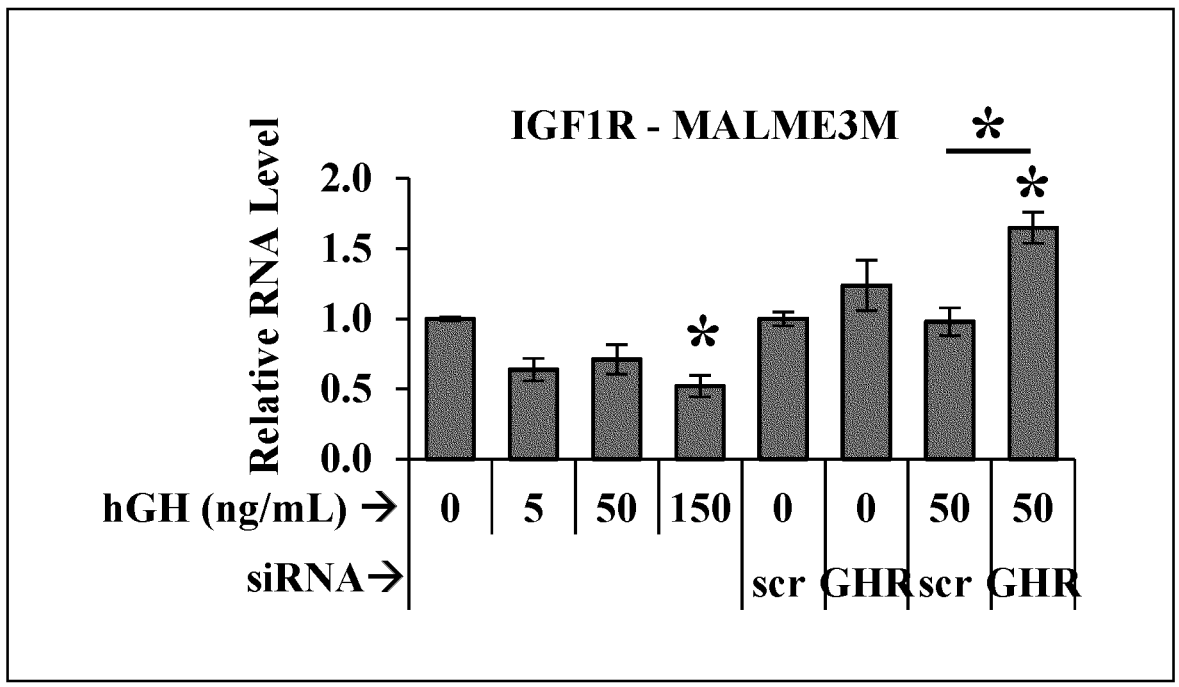
Figure 18E:
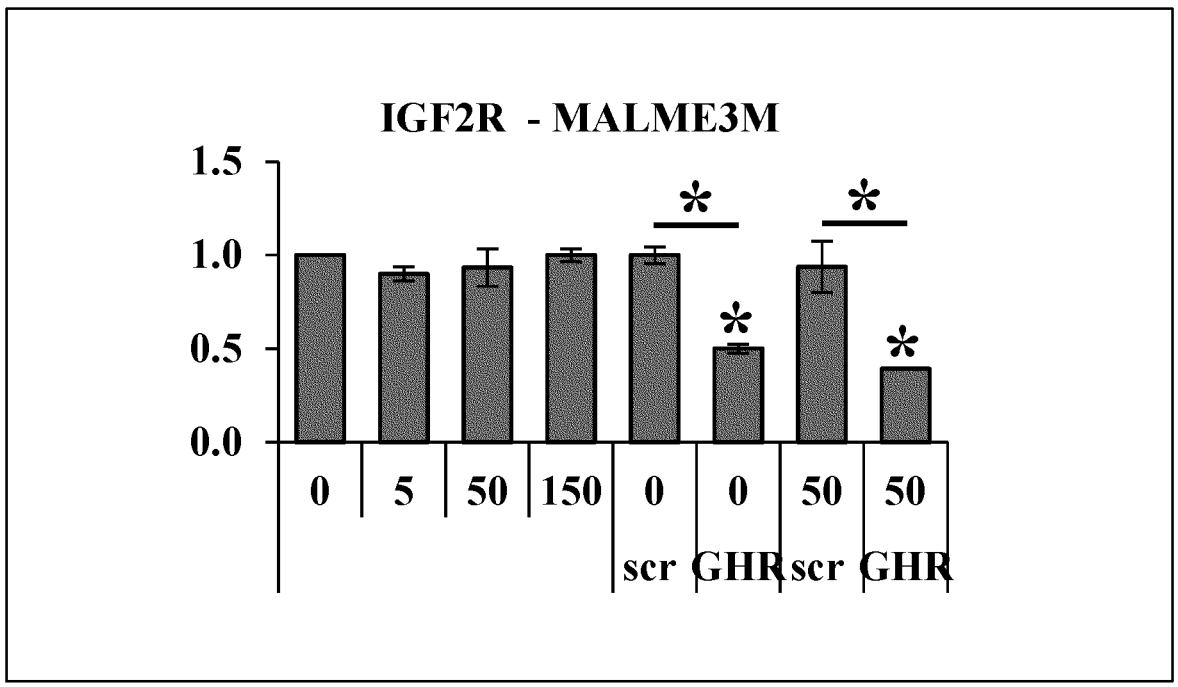
Figure 18F:
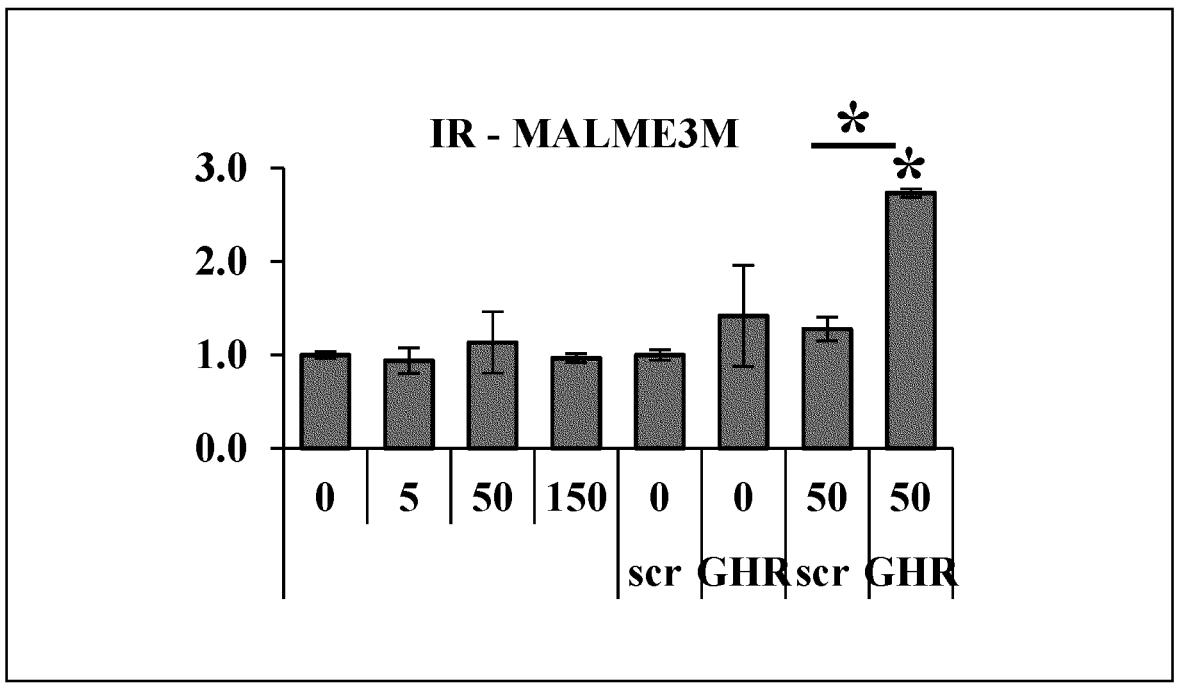
Figure 19A:
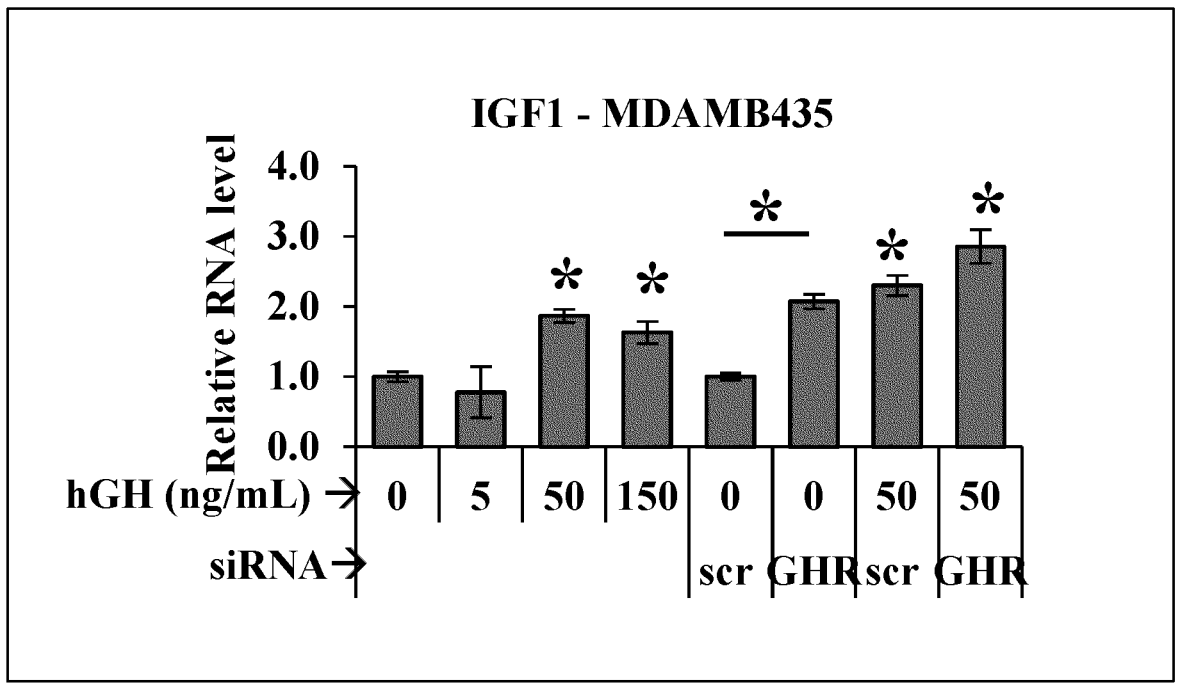
FIGS. 19A-19F include graphs showing RT-qPCR analysis of components of IGF axis in MDA-MB-435 cells.
Figure 19B:
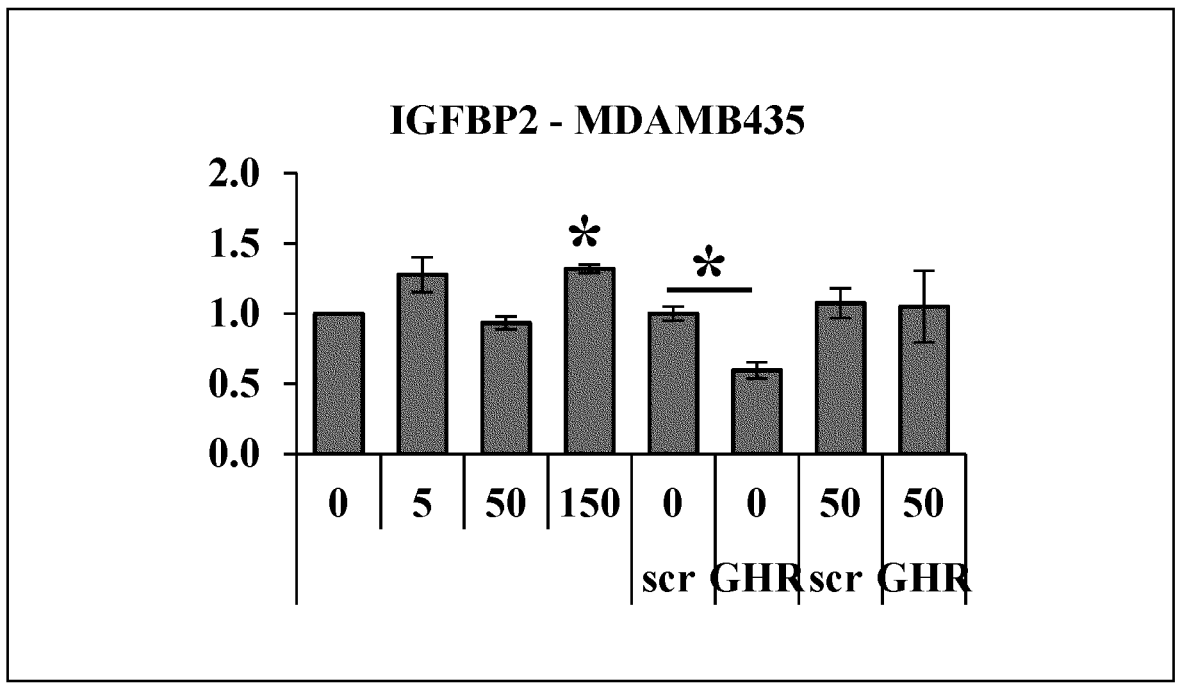
Figure 19C:
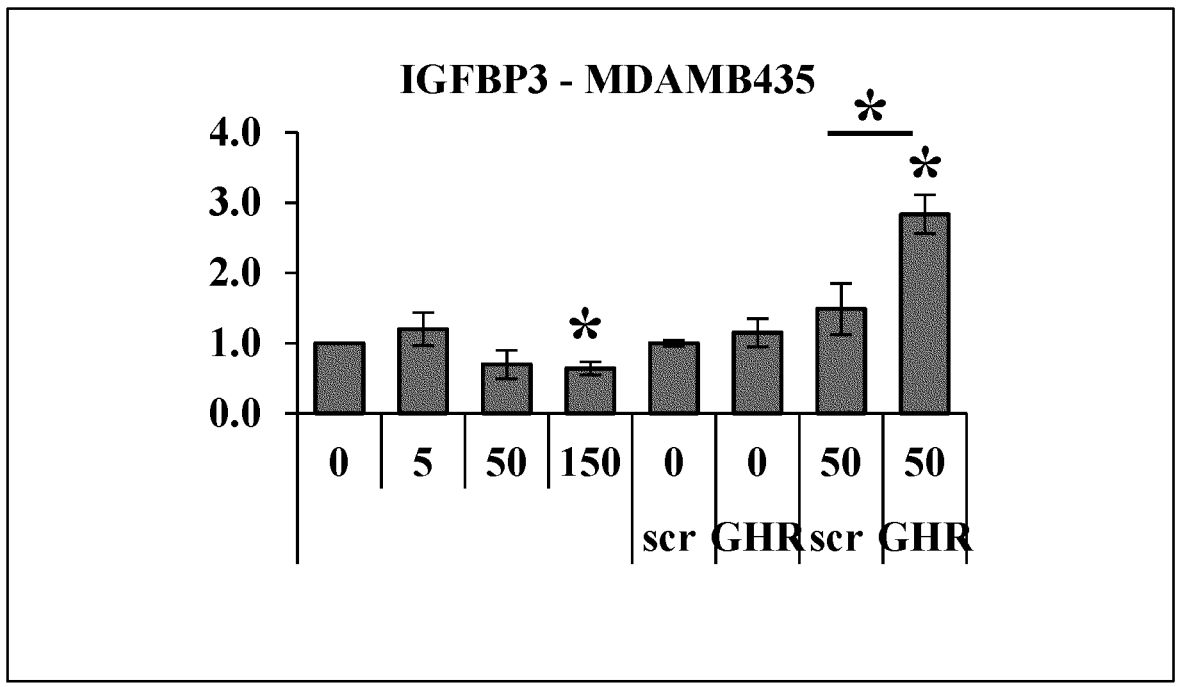
Figure 19D:
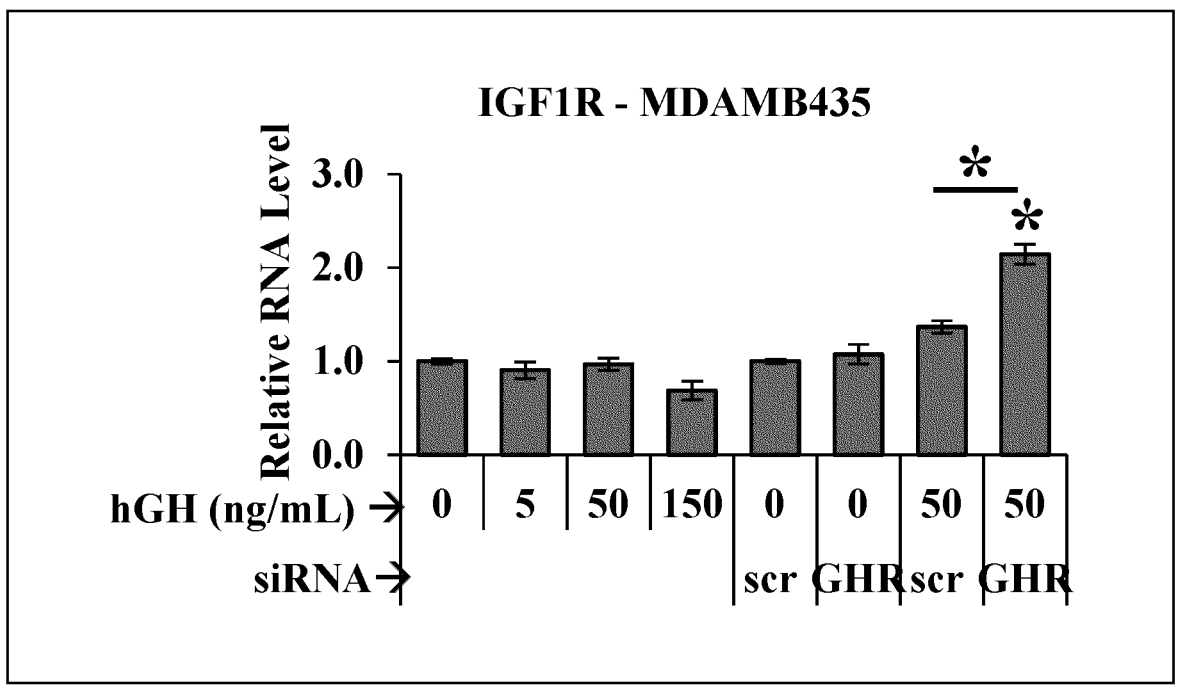
Figure 19E:
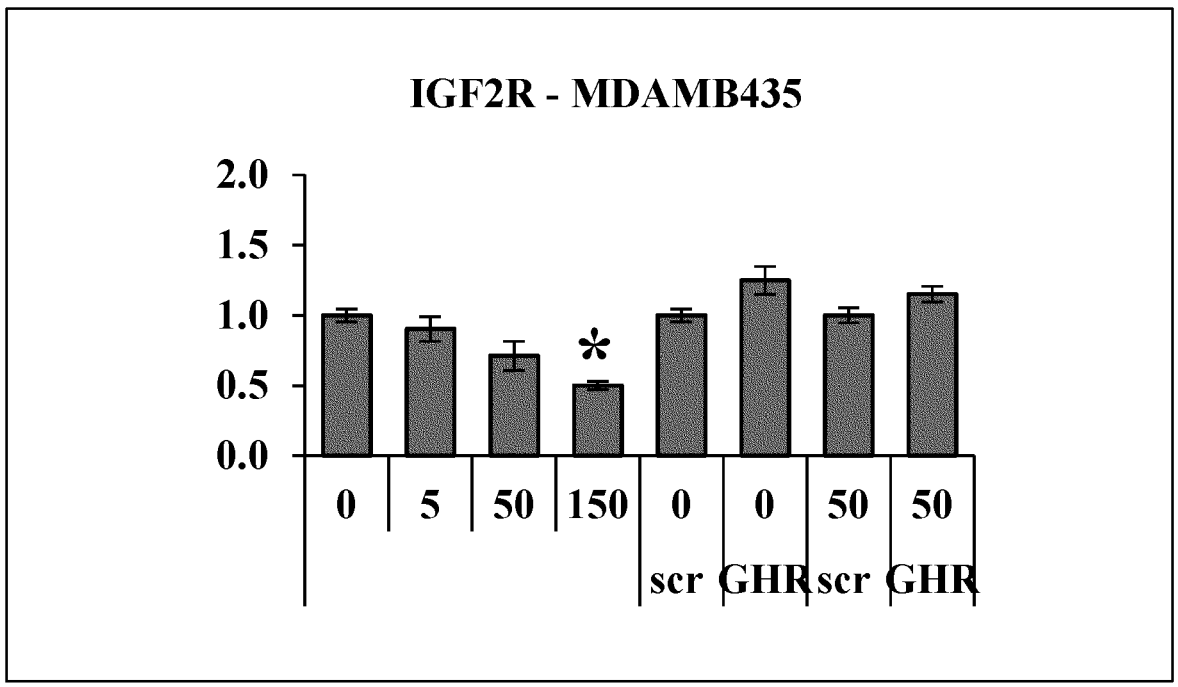
Figure 19F:
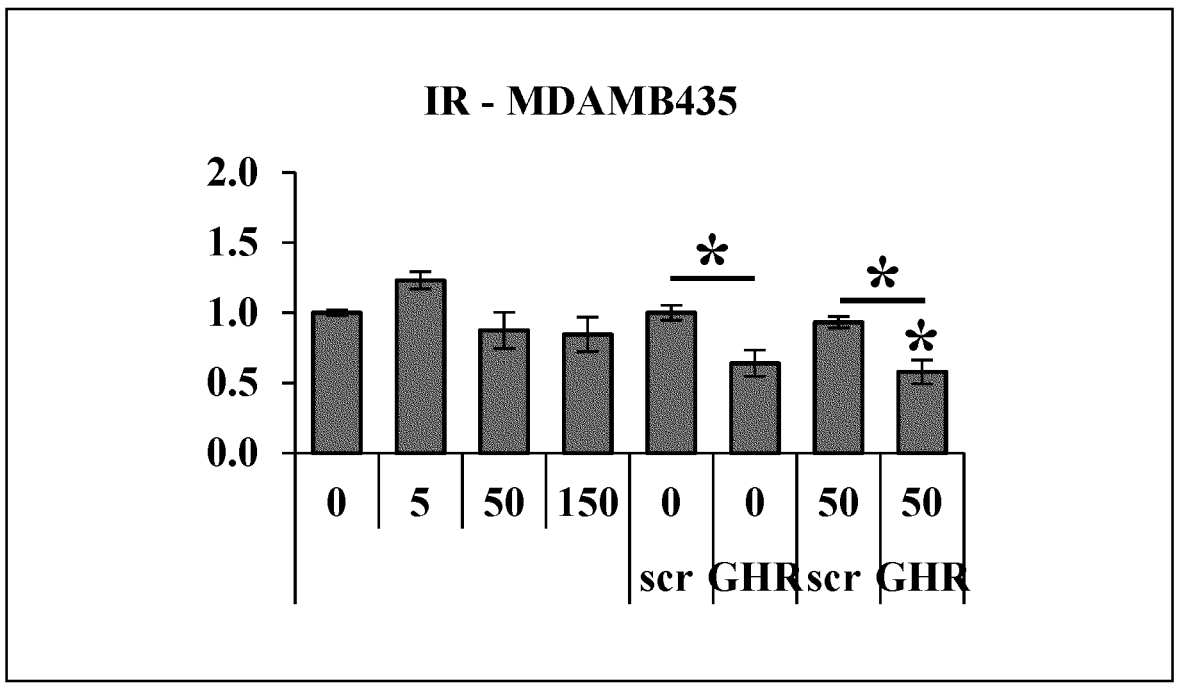
Figure 20A:
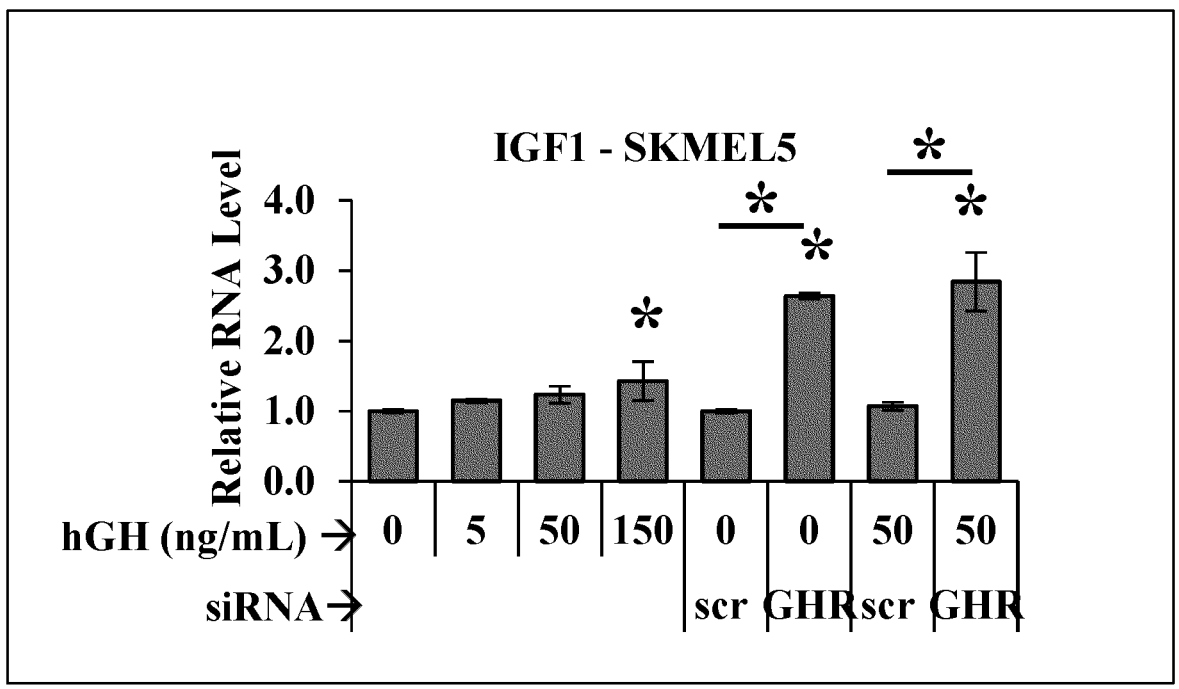
FIGS. 20A-20F include graphs showing RT-qPCR analysis of components of IGF axis in SK-MEL-5 cells.
Figure 20B:
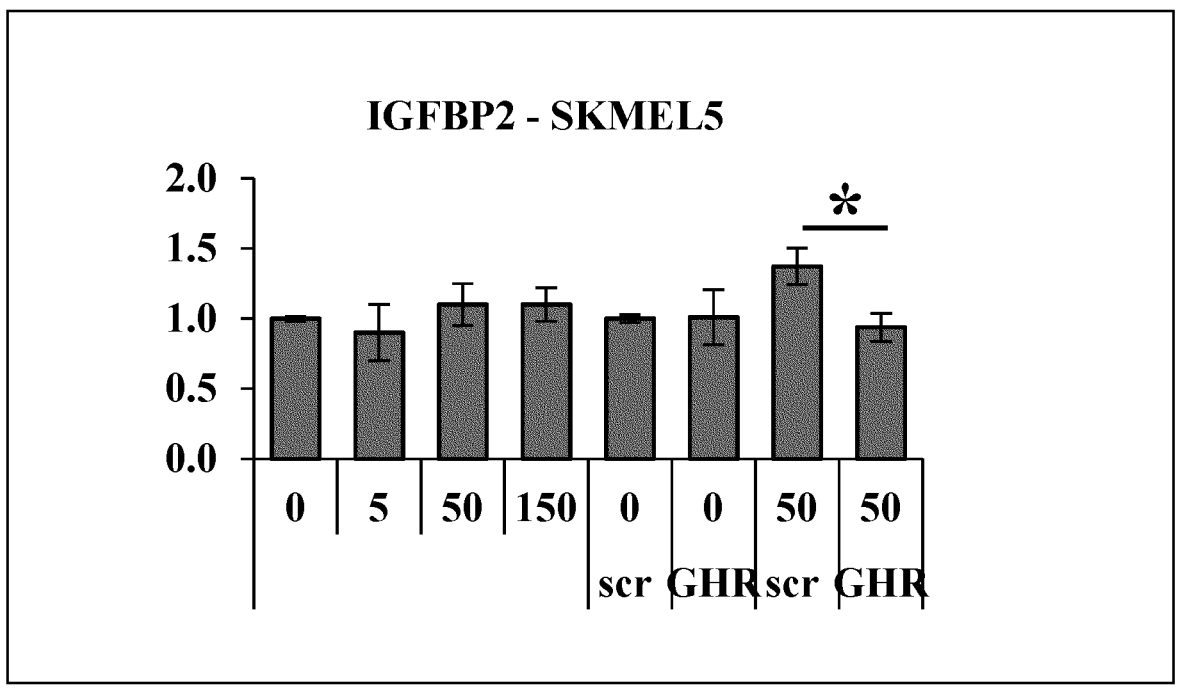
Figure 20C:
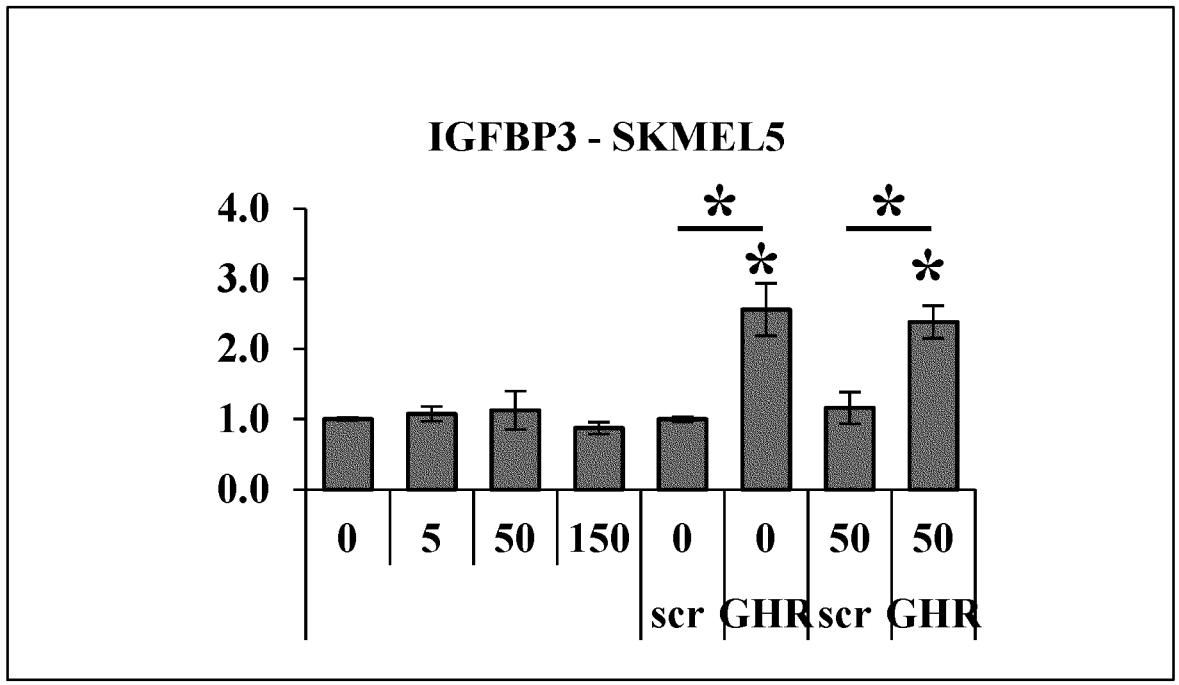
Figure 20D:
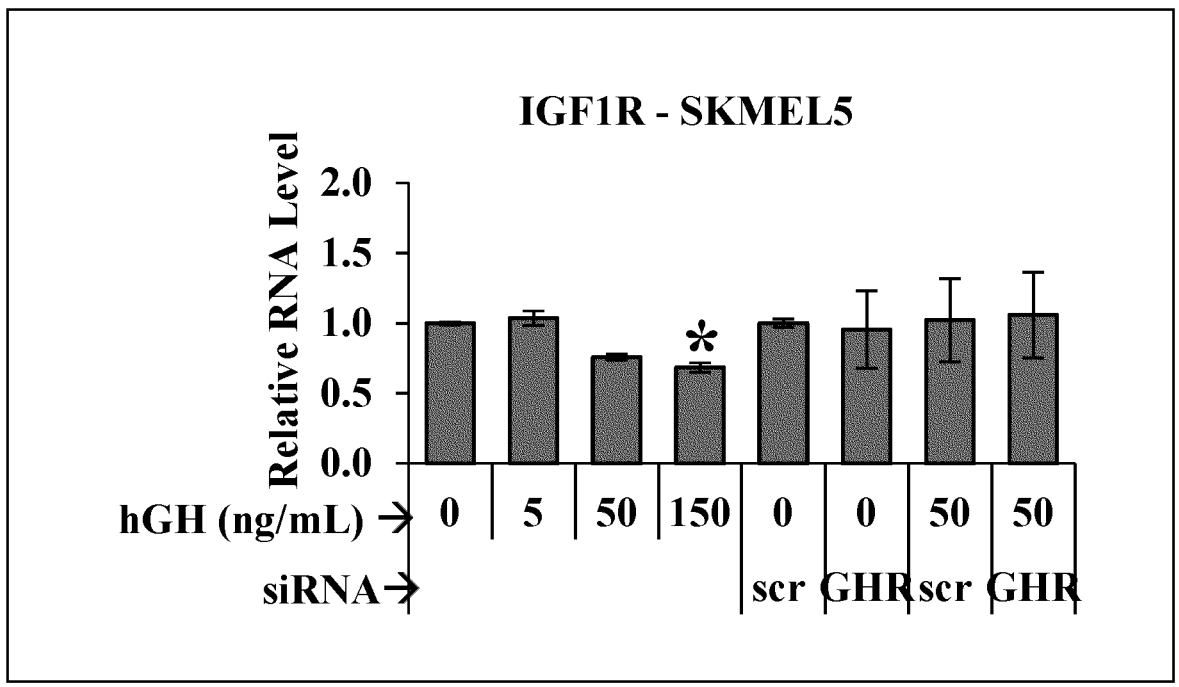
Figure 20E:
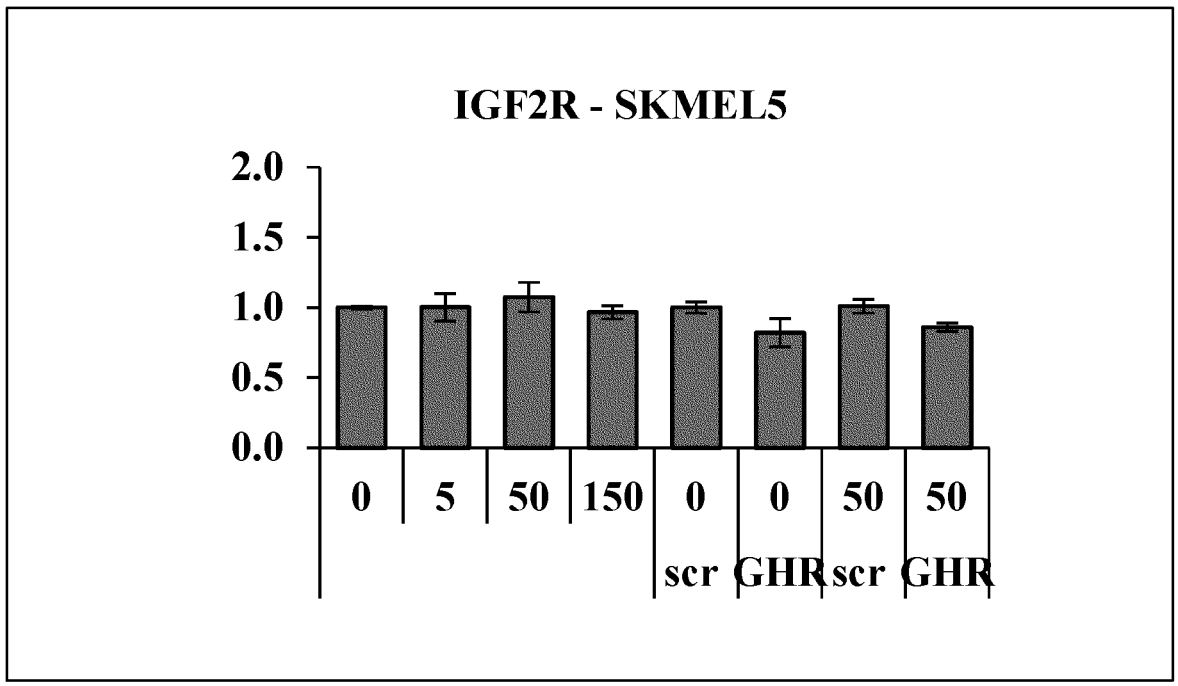
Figure 20F:
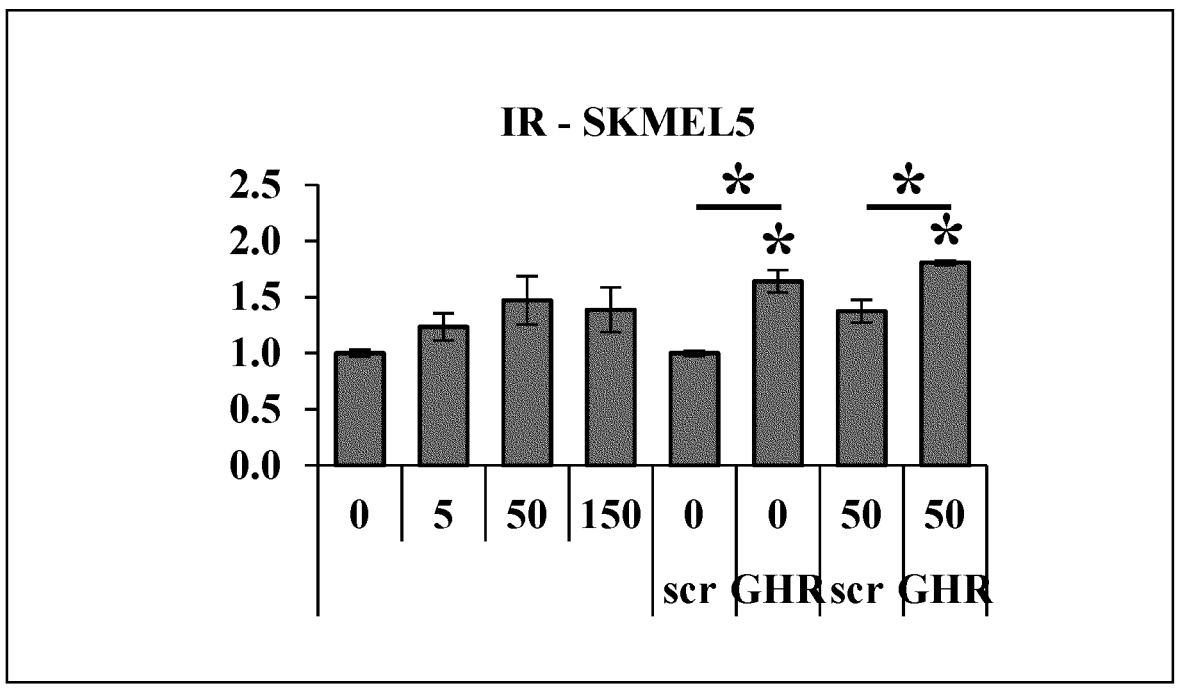
Figure 21A:
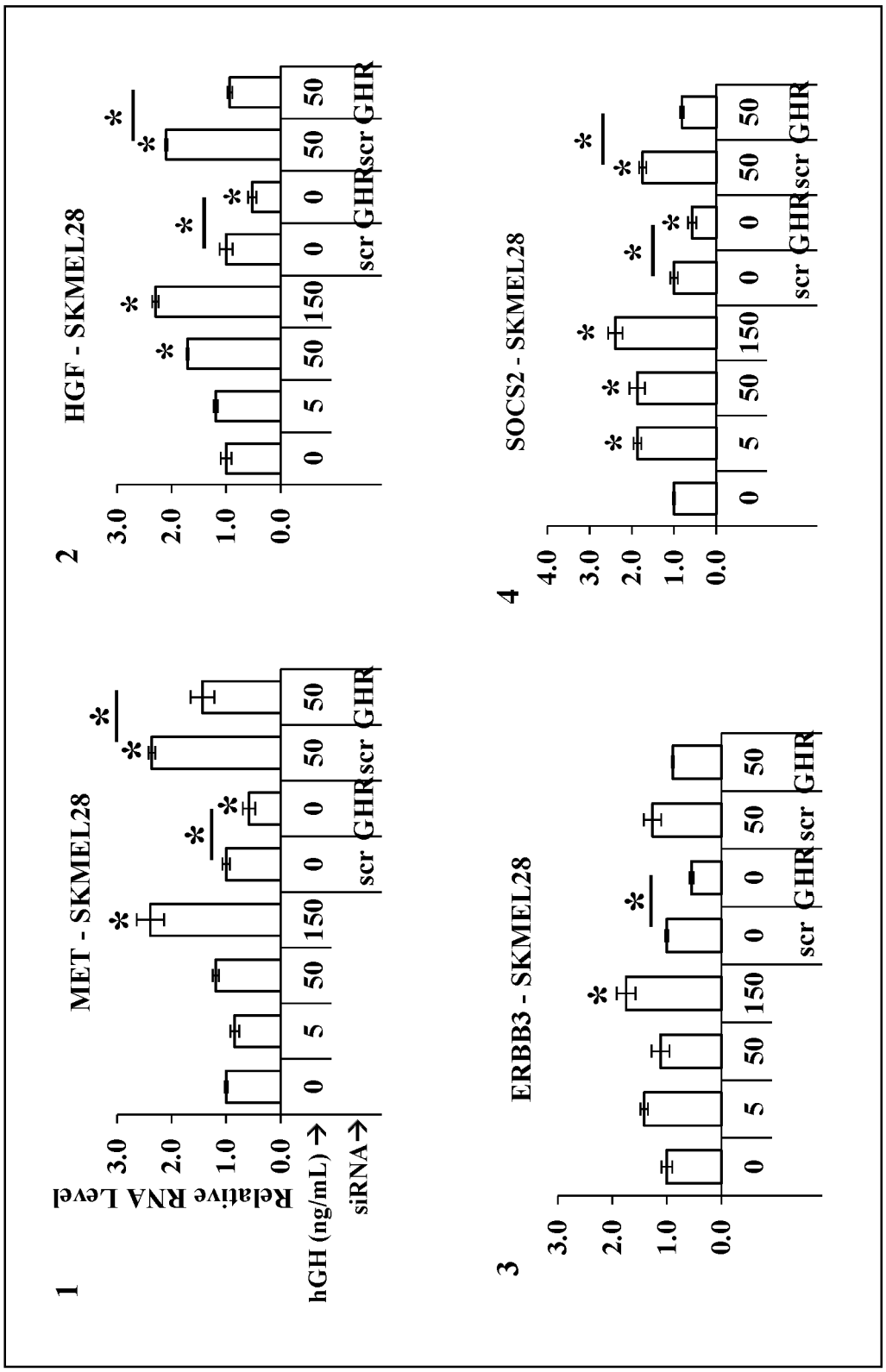
FIGS. 21A-21D include graphs showing that GH-excess increases and GHR-KD decreases HGF, MET, ERBB3 RNA-levels in human melanoma cells.
Figure 21B:
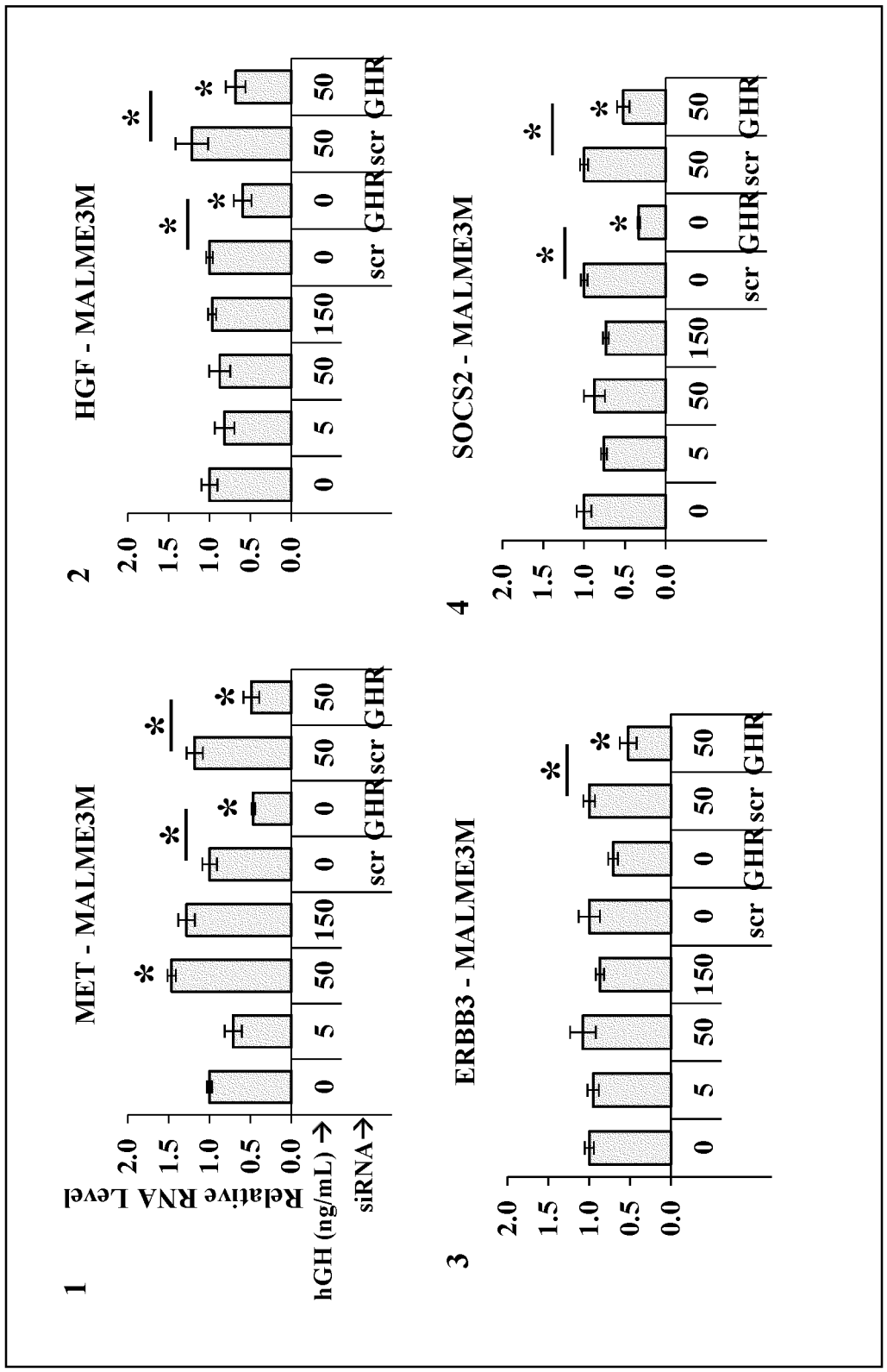
Figure 21C:
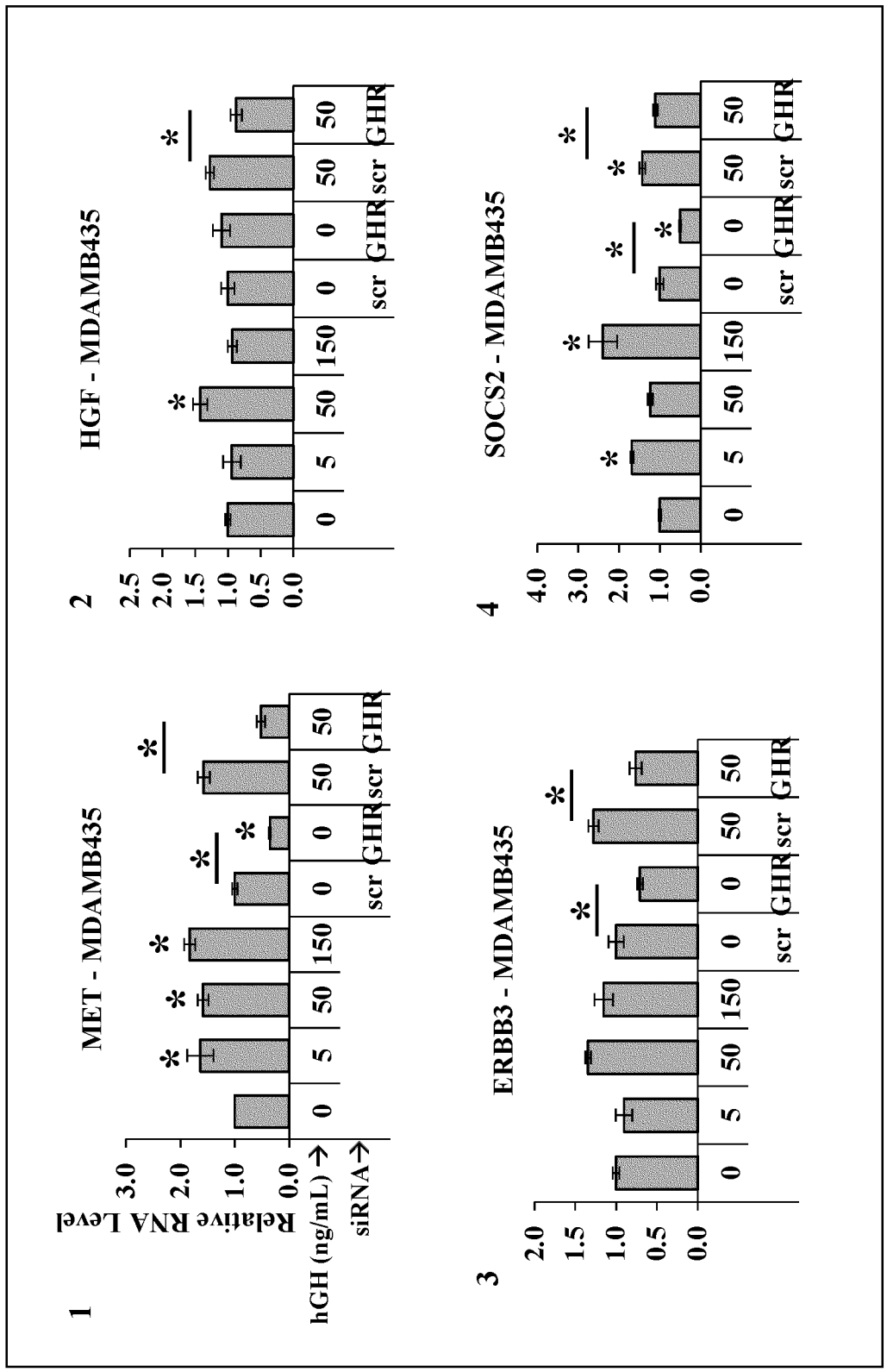
Figure 21D:
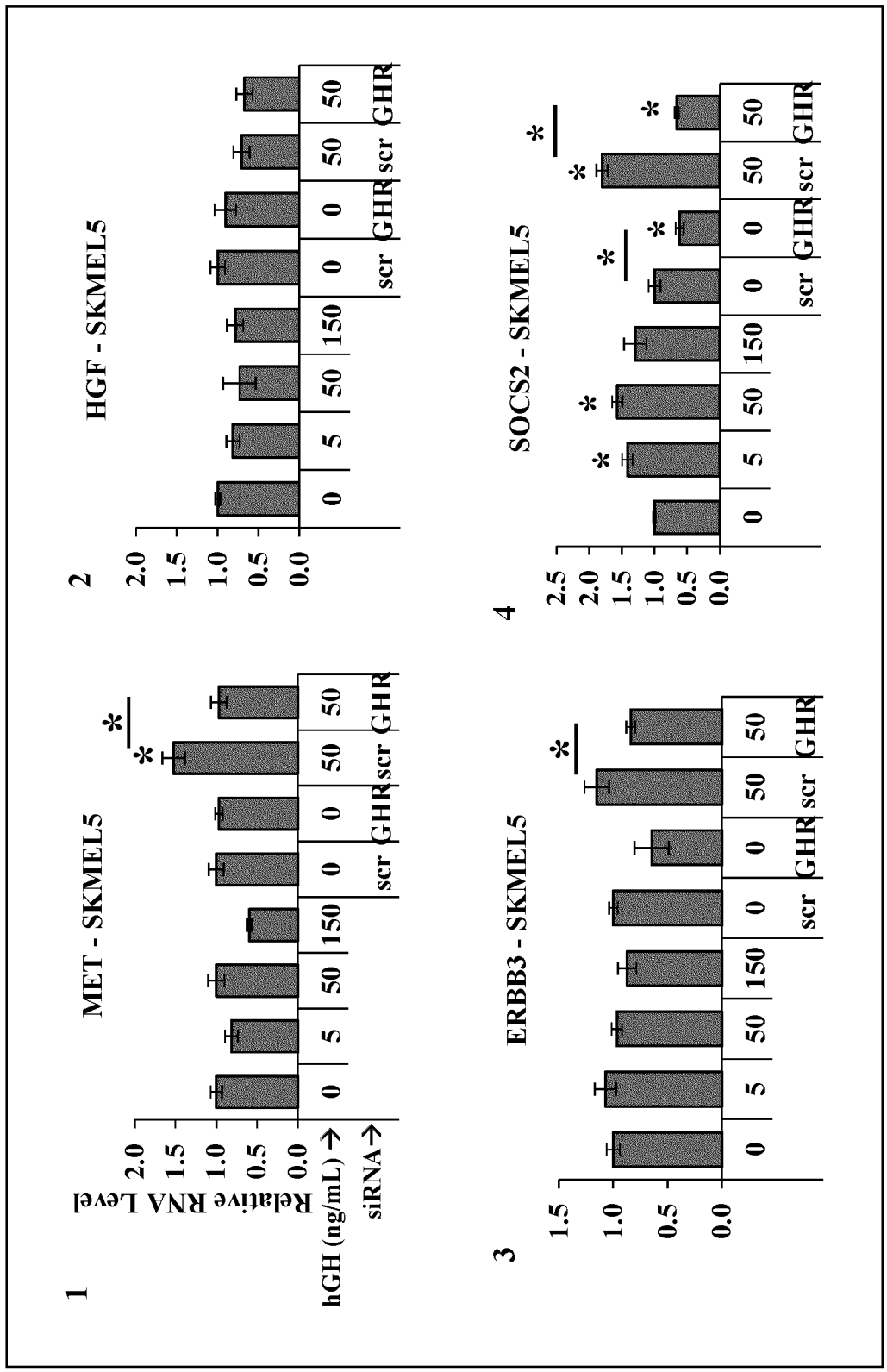

IGFBP3 may bind IGF1 as well as IGF2 and may have an anti-tumor effect in several types of cancers. Indeed, its concentration decreases markedly in circulation of cancer patients. However, IGFBP3 has also been shown to have an oncogenic potential with drastic increase in expression in cultured human melanoma cells. With the exception of SK-MEL-28 cells (FIG. 12B, panel 3), GHR-KD increased IGFBP3 levels by as much as 3-fold (FIGS. 18C, 19C, and 20C). Thus, RNA analysis of IGF axis in human melanoma, in response to variations in GH action, reflects an intricate pattern of regulation. The overall change in responsiveness to circulating or paracrine insulin and IGFs, induced by blockade of GH action is, therefore, of interest.

In the course of studying two spectra of GH action, i.e., GH excess and GHR-KD, on human melanoma cells, significant modulation was observed with response to changes in GH action in a set of three genes, i.e., the autocrine system of HGF and its cognate receptor MET and the Erb-B2 receptor tyrosine kinase 3 (ERBB3 or HER3), believed to be induced by GH in different tissues and to be drivers of aggressive disease progression and melanoma drug resistance. RT-qPCR analysis of 17 human melanoma samples identified the existence of a tumor driving HGF-MET axis. To that end, FIGS. 21A-21D show relative RNA levels of MET, HGF, and ERBB3 following RT-qPCR of RNA extracted from SK-MEL-28, MALME-3M, MDA-MB-435, and SK-MEL-5 cells following addition of 0, 5, 50 and 150 ng/mL hGH or following GHR-KD, in presence or absence of 0 and 50 ng/mL hGH. SOCS2 was used as an internal control for GH action. Results are discussed below and shown in FIGS. 21A-21D. In all cases, exogenous hGH treatment was for 24 hr. RNA levels were normalized against expression of β-actin and GAPDH as reference genes. [*, $p<0.05$, Wilcoxon sign rank test, n=4]

Low levels of HGF and consistently high levels of MET and ERBB3 RNA were observed in the four melanoma cell lines (FIG. 12A, panel 1), Both HGF and MET expression levels were significantly upregulated in a dose-dependent manner with added GH in SK-MEL-28 (FIG. 21A, panels 1 and 2) and MALME-3M (FIG. 21B, panels 1 and 2) cells to more than 2-fold at maximum GH concentrations. In comparison, this GH-excess mediated increase in expression was more than 50% reduced by GHR-KD in all the four cell lines (see panels 1 and 2 of FIGS. 21A-21D). ERBB3 showed a similar upregulation under GH stimulation while GHR-KD caused a drop in its levels (see panel 3 of FIGS. 21A-21D). SOCS2 was used as an internal control to monitor GHR-KD effects in all RT-qPCR experiments (see panel 4 of FIGS. 21A-21D). Therefore, mechanistic details of GH-GHR activity in melanoma are provided in this example and this activity is also validated as therapeutic targets to abrogate melanoma growth and proliferation.

Discussion of the Above Results

Human melanoma continues to be a serious cause of global mortality. The example provided above (Example 1) presents mechanistic details of GH-GHR action in human melanoma cells. Detectable levels of hGH RNA and protein, as well as its cognate GHR, were observed on human melanoma cells. Basal level phosphorylation of GH-regulated intracellular signaling networks, such as JAK2, STATs 1, 3, 5, ERK1/2, SRC, AKT, and mTOR, in absence of externally added GH, suggested the presence of an autocrine ligand-receptor loop existent and critical in these four melanoma cell lines, although there is no intention to be bound by any particular theory. This observation indicates that GH-GHR pair could be an important marker of metastatic melanoma.

Without intending to be bound by any particular theory, endocrine as well as paracrine/autocrine GH appears to directly activate certain intracellular signaling pathways and drive aggressive tumor phenotypes and EMT in human melanoma, as shown above. Further dissecting the autocrine vs. intracrine roles of this ligand-receptor pair using human melanoma as a model might be of substantial interest. Skin is an extra-pituitary site of GH as well as PRL expression and autocrine effect. PRL and expression of PRLR on tumor tissues are implicated in breast and prostate cancers for a considerable time via its mitogenic and angiogenic properties. Low but consistent RNA levels of both PRL and PRLR were observed in the example above, as was a consistent marked rise in PRLR levels following GHR-KD in SK-MEL-28 MALME-3M, and MDA-MB-435 cells. The presence of excess GH potentiated the effect. PRL-PRLR signaling engages intracellular mediators, such as JAK2, PI3K, ERK1/2, and STAT5, which overlaps with GHR signaling pathway.

The siRNA mediated GHR-KD could lead to a compensatory non-canonical binding of GH-PRLR and subsequent downstream signaling. Basal phosphorylation of the ERK1/2 and AKT/mTOR components was observed in all four melanoma cell lines. Without intending to be bound by any theory, a constitutively active RAS, harboring the V600E mutation in these cell lines, is believed to be the cause of this observation. However, on GHR-KD, a decrease in ERK1/2, AKT, and mTOR was observed in all cases, often below the basal levels, irrespective of presence of hGH. Without intending to be bound by any particular theory, this significant downregulation may indicate that suppression of an active autocrine GH-GHR interaction contributes significantly to down regulation of the basal phosphorylation states of these signaling pathways. The residual phosphorylation observed following GHR-KD, although significantly low, could be induced by GH binding and activation of PRLR as well as other shared signaling pathways. Importantly, exogenous GH and GHR-KD had significant enhancing and suppressing effects respectively, on relevant intracellular signaling pathways. Similarly, the effect of increased PRLR from endocrine or paracrine PRL is of continued interest. However, observed RNA levels of PRLR in these melanoma cells were more than 100-fold lower than the observed GHR RNA levels, and no significant variation was observed due to altered autocrine PRL-PRLR level on GHR-KD-induced effects in either the phosphorylation levels of intracellular signaling intermediates or in the tumoral phenotypes of migration, invasion, and proliferation.

The role of IGF axis in human melanoma prompted an analysis of RNA levels of insulin-IGF axis in human melanoma cells during GH-excess and GHR-KD. No endogenous insulin or IGF2 RNA or protein levels were detected in any of the four melanoma cells tested, but RT-qPCR studies revealed the presence of IGF1 RNA. IGF1 & IGF2 and their cognate receptors are believed to be important regulators of multiple human cancers, including melanoma. High levels of RNA of the corresponding cognate receptors, i.e., IR, IGF1R, and IGF2R, were observed in all four melanoma cells studied in the above example. Significant suppression of IGF2R on all melanoma cells was observed following GHR-KD, but a significant rise in IGF1R and IR RNA levels was observed following GHR-KD, especially when treated with excess GH.

The melanoma cells also appear to be in a state of heightened insulin/IGF sensitivity via abundant expression of IR, IGF1R, and IGF2R, as seen in all four melanoma cells in the above example. Increased levels of IGFBP3 were observed following GHR-KD for the four cell lines, along with a concomitant increase in IGF1 levels. Without intending to be bound by any particular theory, it is speculated that this could possibly be an IGF1 mediated increase in IGFBP3 levels. However, the regulatory role of IGF axis in human melanoma appears to be limited at the early stage of disease progression and not in the case of metastatic malignant melanoma. Additionally, as with PRL and PRLR, the basal RNA levels of IGF1 were 3-fold lower than GH levels, and the GH induced changes in members of the IGF family apparently had no observable variation on intracellular signaling or tumor phenotypes, as described above.

Overall, in most cancer treatments, achieving a therapeutic reduction in endocrine IGF1 levels appears to be favored in halting tumor progression. Moreover, starvation or diet restriction induces a reduction in circulating IGF1 and may preferentially protect normal cells while sensitizing melanoma cells to chemotherapy. Thus, the use of GHR-antagonists or any therapeutic modality which decreases GH induced intracellular signaling, including but not limited to siRNAs, antibodies to GH or the GHR, and inhibitors of JAK, JAK2, STATs, STAT5, SRC, AKT ERK1/2, and mTOR, in melanoma therapy.

Targeting GHR elevates insulin and IGF1 receptors, meaning that GHR antagonism, including with concurrent administration of IGF1R inhibitors, provides a pathway towards melanoma therapy. Reduction in tumor cell proliferation can either be caused by a direct decrease in the levels of GHR, by downstream signaling, or by reducing circulating IGF1 levels by decreasing hepatic and other cellular IGF1 output. Therefore, the above example predicts a mechanistic rationale of combining GHR antagonism with IGF1R inhibition as a logical combination treatment in malignant human melanoma.

Also, the example above shows GH regulation of the autocrine hepatocyte growth factor (HGF) and its cognate receptor MET (or c-MET) on the four melanoma cell lines. Although intrinsic RNA levels of HGF were low, there was significant increase when treated with added hGH in SK-MEL-28 and MDA-MB-435 cells, as well as a significant downregulation following GHR-KD. Moreover, high RNA levels of the HGF-receptor MET were observed on all four melanoma cells, which high RNA levels exhibited a dose dependent rise with added hGH. On the other hand, GHR-KD significantly suppressed the same, even in presence of relatively high levels of hGH. This set of results suggest a possible transcriptional control of MET and HGF expression by hGH.

Additionally, the ERBB family members, EGFR, ERBB1, ERBB2, and ERBB3 may drive several oncogenic processes in melanoma. RNA levels of ERBB3 were upregulated in response to excess GH in SK-MEL-28 and MDA-MB-435, and a consistent suppression occurred following GHR-KD. Both MET and EGFR may strongly activate the SRC signaling pathway. GH may activate EGFR in liver regeneration. Thus, the results provided in Example 1 indicate a regulatory role of GH on expression of HGF, MET, and ERBB3 in human melanoma cells. Identifying the underlying mechanisms of transcriptional regulation and downstream intracellular targets can add value to the extent of dependence of malignant metastatic melanoma on the GH-GHR axis.

STAT3 activation in melanoma may drive multiple transformations, including EMT, angiogenesis, and inhibition of apoptosis by increasing expressions of intrinsic oncogenic factors, such as microphthalmia associated transcription factor (MITF). STAT3 activation may also cooperatively induce downstream factors, such as c-fos, Robust GH-mediated STAT3 regulation is of further interest, including in melanoma, and commends itself to new studies investigating role of GH in cellular reprogramming and cancer initiating cells. STAT3 is also a converging point in signaling networks for multiple different upstream regulators, e.g. SRC and JAK2, as well as ERBB family members, such as EGF4 and ERBB3. The results obtained in the above example show the presence of constitutive activation of SRC and STAT1, 3, and 5 proteins in melanomal tumors. GH-induced activation of STAT proteins was found to be active in melanoma. A significant decrease of STAT activation was observed below basal levels, even in presence of added GH, with GHR-KD, suggesting (i) attenuation of the autocrine GH-mediated activation, as well as (ii) sensitivity and dependence of the melanoma cells on GH-GHR interaction and activation of either JAK2 or SRC or both. The presence of basal phosphorylation of both JAK2 and SRC kinases, as well as their respective changes with GHR-KD and/or added exogenous GH, as observed in all cell lines, may indicate that both signaling mediators may be highly responsive to GH in melanoma. Upregulation of the basal STAT1 phosphorylation levels suggests GH action as an explanation for observations in recurrent melanoma phenotypes. The STAT5 dependence on GH-GHR induced activation, as noted above, also suggests the role of GH-GHR action in activating STAT5, which is believed to be an oncogenic driver in melanoma and believed to protect the cell against interferon-based immunotherapies. In melanoma cells, STAT5 acts to mediate resistance to apoptosis and may be activated by both JAK2 and SRC kinases. Thus, without intending to be bound by any particular theory, the above results indicating significant basal activation of JAK2, SRC, STATs 1, 3, and 5, in melanoma suggests that these pathways might be under the control of an autocrine GH-GHR system that was affected by GHR-KD. Therefore, along with GHR-KD, these can be evaluated from a new perspective as therapeutic targets in future studies.

In general, the above Example 1 suggests that melanoma cells orchestrate increased proliferation, invasion, and migration directed by GH, and the interaction of GH with the GHR regulates intracellular signaling pathways and also upregulates oncogenic pathways, such as HGF-MET and ERBB3. In summary, this example presents a mechanistic model of GH regulation in human malignant melanoma cells. Without intending to bound by any particular theory, endocrine or paracrine or autocrine GH binds to abundantly expressed. GHR on human melanoma and activates JAK2 as well as SRC kinases. This activation leads to phosphorylation of STAT1 STAT3, STAT5, ERK1/2, AKT, and mTOR and further promotes invasion, migration, and proliferation for tumor progression. Together these results identify novel regulatory roles of GH in one of the most aggressive and disease-resistant fomrs of cancer. Using GHR-KD, the results demonstrate that targeting GHR can be a point of intervention in melanoma therapeutics and may be useful even in the context of continual occurrence of chemotherapy resistance. In the following Example 2, this unique relationship between GHR levels and drug resistance mechanisms in human melanoma is investigated.

Example 2

In this Example 2, the inventors demonstrated that (1) GHR knock-down significantly suppresses expression of ABC transporter pumps in human melanoma cells; (2) GHR knock-down significantly suppresses RNA levels of melanogenesis regulators in human melanoma cells; and (3) GHR knock-down significantly modulates markers of EMT in human melanoma cells. The results of this Example 2 provide data not only in the context of the effect of GHR-KD on expression of ABC transporters mediating multi-drug resistance in human melanoma, but also identify cell-specific and multiple drug-specific variations of seven different ABC transporters in melanoma. The results reveal a specific expression profile of several ABC transporter pumps in melanoma cells following exposure to specific anti-tumor compounds in the context of decreased GHR, and establish a novel role of regulation of GH in multi-drug resistance in melanoma.

Materials and Methods

Cell Culture

Human melanoma cells SK-MEL-5 (#HTB-70), SK-MEL-28 (#HTB-72), MALME-3M (#HTB-64), and MDA-MB-435S (#HTB-129), as well as normal melanocyte ST-MEL (ATCC # 30-2001), were purchased from American Type Culture Collection (ATCC; Manassas, Va.) and grown in the recommended media with 5% fetal bovine serum (FBS; ATCC # 30-2020) and 1× antibiotic-antimycotic (Thermo Fisher Scientific #15240) at 37° C. in 5% $CO_2$ in a humidified incubator. Recombinant human GH (Antibodies Online # ABIN2017921) was added to the media at 50 ng/ml.

Drug Treatments

For treatment of melanoma cells, the following five anti-tumor compounds were obtained from the sources mentioned: cisplatin (Calbiochem #232120, Darmstadt, Germany), doxorubicin (Sigma Aldrich #D-1515, St. Louis, Mo.), oridonin (Sigma-Aldrich #O-9639, St. Louis, Mo.), Paclitaxel (Sigma-Aldrich #C-7191), and vemurafenib/PLX4032 (ApexBio #A-3004, Houston, Tex.). $EC_{50}$ values were determined for each drug in every cell line, providing the following $EC_{50}$ ranges for the four melanoma cell lines: cisplatin (3-15 µM), doxorubicin (25-100 nM), oridonin (2-8 µM), paclitaxel (2-8 nM), and vemurafenib (2-20 nM). In the subsequent experiments, the following drug concentrations were used unless specified otherwise: cisplatin (0.5 µM), doxorubicin (10 nM), oridonin (0.5 µM), paclitaxel (1 nM), vemurafenib (2 nM). Treatments were performed for 24 hours starting 48 hours post-transfection with siRNA.

Transfection

Transfection was performed using siLentFect lipid reagent (Biorad #170-3360, Hercules, Calif.) following the manufacturer's protocol. Pre-designed siRNA duplex against human GHR (Origene #SR301794, Rockville, Md.) at 20 nM was used (siRNA-B: AGCUAGAAUUGAGU-GUUUAAAGUTC) to decrease GHR transcripts by >80% in all four melanoma cells, while a universal scrambled siRNA-duplex (Origene #SR30004) was used as a control. Cells were seeded at 25,000-30,000 cells/cm², incubated overnight for complete attachment to substratum, and a pre-incubated mix of 20 nM siRNA duplex (scramble or GHR specific) and siLentFect reagent at 1:1 molar ratio were then added to the cells and incubated at 37° C. in 5% $CO_2$. Media was changed after 24 hours. RNA levels were analyzed 48 hours post transfection while protein levels were analyzed at 60 hours post-transfection. For drug treatment, drugs at the specified concentrations noted above were added to the cells 48 hours post-transfection and treated for 24 hours prior to quantitation of RNA expressions.

RNA Extraction, RT-qPCR, and Protein Extraction

RNA extraction, RT-qPCR, and protein extraction were performed as described in Example 1, above.

Western Blot (WB)

Western-blot was performed following standard laboratory protocol with few modifications. Briefly, intracellular proteins were separated by SDS-PAGE and transferred onto a PVDF membrane, then blocked with 5% bovine serum albumin (BSA) in 1× TBS-T (Tris buffered saline, pH 7.2 with 0.1% Triton-X100) for 12-16 hours at 4° C. Membranes were then incubated with primary antibody (at specific dilutions mentioned below) for 12-16 hours at 4° C., followed by wash and incubation with corresponding secondary antibodies (at specific dilutions mentioned below) for 2 hours at 25° C. Membranes were then washed and treated with WestFemto Chemilumiscence detection reagents (Thermo Fisher Scientific), and the chemiluminiscent signal was captured using a GelDoc (Biorad) fluorescence reader. Densitometry analysis of the blots was performed using ImageJ software.

Primary antibodies were used to detect the following human proteins: GHR (Mouse, 1:300, scar #137185; Goat, 1:100, R&D Systems #AF1210; Rabbit, 1:200, Abcam #ab134078), Actin (Goat, 1:3000, SCBT #sc1616), GAPDH (Goat, 1:3000, SCBT #sc20357), Vimentin (Rabbit, 1:3000, CST #5741), E-cadherin (Rabbit, 1:1000, CST #3195), N-cadherin (Rabbit, 1:500, CST #13116), Vimentin (Rabbit, 1:3000, CST #5741), ABCG1 (Rabbit, 1:100, Abiocode #R0254), ABCB8 (Rabbit, 1:100, SAB #31025), and ABCB1/MDR1 (Mouse, 1:100, SCBT #sc55510). Secondary antibodies used: anti-rabbit HRP-linked IgG (Donkey, 1:2000, CST #7074P2), anti-goat HRP-linked IgG (Donkey, 1:1000, SCBT #sc2020), anti-rabbit HRP-linked IgG (Donkey, 1:2000, GE #NA934), and anti-mouse HRP-linked IgG (Rat, 1:1000, Antibodies Online #ABIN1589975).

Immunofluorescence (IF)

Cells were seeded at 10,000 cells/cm² in 8-well chamber slides, and transfection was performed as described above. The cells were treated for 24 hours with 10 nM doxorubicin or 1 nM paclitaxel, 48 hours post-transfection. Subsequently cells were fixed with 100% methanol, permeabilized with 0.2% Triton-X100 in 1× PBS for 15 min. at 25° C., and blocked with 1% BSA for 4 hours at 25° C. Incubation time was 12 hours at 4° C. for the primary antibody and 2 hours at 25° C. for the secondary antibody. Finally, the slides were washed four times with 1× PBS, and the sample was mounted with Fluoroshield mounting medium containing DAPI (Abcam #ab104139, Cambridge, UK), covered with a 60 mm coverslip, the edges of which were sealed with nail-polish. The mounted sample was then stored at 4° C. for microscopy. Microscopic imaging was performed using a Nikon Eclipse E600 compound fluorescent microscope fitted with a Nikon DS-Fi1CC camera (Nikon, Tokyo, Japan) and NIS-Elements BR3.2 imaging software. The antibodies used were Rabbit anti-human-Ki67 monoclonal antibody with AlexaFluor488 tag (Abcam #ab154201, 1:300 dilutions); and Goat anti-rabbit secondary antibody with AlexaFluor488 tag (Life Technologies #R37116, 1:500 dilution).

Cell Proliferation Assay

The cell proliferation assay was performed as described in Example 1, above.

Drug Retention Assay

The presence of multiple drug resistance pumps along the cellular membrane is key to the resistance against chemotherapy in certain cells such as melanoma. ATP-binding cassette (ABC) transporter pumps in the MDR and MRP family are involved in exclusion of xenobiotics from inside the cells to outside. This reduces the retention time of drugs inside a cell and confers decreased sensitivity to the drug-effects. In this example, the Vybrant multidrug resistance assay kit (Molecular Probes #V13180, Eugene, Oreg.) was used for the drug retention assay. The assay uses the non-fluorescent calcein acetoxymethylester (calcein-AM) as a drug-mimic and a substrate for the melanoma cell efflux pumps. Calcein-AM is highly lipid soluble and permeates the cell membrane where it is converted to a fluorescent calcein by the intracellular esterases. In the absence of (or even decreased) activity of the efflux pumps, the intensely fluorescent calcein is retained and can be measured as an indication of drug retention inside the cell. The assay was performed as per the manufacturer's protocol with some modifications.

Briefly, the siRNA treated cells were trypsinized 48 hours after transfection, counted, and seeded at 50,000 cells/well in a black, clear bottom Costar 96-well plate (Corning #3603, Corning, N.Y.). Then, calcein-AM was added at a final concentration of 2 µM, and the cells were incubated at 37° C. for 2 hours. After thorough washing, the fluorescence was measured at 494 (exc)/517 nm (emi) in a spectramax M2 fluorescence plate reader (Molecular Devices, Sunnyvale, Calif.) with the aid of SoftMax Pro v6.2.1 software. Experiments were performed in quadruplicate.

Statistical Analyses

Statistical analyses were performed as described in Example 1, above.

Results

GHR knock-down significantly suppresses expression of ABC transporter pumps in human melanoma cells: Various levels of RNA for seven ABC transporter pumps were found in the four melanoma cell lines used in this study. The RNA levels of ABCB8, ABCC1 and ABCC2 were relatively high while ABCB1, ABCB5, ABCG1 and ABCG2 were lower in these melanoma cells. The melanoma cells were then treated with sub-$EC_{50}$ doses of cisplatin, doxorubicin, oridonin, paclitaxel, and vemurafenib, all of which have been reported and used for their anti-tumor effects on different classes of cancer cells, especially melanoma. The results for each transporter are presented separately below.

Figure 22A:
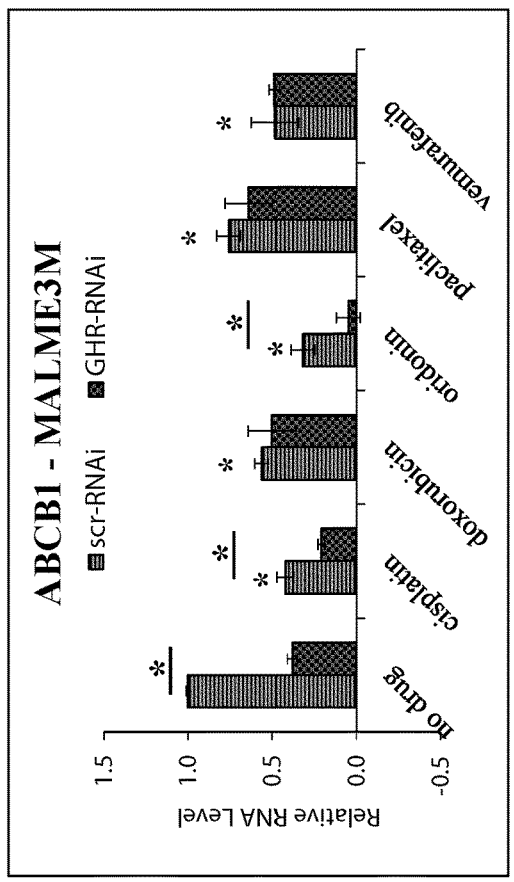
FIGS. 22A-22D include graphs showing the effect of GHR-KD on ABCB1 expression following drug treatment in human melanoma cells.
Figure 22B:
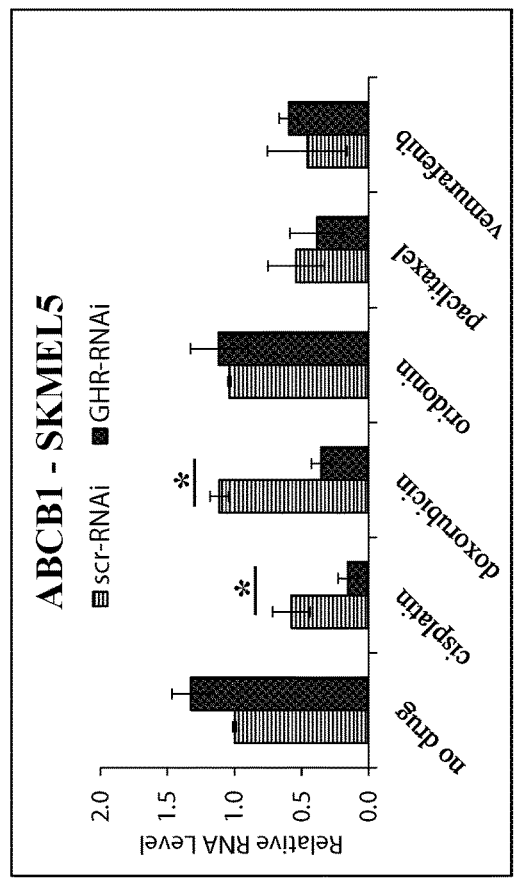
Figure 22C:
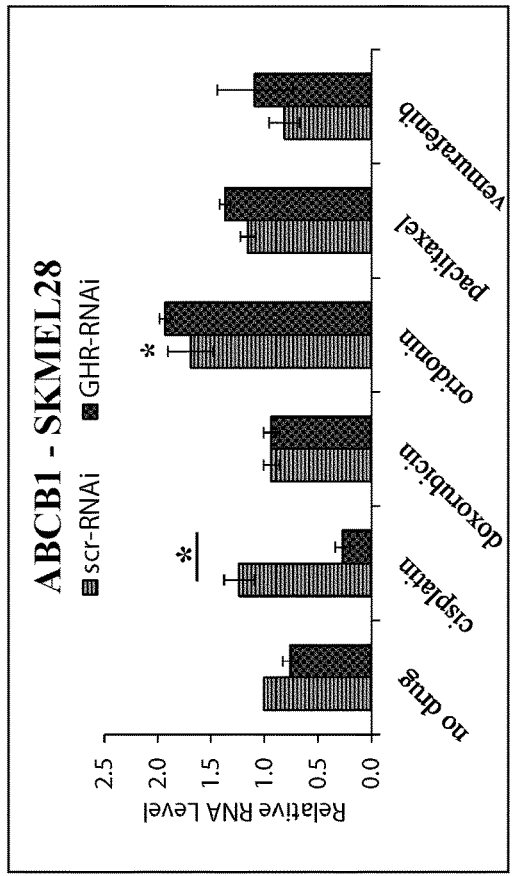
Figure 22D:
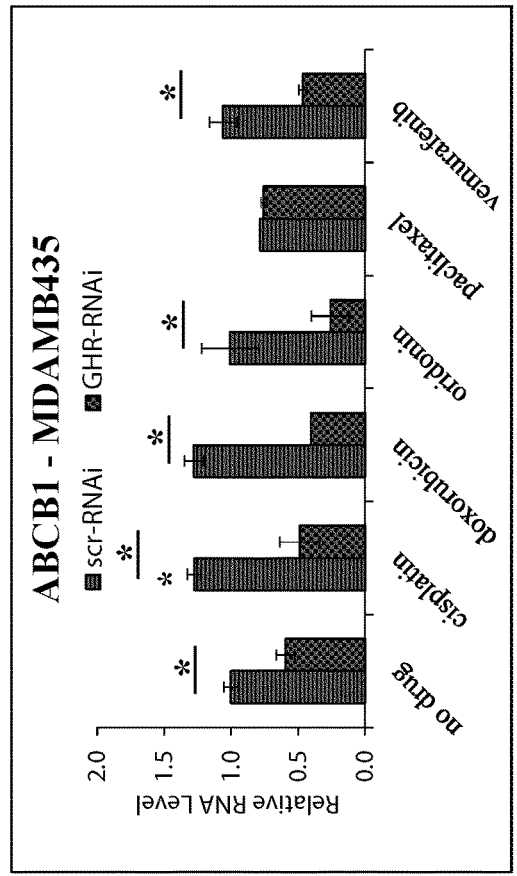

ABCB1: The effect of GHR-KD on ABCB1 expression following drug treatment in human melanoma cells is shown in FIGS. 22A-22D, based on relative RNA expression of ABCB1 in SK-MEL-28 (FIG. 22A), MALME-3M (FIG. 22B), MDA-MB-435 (FIG. 22C), and SK-MEL-5 (FIG. 22D) melanoma cells following scr- or GHR-siRNA mediated knock-down of GHR levels. Experiments were conducted in presence of 50 ng/mL hGH. In all cases, drug treatment was for 24 hr. starting 48 hr. post-transfection. Expressions were normalized against expression of ACTB and GAPDH as reference genes [*, $p<0.05$, Wilcoxon sign rank test, n=3]. Significant upregulation of ABCB1 RNA levels was observed in response to cisplatin in SK-MEL-28 (FIG. 22A) and MDA-MB-435 (FIG. 22C) cells and in response to oridonin in SK-MEL-28 cells (FIG. 22A). Interestingly, the intrinsic RNA level of ABCB1 was significantly downregulated following GHR-KD in presence of cisplatin for all four melanoma cell lines. ABCB1 expression was markedly reduced following GHR-KD also on exposure to doxorubicin (in MDA-MB-435 and SK-MEL-5), oridonin (in MALME-3M and MDA-MB-435), and vemurafenib (in MDA-MB-435) (FIGS. 22A-22D).

Figure 23A:
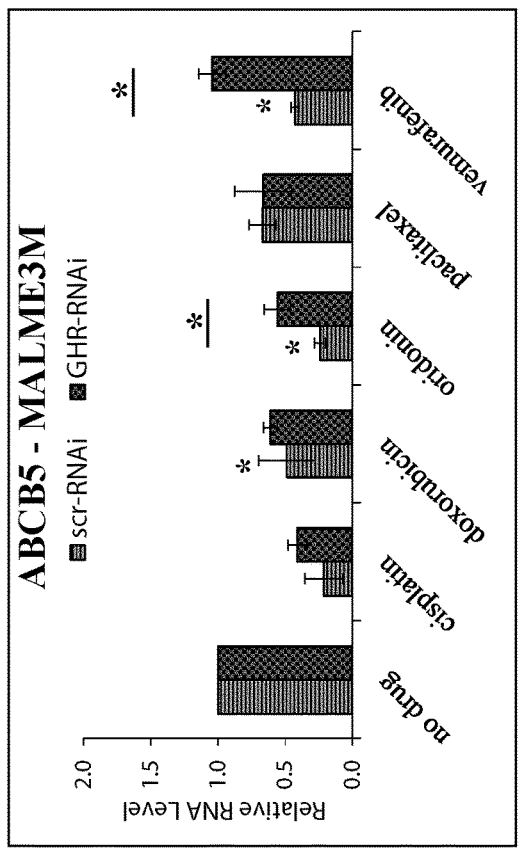
FIGS. 23A-23D include graphs showing the effect of GHR-KD on ABCB5 expression following drug treatment in human melanoma cells.
Figure 23B:
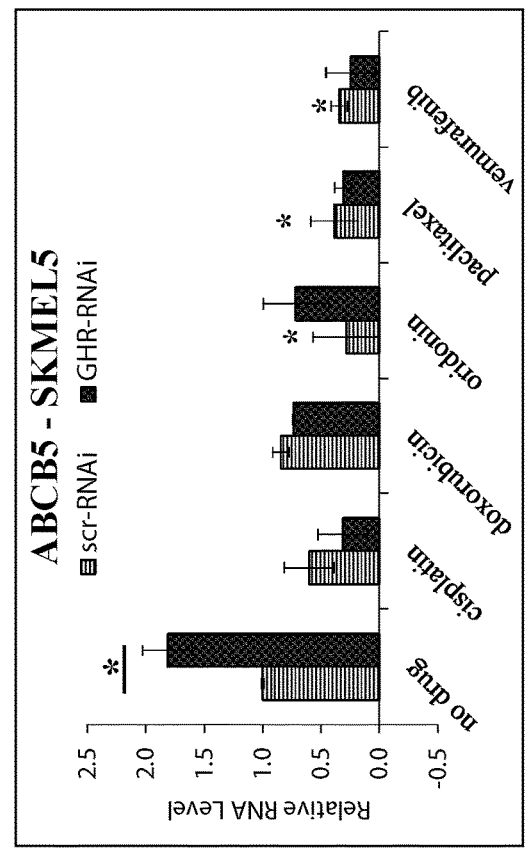
Figure 23C:
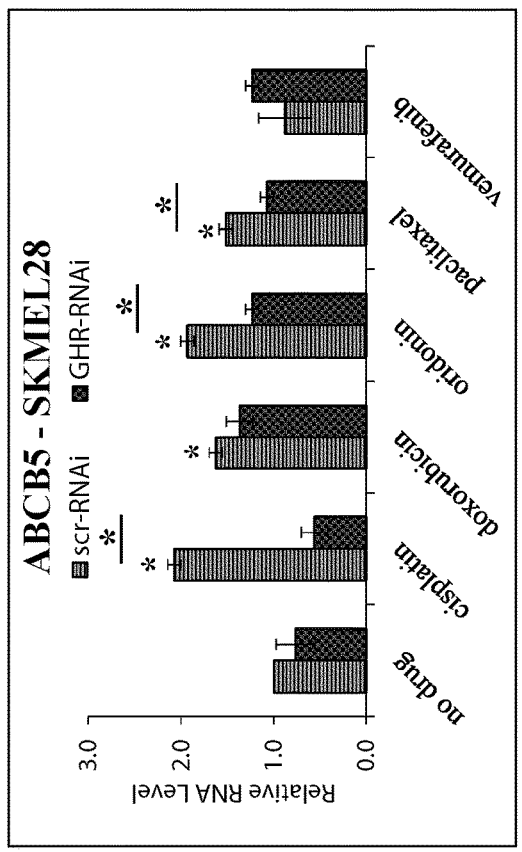
Figure 23D:
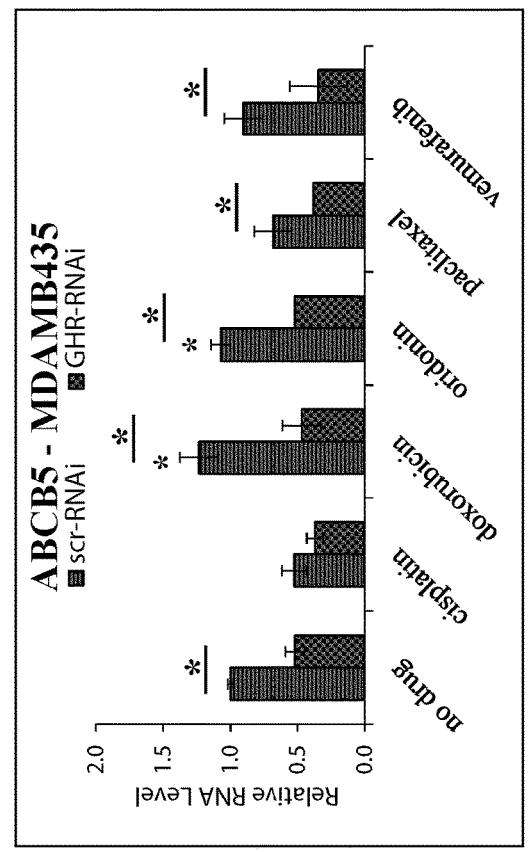
Figure 24B:
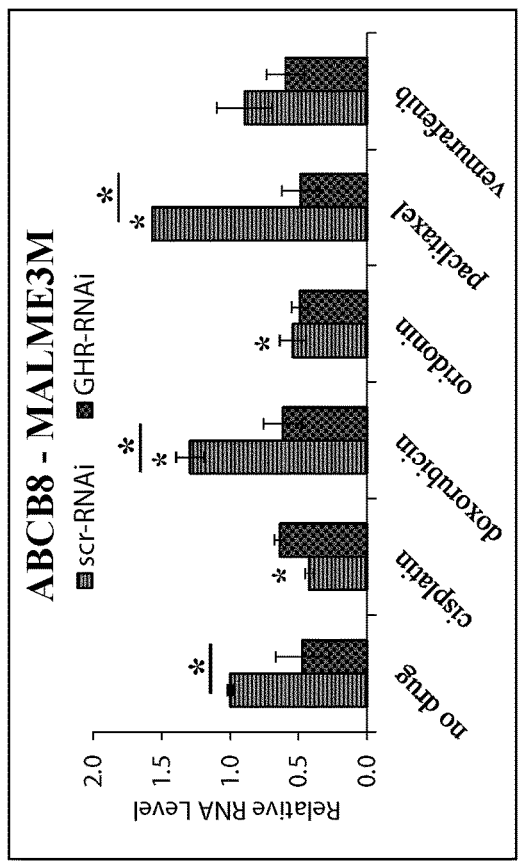
FIGS. 24A-24D include graphs showing the effect of GHR-KD on ABCB8 expression following drug treatment in human melanoma cells.
Figure 24D:
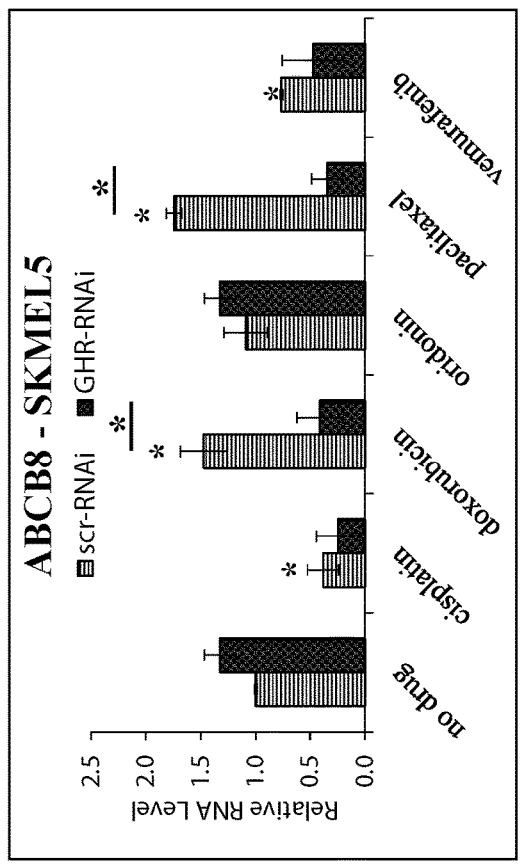
Figure 24A:
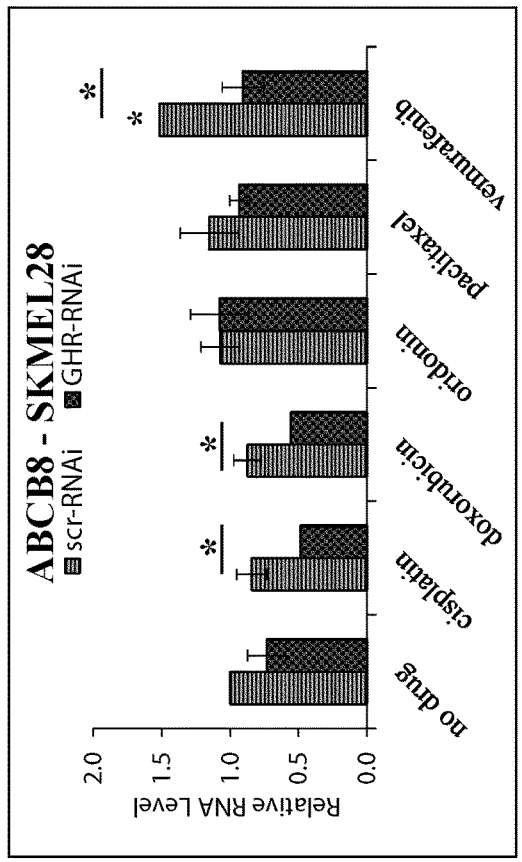
Figure 24C:
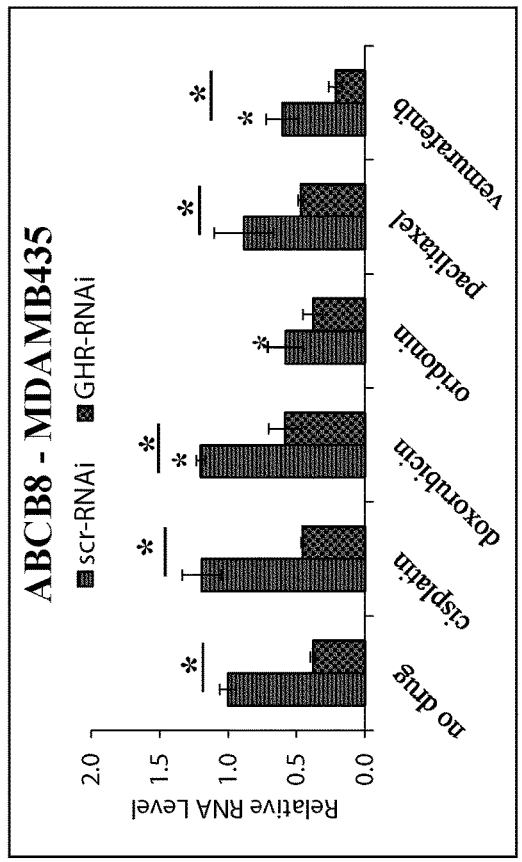

ABCB5: The effect of GHR-KD on ABCB5 expression following drug treatment in human melanoma cells is shown in FIGS. 23A-23D, based on relative RNA expression of ABCB5in SK-MEL-28 (FIG. 23A), MALME-3M (FIG. 23B), MDA-MB-435 (FIG. 23C), and SK-MEL-5 (FIG. 23D) melanoma cells following scr- or GHR-siRNA mediated knock-down of GHR levels. Experiments were conducted in presence of 50 ng/mL hGH. In all cases, drug treatment was for 24 hr. starting 48 hr. post-transfection. Expressions were normalized against expression of ACTB and GAPDH as reference genes. [*, $p<0.05$, Wilcoxon sign rank test, n=3]. As can be seen, RNA levels of ABCB5 were significantly upregulated following treatment with cisplatin, doxorubicin, oridonin and paclitaxel in SK-MEL-28 cells (FIG. 23A). The same was observed for doxorubicin and oridonin treatment in MDA-MB-435 cells (FIG. 23B), indicating a role of ABCB5 in mediating multi-drug resistance specifically in these two cell lines. Also, GHR-KD caused significant downregulation of ABCB5 expression compared to scr-siRNA treated controls, on exposure to cisplatin (in SK-MEL-28), doxorubicin (in MDA-MB-435), oridonin (in SK-MEL-28 and MDA-MB-435), paclitaxel (in SK-MEL-28 and MDA-MB-435) and vemurafenib (in MDA-MB-435) (FIGS. 23A-23D). A rise was observed in ABCB5 levels in MALME-3M cells following GHR-KD in response to oridonin and vemurafenib treatments (FIG. 23B) while GHR-KD significantly decreased even the basal expression levels of ABCB5 in absence of any drug in MDA-MB-435 cells (FIG. 23C).

ABCB8: The effect of GHR-KD on ABCB8 expression following drug treatment in human melanoma cells is shown in FIGS. 24A-24D, based on relative RNA expression of ABCB8 in SK-MEL-28 (FIG. 24A), MALME-3M (FIG. 24B), MDA-MB-435 (FIG. 24C), and SK-MEL-5 (FIG. 24D) melanoma cells following scr- or GHR-siRNA mediated knock-down of GHR levels, Experiments were conducted in presence of 50 ng/mL hGH. In all cases, drug treatment was for 24 hr. starting 48 hr. post-transfection. RNA expressions were quantified by RT-qPCR and normalized against expression of ACTB and GAPDH as reference genes, [*, p<0.05, Wilcoxon sign rank test, n=3]. ABCB8 is known to induce doxorubicin resistance in human melanoma cells, including MDA-MB-435. Consistent with previous observations, significant upregulation of ABCB8 levels was observed following exposure to doxorubicin in MDA-MB-435 (FIG. 24C), MALME-3M (FIG. 24B), and SK-MEL-5 (FIG. 24D) cells. A significant upregulation of ABCB8 was also observed on treatment with paclitaxel in MALME-3M (FIG. 24B) and SK-MEL-5 (FIG. 24D) cells, while vemurafenib induced a robust increase in ABCB8 in SK-MEL-28 cells (FIG. 24A), When the GHR was knocked down, a strong downregulation of ABCB8 to below basal levels was observed following exposure to cisplatin (in SK-MEL-28 and MDA-MB-435), doxorubicin (in all four cell lines), paclitaxel (in MALME-3 M, MDA-MB-435 and SK-MEL-5), and vemurafenib (in SK-MEL-28 and MDA-MB-435) (FIGS. 24A-24D).

Figure 25A:
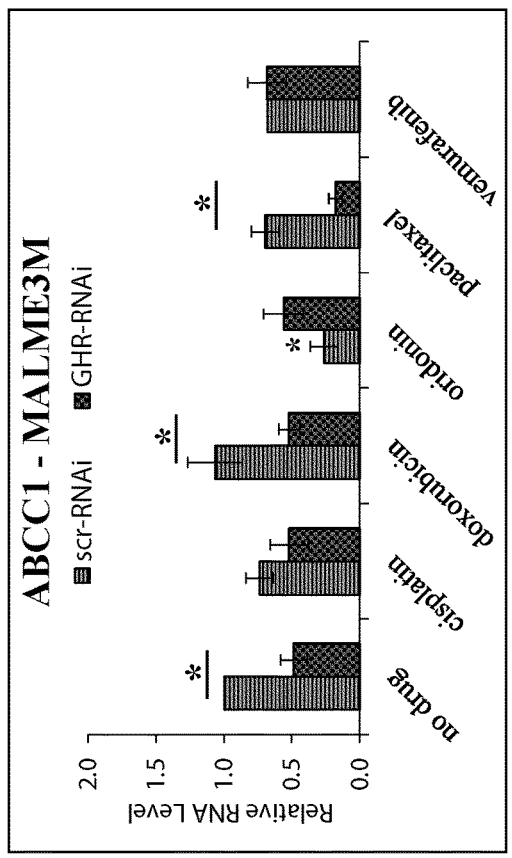
FIGS. 25A-25D include graphs showing the effect of GHR-KD on ABCC1 expression following drug treatment in human melanoma cells.
Figure 25B:
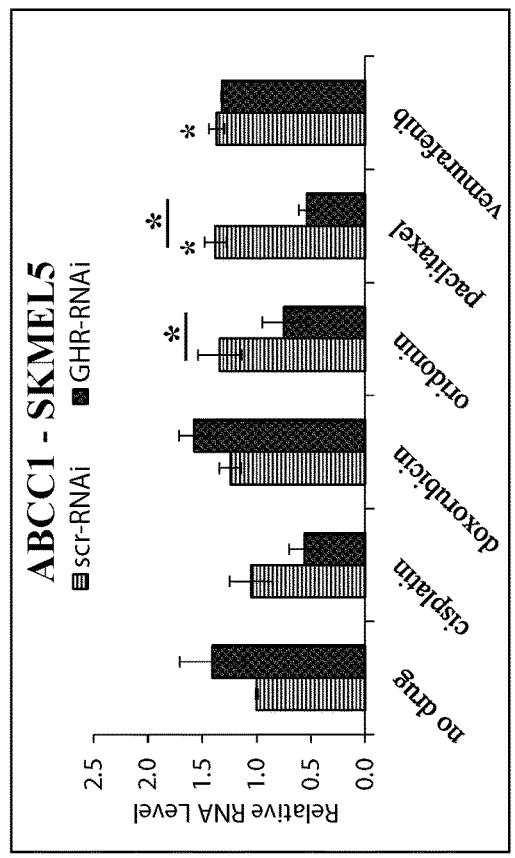
Figure 25C:
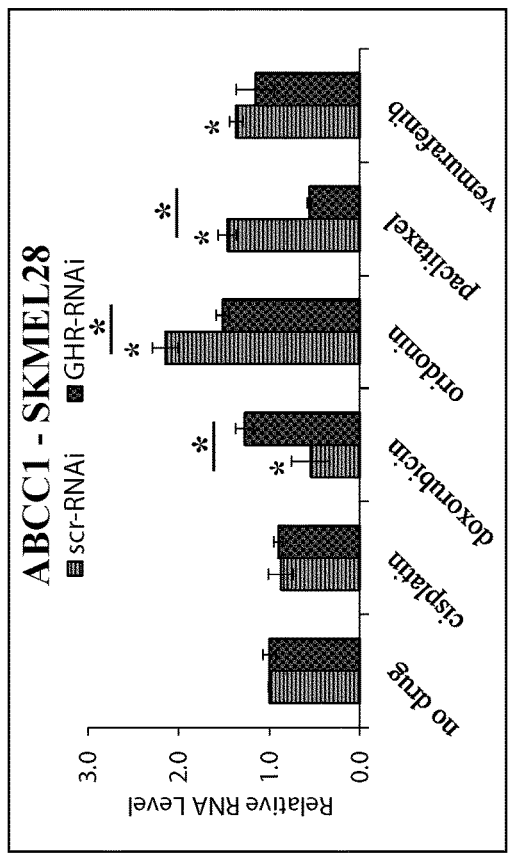
Figure 25D:
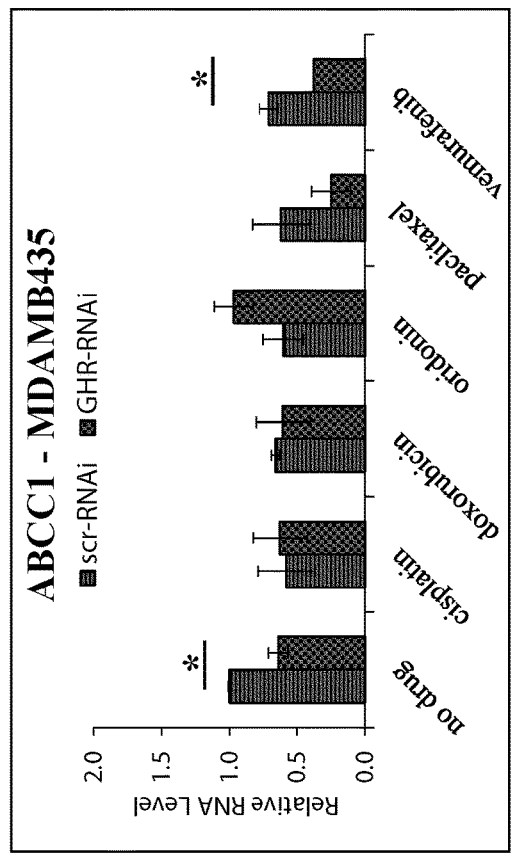

ABCC1: The effect of GHR-KD on ABCC1 expression following drug treatment in human melanoma cells is shown in FIGS. 25A-25D, based on relative RNA expression of ABCC1 in SK-MEL-28 (FIG. 25A), MALME-3M (FIG. 25B), MDA-MB-435 (FIG. 25C) and SK-MEL-5 (FIG. 25D) melanoma cells following scr- or GHR-siRNA mediated knock-down of GHR levels. Experiments were conducted in presence of 50 ng/mL hGH. In all cases, drug treatment was for 24 hr. starting 48 hr. post-transfection. Expressions were normalized against expression of beta-actin and GAPDH as reference genes. [*, p 21 0.05, Wilcoxon sign rank test, n=3]. As can be seen, ABCC1 levels were particularly upregulated in response to paclitaxel treatment in SK-MEL-28 and SK-MEL-5 cells (FIGS. 25A and 25D). However, following GHR-KD significant suppression of ABCC1 RNA levels was observed in response to doxorubicin (in MALME-3M), oridonin (in SK-MEL-28 and SK-MEL-5), paclitaxel (in SK-MEL-28, MALME-3M and SK-MEL-5), and vemurafenib (in MDA-MB-435) (FIGS. 25A-25D).

Figure 26A:
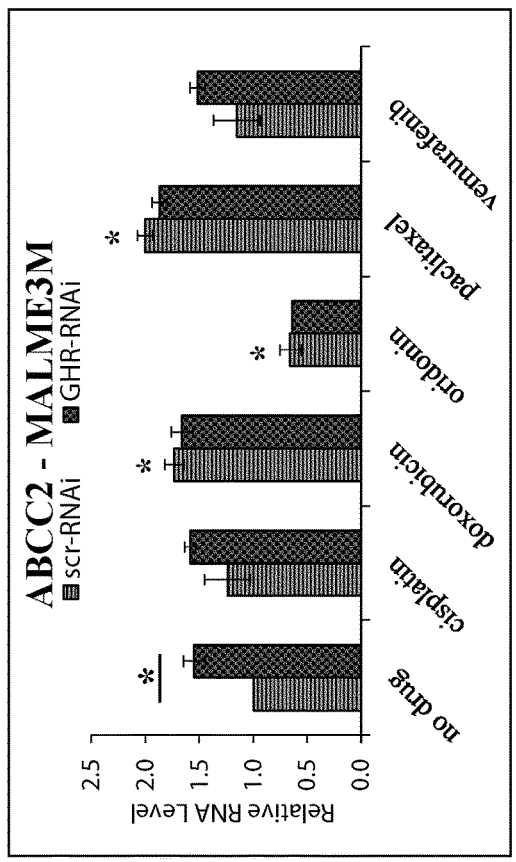
FIGS. 26A-26D include graphs showing the effect of GHR-KD on ABCC2 expression following drug treatment in human melanoma cells.
Figure 26B:
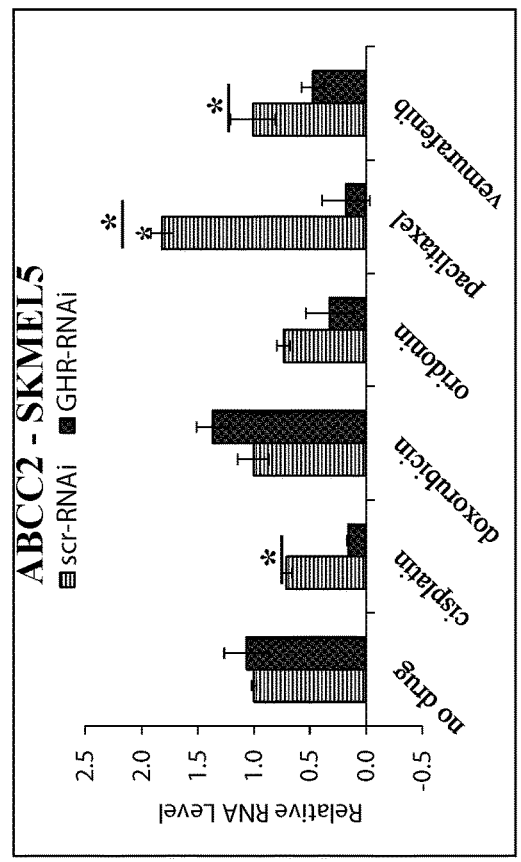
Figure 26C:
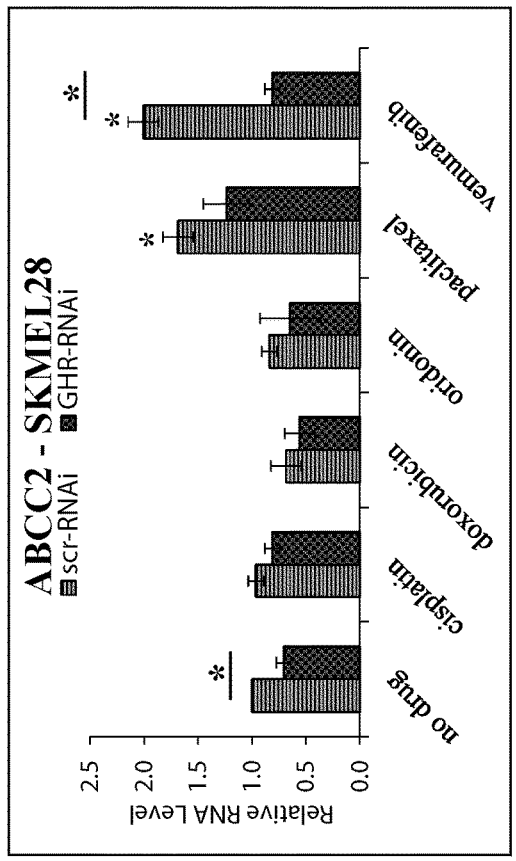
Figure 26D:
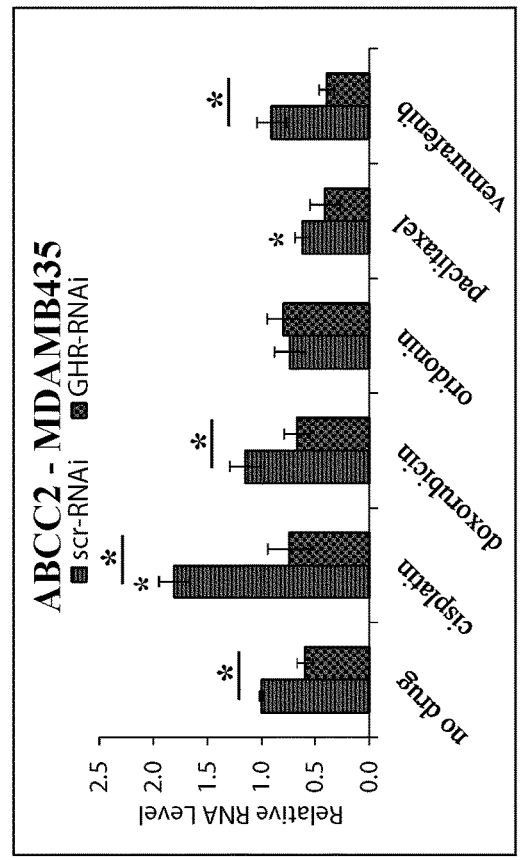

ABCC2: The effect of GHR-KD on ABCC2 expression following drug treatment in human melanoma cells is shown in FIGS. 26A-26D, based on relative RNA expression of ABCC2in SK-MEL-28 (FIG. 26A), MALME-3M (FIG. 26B), MDA-MB-435 (FIG. 26C), and SK-MEL-5 (FIG. 26D) melanoma cells following scr- or GHR-siRNA mediated knock-down of GHR levels. Experiments were conducted in presence of 50 ng/mL hGH. In all cases, drug treatment was for 24 hr. starting 48 hr. post-transfection. Expressions were normalized against expression of beta-actin and GAPDH as reference genes. [*, p<0.05, Wilcoxon sign rank test, n=3] As can be seen, paclitaxel significantly increased RNA levels of ABCC2 transporter in SK-MEL-28 (FIG. 26A), MALME-3M (FIG. 26B), and SK-MEL-5 (FIG. 26D). The same effect was observed for vemurafenib in SK-MEL-28 (FIG. 26A) and cisplatin in MDA-MB-435 (FIG. 26C) melanoma cells. GHR-KD resulted in a decrease in ABCC2 levels on exposure to cisplatin (in MDA-MB-435 and SK-MEL-5 cells), doxorubicin (in MDA-MB-435), paclitaxel (in SK-MEL-28 and MDA-MB-435), and vemurafenib (SK-MEL-28, MDA-MB-435 and SK-MEL-5 cells) (FIGS. 26A-26D).

Figure 27A:
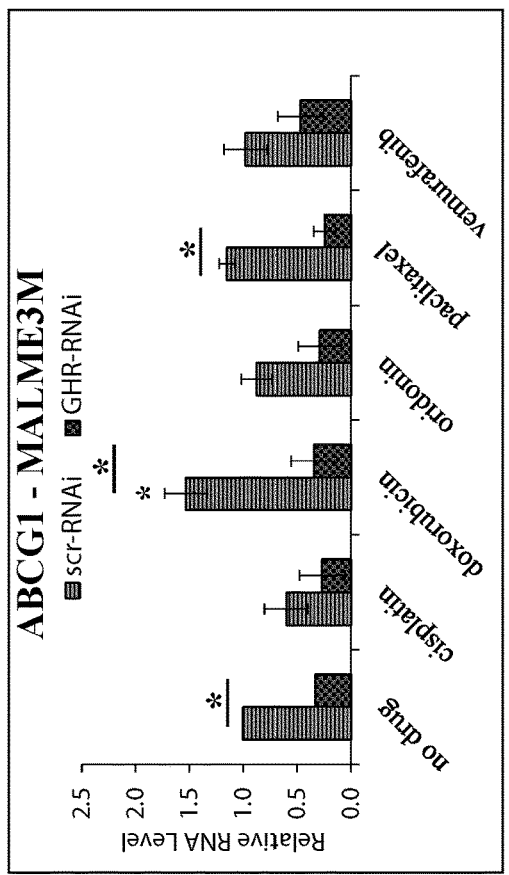
FIGS. 27A-27D include graphs showing the effect of GHR-KD on ABCG1 expression following drug treatment in human melanoma cells.
Figure 27B:
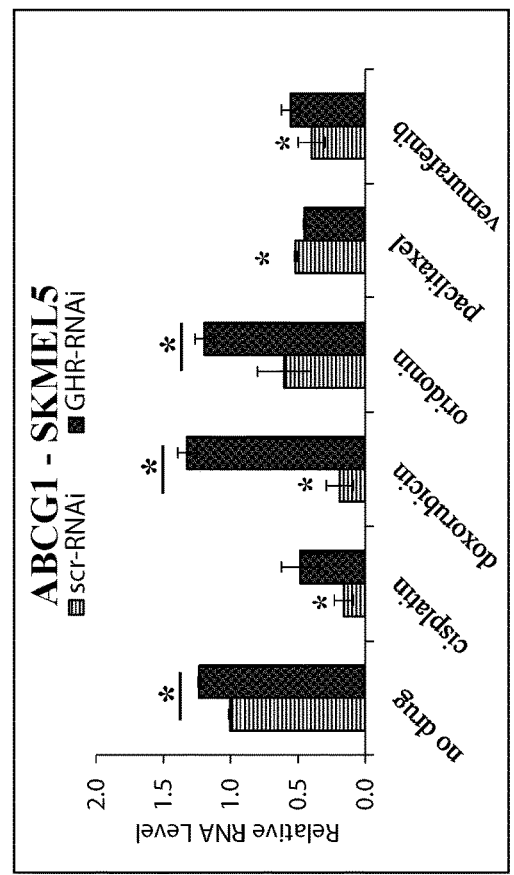
Figure 27C:
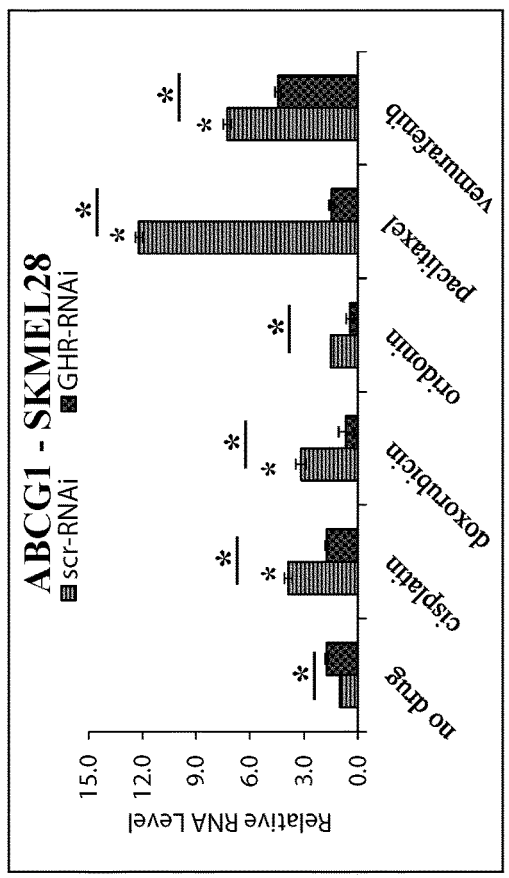
Figure 27D:
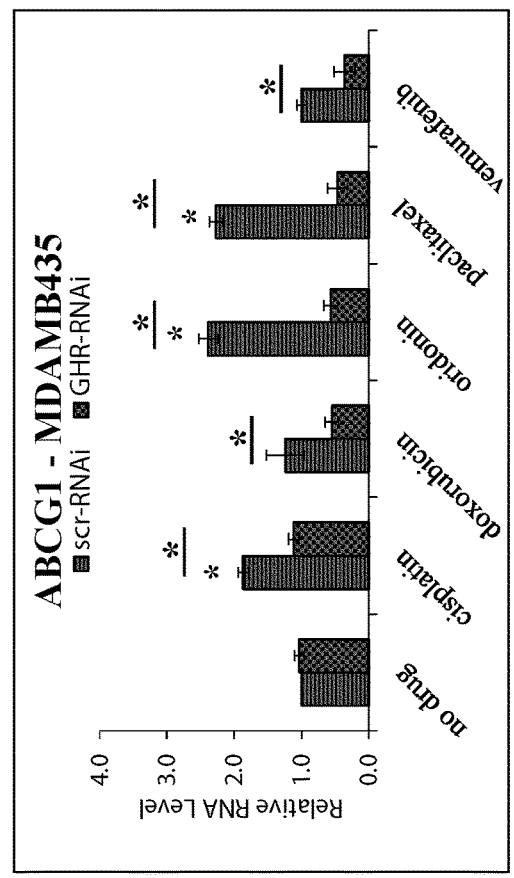

ABCG1: The effect of GHR-KD on ABCG1 expression following drug treatment in human melanoma cells is shown in FIGS. 27A-27D, based on relative RNA expression of ABCG1 in SK-MEL-28 (FIG. 27A), MALME-3M (FIG. 27B), MDA-MB-435 (FIG. 27C) and SK-MEL-5 (FIG. 27D) melanoma cells following scr- or GHR-siRNA mediated knock-down of GHR levels. Experiments were conducted in presence of 50 ng/mL hGH. In all cases, drug treatment was for 24 hr. starting 48 hr. post-transfection. RNA expressions were quantified by RT-qPCR and normalized against expression of ACTB and GAPDH as reference genes. [*, p<0.05, Wilcoxon sign rank test, n=3]. In the four melanoma cell lines tested, ABCG1 was significantly upregulated consistently for a number of drugs. ABCG1 levels surged in SK-MEL-28 in response to cisplatin, doxorubicin, paclitaxel, and vemurafenib treatment (FIG. 27A), in MALME-3M cells in response to doxorubicin (FIG. 27B), and in MDA-MB-435 cells in response to cisplatin, oridonin and paclitaxel (FIG. 27C). On the other hand, GHR-KD had an equally drastic effect in significantly downregulating ABCC2 following exposure to cisplatin (in SK-MEL-28 and MDA-MB-435), doxorubicin (in SK-MEL-28, MALME-3M and MDA-MB-435), oridonin (in SK-MEL-28 and MDA-MB-435), paclitaxel (in SK-Mel-28, MALME-3M and MDA-MB-435), and vemurafenib (in SK-MEL-28 and MDA-MB-435). Only in the case of SK-MEL-5 was a rise in ABCG1 levels observed following GHR-KD basally as well as in presence of all drugs tested (FIG. 27D).

Figure 28A:
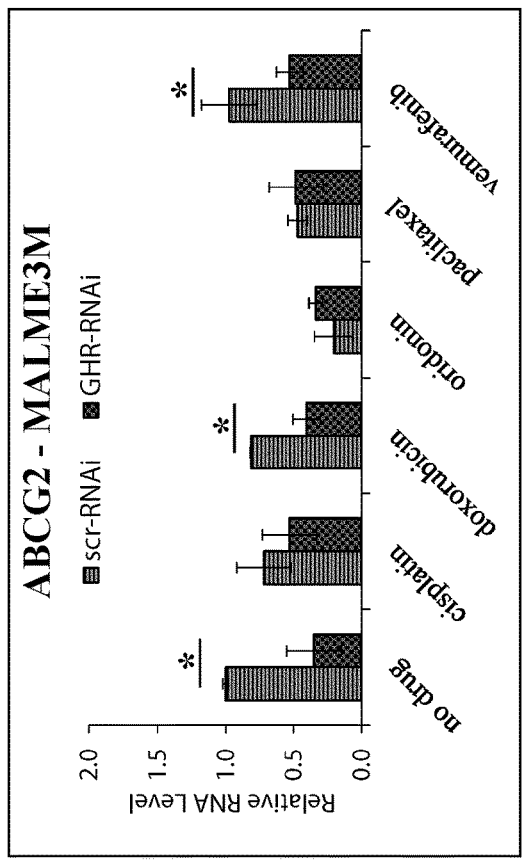
FIGS. 28A-28D include graphs showing the effect of GHR-KD on ABCG2 expression following drug treatment in human melanoma cells.
Figure 28B:
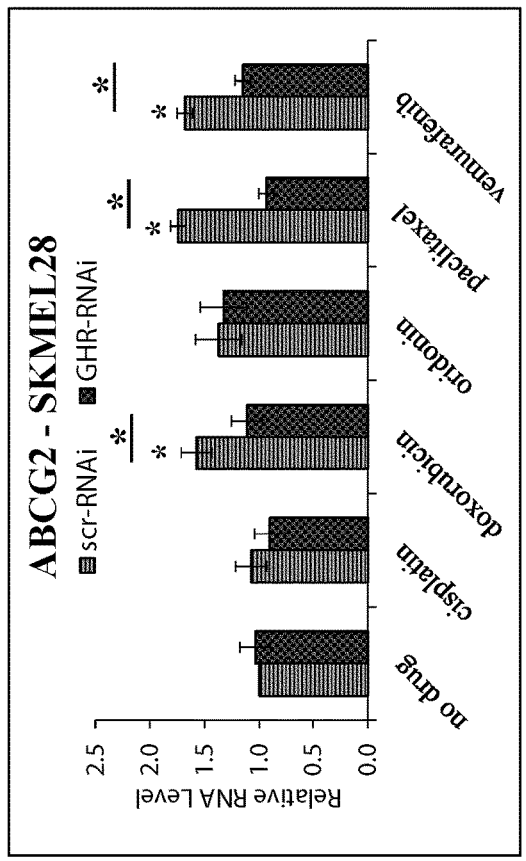
Figure 28C:
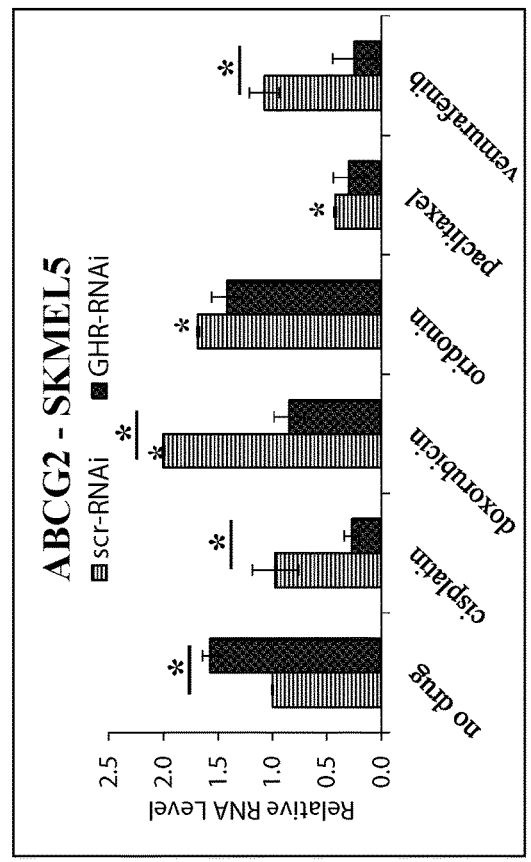
Figure 28D:
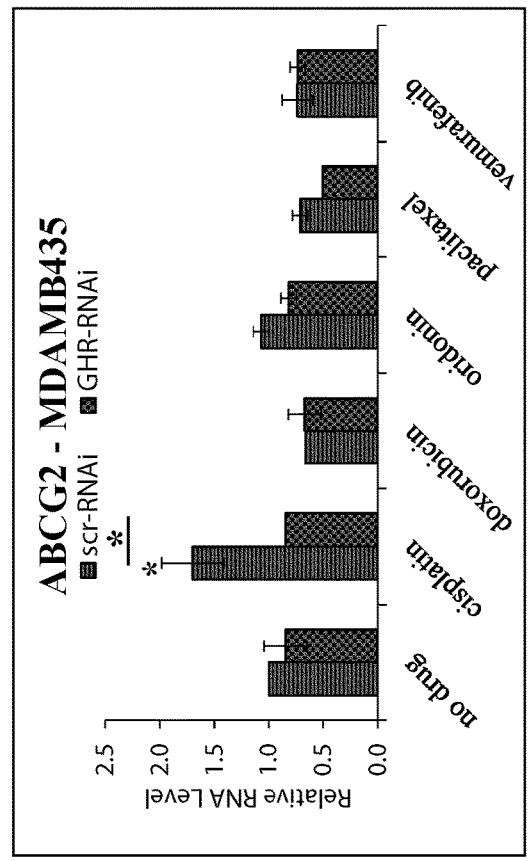

ABCG2: The effect of GHR-KD on ABCG2 expression following drug treatment in human melanoma cells is shown in FIGS. 28A-28D, based on relative RNA expression of ABCG2in SK-MEL-28 (FIG. 28A), MALME-3M (FIG. 28B), MDA-MB-435 (FIG. 28C), and SK-MEL-5 (FIG. 28D) melanoma cells following scr- or GHR-siRNA mediated knock-down of GHR levels. Experiments were conducted in presence of 50 ng/mL hGH. In all cases, drug treatment was for 24 hr. starting 48 hr. post-transfection. Expressions were normalized against expression of beta-actin and GAPDH as reference genes. [*, p<0.05, Wilcoxon sign rank test, n=3]. As can be seen, ABCG2 levels were significantly upregulated in SK-MEL-28 cells on exposure to doxorubicin, paclitaxel and vemurafenib (FIG. 28A), while the same was observed in MDA-MB-435 cells in response to cisplatin (FIG. 28C) and in SK-MEL-5 cells in response to doxorubicin and oridonin (FIG. 28D). GHR KD caused a significant decrease in ABCG2 levels on exposure to cisplatin (in MDA-MB-435 and SK-MEL-5), doxorubicin (in SK-MEL-28, MALME-3M and SK-MEL-5), paclitaxel (in SK-MEL-28), and vemurafenib (in SK-MEL-28, MALME-3M and SK-MEL-5) (FIGS. 28A-28D). The results of GHR-KD on seven different ABC transporter pumps on all four melanoma cell lines on exposure to cisplatin (0.5 μM), doxorubicin (10 nM), oridonin (0.5 μM), paclitaxel (1 nM), and vemurafenib (15 nM) are listed in Table 1.

TABLE 1

List of ABC-transporter pumps with significantly down-regulated RNA expressions following 24 hr. exposure to anti-tumor compounds in GHR-siRNA transfected melanoma cells compared to corresponding scr-siRNA transfected controls.

| Cell Line | Drug Treatment | Efflux Pumps (expression level change, p < 0.05) |
|---|---|---|
| SK-MEL-28 | Cisplatin | ABCB1, ABCB5, ABCB8, ABCG1 |
| | Doxorubicin | ABCB8, ABCC1, ABCG1, ABCG2 |
| | Oridonin | ABCB5, ABCC1, ABCG1 |
| | Paclitaxel | ABCB5, ABCC1, ABCG1, ABCG2 |
| | Vemurafenib | ABCB8, ABCC2, ABCG1, ABCG2 |
| MALME-3M | Cisplatin | ABCB1 |
| | Doxorubicin | ABCB8, ABCC1, ABCG1, ABCG2 |
| | Oridonin | ABCB1, ABCB5, ABCG1 |
| | Paclitaxel | ABCB8, ABCC1, ABCG1 |
| | Vemurafenib | ABCB5, ABCG2 |

TABLE 1-continued

List of ABC-transporter pumps with significantly down-regulated RNA expressions following 24 hr. exposure to anti-tumor compounds in GHR-siRNA transfected melanoma cells compared to corresponding scr-siRNA transfected controls.

| Cell Line | Drug Treatment | Efflux Pumps (expression level change, p < 0.05) |
| --- | --- | --- |
| MDA-MB-435 | Cisplatin | ABCB1, ABCB8, ABCC2, ABCG1, ABCG2 |
| | Doxorubicin | ABCB1, ABCB5, ABCC2, ABCG1 |
| | Oridonin | ABCB1, ABCB5, ABCG1 |
| | Paclitaxel | ABCB5, ABCB8, ABCG1, ABCG2 |
| | Vemurafenib | ABCB1, ABCB5, ABCB8, ABCC1, ABCC2, ABCG1 |
| SK-MEL-5 | Cisplatin | ABCB1, ABCC1, ABCC2, ABCG2 |
| | Doxorubicin | ABCB1, ABCB8, ABCG2 |
| | Oridonin | ABCC1 |
| | Paclitaxel | ABCB8, ABCC1, ABCC2 |
| | Vemurafenib | ABCC2, ABCG2 |

Figure 29A:
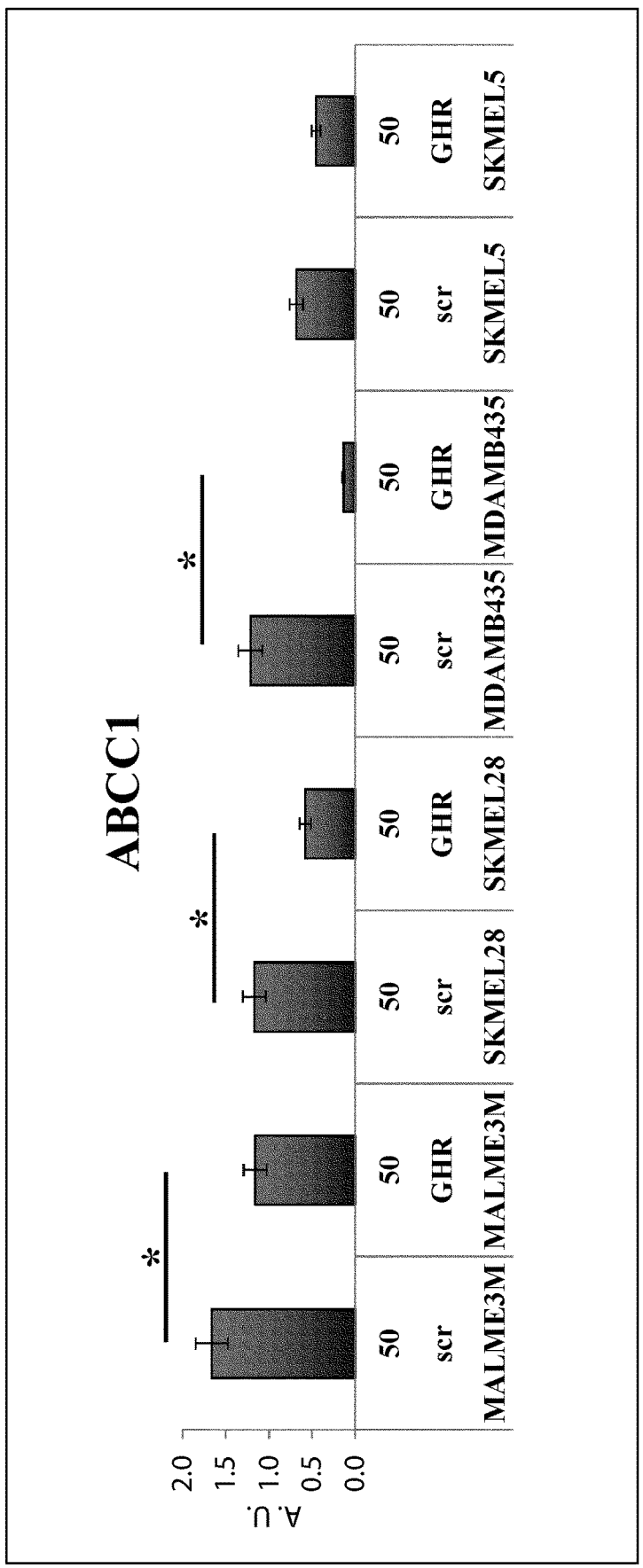
FIGS. 29A-29C include graphs and photographs showing a change in ABC transporter pumps following GHR-KD.
Figure 29B:
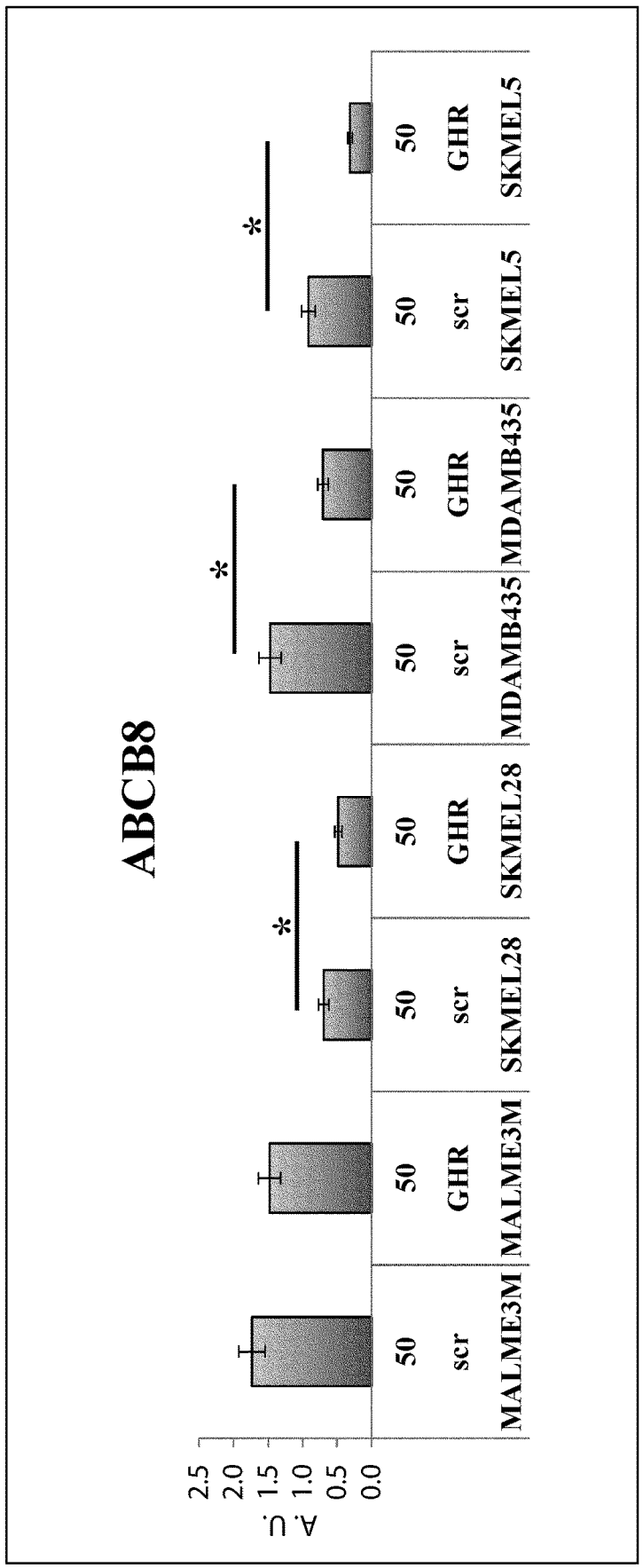
Figure 29C:
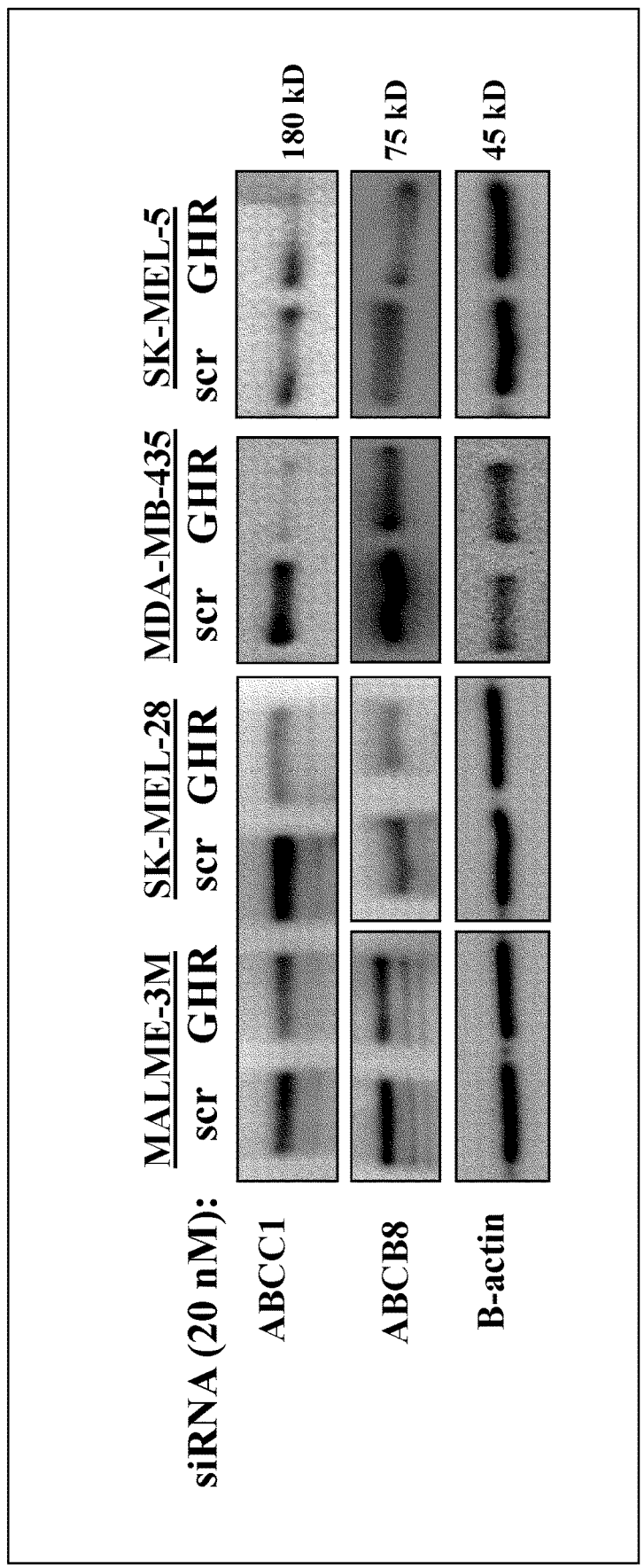

FIGS. 29A-29C then show the change in ABC transporter pumps following GHR-KD. To show this, changes in protein expressions of ABCG1 and ABCB8 were analyzed. Western blot comparison was done for protein extracted from all four melanoma cells, 60 hr. post-transfection with scr-siRNA. Blots were quantified using ImageJ software and mean of three blots per sample was taken. Expressions were normalized against expression of ACTB (β-actin). [*, p<0.05, Students t test, n=3]. This WB analysis showed significantly lower ABCC1 levels in SK-MEL-28, MALME-3M and MDA-MB-435, (FIGS. 29A and 29C), while protein levels of ABCB8 were found to significantly lower in GHR-KD samples of MALME-3M, MDA-MB-435 and SK-MEL-5 cells (FIGS. 29B and 29C). These results are consistent with the levels of RNA expression observed herein.

It was noted in the Example 1 that externally added GH did not produce a marked or consistent effect on the aggressive tumor phenotypes in melanoma. Without intending to be bound by any particular theory, this may be ascribed to the melanoma cells expressing GH RNA and having an intrinsic (autocrine) ligand-receptor loop wherein the autocrine-GH may have a much more pronounced effect than exogenously added GH. Regardless, the effects of 24-hour exposure to added GH (50 ng/ml) on the ABC-transporter RNA expressions were assessed in presence of the above mentioned anti-tumor agents at the specified concentrations.

Figure 30A:
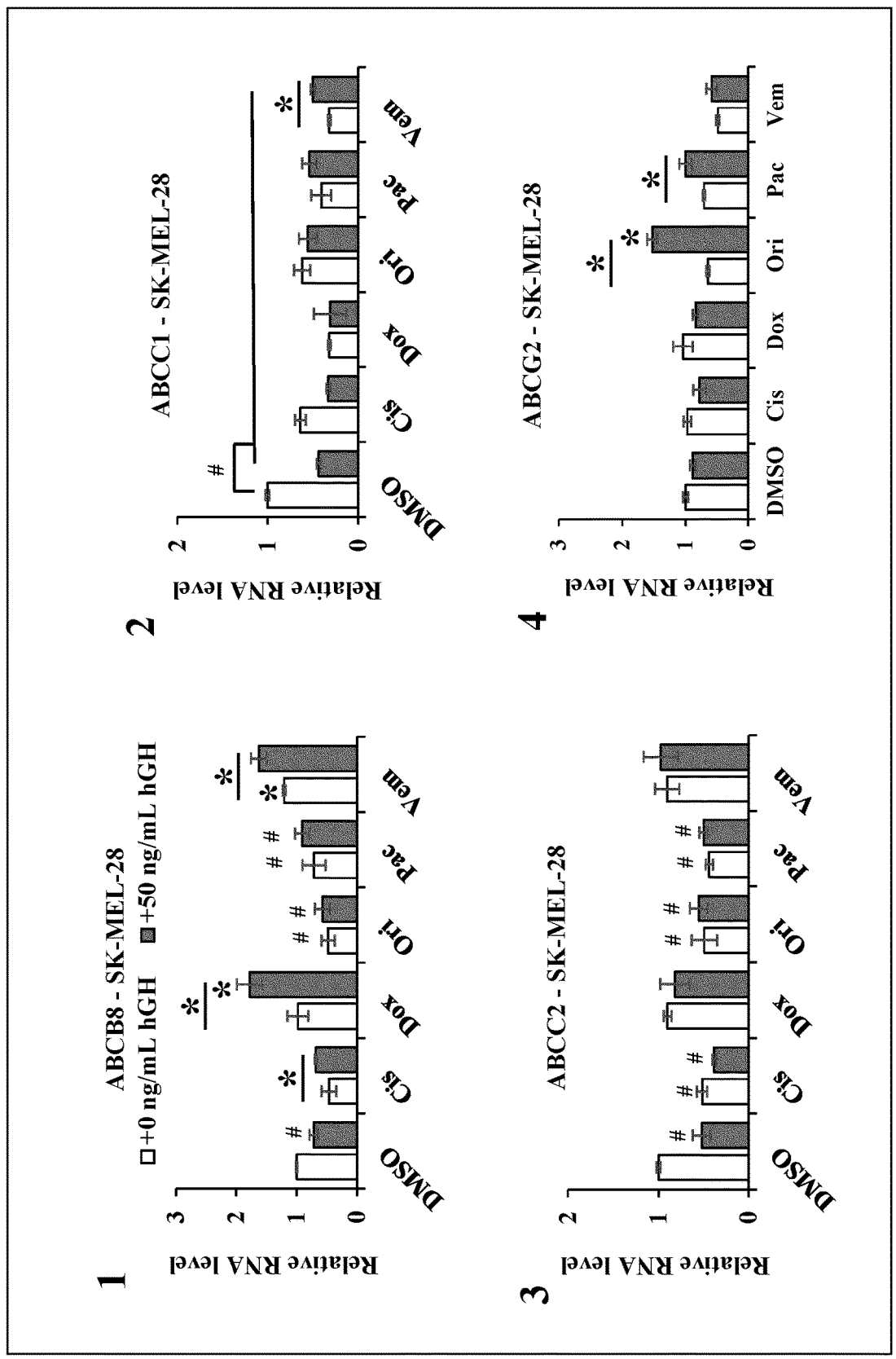
FIGS. 30A-30C include graphs showing the effect of GHR excess on ABCB8, ABCC1, ABCC2 and ABCG2 expressions following drug treatment in human melanoma cells.
Figure 30B:
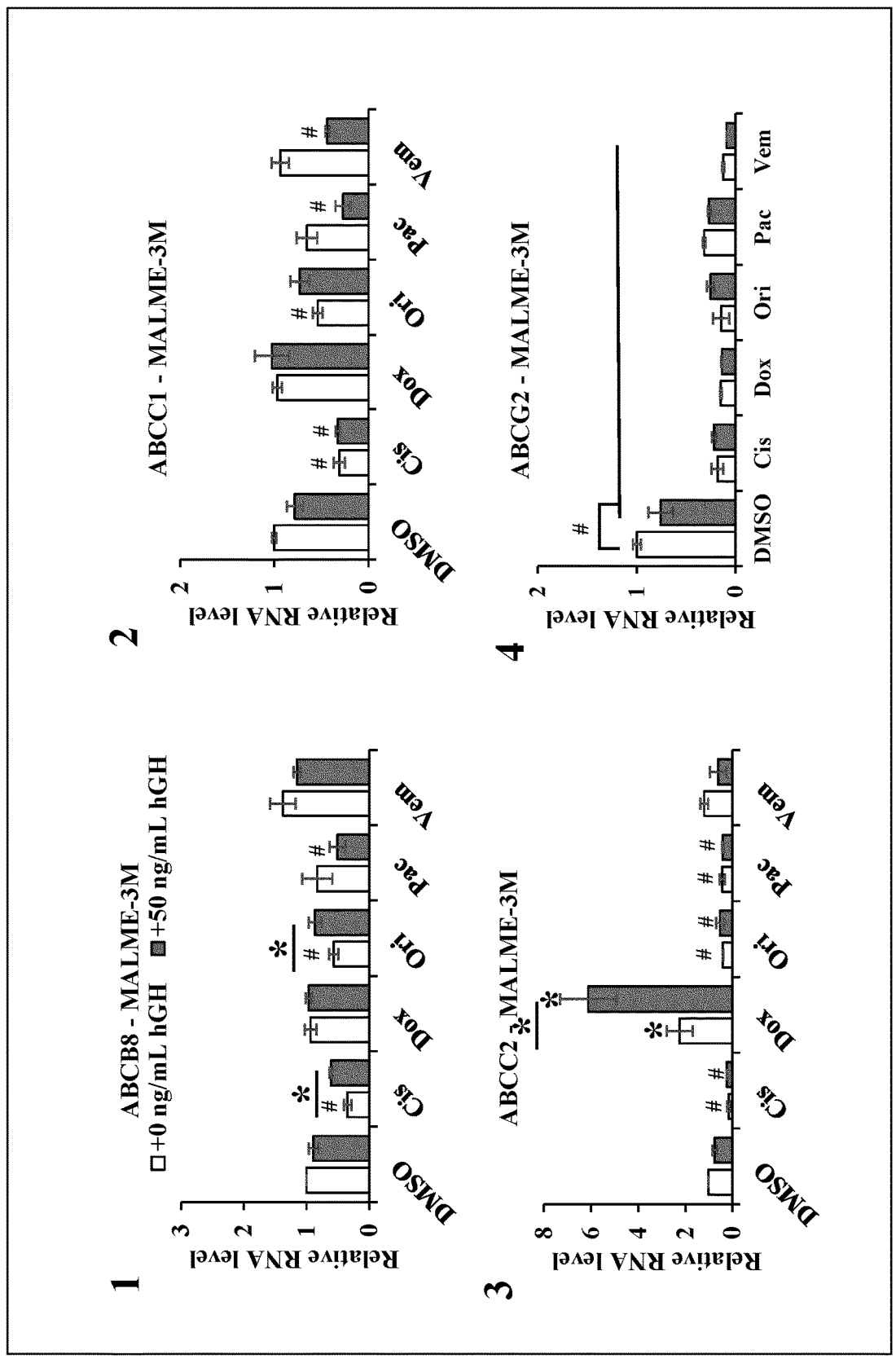
Figure 30C:
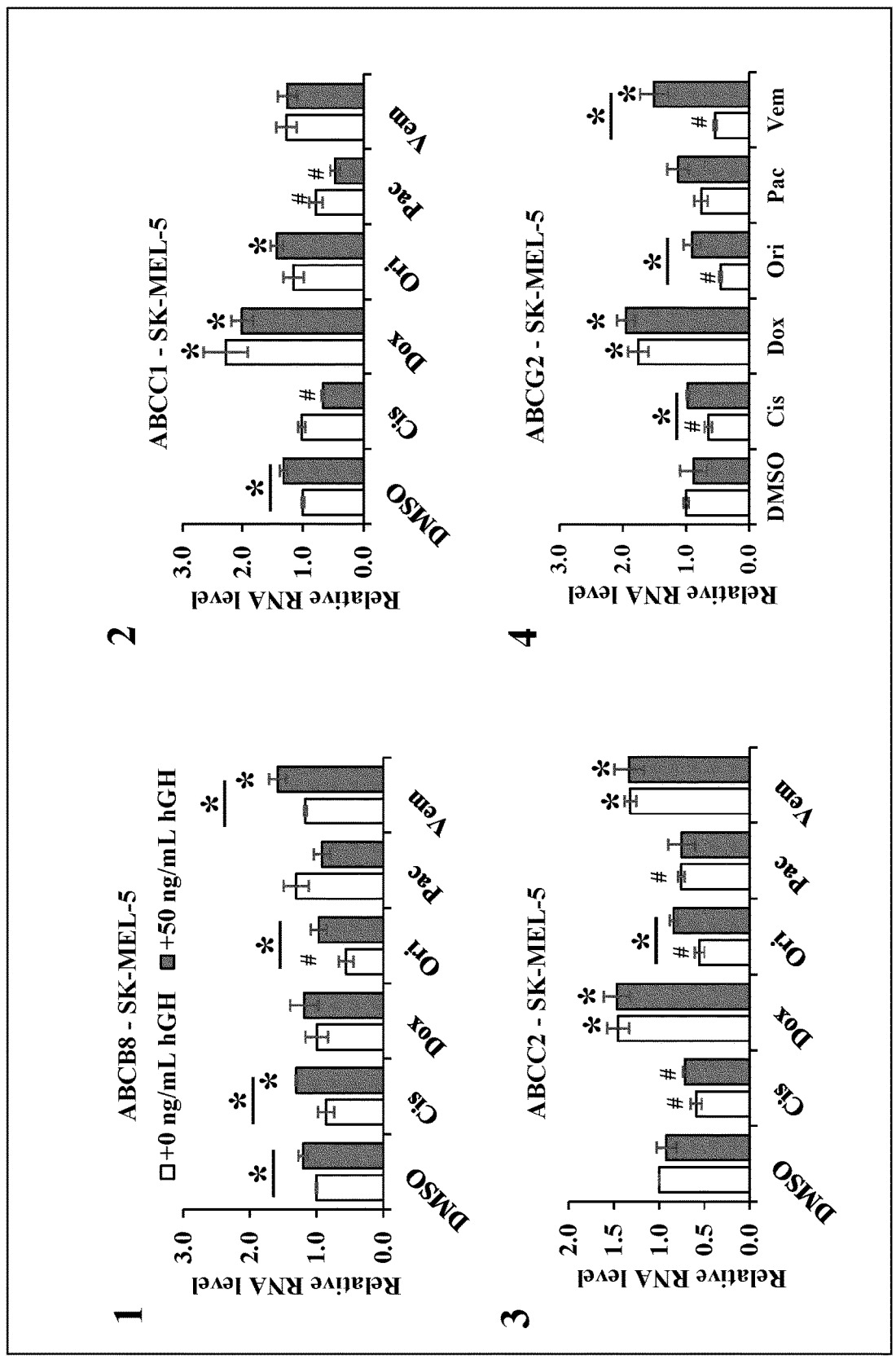
Figure 31A:
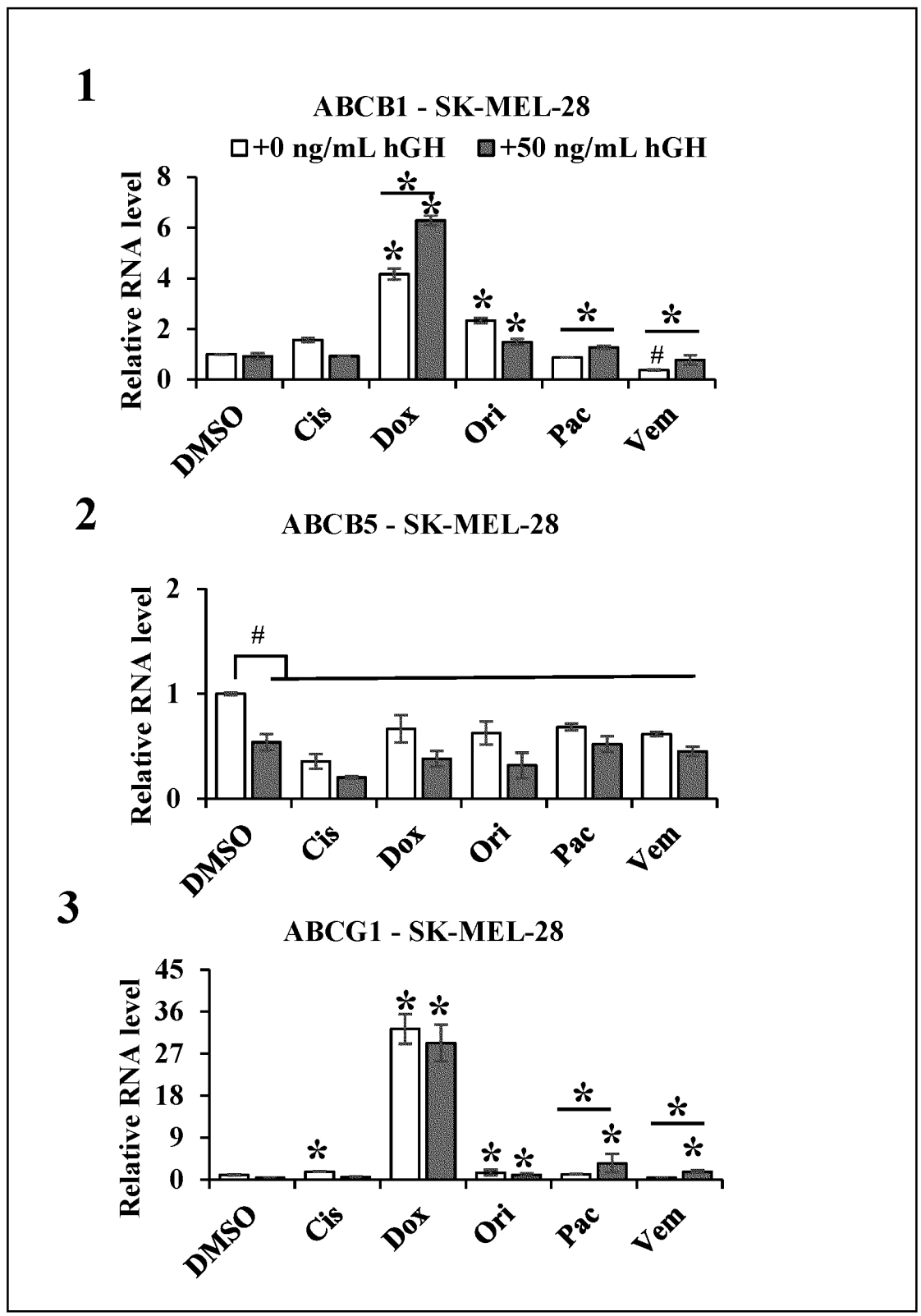
FIGS. 31A-31C include graphs showing the effect of GHR excess on ABCB1, ABCB5, and ABCG1 expressions following drug treatment in human melanoma cells.
Figure 31B:
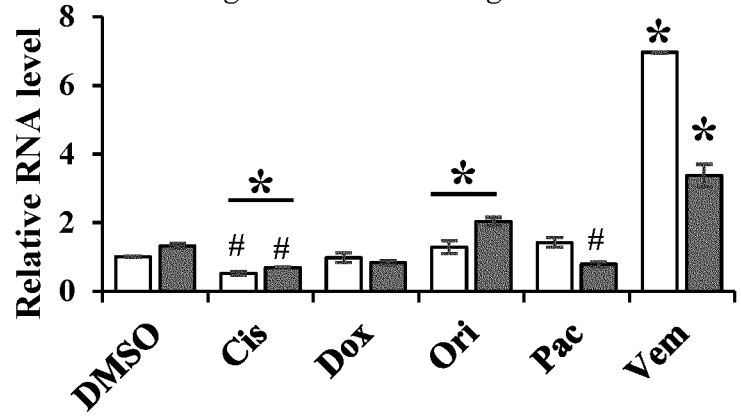
Figure 31B:
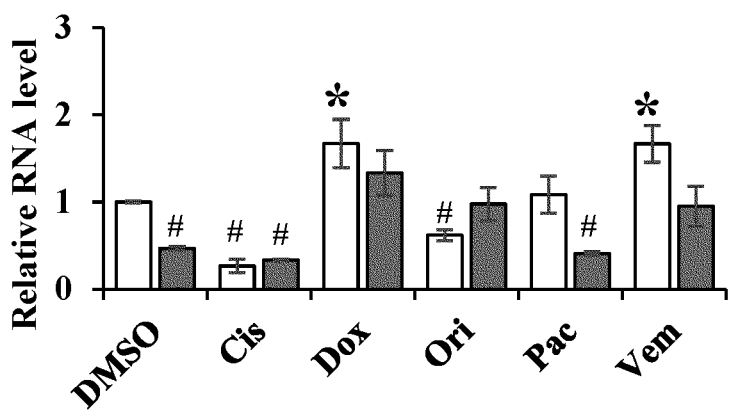
Figure 31B:
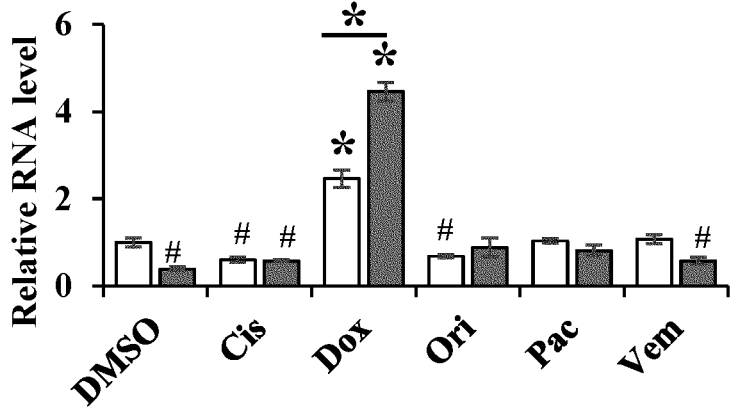
Figure 31C:
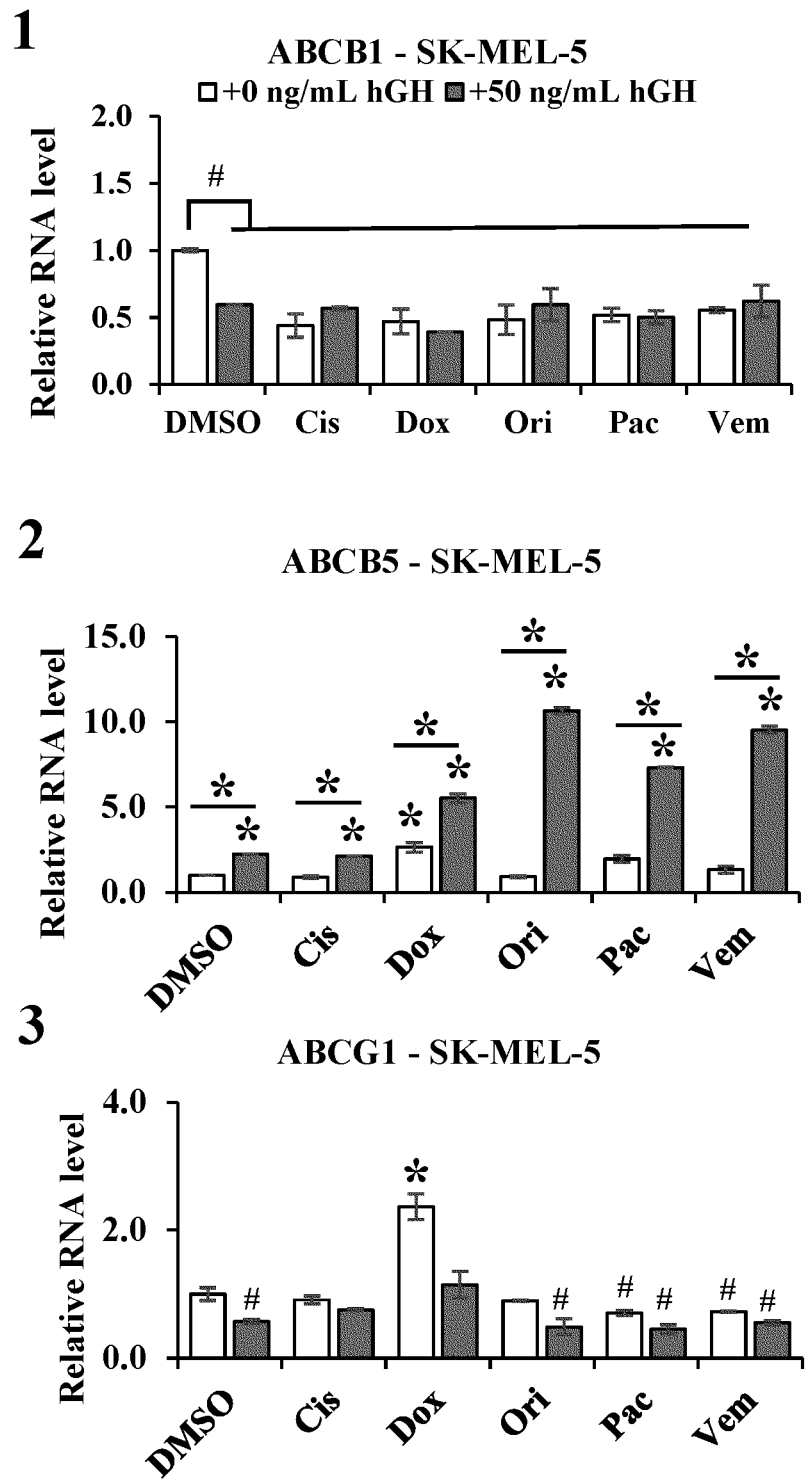

Referring now to FIGS. 30A-30C and 31A-31C, FIGS. 30A-30C show the effect of GHR excess on ABCB8, ABCC1, ABCC2 and ABCG2 expressions following drug treatment in human melanoma cells, and FIGS. 31A-31C show the effect of GHR excess on ABCB1, ABCB5, and ABCG1 expressions following drug treatment in human melanoma cells. More specifically, FIGS. 30A-30C shows relative RNA expression of the four most abundantly expressed drug transporters of the ABC-family transporters in SK-MEL-28 (FIG. 30A), MALME-3M (FIG. 30B), and SK-MEL-5 (FIG. 30C) melanoma cells following 24-hour exposure to different anti-cancer drugs in absence or presence of 50 ng/mL GH was done. (Cis=cisplatin, dox=doxorubicin, ori=oridonin, pac=paclitaxel, vem=vemurafenib). Expressions were normalized against expression of beta-actin and GAPDH as reference genes. [*, p<0.05, Wilcoxon sign rank test, n=3]. And FIGS. 31A-31C more specifically shows relative RNA expression of the ABC-family of drug transporters in SK-MEL-28 (FIG. 31A), MALME-3M (FIG. 31B), and SK-MEL-5 (FIG. 31C) melanoma cells following 24-hour exposure to different anti-cancer drugs in absence or presence of 50 ng/mL GH was done. (Cis=cisplatin, dox=doxorubicin, ori=oridonin, pac=paclitaxel, vem=vemurafenib), Expressions were normalized against expression of beta-actin and GAPDH as reference genes. [*, p<0.05, Wilcoxon sign rank test, n=3]. As can be seen from the figures, SK-MEL-28 cells showed an upregulation in ABCB8 (in response to Doxorubicin and vemurafenib) (FIG. 30A, panel 1), ABCC1 (in response to vemurafenib) (FIG. 30A, panel 2), ABCG2 (in response to oridonin and paclitaxel) (FIG. 30A, panel 4), and ABCB1 (in response to doxorubicin and vemurafenib) (FIG. 31A, panel 1) in presence of GH. MALME-3M cells showed a similar increase in ABCB8 (in response to cisplatin) (FIG. 30B, panel 1), ABCC2 (in response to doxorubicin) (FIG. 30B, panel 3), ABCB1 (in response to oridonin) (FIG. 31B, panel 1), and ABCG1 (in response to doxorubicin) (FIG. 31B, panel 3). In SK-MEL-5 melanoma cells too, excess GH also caused an increase of ABCB8 (in response to cisplatin and vemurafenib) (FIG. 30C, panel 1), ABCC2 (in response to oridonin) (FIG. 30C, panel 3), ABCG2 (in response to cisplatin, oridonin and vemurafenib) (FIG. 30C, panel 4), and ABCB5 (in response to cisplatin, doxorubicin, oridonin, paclitaxel and vemurafenib) (FIG. 31C, panel 2). The presence of GH also caused downregulation of some ABC-transporters (FIGS. 30A-30C and 31A-31C). However, the level of decrease was ~2-fold and not consistently observed to increase on GHR-KD.

Figure 32A:
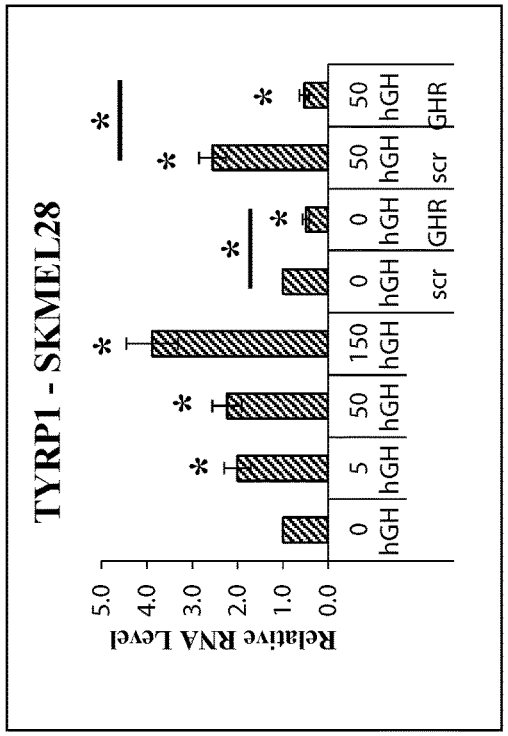
FIGS. 32A-32H include graphs showing that regulators of melanogenesis pathway are influenced by GH action in melanoma cells.
Figure 32B:
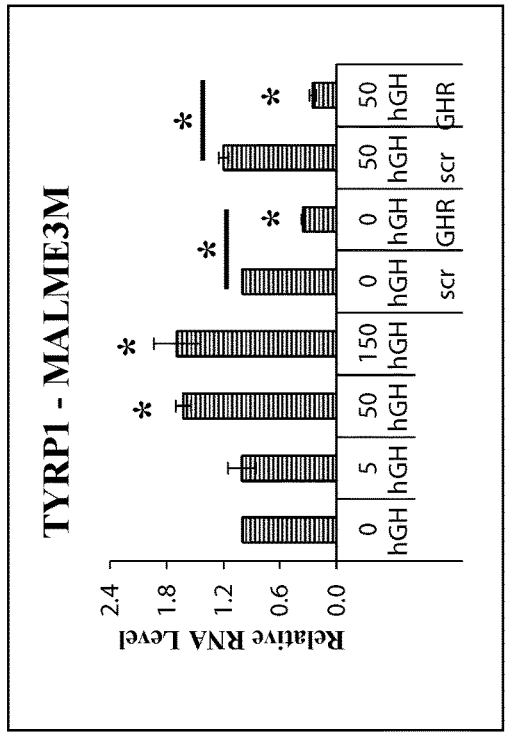
Figure 32C:
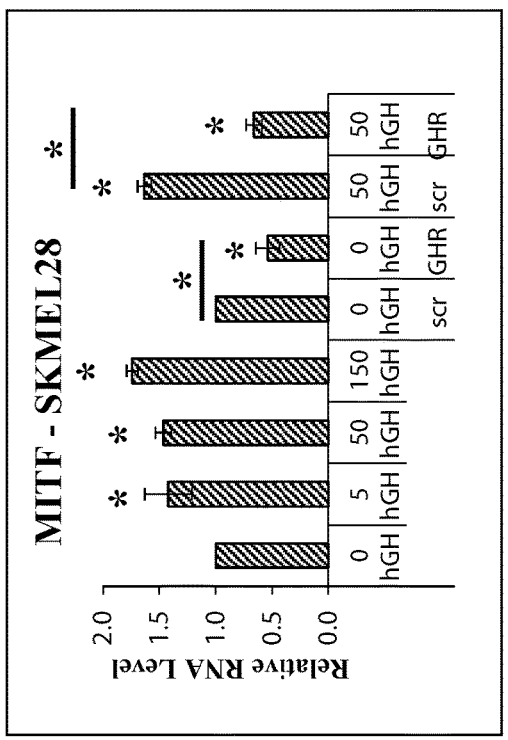
Figure 32D:
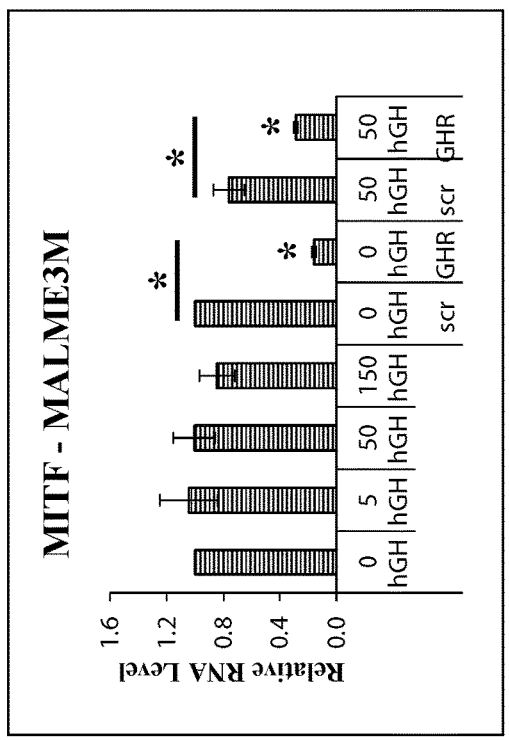
Figure 32E:
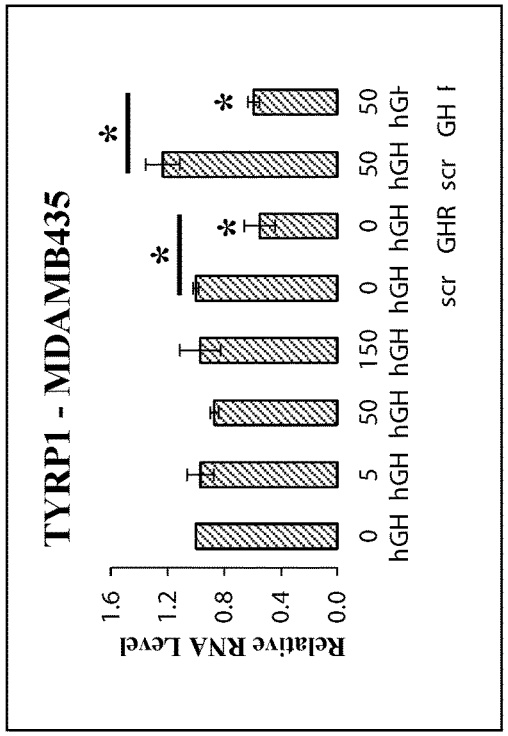
Figure 32F:
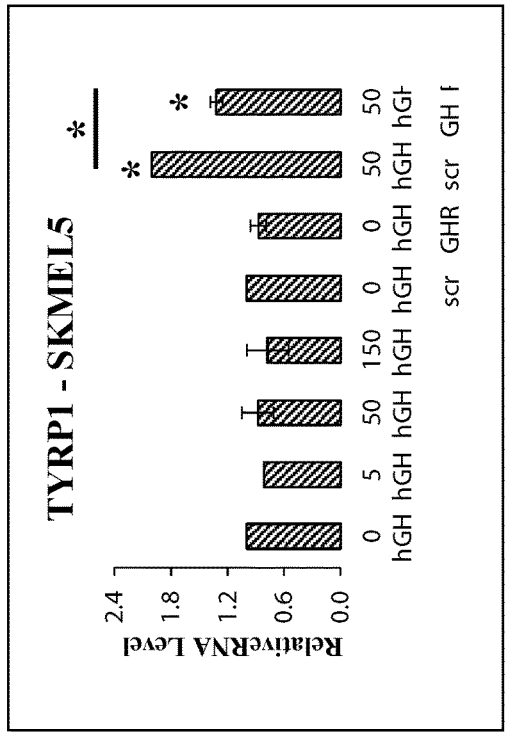
Figure 32G:
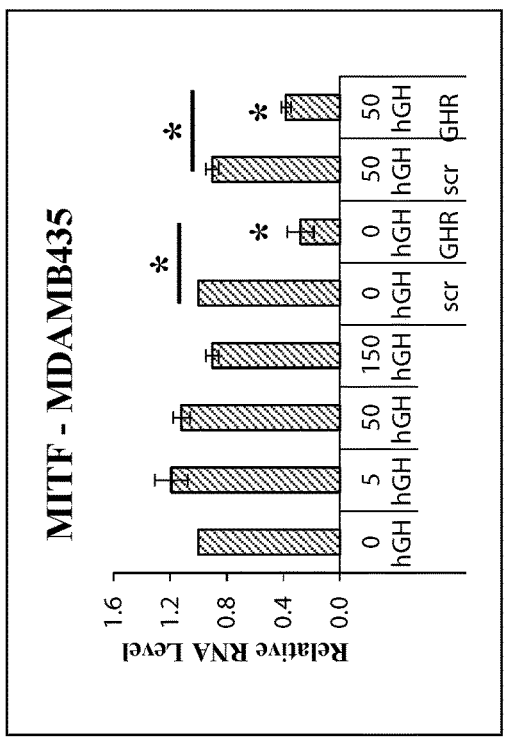
Figure 32H:
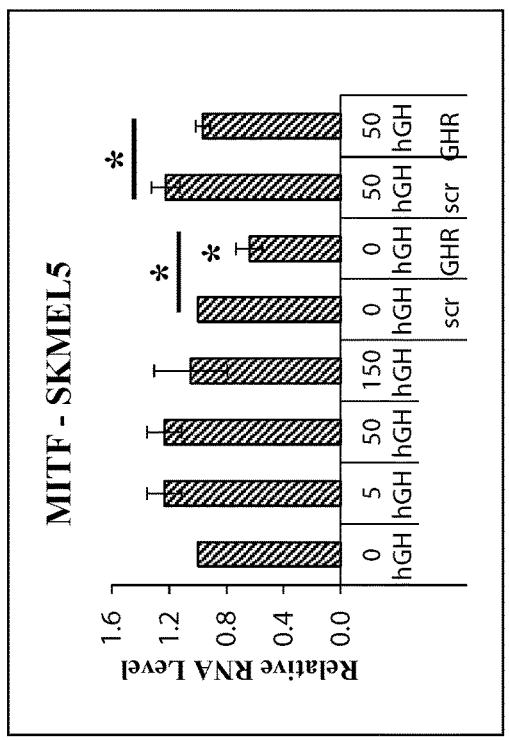
Figure 33A:
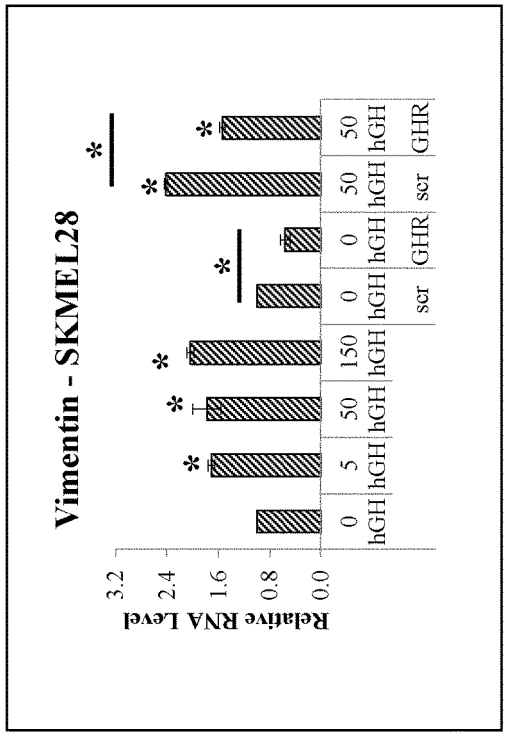
FIGS. 33A-33L include graphs showing that markers of EMT are strongly modulated by GH action in melanoma cells.
Figure 33B:
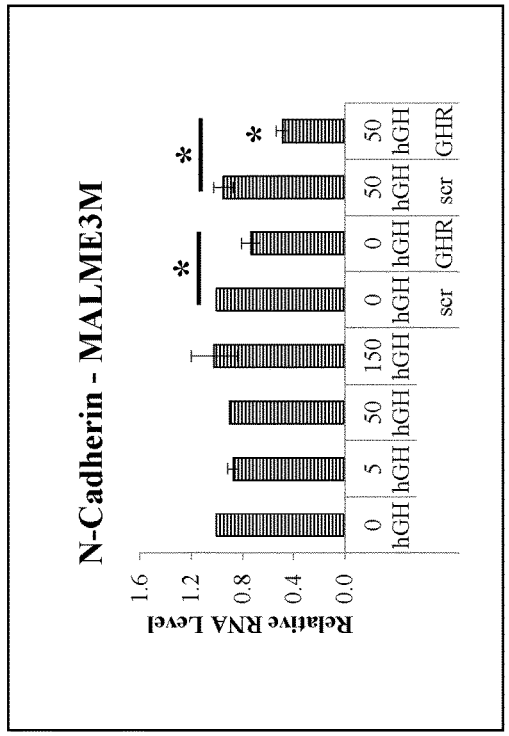
Figure 33C:
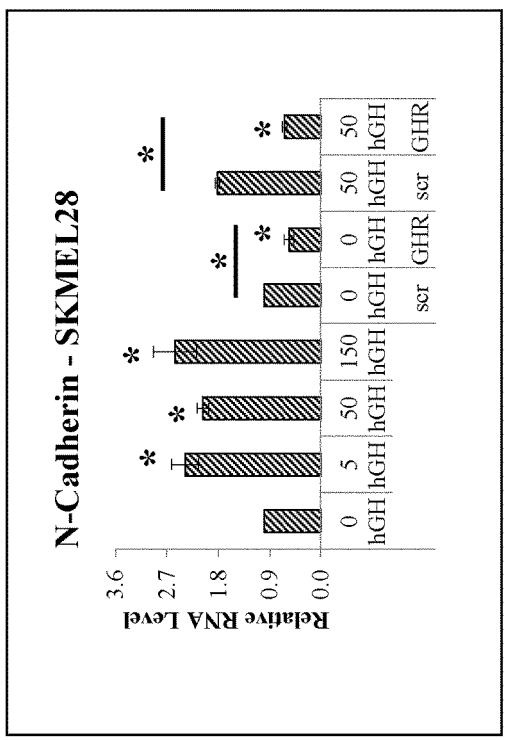
Figure 33D:
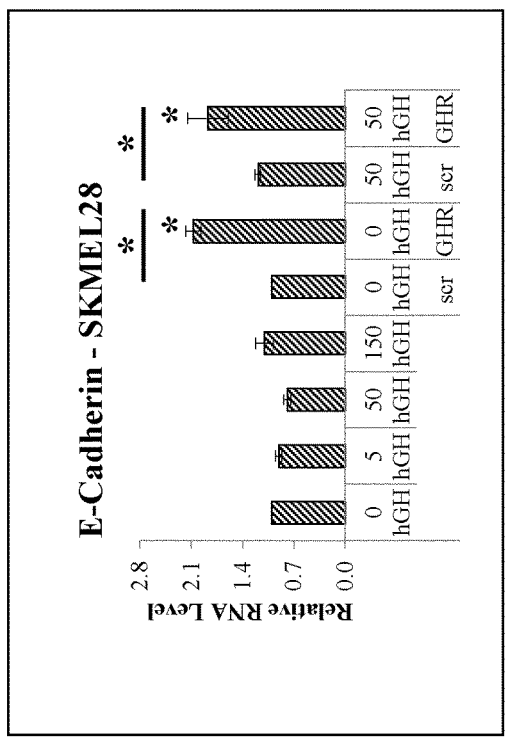
Figure 33E:
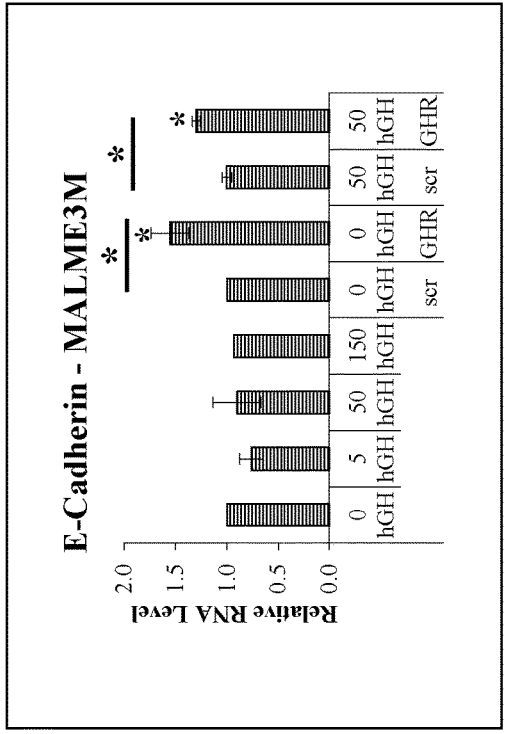
Figure 33F:
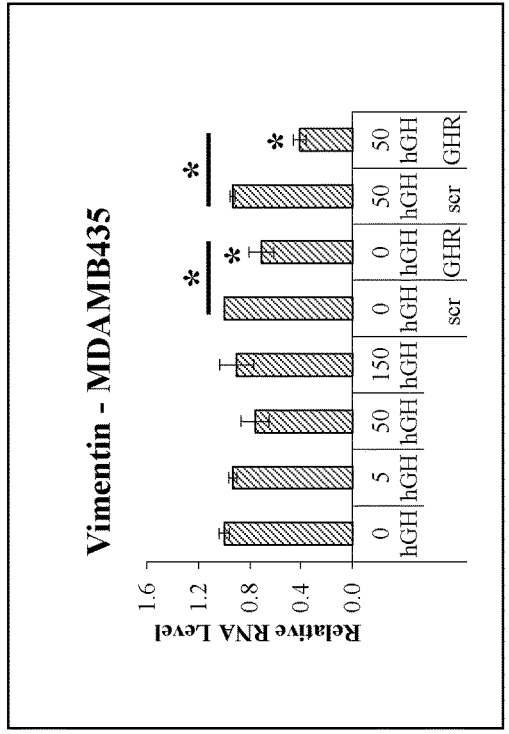
Figure 33G:
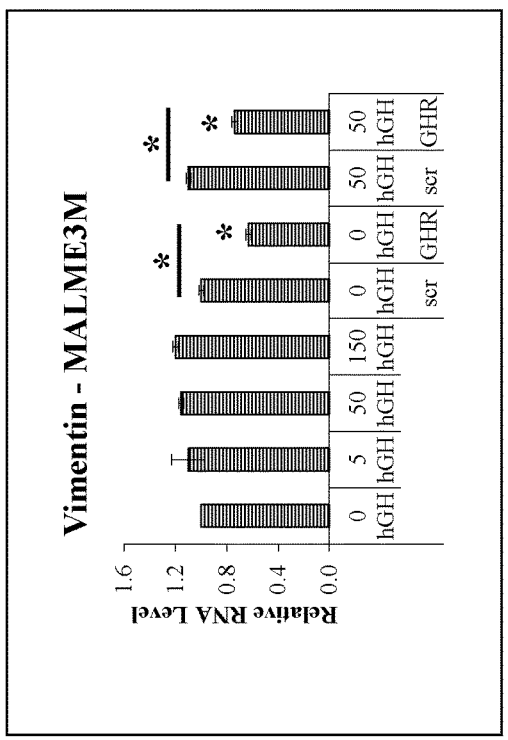
Figure 33H:
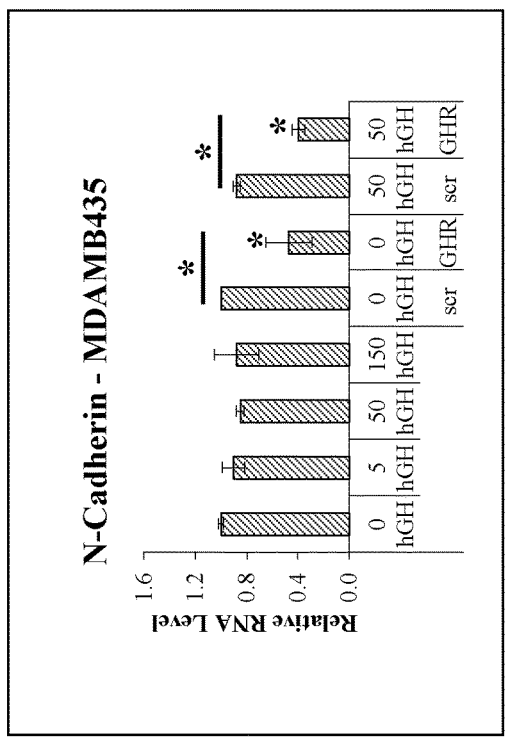
Figure 33I:
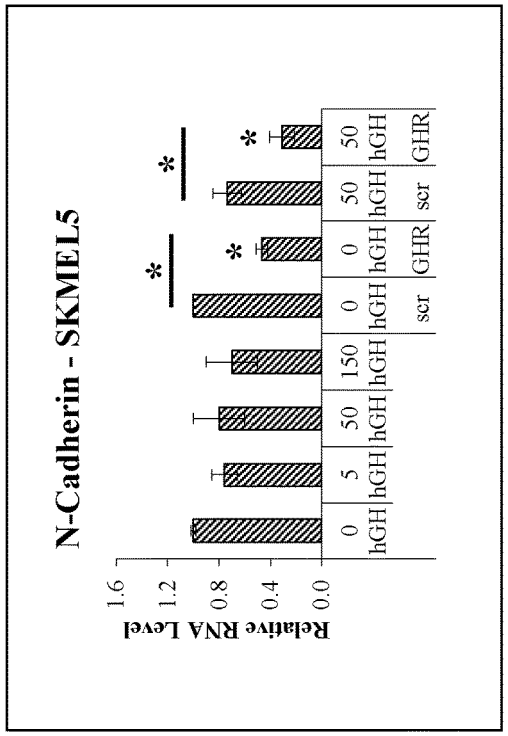
Figure 33J:
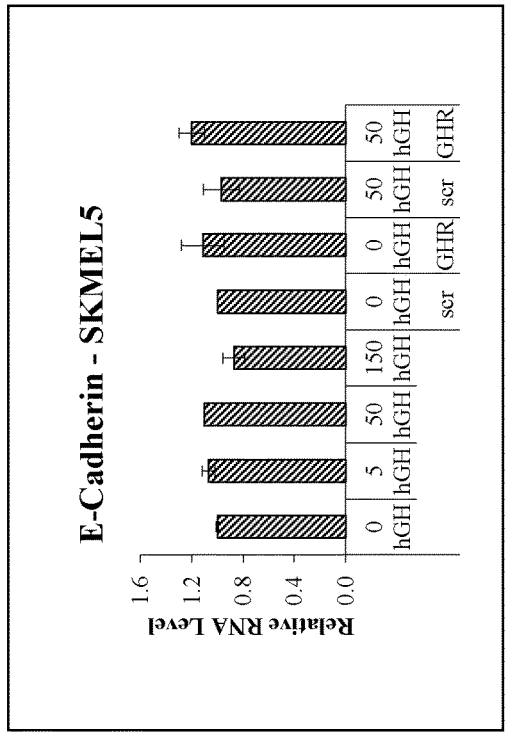
Figure 33K:
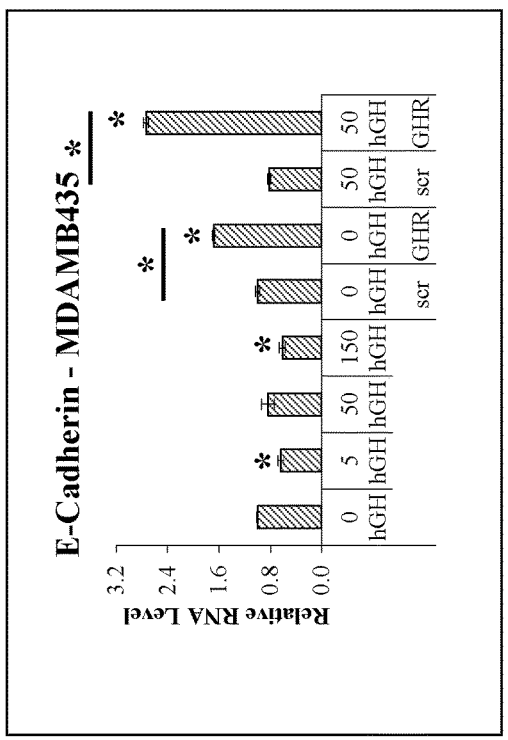
Figure 33L:
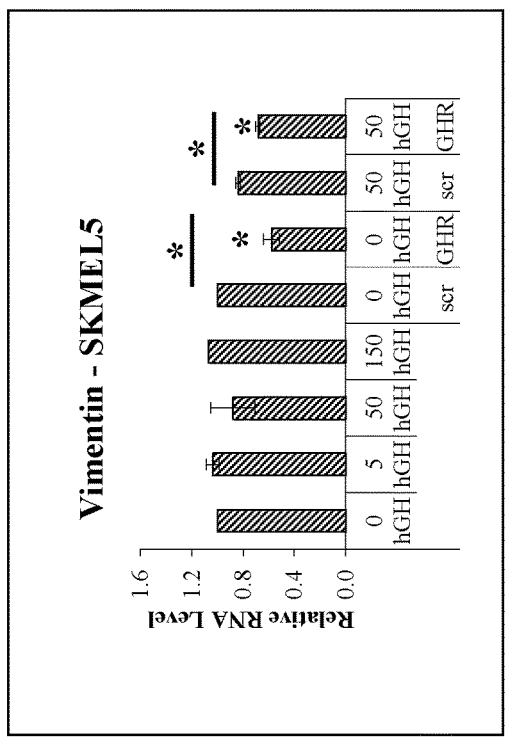

GHR knock-down significantly suppresses RNA levels of melanogenesis regulators in human melanoma cells: The RNA levels of two key components of the melanogenesis pathway MITF and TYRP1 with modulation of the GH/GHR levels were investigated. Referring to FIGS. 32A-32H, relative RNA expression was quantified for MITF (FIGS. 32A, C, E, and G) and TYRP1 (FIGS. 32B, D, F, and H) in SK-MEL-28 (FIGS. 32A-32B), MALME-3M (FIGS. 32C-32D), MDA-MB-435 (FIGS. 32E-32F) and SK-MEL-5 (FIGS. 32G-32H) melanoma cells following addition of 0, 5, 50 and 150 ng/mL hGH or following GHR-KD, in presence or absence of 0 and 50 ng/mL hGH. In all cases, exogenous GH treatment was for 24 hr. RNA expressions were quantified by RT-qPCR and normalized against expression of ACTB and GAPDH as reference genes. [*, p<0.05, Wilcoxon sign rank test, n=4]. A robust downregulation of MITF expression was observed in all four GHR-KD melanoma cells relative to the scramble siRNA-treated controls, irrespective of added GH (FIGS. 32A, 32C, 32E, and 32G). SK-MEL-28 cells also exhibited a GH dose dependent increase in RNA levels of MITF (FIG. 32A). A GH dose-dependent increase in RNA levels was also observed for the MITF target TYRP1 in SK-MEL-28 (FIG. 32B), as well as in MALME-3M cells (FIG. 32D). Additionally, reduced GHR expression correlated with a significant decrease in TYRP1 levels in all four melanoma cell lines (FIGS. 32B, 32D, 32F, and 32H).

GHR knock-down significantly modulates markers of EMT in human melanoma cells: Referring now to FIGS. 33A-33L and 34A-34D, the changes in important markers of epithelial mesenchymal transition (EMT) in melanoma cells, following a modulation in the GH-GHR axis, were investigated. As shown in FIGS. 33A-33L, relative RNA expression was quantified for N-Cadherin, E-Cadherin, and vimentin in SK-MEL-28, MALME-3M, MDA-MB-435 and SK-MEL-5 melanoma cells following addition of 0, 5, 50 and 150 ng/mL hGH or following GHR-KD, in presence or absence of 0 and 50 ng/mL hGH. In all cases, exogenous hGH treatment was for 24 hr. RNA expressions were quantified by RT-qPCR and normalized against expression of ACTB and GAPDH as reference genes. [*, p<0.05, Wilcoxon sign rank test, n=4]. And, as shown in FIGS. 34A-34D, changes in protein expressions of vimentin (FIG. 34A), E-cadherin (FIG. 34B) and N-cadherin (FIG. 34C) were analyzed. WB comparison (FIG. 34D) was done in all four melanoma cells, 60 hr. post-transfection with GHR- or scr-siRNA. Blots were quantified using ImageJ software and mean of three blots per sample was taken. Expression levels were normalized against expression of ACTB (B-actin), [*, p<0.05, Students t test, n=3].

Figure 34A:
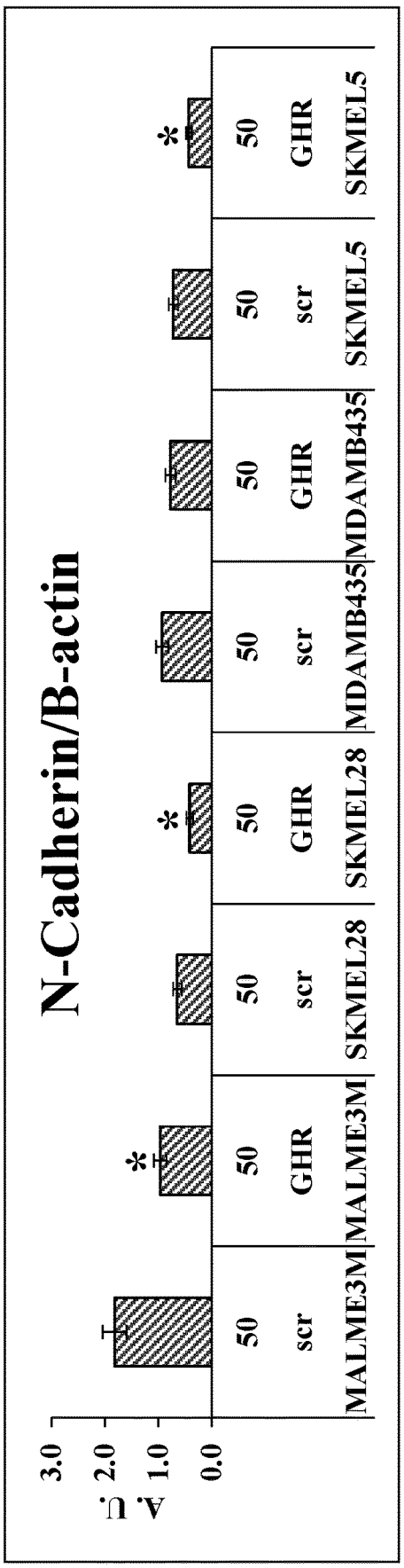
FIGS. 34A-34D include graphs and photographs showing a change in markers of epithelial mesenchymal transition (EMT) following GHR-KD.
Figure 34B:
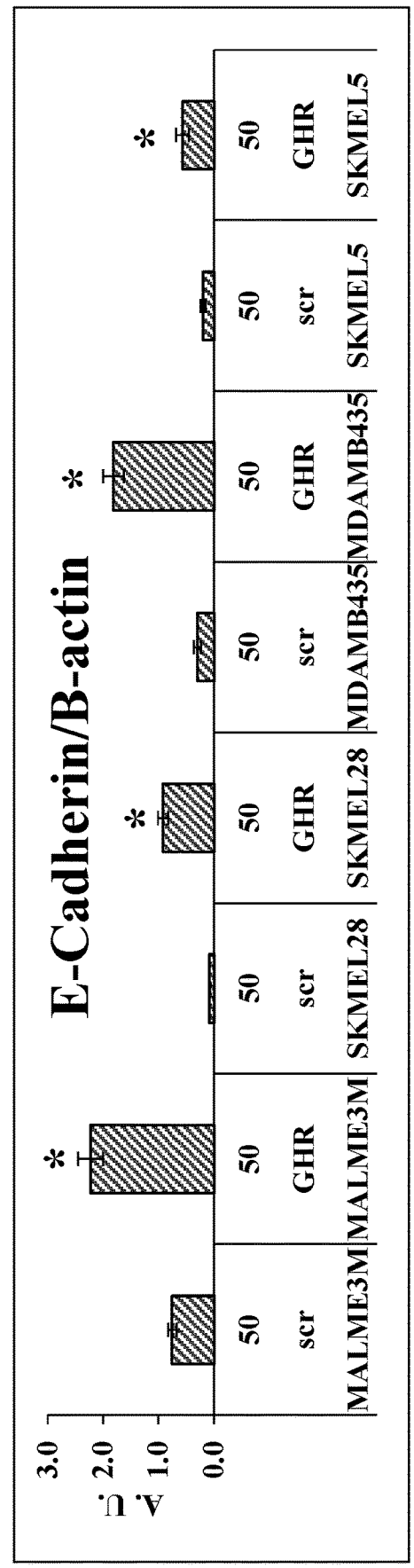
Figure 34C:
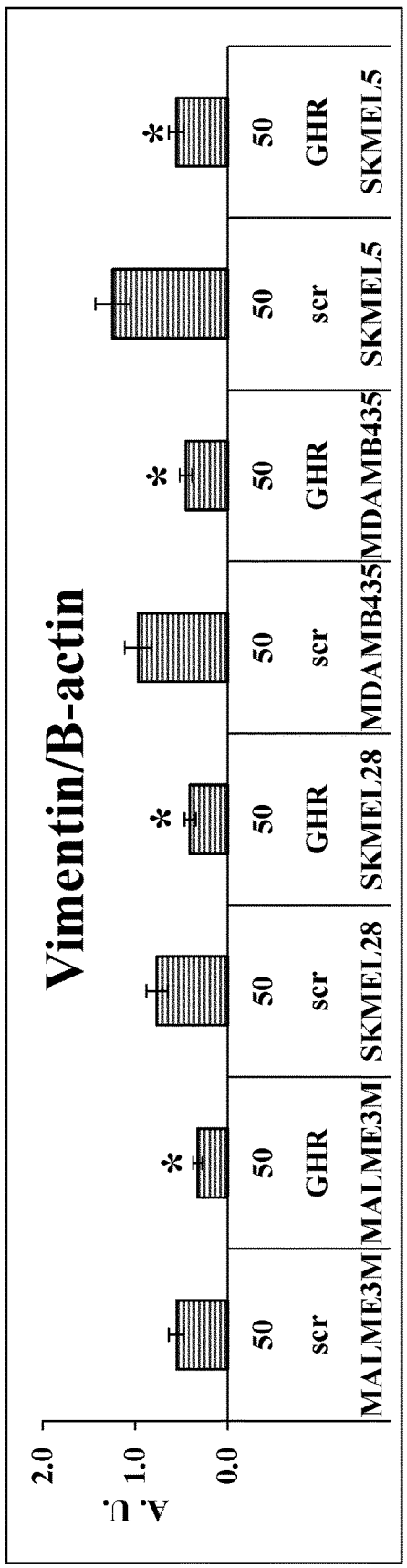

In those analyses, a significant dose-dependent increase of N-cadherin and vimentin RNA levels was observed with increase of GH (FIGS. 33A and 33B) in SK-MEL-28 cells, while the same remained constant for the other three cell lines. The epithelial marker E-cadherin RNA levels were low for all four cell lines, which levels decreased significantly (FIG. 33I) with increasing GH for MDA-MB-435 cells but not for the other cell lines. Increased levels of E-cadherin RNA levels were observed following GHR-KD, which levels are normally found in low levels in the human malignant melanoma cells (FIGS. 33A-33L and 34A-34D). A concomitant significant decrease was observed in the RNA levels of N-cadherin (FIGS. 33A, 33D, 33G, and 33J) and vimentin (FIGS. 33B, 33E, 33H, and 33K) with GHR-KD consistently in all four melanoma cell lines in this example. Western blot analysis showed results consistent with the RNA level variations of E-cadherin, N-cadherin and vimentin following GHR-KD (FIGS. 34A, 34B, and 34C). This is the first report on the variations of EMT markers under decreased GHR or increased GH levels in human melanoma cells.

Figure 35A:
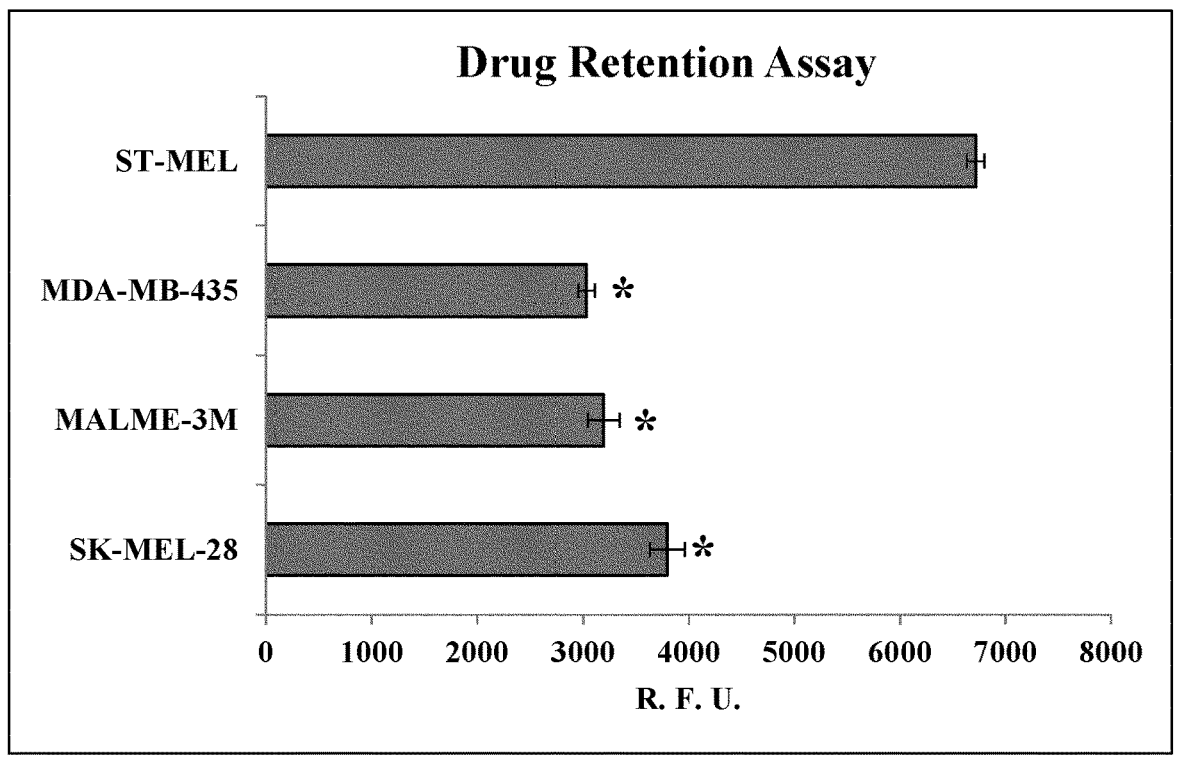
FIGS. 35A-35D include graphs showing that GHR-KD resulted in increased drug retention and drastically reduced proliferation of melanoma cells, FIG. 36 includes microphotographs showing the effect of drug treatment on level of Ki-67-cell proliferation marker in SK-MEL-28 cells following GHR-KD and drug treatment.
Figure 35B:
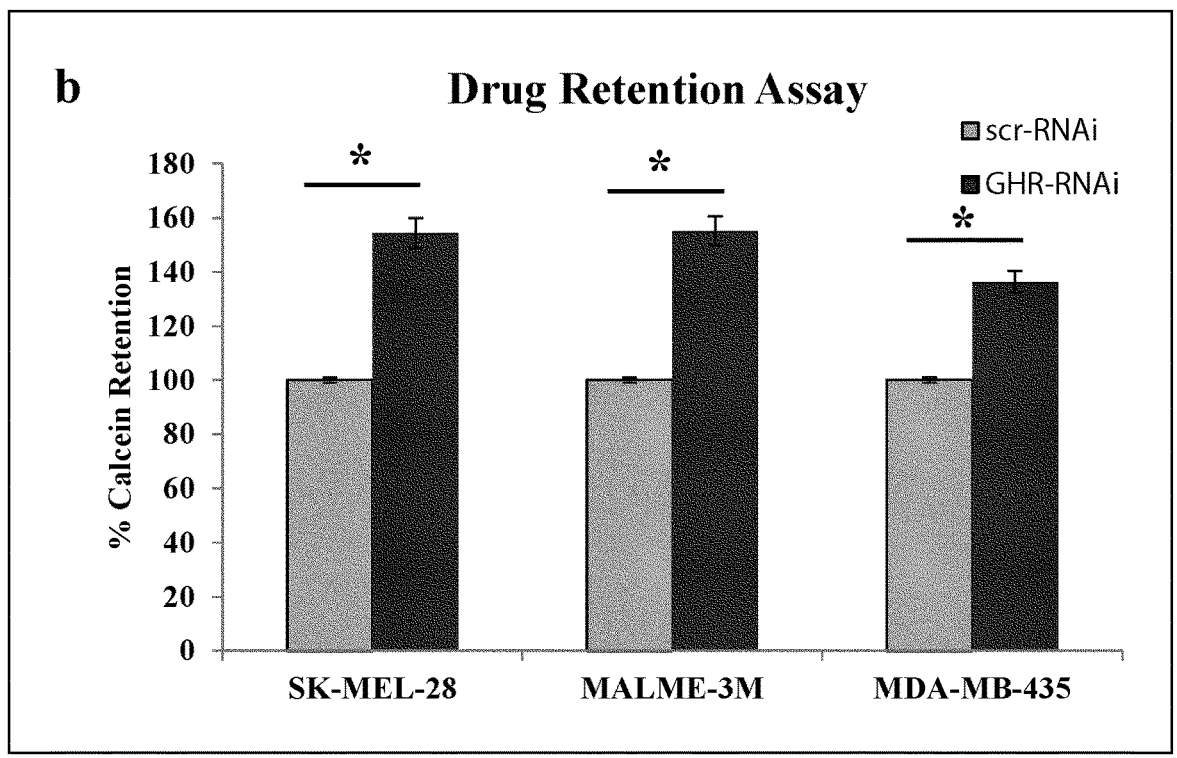

GHR knock-down leads to significantly higher drug retention and dramatically suppresses cell proliferation in response to sub-$EC_{50}$ doses of chemotherapy in human melanoma cells: A significant suppression of expression of several efflux pumps, as observed herein, should translate into a longer retention of xenobiotic (chemotherapeutic) compounds inside the GHR-KD melanoma cells relative to the scramble siRNA-treated controls. To determine this, and referring now to FIGS. 35A-35D, changes in amounts of calcein retained inside cells following treatment with calcein-AM ester was analyzed by the fluorescence readout from intracellular calcein. Increased abundance of transporter pumps is reflected by decreased levels of intracellular calcein. In the reported fluorometric calcein retention assay, which is sensitive to ABCB1 and ABCC1 mediated drug efflux activity, a significantly lower concentration of retained calcein was observed in the human melanoma cells compared to melanocytes (FIG. 35A), Following GHR-KD, significantly higher concentration of calcein was retained inside GHR-siRNA transfected melanoma cells relative to the scramble siRNA transfected controls (FIG. 35B). The result corroborated the above observations demonstrating the importance of the GH-GHR interaction in multi-drug resistance in melanoma. More specifically, in FIG. 35A, there was significantly lower calcein retention in human melanoma cells compared to human melanocyte ST-MEL; and in FIG. 35B, humanmelanoma cells exhibit significantly higher levels of intracellular calcein following GHR-KD. Assays were performed 48 hr. post-transfection with either scr-siRNA or GHR-siRNA. Effect of GHR-KD on cell proliferation following 24 hr. exposure to $EC_{50}$ levels of cisplatin and paclitaxel was tested. SK-MEL-28 (FIG. 35C) and MALME-3M (FIG. 35D) cells were exposed to DMSO (vehicle), or 10 um cisplatin (Cis), or 5 nM paclitaxel (Pac) for 24 hr. Treatments were done 48 hr. post-transfection with either scr-siRNA (scr) or GHR-siRNA (GHR). Mean of three independent experiments performed in triplicate was taken. [*, p<0.05, Students t test, n=3]

Figure 36:
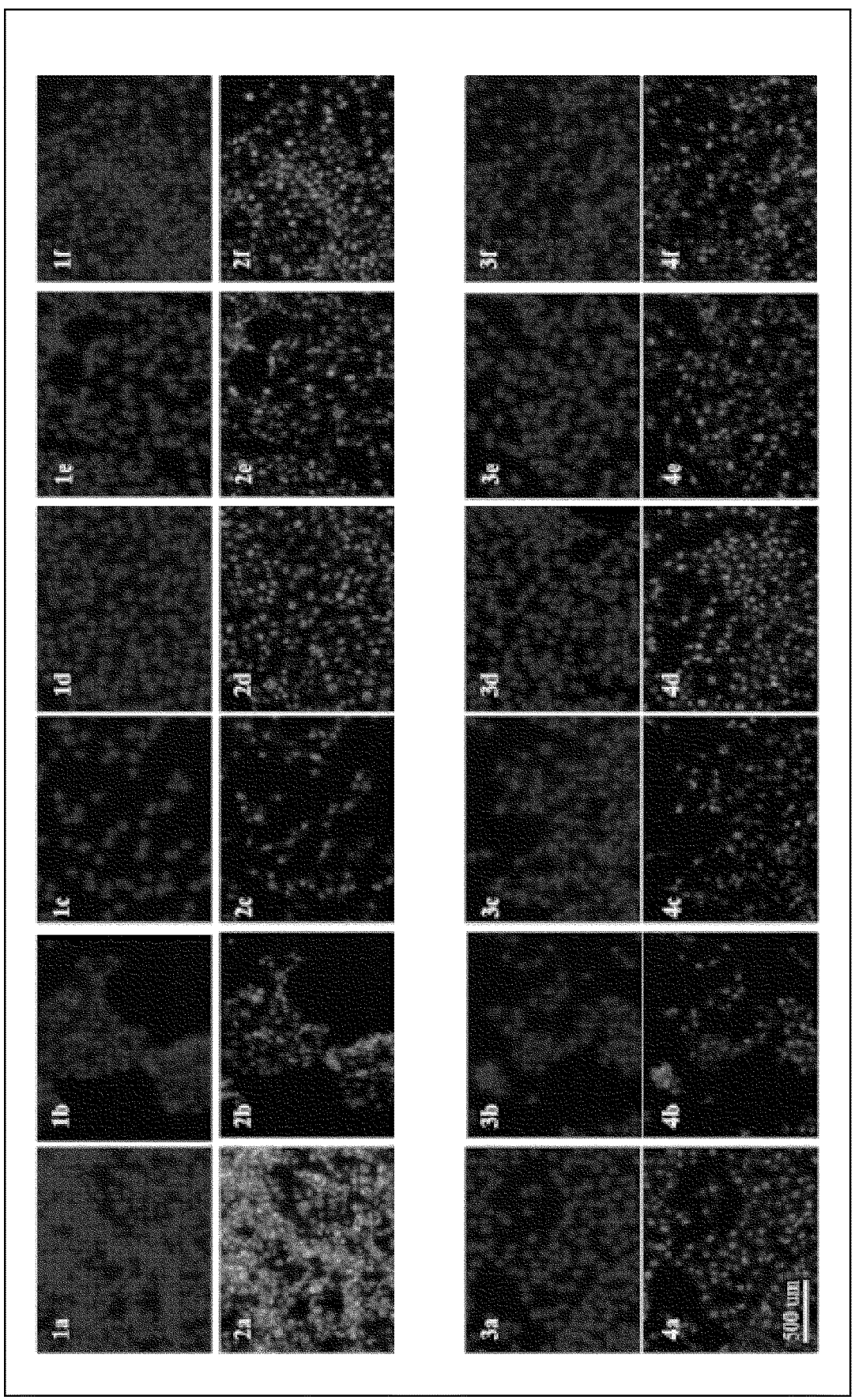

In order to evaluate the effects of decreased levels of drug efflux pumps and significantly higher drug retention times in GHR-KD melanoma cells, an immunofluorescence analysis was performed of the expression of Ki-67, an abundantly expressed marker of cell proliferation routinely used to observe changes in cell viability, including cancer cell viability. The Ki-67 fluorescence levels in GHR-KD were compared to those of scramble siRNA treated melanoma cells, following a 24 hour treatment with cisplatin (0.5 μM), doxorubicin (10 nM), oridonin (0.5 μM), paclitaxel (1 nM), and vemurafenib (2 nM). More specifically, and referring now to FIG. 36, the effect of drug treatment on level of Ki-67-cell proliferation marker in SK-MEL-28 cells following GHR-KD and drug treatment is shown. SK-MEL-28 cells were exposed to DMSO (FIG. 36 pictures designated with letter a), 0.5 um cisplatin (FIG. 36 pictures designated with letter b), 10 nM doxorubicin (FIG. 36 pictures designated with letter c), 0.5 uM oridonin (FIG. 36 pictures designated with letter d), 1 nM paclitaxel (FIG. 36 pictures designated with letter e) or 15 nM vemurafenib (FIG. 36 pictures designated with letter f) for 24 hr. Treatments were done 48 hr. post-transfection with either scr-siRNA (panels 1 and 2 of FIG. 36) or GHR-siRNA (panels 3 and 4 of FIG. 36). Panels 1 and 3 show cellular DNA stained with DAPI while panels 2 and 4 show fluorescence signals from AF488-tagged anti-Ki67 antibody. In FIG. 36, picture was taken at 40× magnification; and scale bar represents 500 μm. A dramatic decrease in Ki-67 markers was observed across all four melanoma cells following GHR KD at dosages 2-10-fold lower than the $EC_{50}$ doses of the drugs. SK-MEL-28 cells showed particularly consistent decrease in Ki-67 levels following GHR KB when exposed to sub-$EC_{50}$ levels of cisplatin and vemurafenib (FIG. 36).

Figure 35C:
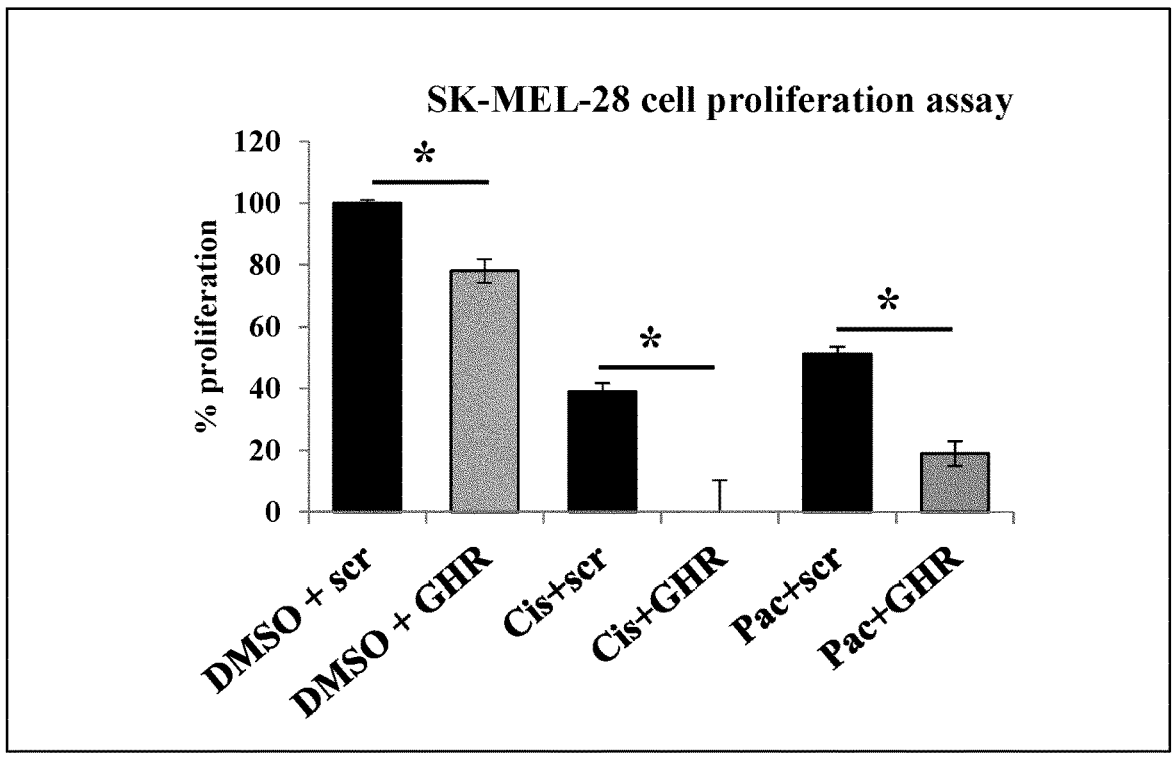
Figure 35D:
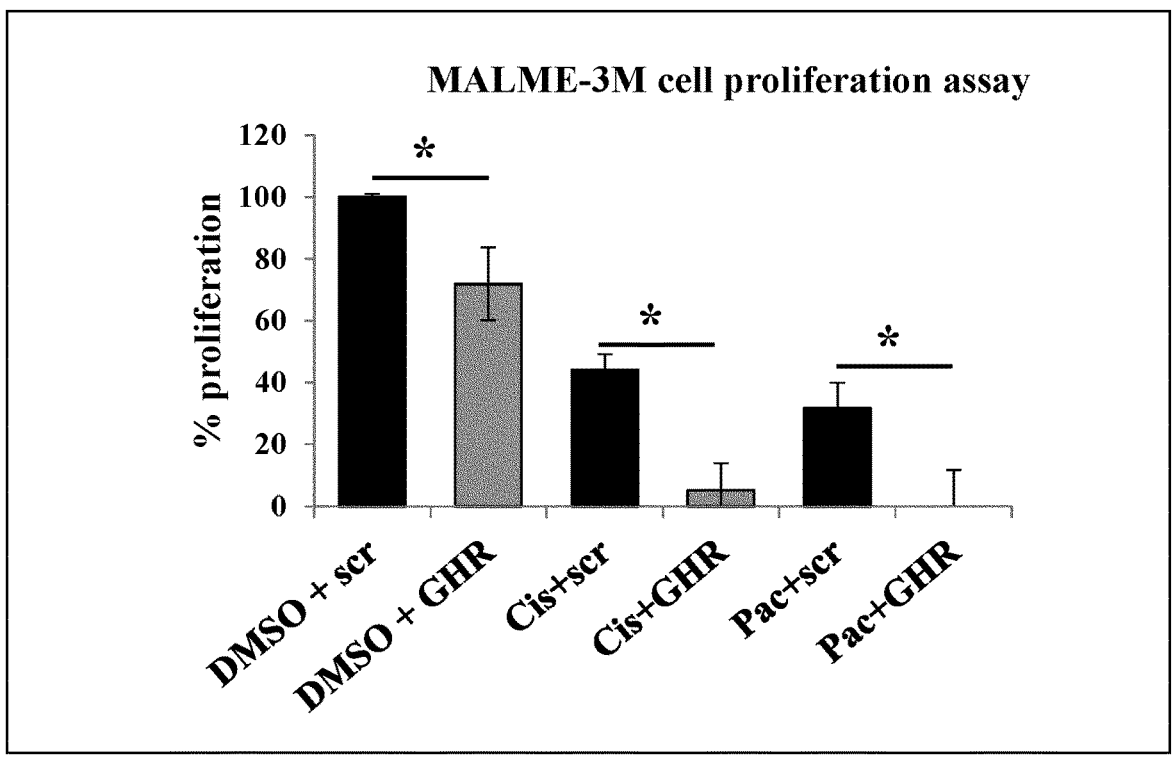
Figure 37:
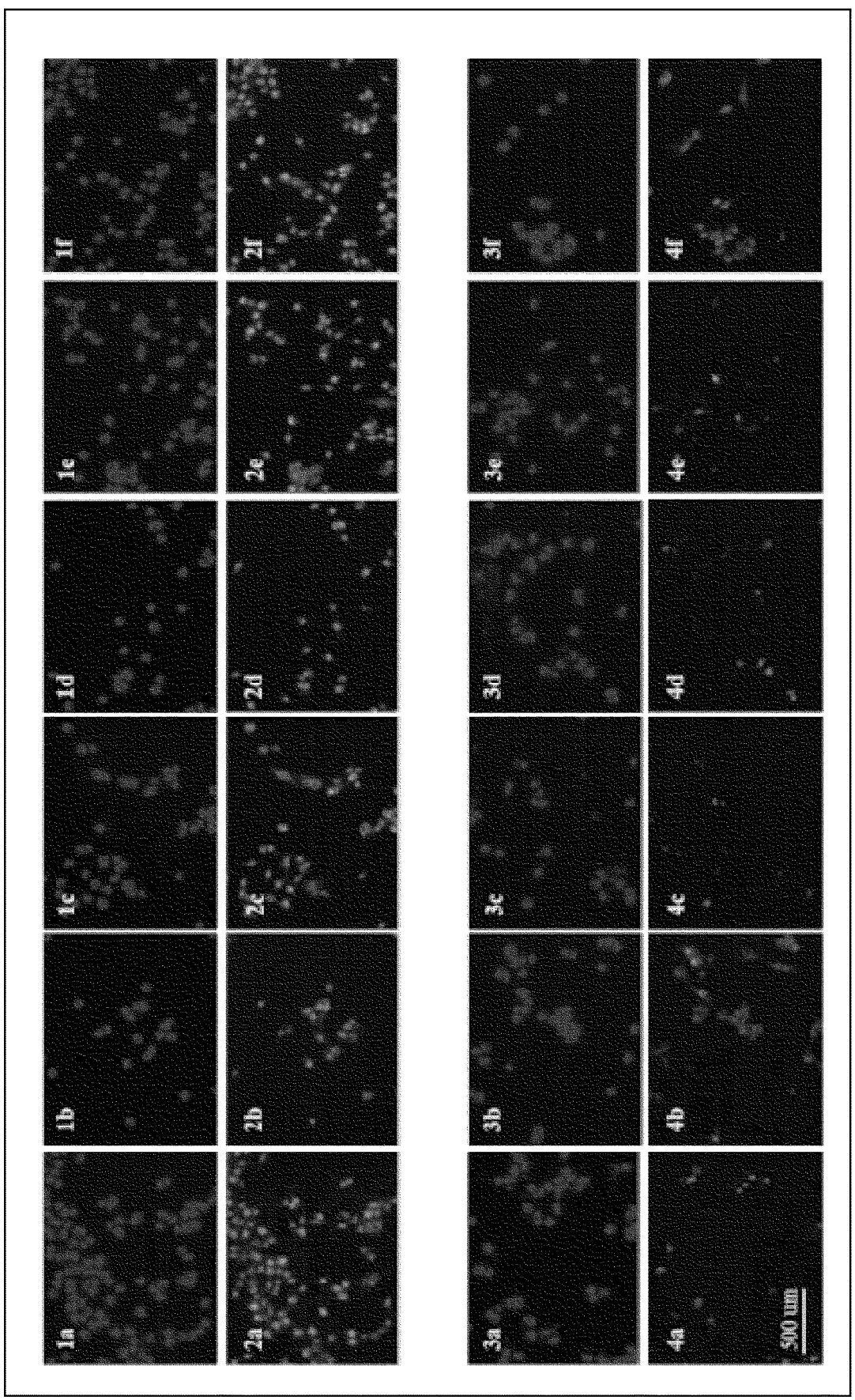
FIG. 37 includes microphotographs showing the effect of drug treatment on level of Ki-67-cell proliferation marker in MALME-3M cells following GHR-KD and drug treatment.
Figure 38:
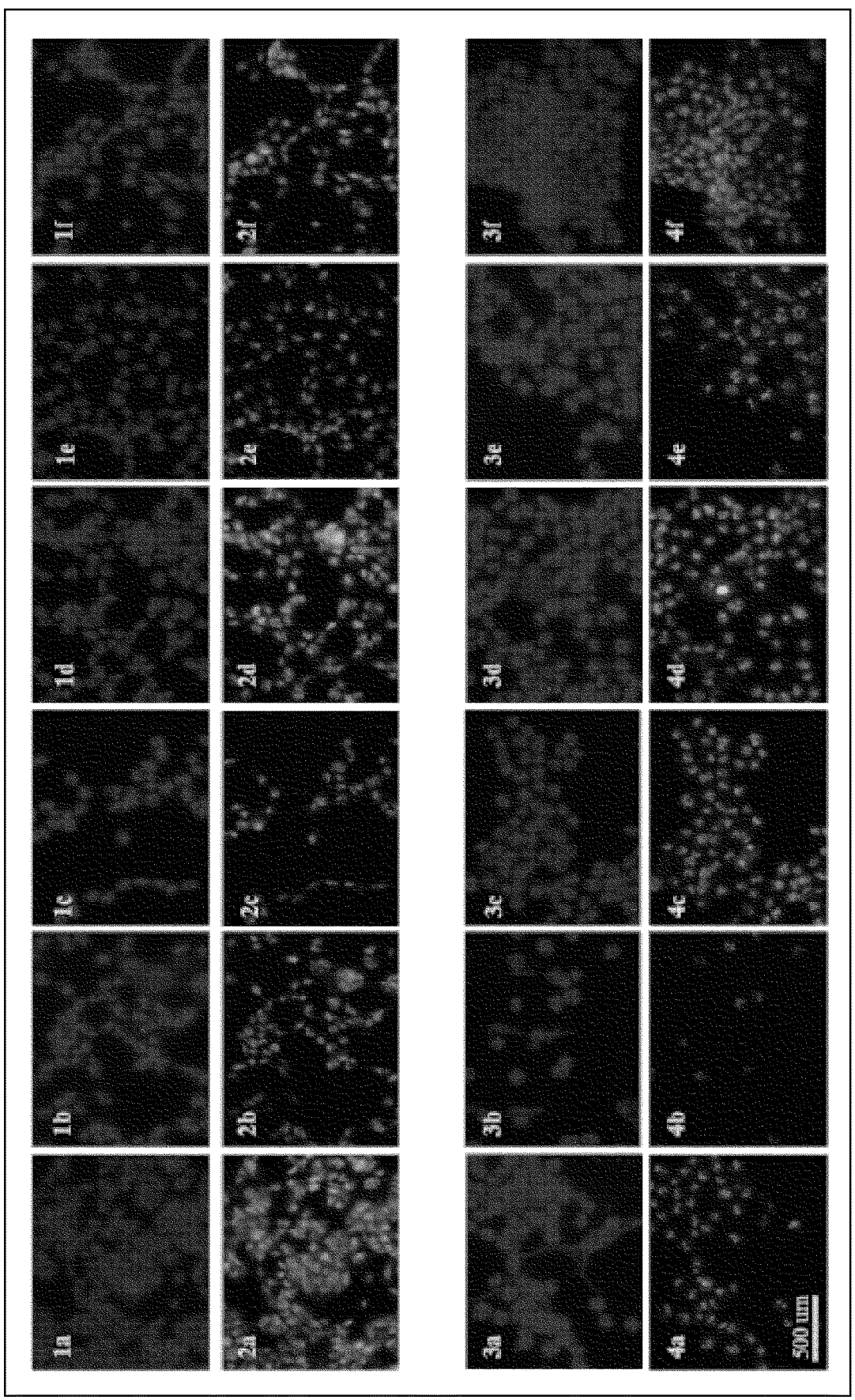
FIG. 38 includes microphotographs showing the effect of drug treatment on level of Ki-67-cell proliferation marker in MDA-MB-435 cells following GHR-KD and drug treatment.
Figure 39:
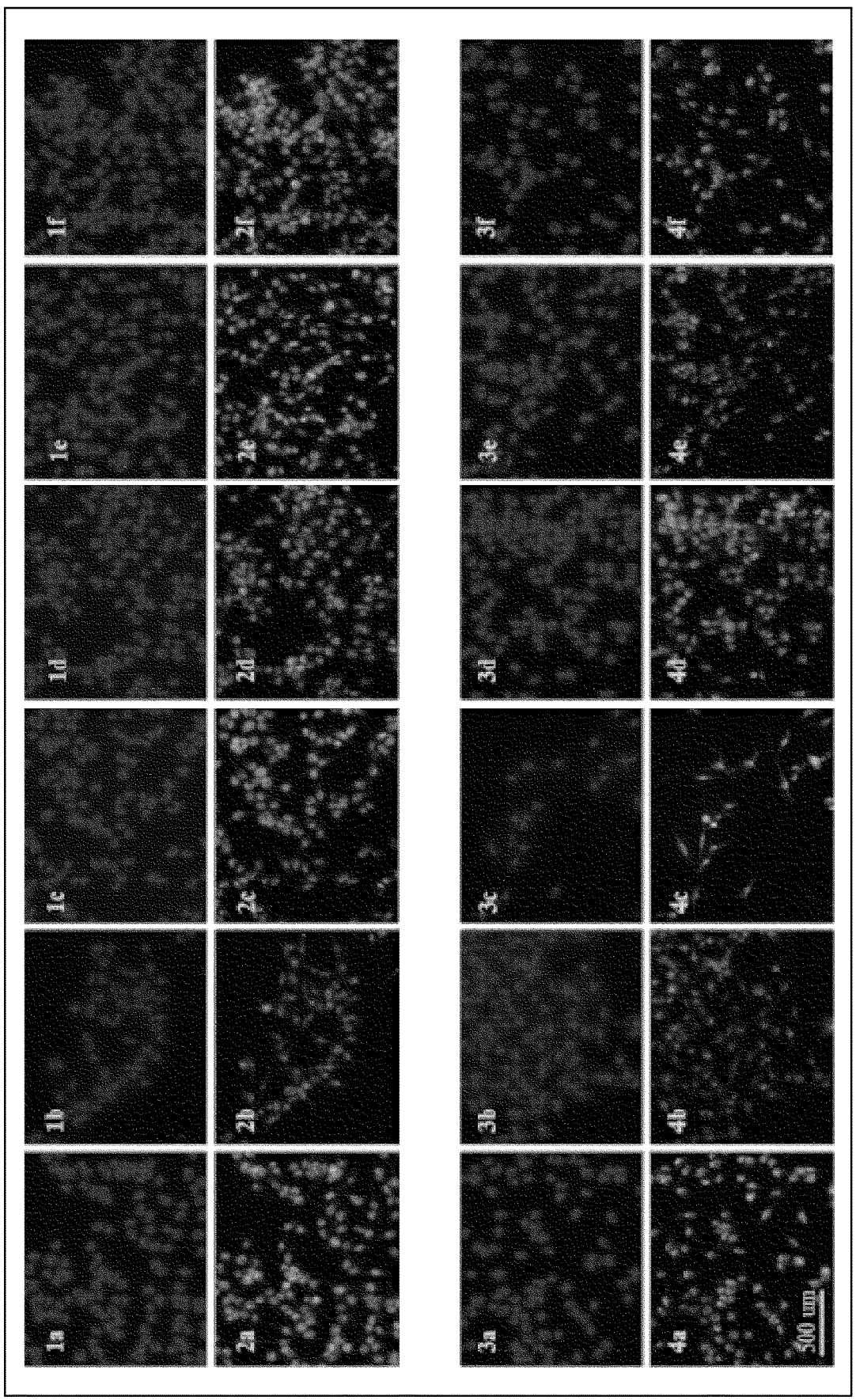
FIG. 39 includes microphotographs showing the effect of drug treatment on level of Ki-67-cell proliferation marker in SK-MEL-5 cells following GHR-KD and drug treatment.

Similar analyses were performed on MALME-3M cells (shown in FIG. 37), MDA-MB-435 cells (shown in FIG. 38), and SK-MEL-5 cells (shown in FIG. 39). MALME-3M cells showed the most drastic and consistent decrease in Ki-67 levels following GHR-KD when exposed to all five anti-tumor compounds tested (FIG. 37). Similar reduction in cell proliferation was observed in MDA-MB-435 cells on exposure to cisplatin (FIG. 38). FIG. 39 shows results in SK-MEL-5 cells, as well. When the cell proliferation levels of SK-MEL-28 and MALME-3M cells were quantified following exposure to $EC_{50}$ levels of cisplatin (10 μM) and paclitaxel (5 nM), with and without siRNA mediated KD of GHR, drastic inhibition (>90%) was observed in all cases (FIGS. 35C and 35D). The results emphasized a net result of sensitization of the human melanoma cells to low doses of anti-cancer drugs following GHR-KD.

Discussion of Above Results

The ABC transporter pumps are ATP dependent xenobiotic efflux pumps which are employed by various cancer cells as an important mechanism of lowering the intracellular accumulation of cytotoxic anti-cancer drugs. Melanoma expresses a number of ABC efflux pumps, the RNA levels of which were specifically investigated for ABCB1, ABCB5, ABCB8, ABCC1, ABCC2, ABCG1, and ABCG2 based on reports of their presence and drug-resistance activity in human melanoma. The results of the investigation of ABC transporters reported above and compiled in Table 1 provides data not only in the context of the effect of GHR-KD on expression of ABC transporters mediating multi-drug resistance in human melanoma, but also identifies cell-specific and multiple drug-specific variations of seven different ABC transporters in melanoma. The results reveal a specific expression profile of several ABC transporter pumps in melanoma cells following exposure to specific anti-tumor compounds in the context of decreased GHR, and establish a novel role and regulation of GH in multi-drug resistance in melanoma.

Recent studies in GHR knock-out (GHRKO) mice identified decreased levels of melanocyte stimulating hormone (MSH) compared to their wild-type littermates. Since MSH is a potent regulator of melanogenesis in melanocytes as well as melanoma, it is reasonable to speculate a GH-dependent variation in melanogenesis in these cells. To that end, the levels of two key regulators of melanogenesis, i.e. tyrosinase related protein 1 (TYRP1) and its transcriptional regulator the microphthalmia associated transcription factor (MITF), were investigated. TYRP1 is a rate limiting enzyme in melanin synthesis pathway. A potent downregulation of the phosphorylation states of ERK1/2 and AKT/mTOR pathways with GHR-KD has been observed, as has a dose-dependent increase with additional GH. See Example 1, above. This is especially relevant with respect to MITF regulation, following reports of an ERK1/2 binding domain in the MITF gene. MITF is the principal driver of melanocyte differentiation and development from neural crest cells and occupies a central role as a driver of melanoma to metastasis as well as in the interaction of melanoma with its microenvironment. Therefore, identification of a GH-regulation of MITF could be of substantial importance. The finding of upregulation of MITF and TYRP1 levels with increasing exogenous GH, as well as marked downregulation of the same following GHR-KD, strongly implicates GH action in control of the melanogenesis pathway used in the melanoma cell lines for active sequestration of drugs via ABC transporters present on the cell membrane and the melanosomal boundary.

EMT plays a physiological role in wound-healing, fibrosis, and in the progression of cancer. Melanomas break free from the homeostatic control of keratinocytes by loss in expression of E-cadherin, upregulation of expression of fibroblast interacting cadherins such as N-cadherin, and upregulation of mesenchymal markers such as vimentin. Numerous studies have reviewed the importance of EMT in cancer metastasis. EMT is a regulator of drug resistance in lung cancer. Also, activation of the miRNA-96-182-183 cluster may cause an autocrine GH mediated direct regulation of EMT. The above observations of reappearance or increase of epithelial markers (E-cadherin) and concomitant downregulation of mesenchymal markers, such as N-cadherin and vimentin, following GHR-KD, at both RNA and protein levels thus describe a role of GH as a regulator of EMT and the aggressive phenotypes of melanoma multi-drug resistance and metastasis.

Melanomas have the unique property of resisting drug action by multiple processes involving active drug efflux, increased melanogenesis, and concomitant packaging away of drugs in melanosomes, as well as upregulation of the epithelial-mesenchymal-transition markers as means of decreased keratinocyte control and increased fibroblast interaction. Melanomas were also found to express one of the highest levels of GHR expression among all human cancers in the NCI's panel of human cancer cell lines. These two unique properties of human melanoma were investigated, and distinct regressive effects of GHR KD on critical aspects of all the above drug-evading processes were observed. Significant reduction in expression of multiple different ABC transporter pumps following a decrease in GHR indicates a GH action dependent mechanism regulating drug efflux from melanoma. In fact, the existence of GH-GHR mediated regulation of the mTOR pathway in melanoma cells is shown in Example 1, above, and GH induced activation of the pathway is known to be necessary for rapid activation of protein synthesis, as might be expected to be required in case of expression of transporter pumps in response to exposure to drugs. These observations may be experimentally confirmed in vivo using appropriately designed mouse models of growth hormone transgenic (bGH) or GHR deficient (GHR$^{-/-}$) mice. Further, the detailed effects of GHR on induction of apoptotic and/or necrotic cell death, as well as DNA damage, can add significant value to our results.

Described above is a mechanistic model of GH action in mediating multi-drug resistance in human melanoma through possible transcriptional regulation of expression of multiple mediators. Indeed, a significant GH-dependent variation in transcription and protein expression of several intracellular mediators of oncogenic signaling pathways in melanoma was observed (See Example 1), and this observation adds unknown information of the downstream effects of the earlier findings.

Decreased drug efflux machinery, increased drug retention, a reversal in EMT markers and a reduced cell proliferation at low doses of chemotherapy following GHR-KD supports the idea of approaching GH-GHR interaction as a suitable chemotherapeutic target of intervention as a combination therapy for several classes of anti-tumor compounds. Thus, this approach may have several downstream effects in cancer therapy. First, a lower drug dose applied in combination or following pretreatment with GHR antagonists can potentially lower the dose and duration of chemotherapy. This, in effect, may reduce the harsh side-effects associated with chemotherapy. Second, employing GHR inhibition as a means of sensitizing the tumor cells to other chemotherapeutic compounds may be one approach in the area of drug development. Third, a combination of GHR inhibition and chemotherapy can not only improve the efficacy of available anti-melanoma drugs but can also assist the development of candidate compounds under development. Decreased drug retention in tumors is a hurdle in establishing efficacy of thousands of good drug candidates in pharmaceutical research and development. The above Examples directly indicate a breakthrough in this problem by establishing that GH-GHR interaction is a mediator of drug-resistance and that targeting the same can successfully lead to improved drug action.

Example 3

In the above Examples 1 and 2, the role of the GH-GHR axis in human melanoma cells, using extensive in vitro studies, was described. The inventors have described a detailed mechanism of GH-dependence of human melanoma cells for eliciting resistance to the effects of chemo- and targeted therapies. In this Example 3, two additional sets of results are presented, which further support the inventors' concept of attenuation of GHR activation in human cancers like melanoma to efficiently counteract their therapy refractoriness.

In the first set, the in vivo effect of high levels of GH on xenografted melanoma tumor in syngeneic mice with supraphysiological levels of circulating GH is presented. For this purpose, a syngeneic mouse melanoma model was used—B16F10 mouse melanoma cells (that express GHR but not GH) xenografted in either of two C57BL/6J mouse strains, with altered GH/GHR axis—transgenic bGH expressing mice (bGH) or GHR knock-out mice (GHRKO)—both with high circulating GH levels. The RNA and protein expression levels of multidrug efflux pumps of ABC-transporter family and known markers of EMT, in the xenografted tumors in bGH or GHRKO mice, were analyzed and compared against xenografts in corresponding wild-type littermate controls.

In the second set, the inventors performed in vitro analyses of GH induced transcription level changes (mRNA) in the mediators of drug efflux and EMT in two highly drug-resistant and GHR-expressing human cancers—hepatocellular carcinoma (HCC/liver cancer) and melanoma. Very recently, others have described a role of autocrine GH in promoting cancer stem cell properties in human liver cancer cells[Chen Y-J, You M-L, Chong Q-Y, Pandey V, Zhuang Q-S, Liu D-X, Ma L, Zhu T, Lobie P. Autocrine Human Growth Hormone Promotes Invasive and Cancer Stem Cell-Like Behavior of Hepatocellular Carcinoma Cells by STAT3 Dependent Inhibition of CLAUDIN-1 Expression. Int J Mol Sci [Internet]. 2017; 18: 1274. doi: 10.3390/ijms18061274.]. The inventors in vitro results here independently demonstrate the existence of a robust autocrine GH-GHR axis in human melanoma and HCC cells, markedly upregulated following drug exposure, which in turn drives drug efflux and EMT in these cancer cells.

Materials and Methods

Cell Culture

SK-MEL-28, SK-MEL-5, Hep-G2, SK-HEP-1, PANC-1, H1299, and MCF7 cells were purchased from American Type Culture Association (ATCC). SK-MEL-5, SK-MEL-28, SK-HEP-1, Hep-G2, and MCF7 cells were maintained in EMEM media (ATCC); PANC-1 was maintained in DMEM (ATCC); H1299 was maintained in RPMI1640 media. Complete growth medium was supplemented with 10% fetal bovine serum (RMBIO) and 1× antibiotic-antimycotic.

Mouse cDNA

The cDNA from xenografted mouse melanoma tumor B16F10 in GHRKO and UGH male and female mice, was a kind gift from Dr. Yanrong Qian. Briefly, B16F10 mouse melanoma cells, with abundant expression of GHR, was injected subcutaneously into C57BL/6J mice with altered growth hormone axis. This constituted a classical syngeneic mouse model of melanoma with dysregulated GH axis. Tumors could grow for 21 days at the end of which the mice were sacrificed and tumors were collected.

RNA Extraction and RT-qPCR

Following treatments, cells were lysed, and RNA extraction was performed using IBI Tri-isolate kit (IBI), following manufacturer's protocol. RT-qPCR was performed as described previously.

Protein Extraction and Western-Blot

Following treatments, cells were lysed by mild sonication in Ripa lysis buffer as described previously. SDS-PAGE and western-blot was performed using general lab-techniques as described previously.

Cell Viability Assay

Cell viability, following treatments, was performed using Invitrogen's PrestoBlue cell viability assay system. As described previously, it is a resazurin based assay which is reduced to resorufin (absorption at 570 nm) by the reducing environment of metabolically viable cells. It was performed in a 96-well system as described previously.

Results

Figure 34D:
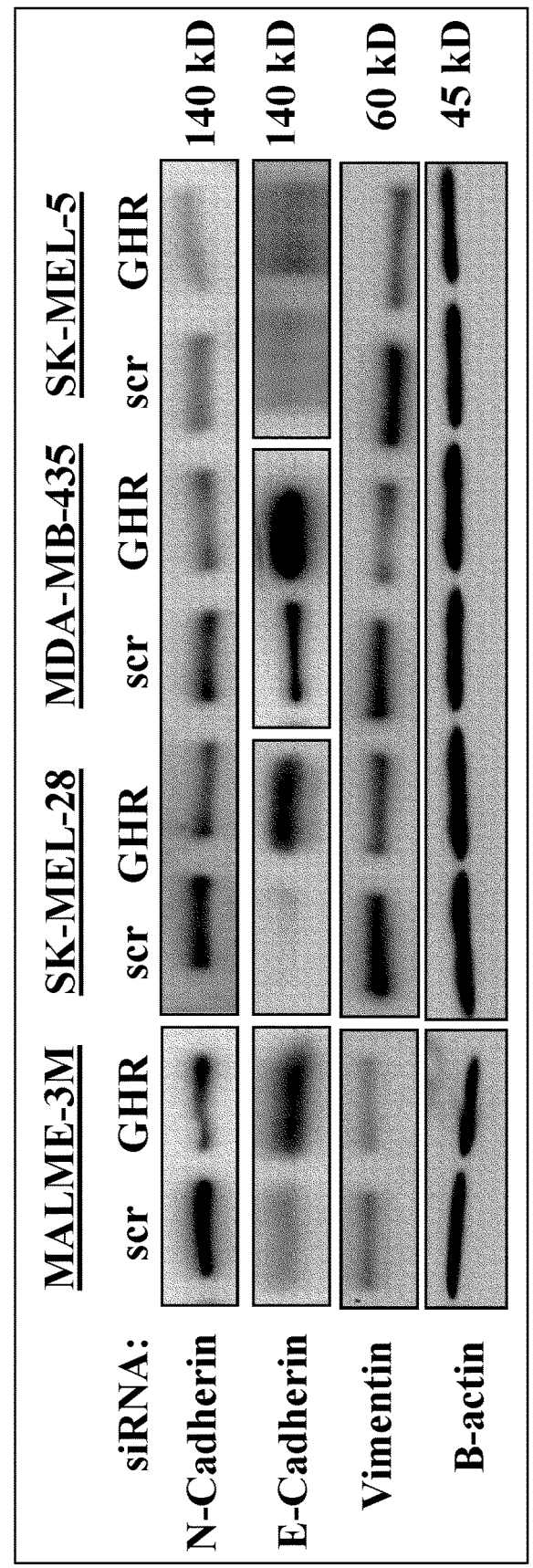
Figure 40A:
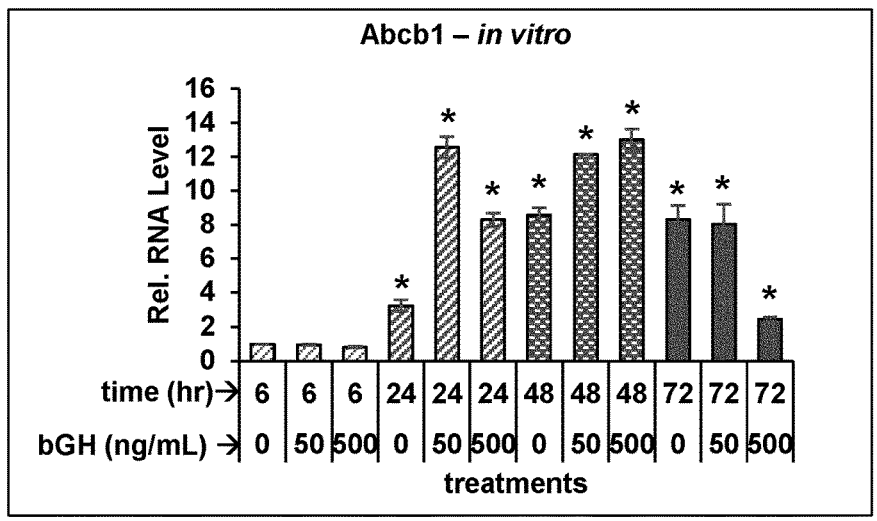
FIGS. 40A-40E include graphs showing that bGH induced higher RNA expression of ABCB1, ABEG1, and ABEG2 in bGH mice (high serum GH) compared to wild-type (WT) littermates.
Figure 40B:
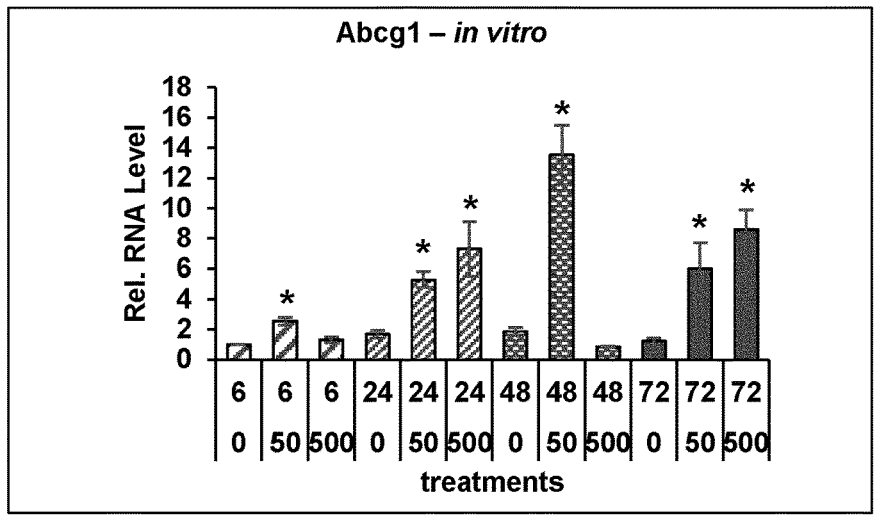
Figure 40C:
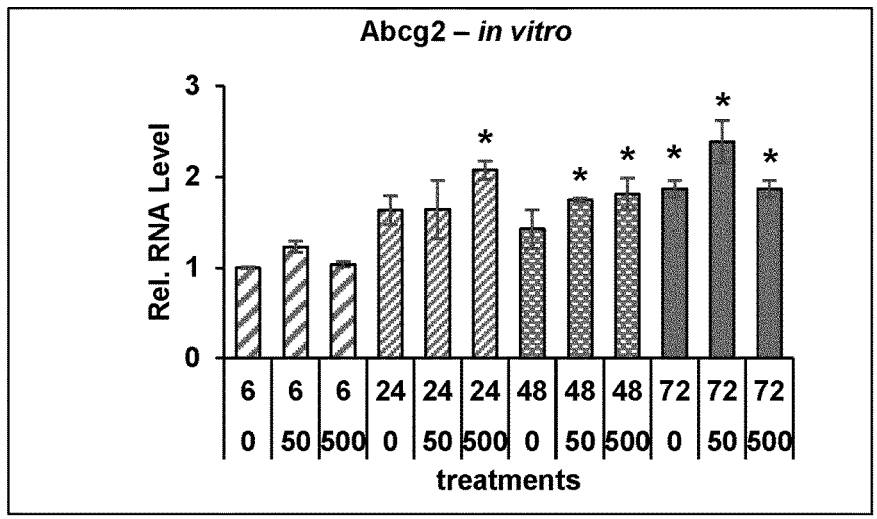
Figure 40D:
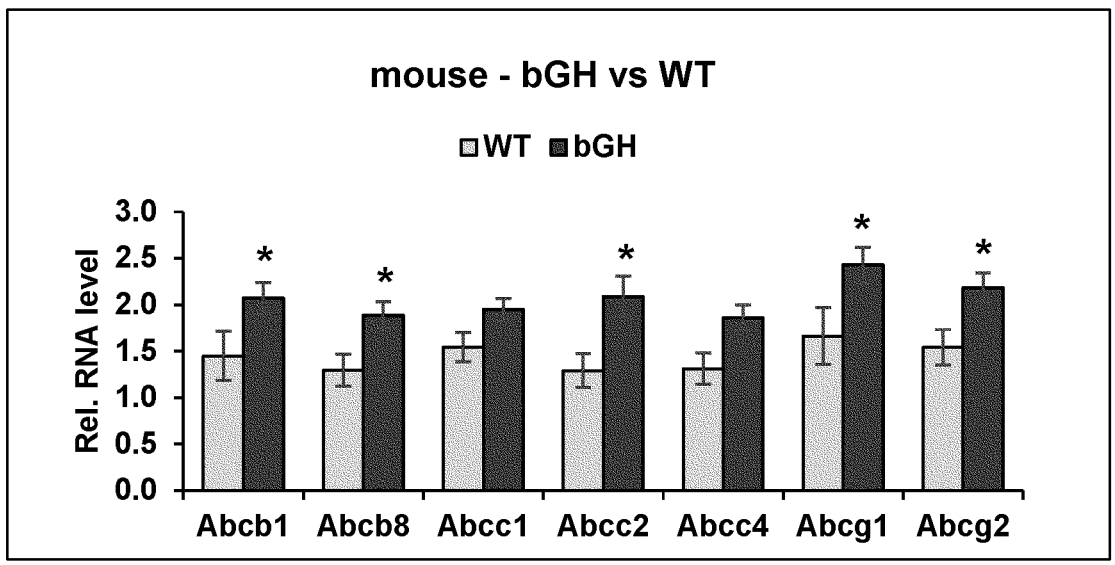
Figure 40E:
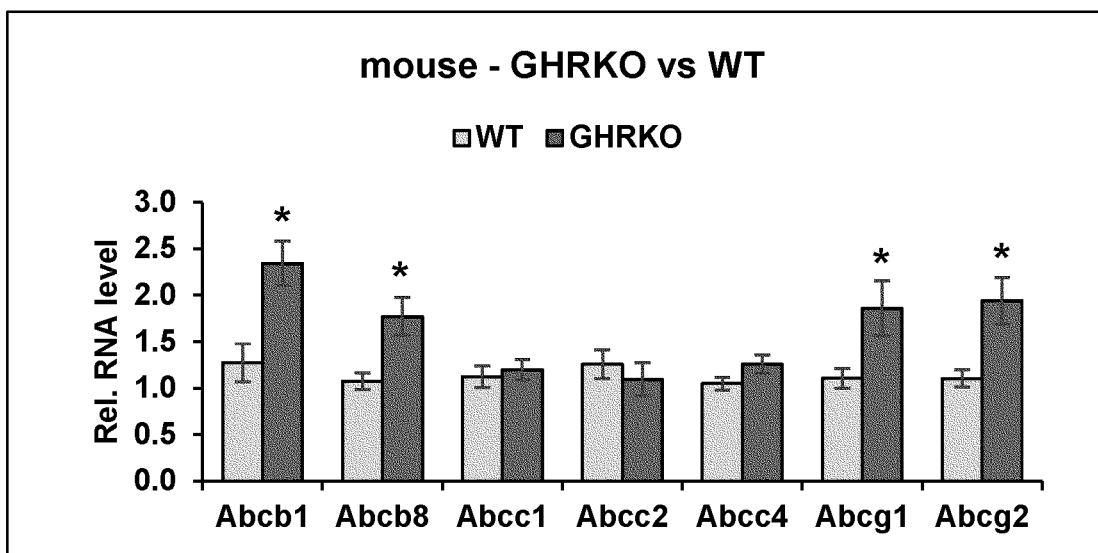

GH upregulates ABC-transporter expression in mouse melanoma B16F10 cells in vitro and in vivo: B16F10 mouse melanoma cells were treated with 50 or 500 ng/mL bGH for 6, 24, 48 or 72 hr and the changes in the RNA levels of specific multidrug exporter pumps were analyzed over time and GH dose. 50 and 500 ng/mL bGH induced a significantly higher RNA expression of Abcb1, Abcg1 and Abcg2 at 24, 48, and 72 hr (FIGS. 40A-C). The levels of Abcb8, Abcc1, Abcc2, and Abcc4 were not significantly different from untreated controls at any dose or time-point in vitro (data not shown). RNA extracted from B16F10 tumors grown in GHRKO or bGH mice were analyzed for the above ABC-transporters. In bGH mice, the tumor cells and resulting tumors were exposed in vivo to high endogenous GH and high IGF-1; while in GHRKO mice, the tumor cells and resulting tumors were exposed in vivo to high GH but low IGF1. In tumors derived from bGH mice, under basal conditions, i.e., in absence any anti-cancer treatment, the levels of Abcb1, Abcb8, Abcc2, Abcg1, and Abcg2 were significantly upregulated compared to tumors in wild-type mice (FIG. 34D). In tumors from GHRKO mice, a similar significant upregulation of Abcb1, Abcb8, Abcg1, and Abcg2 drug transporter RNA levels was observed compared to the same in wild-type mice (FIG. 40E).

Figure 41A:
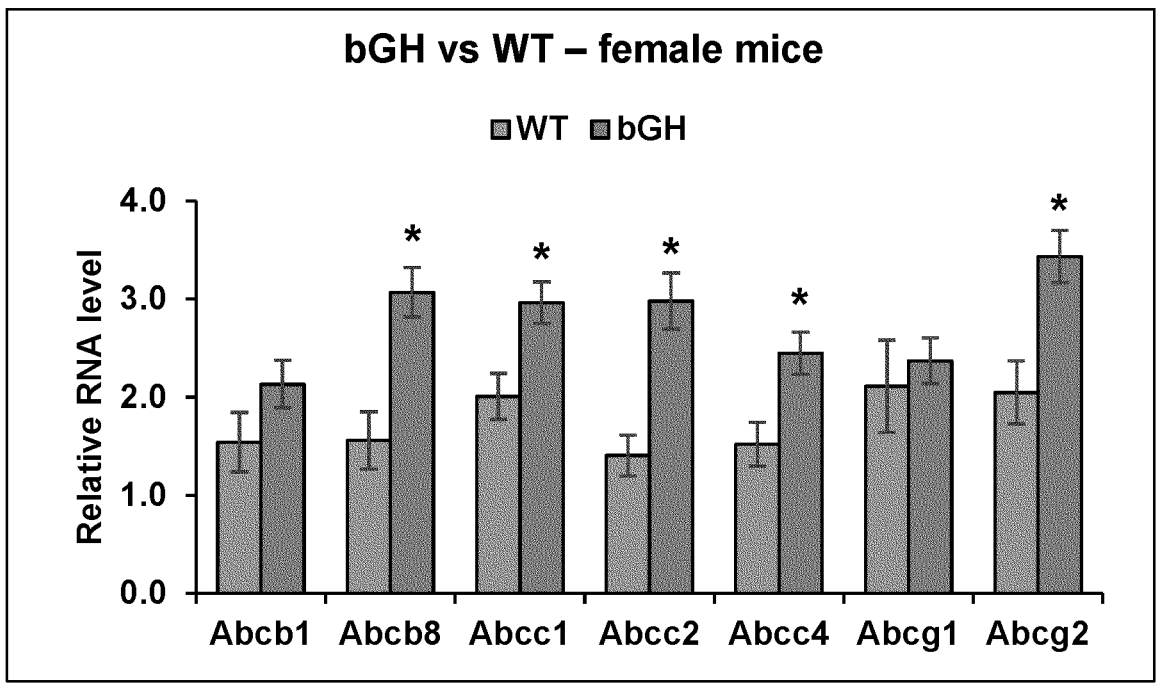
FIGS. 41A-41D include graphs showing in vivo genotypic changes in ABC efflux pump expressions in B16-F10 mouse melanoma xenografted in mouse models of high circulating G-bGH and GHR-KD.
Figure 41B:
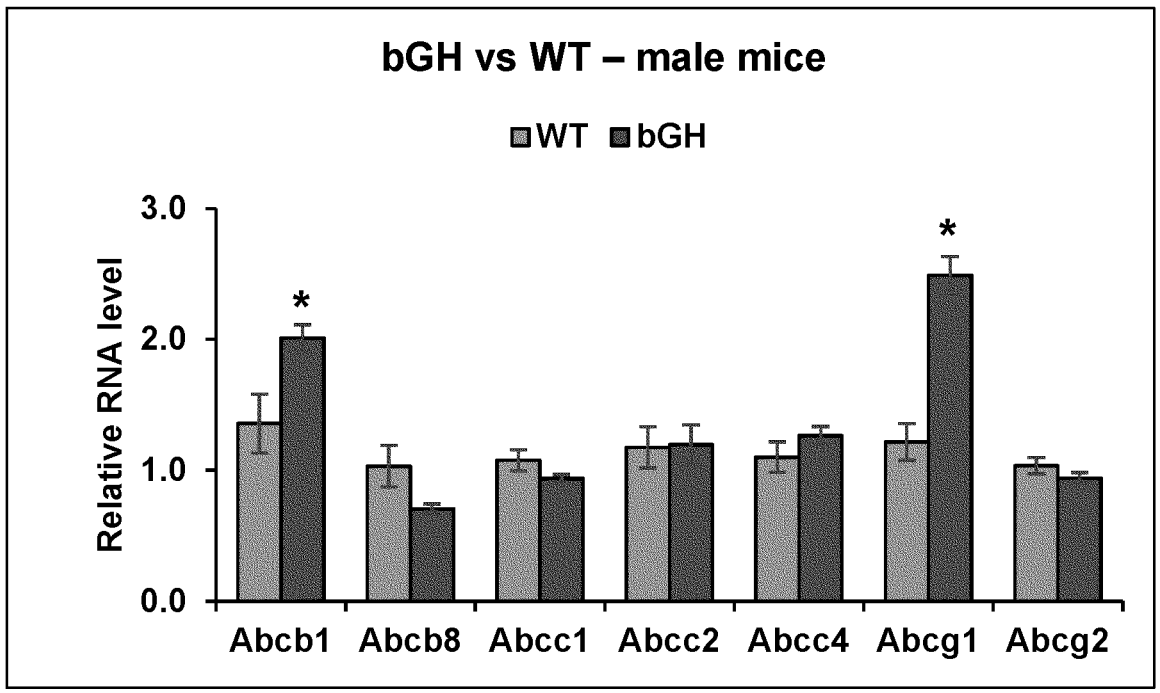
Figure 41C:
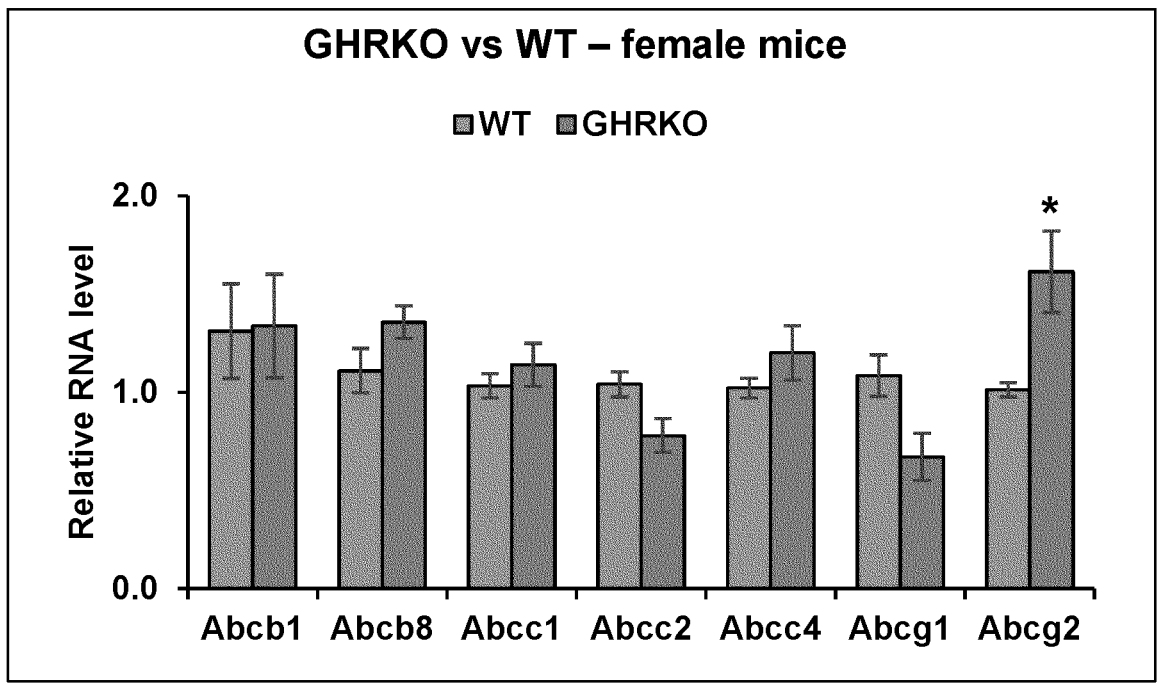
Figure 41D:
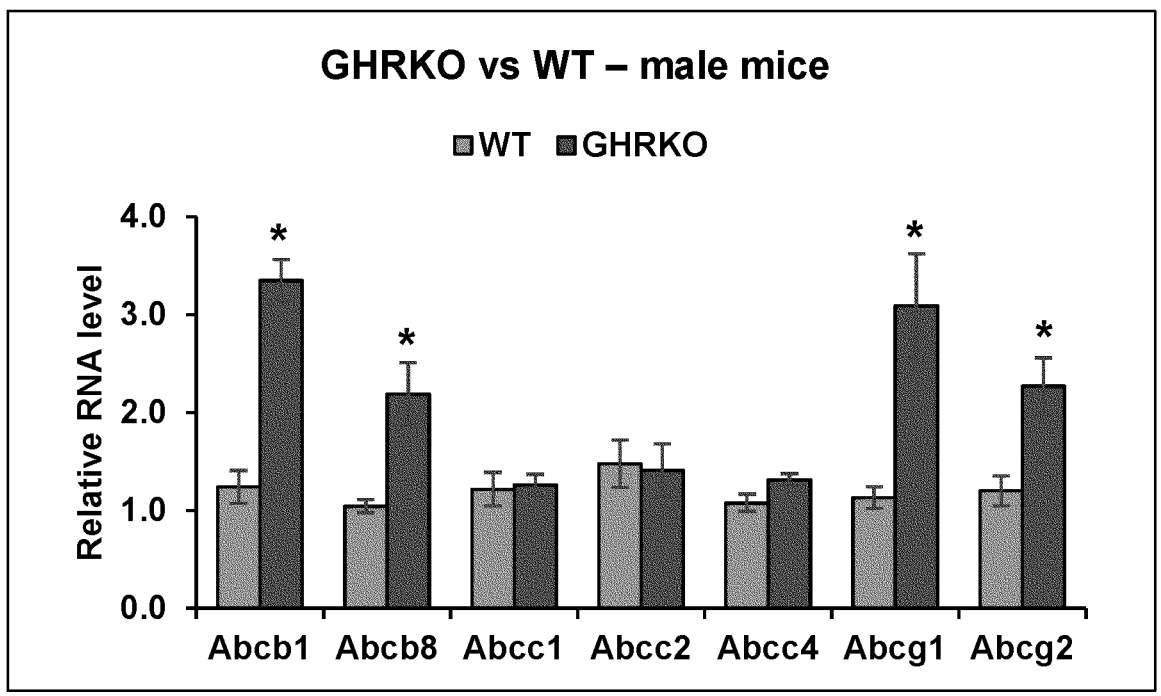
Figure 42A:
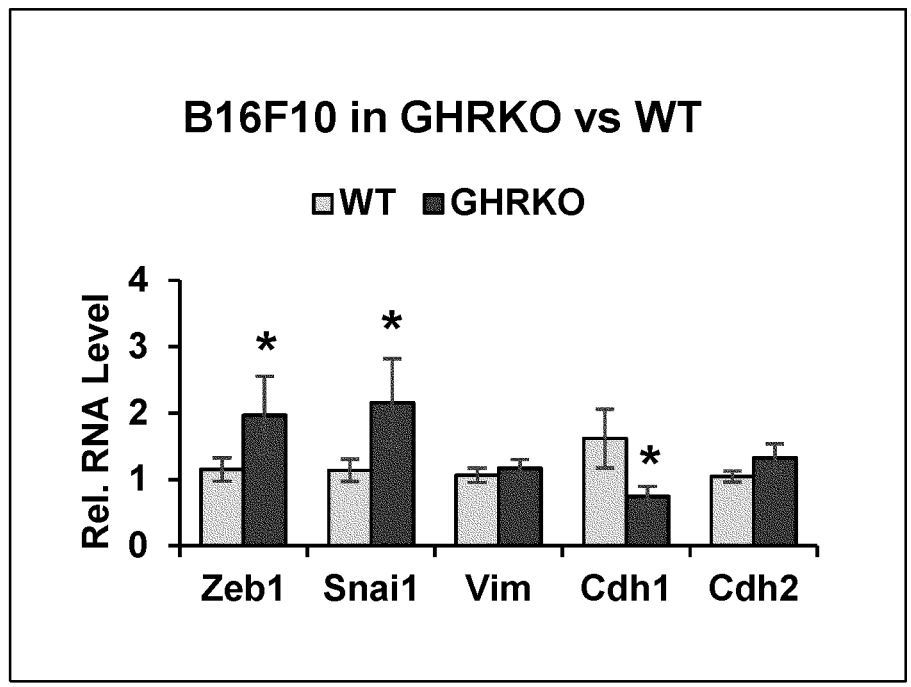
FIGS. 42A-42F include graphs showing in vivo genotypic changes in markers of epithelial-to-mesenchymal transition (EMT) in B16-F10 mouse melanoma xenografted in mouse models of high circulating G-bGH and GHR-KD.
Figure 42B:
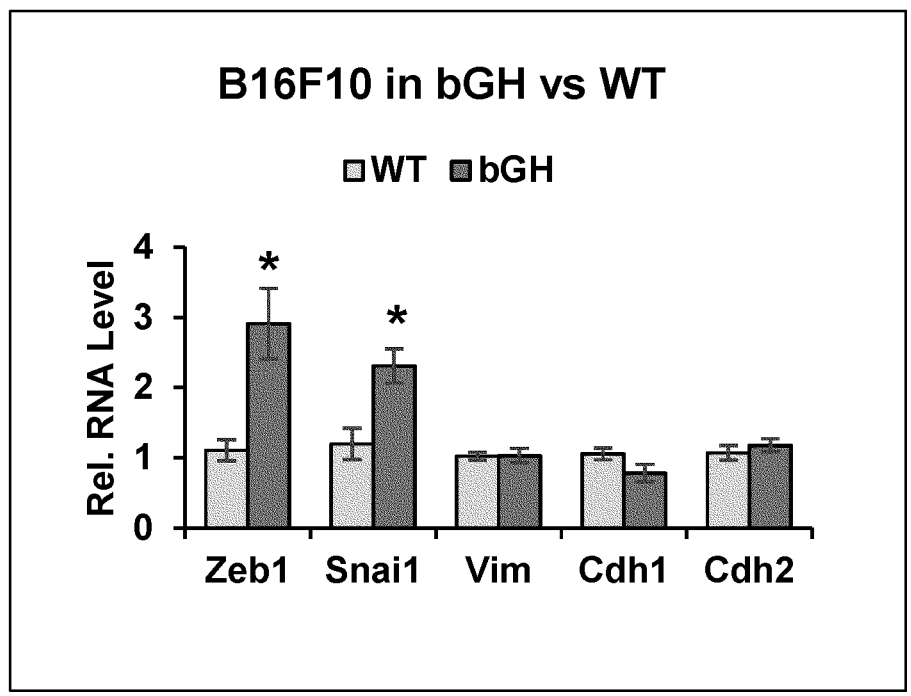
Figure 42C:
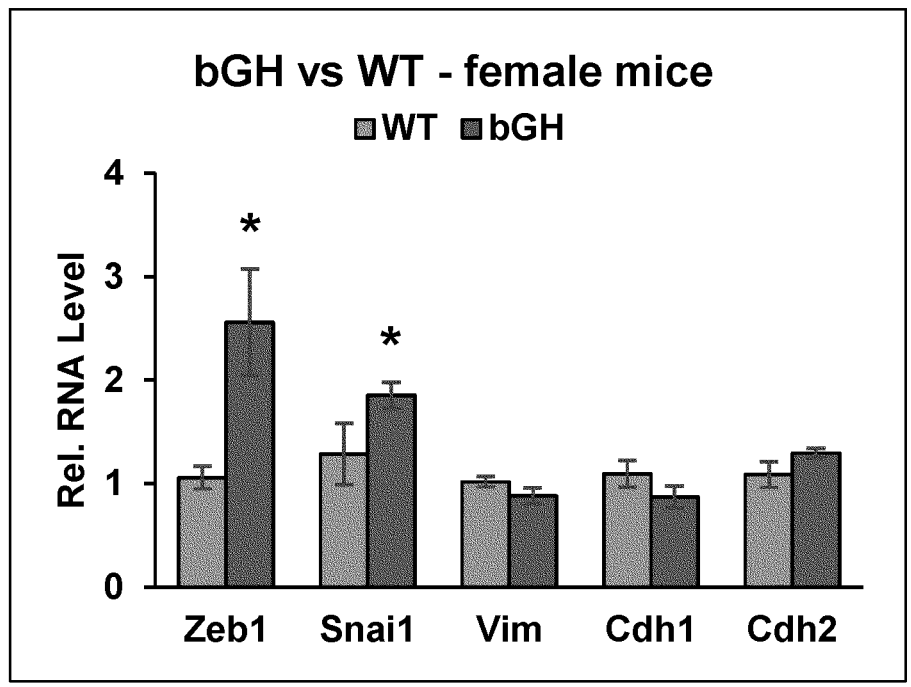
Figure 42D:
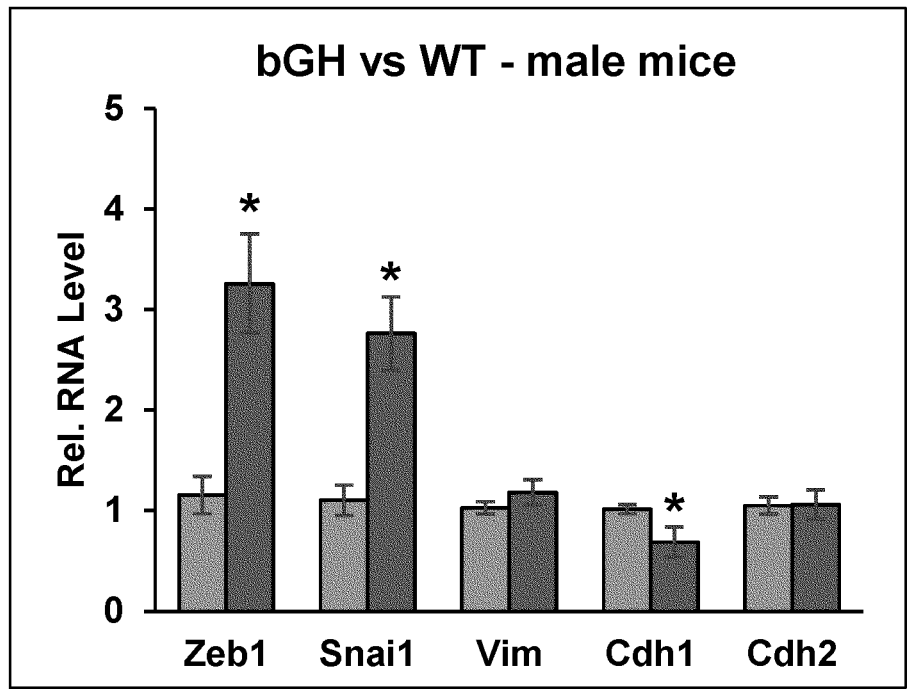
Figure 42E:
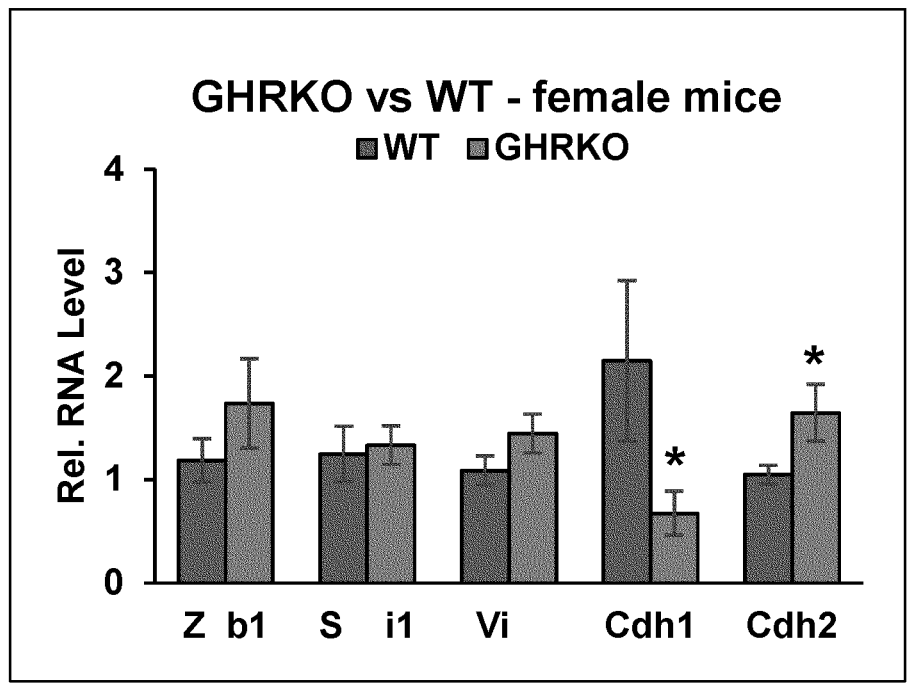
Figure 42F:
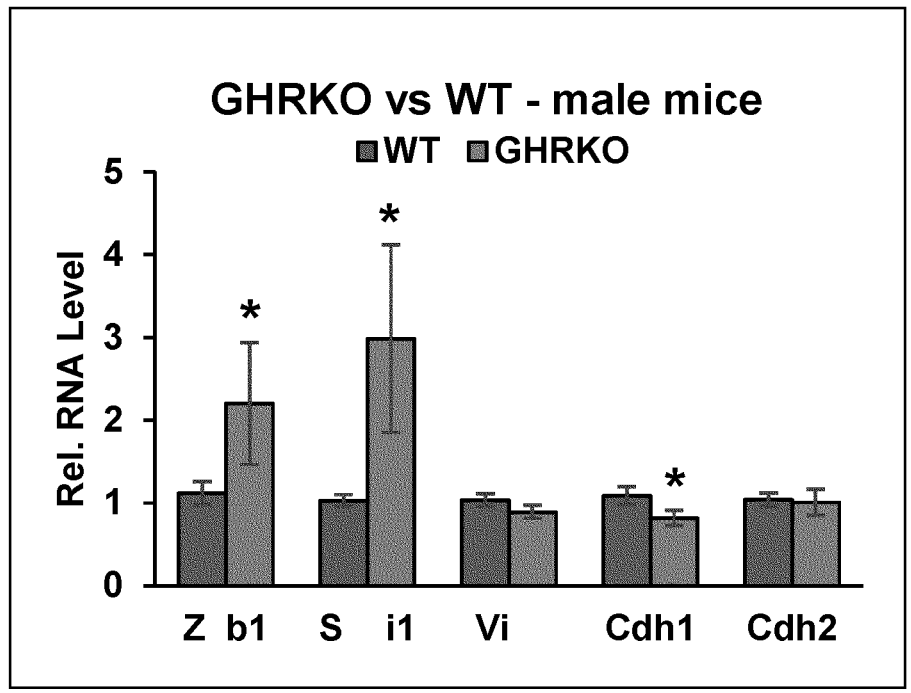

On a closer analysis, a different pattern of GH-induced increase in ABC-transporters was seen between male and female mice. Referring now to FIGS. 41A-41D, the figure includes graphs showing genotypic changes in ABC efflux pump expressions in B16-F10 mouse melanoma in vivo. Here, RNA levels in B16F10 mouse melanoma tumors grown in vivo in bGH female (FIG. 41A), bGH male (FIG. 41B), GHRKO female (FIG. 41C), and GHRKO male (FIG. 41D) mice were queried by RT-qPCR for basal levels of seven different ABC efflux pumps. RNA levels were normalized against expression of β-actin and GAPDH as reference genes [*, $p<0.05$, Wilcoxon sign rank test]. In the bGH group, female mice had significantly higher levels of Abcb8, Abcc1, Abcc2, Abcc4 and Abcg2 RNA levels, while male mice had significantly higher levels of Abcb1 and Abcg1, but not the others (FIGS. 41A and 41B). A similar comparison between GHRKO mice revealed that female GHRKO mice had a significantly higher level of Abcg2 alone at basal level, while the male GHRKO mice had significantly higher level of Abcb1, Abcb8, Abcg1, and Abcg2 levels (FIGS. 41C and 41D). The results clearly indicate that exposure to supra-physiological levels of GH markedly upregulates the levels of ABC-type multidrug efflux pumps in vitro and in vivo.

GH upregulates expression of markers of EMT in mouse melanoma B16F10 cells in vivo: The inventors earlier showed that, in human melanoma cells, exogenously added GH upregulates EMT, while attenuating GHR expression in humanmelanoma cells, leading to re-appearance of E-cadherin (Cdh1) and downregulation of mesenchymal markers. Therefore, here the inventors queried the basal mRNA levels of known epithelial (Cdh1/E-cadherin) and mesenchymal (Cdh2/N-cadherin, Snai1/Snail, Vimentin, Zeb1) markers in the tumors of bGH as well as GHRKO mice relative to that seen in control littermates. Referring now to FIGS. 42A-42F, that figure includes graphs showing genotypic changes in markers of epithelial-to-mesenchymal transition (EMT) in B16-F10 mouse melanoma in vivo. Here, RNA levels in B16F10 mouse melanoma tumors grown in vivo in bGH male (FIG. 42A), bGH female (FIG. 42B), GHRKO male (FIG. 42C), and GHRKO female (FIG. 42D) mice were queried by RT-qPCR for basal levels of five known markers of EMT. RNA levels were normalized against expression of β-actin and GAPDH as reference genes [*, p<0.05, Wilcoxon sign rank test].

Figure 43A:
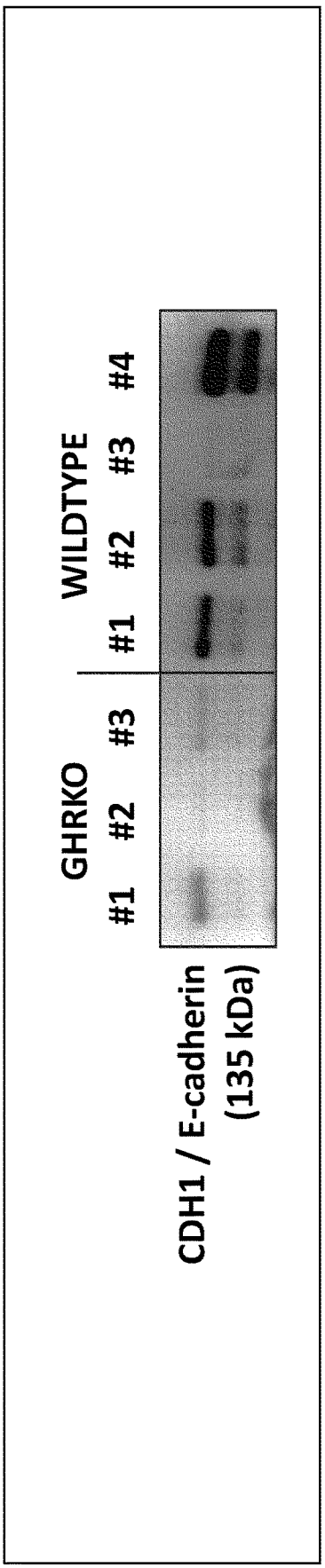
FIGS. 43A-43B includes photographs showing lower protein level expression of epithelial marker Cdh1 in female GHRKO mice, and higher Abcg2 level in GHRKO male mice composed to wild-type littermates.
Figure 43B:
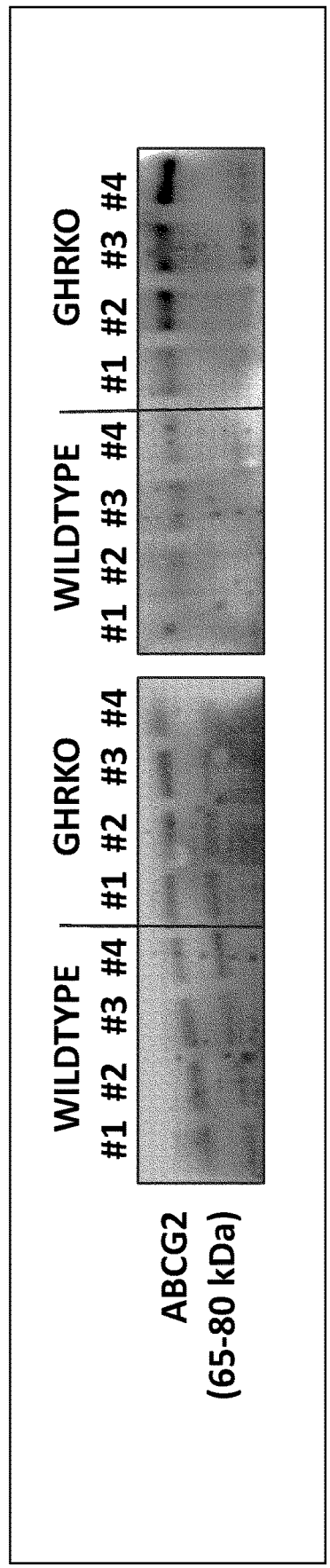

Realtime RT-PCR analyses showed significant upregulation of mRNA levels of the mesenchymal transcription factors Zeb1 and Snai1 in both bGH and GHRKO mice, with a concomitant marked decrease in Cdh1 mRNA levels (FIGS. 42A-42F). A more detailed analysis revealed that the above trend was more consistent in both bGH and GHRKO male mice, than in the female counterparts (FIGS. 42C-42F). Also, the upregulation in Zeb1 and Snai1 levels in GHRKO male mice was suppressed in the female GHRKO mice, although the latter had significantly lower Cdh1 levels than their wild-type littermates. Further, a significantly lower protein level expression of the epithelial marker Cdh1 in female GHRKO mice, and a significantly higher ABCG2 level in GHRKO male mice compared to the tumors in their wild-type littermates (FIGS. 43A and 43B), was observed.

Figure 44:
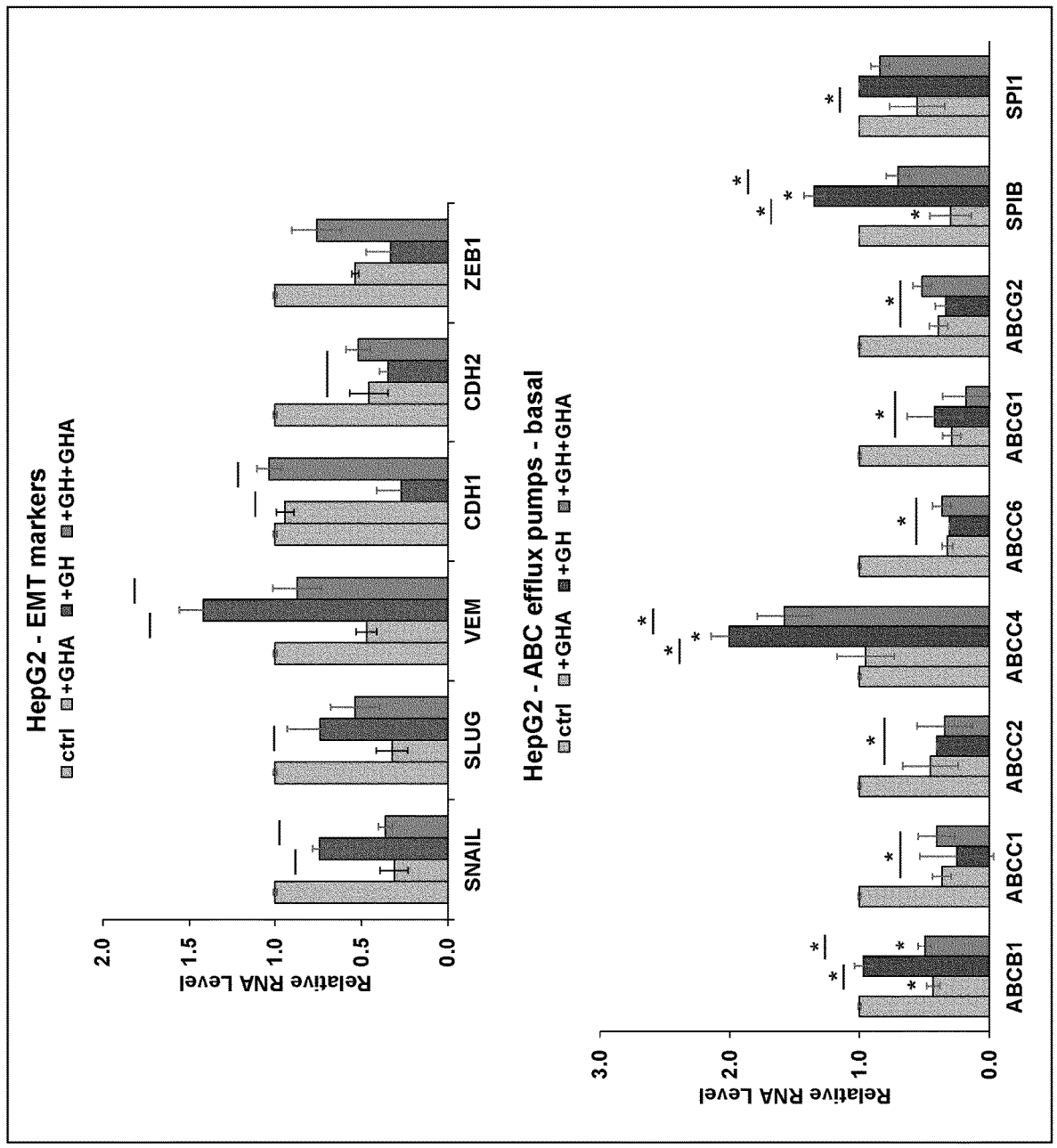
FIG. 44 includes graphs showing the effect of exogenous GH in upregulating, and the effect of GHR antagonists in suppressing, expression of ABC transporters and markers of EMT in human liver cancer cell—HepG2.
Figure 45:
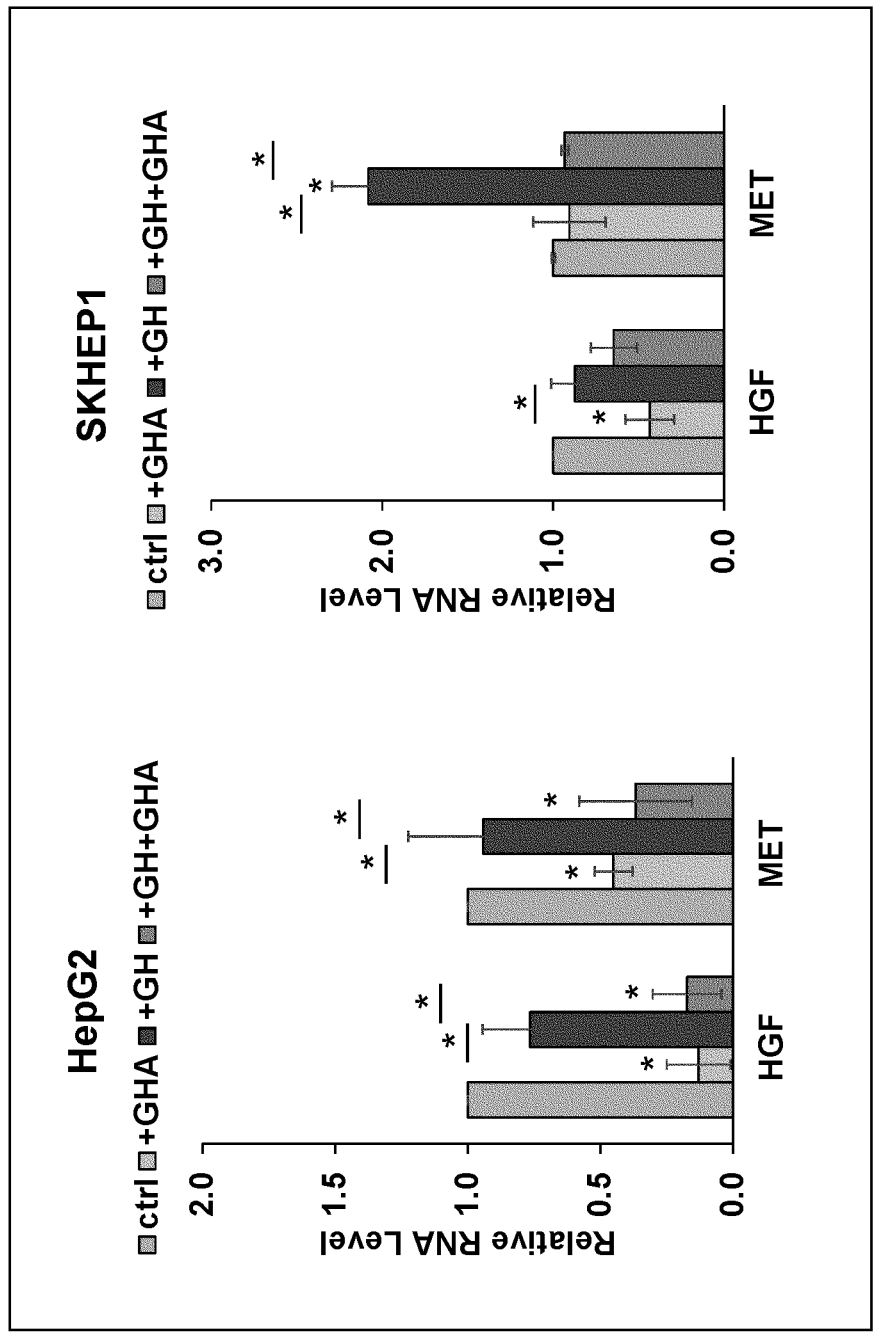
FIG. 45 includes graphs showing the effect of GHR antagonist on HGF levels and MET levels in human liver cancer cells—HepG2 cells and SK-HEP-1.

GH upregulates and GHR-antagonist suppresses the expression of ABC-transporters and markers of EMT in human liver cancer cells in vitro: The inventors earlier showed that in human melanoma cells expressing GHR, exogenous GH drives the expression of known markers of EMT, while blocking the GHR expression using siRNA, inhibits GH induced action and upregulation in EMT marker expressions. And so, the inventors performed a similar experiment with HepG2 and SK-HEP-1 human liver cancer cells, which have been extensively studied and known to express GHR, to verify this observation in human melanoma cells. In vitro, HepG2 cells were treated for 3 days with either 50 ng/mL GH (2.5 nM), or 50 nM GI-IR-antagonist, or both GH and GHR-antagonist, and their RNA expressions were compared against untreated controls at basal condition (i.e. no drug treatment). In Hep-G2 cells, exogenous GH treatment was found to significantly upregulate the RNA levels of mesenchymal marker vimentin, while downregulating CDH1, the epithelial marker (top panel graph of FIG. 44). On the other hand, treatment with GHR-antagonist alone or in presence of GH, markedly lowered the levels of mesenchymal markers—SNAIL (SNAI1), ZEB1, SLUG, CDH2, and VIM (top panel graph of FIG. 44). A similar analysis of ABC-transporter RNA expressions showed that exogenous GH markedly upregulated levels of ABCC4 and that of the transcription factor SPI-B, while addition of GHR-antagonist drastically lowered the basal levels of ABCC4, ABCG1, as well as SPI-B, in HepG2 cells (bottom panel graph of FIG. 44).

Blocking GHR attenuates the oncogenic HGF-MET loop in human liver cancer cells: Hepatocellular carcinoma (HCC) or human liver cancer has one of the highest cancer morbidity rates in the world, with only one FDA approved chemotherapy (sorafenib) available to patients. The hepatocyte growth factor (HGF) and its cognate receptor (MET), both expressed highly on different cancers including melanoma, is known to be an active driver of HCC incidence and progression and have long been implicated as a valuable drug-target [Goyal L, Muzumdar M D, Zhu A X. Targeting the HGF/c-MET Pathway in Hepatocellular Carcinoma, Clin Cancer Res [Internet] 2013; 19: 2310-8. doi: 10.1158/1078-0432.CCR-12-2791; Hu C-T, Wu J-R, Cheng C-C, Wu W-S. The Therapeutic Targeting of HGF/c-Met Signaling in Hepatocellular Carcinoma: Alternative Approaches. Cancers (Basel) [Internet] 2017; 9: 58. doi: 10.3390/cancers9060058]. New generation MET-inhibitors like cabozantinib have had partial success against human HCC, due to cytotoxic effects at high doses in most recent human clinical trials, indicating to unmet needs in countering drug-resistance[Kelley R K, Verslype C, Cohn A L, Yang T-S, Su W-C, Burris H, Braiteh F, Vogelzang N, Spira A, Foster P, Lee Y, Van Cutsem E. Cabozantinib in hepatocellular carcinoma: results of a phase 2 placebo-controlled randomized discontinuation study. Ann Oncol Off J Eur Soc Med Oncol [Internet]. Oxford University Press; 2017 [cited 2017 Oct. 24]; 28: 528-34. doi: 10.1093/annonc/mdw651].

The inventors had previously shown that knock-down of GHR in turn strongly attenuates MET as well as HGF transcript levels in human melanoma. To verify this observation in another GHR expressing human cancer like HCC, the inventors analyzed the effects of GH and GHR-antagonist treatment on the expression of the oncogenic HGF-MET loop in human liver cancer cells. HepG2 and SK-HEP-1 cells were treated for 3 days with either 50 ng/mL GH (2.5 nM), or 50 nM GHR-antagonist, or both, and their RNA expressions were compared against untreated controls at basal levels (i.e. no drug treatment). No additional effect of added GH on the expression levels of HGF or MET in the liver cancer cell lines was observed, except a 2-fold increase in MET levels in SK-HEP-1 cells (FIG. 39). However, added GHR-antagonist had a drastic effect on the HGF-MET loop in both cell lines. Irrespective of presence of added GH, the antagonist lowered HGF levels by >4-fold in Hep-G2 cells and up to 2-fold in SK-HEP-1 cells; while the MET levels were decreased by >2-fold in both Hep-G2 and SK-HEP-1 cells compared to the GH treated samples (FIG. 39). This observed nature of the suppressive effect of GHR-antagonist strongly indicates the existence of a autocrine/paracrine GH action in HCC, as the inventors had found stable GH expression in both Hep-G2 and SK-HEP-1 cells.

Figure 46:
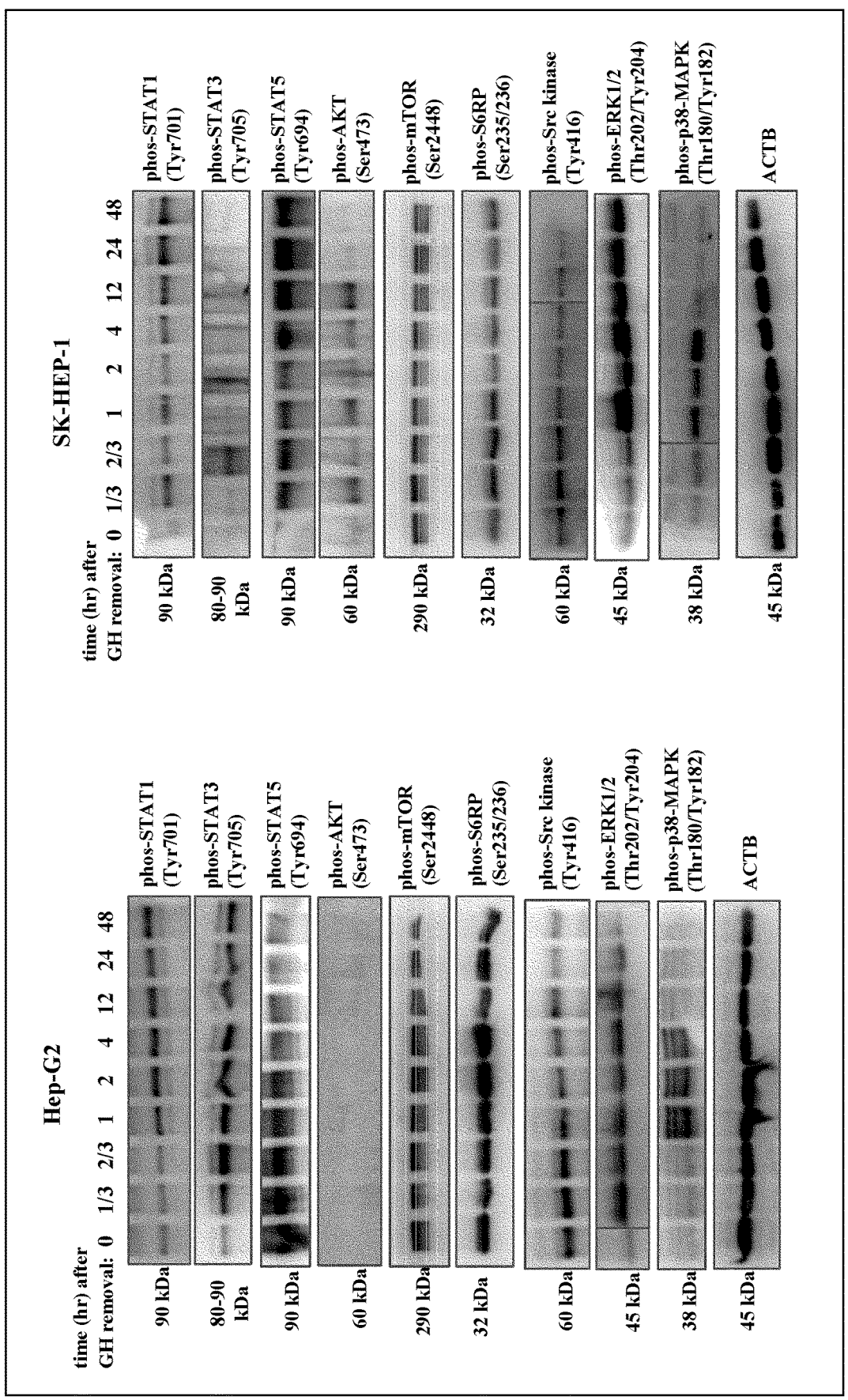
FIG. 46 includes photographs showing that GH increases the phosphorylation states of STAT3, STAT5, SRC, and ERK1/2 in human liver cancer cells—HepG2 cells and SK-HEP-1.

GH-GHR directly activates JAK2, STA5, STAT3, SRC and ERK1/2 pathways in human liver cancer cells: To trace the intracellular signaling pattern or pathways downstream of GH-GHR interaction in human liver cancer cells, the inventors used a time-lapse analysis of the activation states of known GH-regulated signaling pathways, across time, in Hep-G2 and SK-HEP-1 cells stimulated with 50 ng/mL GEL The inventors observed that within 20 minutes of GH addition in both Hep-G2 and SK-HEP-1 cells, the phosphorylation states of STAT3, STAT5, SRC, and ERK1/2 (p44/42 MAPK) were particularly increased significantly, but not that of p38 MAPK, AKT, mTOR, or S6RP (FIG. 46).

Drug-induced autocrine GH-GHR expression drives multiple mechanisms of drug resistance in human melanoma cells: The inventors previously reported the existence of RNA and protein levels of endogenous GH, beside GHR, in human melanoma cells grown in vitro unlike mouse B16F10 cells which express only GHR but no GH. The inventors also reported the existence of a GH-GHR regulated drug resistance mechanism in human melanoma cells. Therefore, the induction of intracellular mechanisms of drug resistance following exposure to chemotherapy in melanoma, could be locally turned on by an autocrine/paracrine GH source, in case of GH-expressing human melanoma cells.

Figure 47:
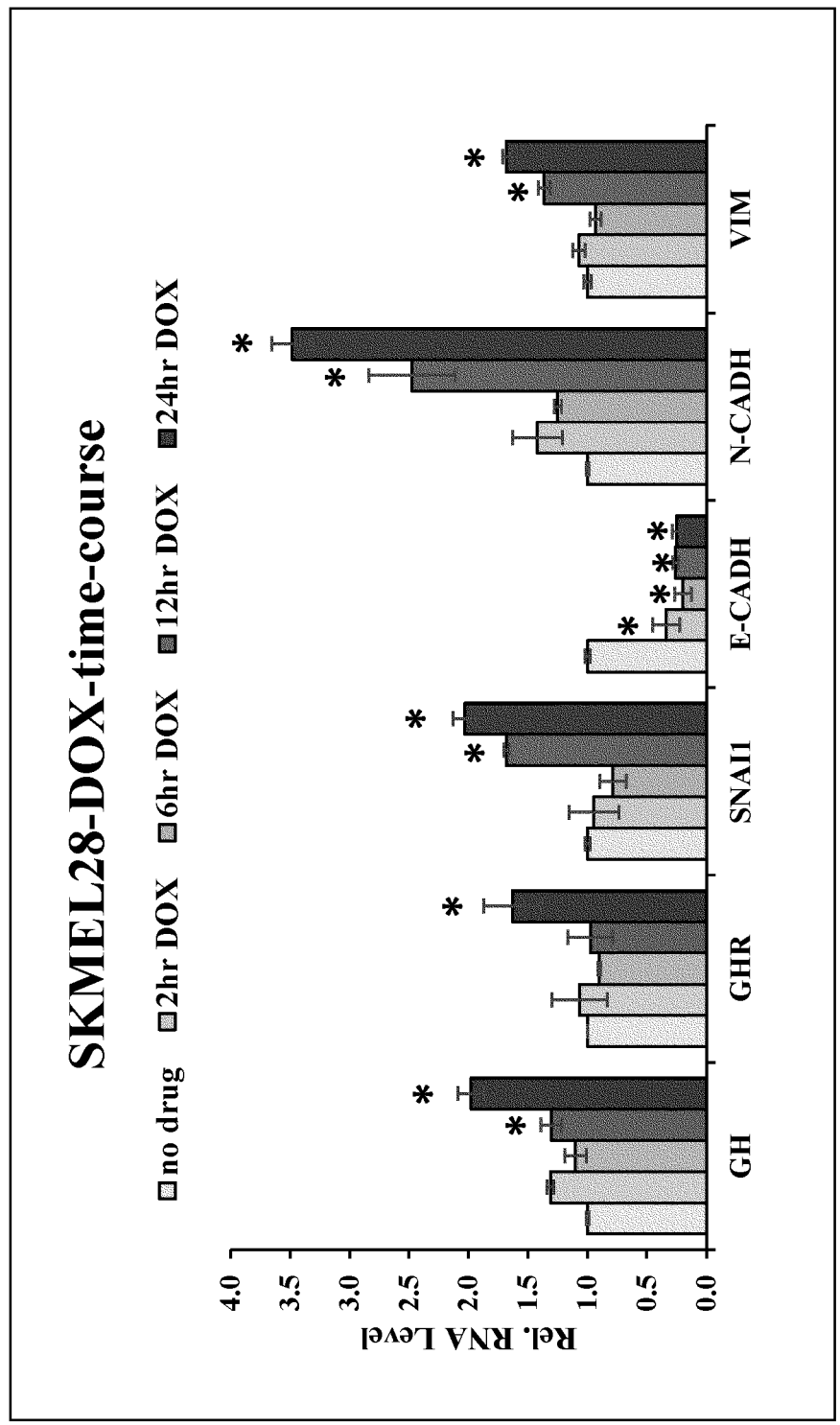
FIG. 47 includes graphs showing that, in human melanoma cells SK-MEL-28, an increase in transcript levels of markers of EMT is observed in synchrony with an increase in autocrine GH and in GHR levels following addition of a chemotherapeutic agent.
Figure 48:
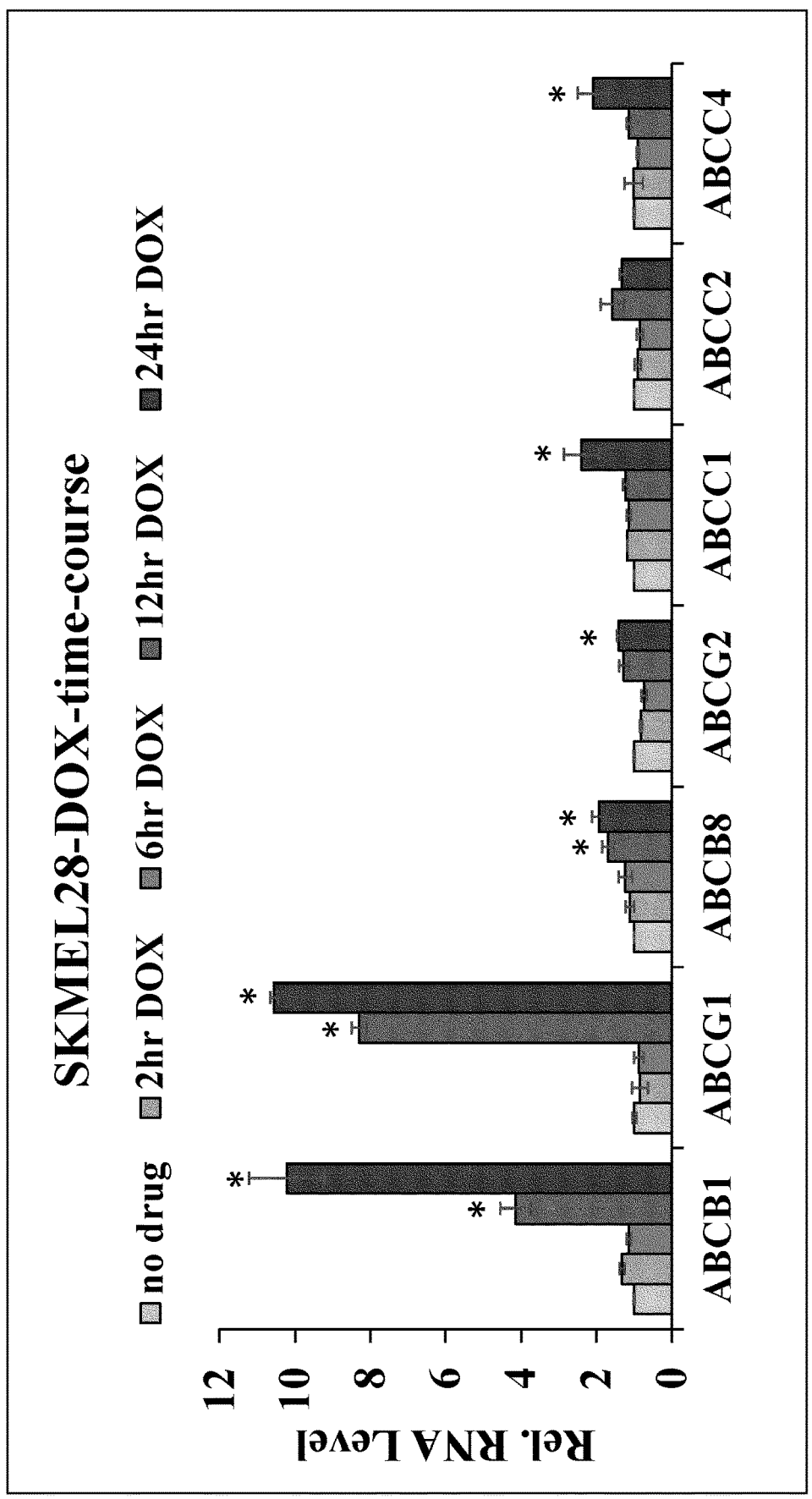
FIG. 48 includes graphs showing that, in human melanoma cells SK-MEL-28, an increase in transcript levels of ABC-type multi-drug efflux pumps is observed in synchrony with an increase in autocrine GH and in GHR levels following addition of a chemotherapeutic agent.

To verify if exposure to chemotherapy alone induces the endogenous levels of GH or GHR, the inventors treated SK-MEL-28 human melanoma cells with 188 nM the chemotherapeutic doxorubicin (=$EC_{50}$ of doxorubicin against SK-MEL-28 cells) and followed the RNA levels of GH and GHR across 2, 6, 12 and 24-hr following drug addition. The inventors parallelly analyzed the changes in transcript levels of known markers of EMT (mesenchymal—SNAI1, CDH2/N-cadherin, VIM; epithelial—CDH1/E-cadherin) and ABC-type multidrug efflux pumps (ABCB1, ABCB8, ABCC1, ABCC2, ABCC4, ABCG1, ABCG2) with time, following doxorubicin addition. A consistent increase in autocrine GH transcript was observed after 12-hr, with a >2-fold rise by 24-hr, with a concomitant rise in GER levels (FIG. 47). In synchrony to this increased GH response, the transcript levels of CDH2, VIM and SNAI1 increased significantly 12-hr after doxorubicin addition, with >2-fold increase in SNAI1 and >3.5-fold increase in CDH2 at the end of 24 hr (FIG. 47). There was a >8-fold reduction in the epithelial marker CDH1/E-cadherin, at the end of 24 hr after doxorubicin addition (FIG. 47), Similarly, following a consistent upregulation of autocrine GH levels at 12-hr, a 4-fold rise in ABCB1 and an 8-fold rise in ABCG1 (both known transporters of doxorubicin in cancer cells) was observed. At the end of 24 hr, the RNA levels of ABCB1 and ABCG1 were even higher with significantly higher levels of ABCB8, ABCC1 and ABCC4 drug efflux pumps as well (FIG. 48).

Discussion of the Above Results

Previously, the inventors found that knocking down GHR attenuated ABC-type multidrug efflux pump gene expression and EMT in multiple human melanoma cell lines. In melanoma, the activation of the epithelial-to-mesenchymal transition (EMT) strongly correlates with a transition to aggressive metastases as well as with upregulation of mechanisms of drug resistance. Our observation in the syngeneic mouse model of melanoma was highly consistent with our earlier observation in human melanoma cells. A significantly upregulated RNA level of markers of EMT as well as that of ABC drug efflux pumps, even in the absence of any drug mediated induction, highlight a critical role of GH in possibly ascertaining the intrinsic nature of the tumor. An elegant study by Caramel et al showed how a switch from a Zeb2-dominant phenotype to an EMT-inducing Zeb1-dominant phenotype is a driver of malignancy in melanoma. Recently Zeb1 was also identified as a critical oncogenic regulator in uveal melanoma. In this study, a marked increase in levels of Zeb1 in vivo was observed, under both conditions of elevated GH (both bGH and GHRKO mice). This data along with our observations of elevated Snai1 and reduced Cdh1 in our syngeneic mouse model additionally points to a hitherto unidentified role of GH action in driving phenotypic plasticity of cancer cells. The current study provides an excellent support to our earlier in vitro observations of attenuating ABC-type multidrug efflux pumps by GHR knockdown in human melanoma cells. Even in absence of drug treatment, the mRNA levels of Abcb1a, Abcg1 and Abcg2, which are some of the most studied drug transporters in cancer, were elevated concomitantly with an elevated GH exposure in bGH and GHRKO mice, relative to that found in their WT littermates controls. Therefore, melanoma cells on exposure to high GH levels might remain at an elevated state of resistance. This in turn might lead to an aggressively drug-resistant phenotype of melanoma. Further, there were some difference between the patterns of altered expression of ABC-type multidrug efflux pumps and EMT markers in male and female mice with elevated GH. The role of estrogen, pattern of GH release between male and female mice, and a putative role of a differential IGF axis could be some potential confounding modulating factors in the observation. Overall, the data from the unique syngeneic mouse melanoma model with altered GH levels provide a confirmation of our previous in vitro observations and bolsters our understanding of the unique regulatory role of GH-GHR pair in specific drug efflux mechanisms in melanoma cells. It provides further insight into the rapidly unfolding nature of GH regulation of the process of EMT and phenotype switches in cancer cells.

Figure 49:
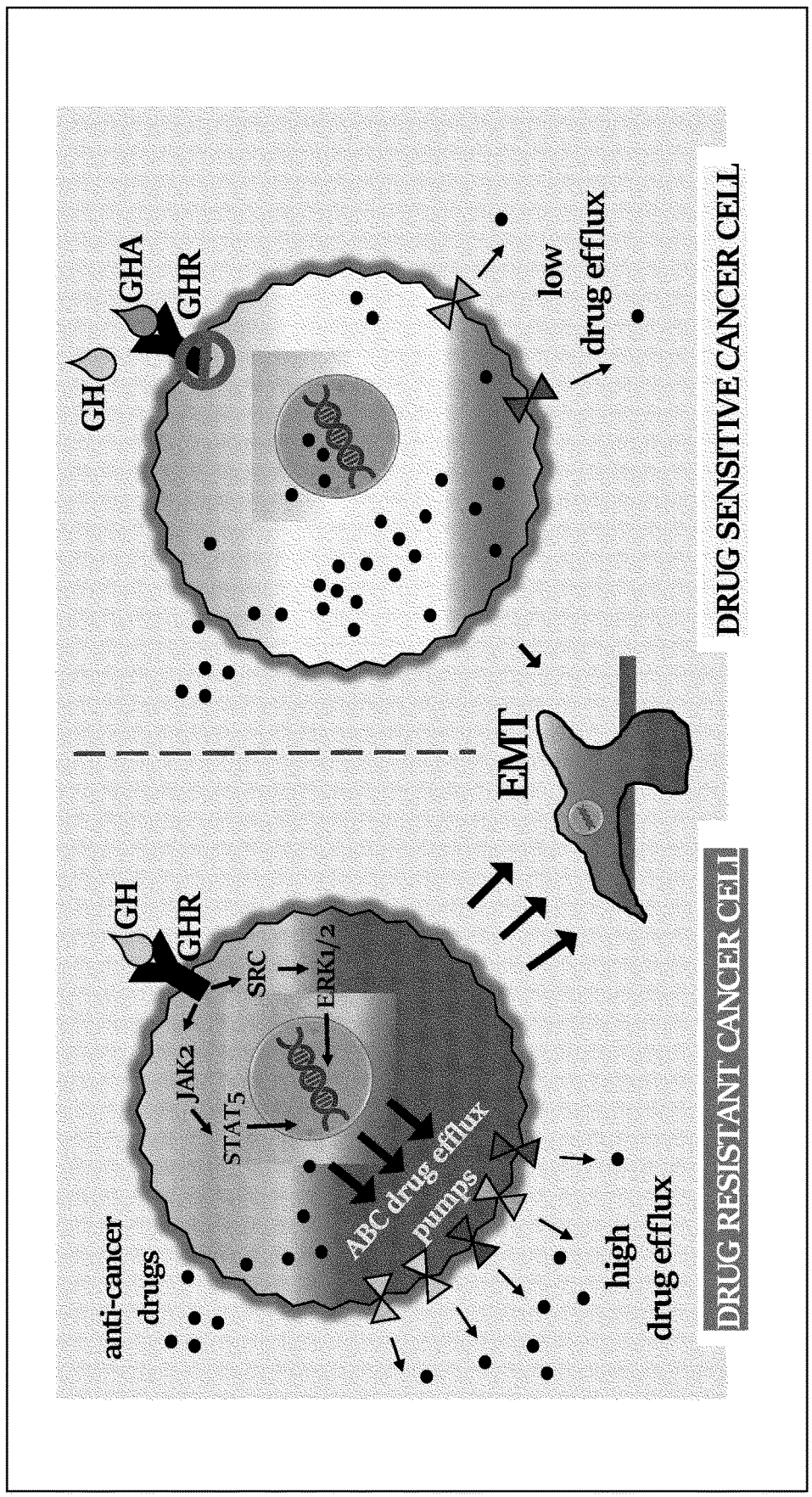
FIG. 49 includes schematic representations of the mechanism of action of GH-GHR regulated drug resistance in cancer cells and how attenuating the GHR by an antagonist would reverse it and sensitize the cancer cell to chemotherapeutics.

Recently, several studies by Peter Lobie's group, indicated a potentially critical role of autocrine GH expression in cancer cells. His group found that human melanoma cells in in vitro express GH, which is significantly upregulated following drug treatment. Our results strongly support this observation and additionally reveal an intrinsic GH-GHR loop activated within 12 hours of exposure of SK-MEL-28 cells to an anti-cancer drug, which is followed by a marked upregulation of EMT and drug efflux mediators. This is significantly corroborated by our observed effects of GHR-antagonist on EMT markers and ABC-transporters in human liver cancer cells which also have endogenous expression of GH as well as GHR. The data bolsters our proposed model of GH-GHR axis as a regulator of drug resistance in GH-responsive or GHR-expressing human cancers (FIG. 49). The effects of GHR-antagonist in reversing the mechanisms of drug resistance in human liver cancer cells, and the role of autocrine GH-GHR loop in driving drug resistance in human melanoma, supports our claim of sensitizing cancer cells to the effect of anti-cancer therapy in combination with methods of GHR antagonism.

While the present invention was illustrated by the description of one or ore embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative product and method, and illustrative examples shown and described. Accordingly, departures may be made from such details without departing from the scope of the general inventive concept embraced by the following claims.

What is claimed is:

1. A method of treating cancer in a subject, wherein the cancer includes cells expressing at least one growth hormone receptor, the method comprising:
   controlling an action of a growth hormone receptor on at least one cancer cell expressing the growth hormone receptor by administering an antagonist of the growth hormone receptor; and
   administering a sub-$EC_{50}$ dose of at least one anti-tumor drug, wherein the anti-tumor drug is a substrate of an ABC transporter.

2. The method of claim 1, wherein the anti-tumor drug is selected from the group consisting of cisplatin, doxorubicin, oridonin, paclitaxel, and vemurafenib.

3. The method of claim 1, wherein the subject is a human.

4. The method of claim 1, wherein the cancer is at least one of breast cancer, colorectal cancer, prostate cancer, hepatic cell carcinoma, and melanoma.

5. The method of claim 1, wherein the controlling an action of the growth hormone receptor includes knock down of the growth hormone receptor.

6. The method of claim 5, wherein the knock down of the growth hormone receptor is performed by siRNA mediated knock down.

7. The method of claim 5, wherein the knock down of the growth hormone receptor is anti-sense RNA directed against the growth hormone receptor.

8. The method of claim 5, wherein the knock down of the growth hormone receptor is caused by an antibody specific to the growth hormone receptor.

9. The method of claim 1, wherein the controlling an action of the growth hormone receptor is caused by inhibiting growth hormone action.

10. The method of claim 9, wherein the inhibiting growth hormone action is caused by antibodies directed against growth hormone.

11. The method of claim 1, wherein the antagonist of the growth hormone receptor is pegvisomant.

12. A method of treating cancer in a subject, wherein the cancer includes cells expressing at least one growth hormone receptor, the method comprising:
reducing serum insulin-like growth factor 1 (IGF1) levels below the normal serum IGF1 level of the subject by controlling an action of the growth hormone receptor by administering an antagonist of the growth hormone receptor; and
administering a sub-$EC_{50}$ dose of an anti-tumor drug to the subject, wherein the anti-tumor drug is a substrate of an ABC transporter.

13. The method of claim 12, wherein the antagonist of the growth hormone receptor is pegvisomant.

14. A method of maintaining an anti-tumor drug in cancer cells of a subject, comprising:
controlling an action of at least one growth hormone receptor in cancer cells expressing growth hormone receptor, wherein the controlling of an action of the growth hormone receptor includes co-administration of:
an antagonist of the growth hormone receptor; and
a sub-$EC_{50}$ dose of the anti-tumor drug, wherein the anti-tumor drug is a substrate of an ABC transporter.

15. The method of claim 14, wherein the anti-tumor drug is selected from the group consisting of cisplatin, doxorubicin, oridonin, paclitaxel, and vemurafenib.

16. The method of claim 14, wherein the subject is a human.

17. The method of claim 14, wherein the cancer cells are attributable to at least one of breast cancer, colorectal cancer, prostate cancer, hepatic cell carcinoma, and melanoma.

18. The method of claim 14, wherein the controlling an action of the growth hormone receptor includes knock down of the growth hormone receptor, and wherein the knock down of the growth hormone receptor is performed by siRNA mediated knock down.

19. The method of claim 18, wherein the knock down of the growth hormone receptor is anti-sense RNA directed against the growth hormone receptor.

20. The method of claim 18, wherein the knock down of the growth hormone receptor is caused by an antibody specific to the growth hormone receptor.

21. The method of claim 14, wherein the controlling an action of the growth hormone receptor is caused by inhibiting growth hormone action.

22. The method of claim 21, wherein the inhibiting the growth hormone action is caused by antibodies directed against growth hormone.

23. The method of claim 14, wherein the antagonist of the growth hormone receptor is pegvisomant.

\* \* \* \* \*